(12) United States Patent
Hernandez et al.

(10) Patent No.: US 8,461,134 B2
(45) Date of Patent: Jun. 11, 2013

(54) BORON-CONTAINING SMALL MOLECULES

(75) Inventors: Vincent S. Hernandez, Watsonville, CA (US); Xianfeng Li, Cupertino, CA (US); Suoming Zhang, Palo Alto, CA (US); Tsutomu Akama, Sunnyvale, CA (US); Yanchen Zhang, Union City, CA (US); Yang Liu, Foster City, CA (US); Jacob J. Plattner, Orinda, CA (US); Michael Richard Kevin Alley, Santa Clara, CA (US); Yasheen Zhou, Moraga, CA (US); James A. Nieman, Sherwood Park, CA (US)

(73) Assignee: Anacor Pharmaceuticals, Inc., Palo Alto, CA (US)

( * ) Notice: Subject to any disclaimer, the term of this patent is extended or adjusted under 35 U.S.C. 154(b) by 22 days.

(21) Appl. No.: 12/944,690

(22) Filed: Nov. 11, 2010

(65) Prior Publication Data
US 2011/0172187 A1 Jul. 14, 2011

Related U.S. Application Data

(60) Provisional application No. 61/260,384, filed on Nov. 11, 2009, provisional application No. 61/260,373, filed on Nov. 11, 2009.

(51) Int. Cl.
*A61K 31/18* (2006.01)
*A61K 31/69* (2006.01)
*C07F 5/02* (2006.01)
*A61P 31/04* (2006.01)

(52) U.S. Cl.
USPC ............... 514/64; 564/8; 564/86; 564/92

(58) Field of Classification Search
None
See application file for complete search history.

(56) References Cited

U.S. PATENT DOCUMENTS

| | | | |
|---|---|---|---|
| 2,260,336 A | 10/1941 | Prescott et al. |
| 3,686,398 A | 8/1972 | Kohn et al. |
| 3,873,279 A | 3/1975 | Singer |
| 4,602,011 A | 7/1986 | West et al. |
| 4,716,035 A | 12/1987 | Sampathkamar |
| 4,766,113 A | 8/1988 | West et al. |
| 4,894,220 A | 1/1990 | Nabi et al. |
| 4,919,934 A | 4/1990 | Deckner et al. |
| 5,348,947 A | 9/1994 | Patel et al. |
| 5,348,948 A | 9/1994 | Patel et al. |
| 5,591,731 A | 1/1997 | Kennedy et al. |
| 5,668,258 A | 9/1997 | Stolowitz |
| 5,688,928 A | 11/1997 | Stolowitz |
| 5,831,045 A | 11/1998 | Stolowitz et al. |
| 5,880,188 A | 3/1999 | Austin et al. |
| 5,962,498 A | 10/1999 | Driedger et al. |
| 6,083,903 A | 7/2000 | Adams et al. |
| 6,221,640 B1 | 4/2001 | Tao et al. |
| 6,306,628 B1 | 10/2001 | Rothschild et al. |
| 6,369,098 B1 | 4/2002 | Pershadsingh et al. |
| 6,521,619 B2 | 2/2003 | Link et al. |
| 6,800,645 B1 | 10/2004 | Cox et al. |
| 6,855,848 B2 | 2/2005 | Scherer et al. |
| 7,169,603 B2 | 1/2007 | Hedley et al. |
| 7,205,425 B2 | 4/2007 | Shibasaki et al. |
| 7,217,701 B2 | 5/2007 | Mikoshiba et al. |
| 7,390,806 B2 | 6/2008 | Lee et al. |
| 7,446,236 B2 | 11/2008 | Naud et al. |
| 7,465,836 B2 | 12/2008 | Lee et al. |
| 7,582,621 B2 | 9/2009 | Baker et al. |
| 7,767,657 B2 | 8/2010 | Baker et al. |
| 7,816,344 B2 | 10/2010 | Baker et al. |
| 8,039,450 B2 | 10/2011 | Akama et al. |
| 8,168,614 B2 | 5/2012 | Baker et al. |
| 2002/0028831 A1 | 3/2002 | Manley |
| 2002/0161230 A1 | 10/2002 | Meudt et al. |
| 2003/0032673 A1 | 2/2003 | Nagy |
| 2004/0077601 A1 | 4/2004 | Adams et al. |
| 2004/0224923 A1 | 11/2004 | Lee et al. |
| 2005/0054644 A1 | 3/2005 | Lee et al. |
| 2005/0125852 A1 | 6/2005 | Caenepeel et al. |
| 2006/0009386 A1 | 1/2006 | Stossel et al. |
| 2006/0222671 A1 | 10/2006 | Weidner |
| 2006/0234981 A1 | 10/2006 | Baker et al. |
| 2007/0155699 A1 | 7/2007 | Baker et al. |
| 2007/0286822 A1 | 12/2007 | Sanders et al. |
| 2007/0293457 A1 | 12/2007 | Baker et al. |
| 2009/0227541 A1 | 9/2009 | Baker et al. |
| 2010/0048570 A1 | 2/2010 | Kim et al. |
| 2010/0256092 A1 | 10/2010 | Xia et al. |

FOREIGN PATENT DOCUMENTS

| | | |
|---|---|---|
| EP | 0969531 | 1/2000 |
| EP | 1155698 A1 | 11/2001 |
| EP | 1 444 981 A1 | 8/2004 |
| WO | WO 9533754 | 5/1995 |
| WO | WO 9622023 A1 | 7/1996 |

(Continued)

OTHER PUBLICATIONS

Williams, D. A., Foye, W. O., Lemke, T. L., Foye's Principles of Medicinal Chemistry, 5th Edition, 2002, Lippincott Williams & Wilkins, p. 59.*
Austin, et al., "Oxaboroles and Salts and their Use of Biocides for Plastics", CAS, vol. 124, pp. 234-024, (1996).
Bailey, et al., "Boron—Containing Antibacterial Agents: Effects on Growth and Morphology of Bacteria Under Various Culture Conditions," Antimicrobial Agents and Chemotherapy, 17(04):549-553, (Apr. 1980).
Baker, et al., "Discovery of New Boron-Containing Antifungal Agent, 5-Fluoro-1,3-dihydro-1-hydroxy-2, 1-benzoxaborole (AN2690) for Potential Treatment of Onychomoycosis", Journal of Medicinal Chemistry, vol. 49, No. 15; pp. 4447-4450, (Jul. 27, 2006).
Bessis, N., "Gene Therapy for Rheumatoid Arthritis," J. Gene Med, vol. 4; pp. 581-591 (2002).

(Continued)

*Primary Examiner* — Sreeni Padmanabhan
*Assistant Examiner* — Irina Neagu
(74) *Attorney, Agent, or Firm* — Morgan, Lewis & Bockius LLP

(57) ABSTRACT

This invention relates to, among other items, 6-substituted benzoxaborole compounds and their use for treating bacterial infections.

25 Claims, 18 Drawing Sheets

FOREIGN PATENT DOCUMENTS

| | | |
|---|---|---|
| WO | WO 9812206 A1 | 3/1998 |
| WO | WO 0027822 | 5/2000 |
| WO | WO 0044387 A1 | 8/2000 |
| WO | WO 0075142 A2 | 12/2000 |
| WO | WO 0114578 A1 | 3/2001 |
| WO | WO 0149303 A1 | 7/2001 |
| WO | WO 0187846 A2 | 11/2001 |
| WO | WO 0244184 | 6/2002 |
| WO | WO 03033002 A1 | 4/2003 |
| WO | WO 03059916 A2 | 7/2003 |
| WO | WO 2004056322 A2 | 7/2004 |
| WO | WO 2005013892 A3 | 2/2005 |
| WO | WO 2005123094 A2 | 12/2005 |
| WO | WO 2006007384 | 1/2006 |
| WO | WO 2006062731 A1 | 6/2006 |
| WO | WO 2006079843 A1 | 8/2006 |
| WO | WO 2006089067 A2 | 8/2006 |
| WO | WO 2006096131 A1 | 9/2006 |
| WO | WO 2007022437 A2 | 2/2007 |
| WO | WO 2007078340 A2 | 7/2007 |
| WO | WO 2007095638 A2 | 8/2007 |
| WO | WO 2007146965 A2 | 12/2007 |
| WO | WO 2008157726 A1 | 12/2008 |
| WO | WO 2009111676 A2 | 9/2009 |
| WO | WO 2009140309 A2 | 11/2009 |
| WO | WO 2010028005 A1 | 3/2010 |
| WO | WO 2010045503 A | 4/2010 |
| WO | WO 2010045505 A1 | 4/2010 |

OTHER PUBLICATIONS

Brown, et al., "Chiral Synthesis Via Organoboranes. 35. Simple Procedures for the Efficient Recycling of the Terpenyl Chiral Auxiliaries and Convenient Isolation of the Homoallylic Alcohols in Asymmetric Allyl- and Crotylboration of Aldehydes," J. Org. Chem., vol. 57, No. 24; pp. 6608-6614, (1992).
Cairns, et al., "Derivatives of 1,4-Xylene-2,5-diboronic acid and 1,4-xylene-2-boronic acid", J. Org. Chem. vol. 29; pp. 2810-2812, (1964).
Chander, et al. "Prevalence of Fungal Corneal Ulcers in Northern India", Infections, vol. 22, No. 3; pp. 207-209, (1994).
Chemical Abstracts Registry No. 845302-09-2, Entered STN Mar. 11, 2005.
Cui, et al., "Organoboron Compounds with an 8-Hydroxyquinolato Chelate and Its Derivatives: Substituent Effects on Structures and Luminescence," Inorganic Chemistry, vol. 44, No. 03; pp. 601-609, (Feb. 7, 2005).
Dale, et al., "Substituted Styrenes VIII Syntheses and some Reactions of the Vinylbenzeneboronic Acids" J. Org. Chem. vol. 27; pp. 2598-2603, (1962).
Denis, "Pharmacology 1104 Lecture: Drug Classifications & Characteristics of Antimicrobials" (2003).
Farfan, et al., "Through-Bond Modulation on N-B Ring Formation Shown by NMR and X-Ray Diffraction Studies of Borate Derivatives of Pyridyl Alcohols," J. Chem. Soc. Perkin Trans, vol. 2; pp. 527-532 (1992).
Ferrer, Targeting Aminocytl-tRNA Synthetases for the Treatment of Fungal Infections, Drug News Perspective, vol. 19, No. 6; pp. 347-348, (Jul./Aug. 2006).
Fungicide: Definition from Answer.com, (1998).
Grassberger, et al., "Degradation of 1,2-dihydro-1-hydroxy-2-(organosulfonyl)2,3,1-benzodiasaborines and -thieno[3,2-d][1,,3]diazaborines in Alkaline Aqueous Solutions", Liebigs Annalen Der Chemie, vol. 4; pp. 683-688, (1985).
Guo-Zheng, et al., "Single Site Transarylation of 2,2'-Dimetalized-1,1'-Binaphthyl to Aminocloroborates and Synthesis of 2-Binaphthyl Boron Compounds," Youji Huaxue/Organic Chemistry, Science Press, vol. 16, No. 02; pp. 139-144, (1996) (English Abstract).
Haynes, et al., "Arylboronic Acids VIII. Reactions of boronphthalide" J. Org. Chem. vol. 29, No. 11; pp. 3229-3233, (1964).
Hauck, et al., "Preparation and Anticonvulsant Activity of Some Arydialkkylsuccinimides" Research Lab of Parke Davis Co. (1967).
He, et al., "Small-Molecule Inhibition of TNF-alpha", Science, vol. 310, No. 5750; pp. 1022-1025, (Nov. 11, 2005).

Lampe, et al., "Synthesis and Protien Kinase Inhibitory Activity of Balanol Analogues with Modified Benzophenone Subunits", J. Med. Chem., vol. 45; pp. 2624-2643, (2002).
Lennarz, et al., "Arylboronic Acids. IV. Reactions of Boronophthalide" J. Am. Chem. Soc. vol. 82; pp. 2172-2175, (1960).
Li, et al., "An Improved Protocol for Preparation of 3-Pyridyl- and Some Arylboronic Acids", J. Org. Chem., vol. 67; pp. 5394-5397, (2002).
Koster, et al., "Cyclisierugen von Bor-Stickstoff-Verbindugen in der Hietz" Liebigs Ann. Chem., vol. 720; pp. 23-31, (1968).
Koster, et al., "Boron Compounds, XXXIX. Alkenoxy(diorgany)boranes Substituted at the Alkeonxy Group from 2-methylacrolein and triorganylboranes," Justus Liebigs Annalen Der Chemie, No. 06; pp. 1116-1134, (1976).
McMillin, et al., "Systemic Aspects of Psoriasis: An Intergrative Model Based on Intestinal Etiology", Int. Med. vol. 2, Issue 2/3, (1999).
Moeder, et al., "Kinetic Analysis of the Asymmetric Amplification exhibited by B-chlorodiisopinocampheylborane," Journal of Physical Organic Chemistry, vol. 17, No. 4; pp. 317-324, (Apr. 2004).
Morissette, et al., "High-throughput Crystallization: Polymorphs, Salts, Co-Crystals and Solvates of Pharmaceutical Solids", Advanced Drug Delivery Reviews, vol. 56; pp. 273-300, (2004).
Mudran, "Drug Delivery to the Nail Following Topical Application", International Journal of Pharmaceutics, vol. 236: pp. 1-26, (2002).
Patani, et al., "Bioterrorism: A Rational Approach to Drug Design", Chem. Rev., vol. 96; pp. 3147-3176 (1996).
Qin, et al., "Luminescent Organoboron Quinolate Polymers," Journal of the American Chemical Society, vol. 126, No. 22; pp. 7015-7018, (Jun. 9, 2004).
Rock, et al., "An Antifungal Agents Inhibits Aminoacyl-tRNA Synthetase by Trapping tRNA in the Editing Site", Science, vol. 316, No. 5832; pp. 1759-1761, (Jun. 22, 2007).
Snyder, et al. "Common Bacteria Whose Susceptibility to Antimicrobials in no longer Predictable" J. Med. Liban, vol. 48 No. 4; pp. 208-214, (2000).
Sugar, et al., "Comparison of Three Methods of Antifungal Susceptibility Testing with the Proposed NCCLS Stardard Broth Macrodilution Assay: Lack of Effect of Phenol Red" Diagn. Microbiol. Infect. Dis. vol. 21; pp. 129-133, (1995).
Tabuchi, et al., "Anticoccidial Activity of some Azacyclo Organoborinates," Heterocycles, vol. 60, No. 01; pp. 177-182, (2003).
Toporcer, et al., "Preparation and Properties of some Tetracoordinate Boron Compounds. The Pseudo-metal Ion Concept," Inorganic Chemistry, vol. 4, No. 11; pp. 649-1655, (Nov. 1965).
Trujillo, et al., "X-Ray Crystallographic Study of Boroxazolidones, Obtained from L-ornithine, L-methionine, Kainic acid and 2,6-pyridinedicarboxylic acid", Journal of Organometallic Chemistry, vol. 571; pp. 21-29, (1998).
Tschampel, et al., "Arylboronic Acids. VII. Some Reactions to o-Formybenzeneboronic Acids", J. Org. Chem. vol. 29, No. 8; pp. 2168-2172, (1964).
Turner, et al., Current Pharmaceutical Design, vol. 2; pp. 209-224 (1996).
Vippagunta, "Crystalline Solids", Advanced Drug Delivery Reviews, vol. 48; pp. 3-26, (2001).
Wang, et al., "Expression, Purification and Characterization of Human cAMP-Specific Phosphodiesterase (PDE4) Subtypes A, B, C, and D", Biochemical and Biophysical Research Communications, vol. 234; pp. 320-324, (1997).
Ye, et al., "Convenient and Versatile Synthesis of formyl-substituted Benzoxaboroles", Tetrahedron, vol. 65; pp. 8738-8744, (2009).
Zhdankin, et al., "Synthesis and Structure of Benzoboroxoles: Novel Organboron Heterocycles," Tetrahedron Letters, vol. 40; pp. 6705-6708, (1999).
Zhou, et al., "Hemodextrin: a Self-assembled Cyclodextrin-Porphyrin Construct That Binds Dioxygen," Biophysical Chemistry, 105:639-648 (2003).
Zhou, et al., "Structure-activity Studies on a Library of Potent Calix[4]arene-based PDGF Antagonists that Inhibit PDGF—stimulated PDGFR Tyrosine Phosphorylation," Org. Biomol. Chem., 4:2376-2386 (2006).

Zhou, et al., "Pattern Recognition of Proteins Based on an Array of Functionalized Porphyrins," J. Am. Chem. Sec., 128:2421-2425 (2006).

Zixing, et al., "Synthesis of Aromatic Nitrogen-containing Heterocyclic Derivatives of Asymmetric Diarylborinic Acids," Wuhan Daxue Xuebo-Wuhan University Journal, vol. 3; pp. 67-71, (1990), (English Abstract).

Adamczyk-Wozniac, et al., "Benzoxaboroles-Old Compounds with new applications", Journal of Organometalic Chemistry 694;3533-3541 (2009).

Akama, et al., "Discovery and structure-activity study of novel benzoxaborole anit-inflammatory agent (AN2728) for the potential topical treatment of psoriasis and atopic dermatitis", Bioorganic & Medicinal Chemistry Letters, (2009) 19: 2129-2132.

Alley, et al., "Recent Progress on Topical Therapy of Onychomycosis" Expert Opinion Investigate Drugs(Feb. 2007) 16(2): 157-67.

Baker, et al., "Identification of a Novel Boron-Containing Antibacterial Agent (AN0128) with Anti-inflammatory activity, for the Potential Treatment of Cutaneous Diseases", Bioorganic & Medicinal Chemistry Letters (2006) 16; 5963-5937.

Baker, et al., "Progress on New Therapeutics for Fungal Nail Infections", Annual Reports in Medicinal Chemistry, vol. 40: pp. 323-335, (2005).

Cusack, S., et al., "The 2 A Crystal Structure of leucyl-tRNA Synthetase and its Complex with a Leucyl-Adenylate Analogue." EMBO Journal, vol. 19; pp. 2351-2361, (2000).

Dian, "International Nomenclature of Organics", China Petrochemical Press, 1st Edition; 50-51 (Jan. 21, 2004).

Goodman, et al., "Goodman & Gilman's Manual of Pharmacology and Therapeutics" Chapter 40;681-694 (2008).

Hui, et al., "In Vitro Penetration of a Novel Oxaborole Antifungal (AN2690) into the Human Nail Plate", Journal of Pharmaceutical Sciences (2007) 96(10): 2622-2631.

Lee, K., et al., "Molecular Study of the Editing Active Site of Escherichia coli Leucyl-tRNA Synthetase: Two Amino Acid Binding Site in the Editing Domain", vol. 54; pp. 693-704, (2004).

Luan, et al., "Inhibition of Experimental Periodontitis by a topical boron-base antimicrobial" J Dent. Res, 87(2):148-152 (2008).

Perola, E., et al., "Successful Virtual Screening of a Chemical Database for Farnesltransferase Inhibitor Leads." vol. 43; pp. 401-4008, (2000).

Silverman, "The Organic Chemistry of Drug Design and Drug Action", 2nd Edition, Northwestern University, Department of Chemistry, Evanston, Illinois, Section 2: 29-32 (2004).

Tatsumi, et al., "Therapeutic Efficacy of Topically applied KP-103 against Experimental Tinea Uguium in Guinea Pigs in Comparison with Amorolfine and Terbinafine", Antimicrobial Agents and Chemotherapy, vol. 46, No. 12; pp. 3797-3801 (2002).

Williams, et al., "Foye's Principles of Medicinal Chemistry", 5th Edition, 2002, Lippincoot Williams & Wilkins, p. 59.

"Structure-Activity Studies led to Discovery of AN2898 in Development for Topical Treatment of Psoriasis and Atopic Dermatitis", Scientific Presentation at the American Academy of Dermatology Annual Meeting, San Francisco, CA Mar. 6-10, 2009.

"AN2898 Inhibits Cytokines Relevant to Topical Treatment of Psoriasis and Atopic Dermatitis", Scientific Presentation at the American Academy of Dermatology Annual Meeting, San Francisco, CA Mar. 6-10, 2009.

"AN2718 has Broad Spectrum Antifungal Activity Necessary for the Topical Treatment of Skin and Nail Fungal Infections", Scientific Presentation at the American Academy of Dermatology Annual Meeting, San Francisco, CA Mar. 6-10, 2009.

"AN2718 Demonstrates Significant Efficacy in Three Phase Ib Psoriasis Microplaque Trials" Scientific Presentation at the American Academy of Dermatology Annual Meeting, San Francisco, CA Mar. 6-10, 2009.

"AN2728 Demonstrates Significant Safety and Efficacy in Phase IIa Double Blind Trial in Plaque Type Psoriasis ", Scientific Presentation at the American Academy of Dermatology Annual Meeting, San Francisco, CA Mar. 6-10, 2009.

"AN2728 Preclinical Studies Demonstrate an Acceptable Safety Profile for the Topical Treatmant of Psoriasis and Atopic Dermatitis", Scientific Presentation at the American Academy of Dermatology Annual Meeting, San Francisco, CA May 6-10, 2009.

"A New Class of Benzoxaborole-based Potent Antitrypanosomal Agents: Probing Effect of Different Linkage Groups in *Trypanosoma brucei* Growth Inhibition", Scientific Presentation at the American Society of Tropical Medicine and Hygiene Conference, New Orleans, LA Dec. 7-11, 2008.

"AN2920, A Novel Oxaborole, Shows In Vitro and In Vivo Activity Against *Trypanosomal brucei*", Scientific Presentation at the American Society of Tropical Medicine and Hygiene Conference, New Orleans, LA Dec. 7-11, 2008.

"A Novel Oxaborole, AN3520, Show Efficacy against Human African Trypanomiasis In Vitro and In Vivo, Including Promise in a Murine CNS Model of *T. brucei* Infection", Scientific Presentation at the American Society of Tropical Medicine and Hygiene Conference, New Orleans, LA Dec. 7-11, 2008.

"Antifungal Activity and Mechanism of Action of a Benzoxaborole, AN2718, which is in Development for the Treatment of Tinea Pedis", Scientific Presentation at the 48th Interscience Conference on Antimicrobial Agents and Chemotherapy, Washington, D.C. Oct. 25-28, 2008.

"AN2728 Ointment, a Novel Oxaborole with Anti-Inflammatory Activity, Demonstrates Safety and Significant Efficacy in a Phase Ib Psoriasis Plaque Test", Scientific Presentation at Montagna Symposium on Biology of Skin, Gleneden Beach, OR, Oct. 2-6, 2008.

"Preclinical Toxicology of AN2728, a Novel Oxaborole in Development for the Topical Treatment of Psoriasis", Scientific Presentation at the International Investigative Dermatology Conference, Kyoto, Japan, May 14-18, 2008.

"AN2898, a Novel Oxaborole Compound with Anti-Inflammatory Activity: Mechanism of Action and in vitro Cytokine Inhibition", Scientific Presentation at the International Investigative Dermatology Conference, Kyoto, Japan, May 14-18, 2008.

"Structure-Activity Studies of AN2728 and AN2898, Novel Oxaborole Compounds with Anti-Inflammatory Activity", Scientific Presentation at the International Investigative Dermatology Conference, Kyoto, Japan, May 14-18, 2008.

"In Vitro Activity and Mechanism of Action of AN2728, a Novel Oxaborole in Development for Treatment of Psoriasis", Scientific Presentation at the International Investigative Dermatology Conference, Kyoto, Japan, May 14-18, 2008.

"AN2898, a Novel Oxaborole Compound with Anti-Inflammatory Activity: Results of In Vivo Efficacy and Preclinical Safety Studies", Scientific Presentation at the International Investigative Dermatology Conference, Kyoto, Japan, May 14-18, 2008.

"AN2728, a Novel Oxaborole in Development for Treatment of Psoriasis, Demonstrates Significant Activity in a Micro Plaque Study", Scientific Presentation at the International Investigative Dermatology Conference, Kyoto, Japan, May 14-18, 2008.

"Preclinical Toxicology of AN2728, a Novel Borinic Acid Ester with Anti-Inflammatory Activity", American Academy of Dermatology, 65th Annual Meeting, Washington, DC, Feb. 2-6, 2007.

"AN2728, a Novel Oxaborole with Broad-Spectrum In Vitro Anti-Inflammatory Activity", American Academy of Dermatology, 65th Annual Meeting, Washington, DC, Feb. 2-6, 2007.

"In Vitro Nail Penetration of AN2690, Effect of Vehicle and Co-Efficient of Efficacy", American Academy of Dermatology, 65th Annual Meeting, Washington, DC, Feb. 2-6, 2007.

"Interim Results of Multi-Center Study to Evaluate the Safety and Efficacy of Topically Applied AN2690 5.0% and 7.5% Solutions for the Treatment of Onychomycosis of the Great Toenail", American Academy of Dermatology, 65th Annual Meeting, Washington, DC, Feb. 2-6, 2007.

"In vivo Nail Residence Time of AN2690, a Novel Broad-Spectrum Antifungal Agent in Development for the Topical Treatment of Onychomycosis", Academy of Dermatology, 65th Annual Meeting, Washington, DC, Feb. 2-6, 2007.

"An Open-Label, Multi-dose Study of Absorption and Systemic Pharmacokinetics of AN2690 Applied as a 7.5% Solution to All Toenails of Adult Patients with Moderate to Severe Onychomycosis", American Academy of Dermatology, 65th Annual Meeting, Washington, DC, Feb. 2-6, 2007.

"Medicinal Chemistry Development of AN2728, a Novel Oxaborole in Development for the Topical Treatment of Psoriasis", American Academy of Dermatology, 65th Annual Meeting, Washington, DC, Feb. 2-6, 2007.

"Skin Penetration and Anti-Inflammatory Activity of AN2728, a Novel Oxaborole", American Academy of Dermatology, 65th Annual Meeting, Washington, DC, Feb. 2-6, 2007.

"Nail Penetration and Nail Concentration of AN2690, a Novel Broad-Spectrum Antifungal Agent in Development for the Topical Treatment of Onychomycosis", Scientific Presentation at the American Associate of Pharmaceutical Scientist, Annual Meeting, San Antonio, TX, Oct. 29-Nov. 2, 2006.

U.S. Appl. No. 13/673,860, filed Nov. 9, 2012.
U.S. Appl. No. 13/607,321, filed Sep. 7, 2012.
U.S. Appl. No. 13/607,405, filed Sep. 7, 2012.
U.S. Appl. No. 13/607,250, filed Sep. 7, 2012.
U.S. Appl. No. 13/356,488, filed Jan. 23, 2012.
U.S. Appl. No. 12/629,753, filed Dec. 2, 2009, now U.S. Patent 8,115,026.
U.S. Appl. No. 11/357,687, filed Feb. 16, 2006, now U.S. Patent 7,582,621.
U.S. Appl. No. 11/505,591, filed Aug. 16, 2006, now U.S. Patent No. 7,767,657.
U.S. Appl. No. 12/507,010, filed Jul. 21, 2009, now U.S. Patent No. 8,039,451.
U.S. Appl. No. 11/676,120, filed Feb. 16, 2007, now U.S. Patent No. 8,168,614.
U.S. Appl. No. 13/453,682, filed Apr. 23, 2012.
U.S. Appl. No. 11/762,038, filed Jun. 12, 2007.
U.S. Appl. No. 11/865,725, filed Oct. 1, 2007, now abandoned.
U.S. Appl. No. 12/142,692, filed Jun. 19, 2008, now U.S. Patent No. 7,816,344.
U.S. Appl. No. 12/752,789, filed Apr. 1, 2010, now abandoned.
U.S. Appl. No. 12/848,051, filed Jul. 30, 2010.
U.S. Appl. No. 12/399,015, filed Mar. 5, 2009, now U.S. Patent No. 8,039,450.
U.S. Appl. No. 13/236,543, filed Sep. 19, 2011.
U.S. Appl. No. 13/062,450, filed Mar. 4, 2011.
U.S. Appl. No. 12/464,829, filed May 12, 2009.
U.S. Appl. No. 13/062,466, filed Mar. 4, 2011.
U.S, Appl. No. 12/641,318, filed Dec. 17, 2009.
U.S. Appl. No. 12/873.036, filed Aug. 31, 2010.
U.S. Appl. No. 12/844,748, filed Jul. 27, 2010.
U.S. Appl. No. 13/062,491, filed Mar. 4, 2011.
U.S. Appl. No. 13/503,016, filed Jun. 25, 2012.
U.S. Appl. No. 12/857,305, filed Aug. 16, 2010.
U.S. Appl. No. 12/852,351, filed Aug. 6, 2010.
U.S. Appl. No. 12/944,690, filed Nov. 11, 2010.
U.S. Appl. No. 13/015,487, filed Jan. 27, 2011.
U.S. Appl. No. 12/944,699, filed Nov. 11, 2010.
U.S. Appl. No. 13/639,594, filed Sep. 7, 2012.
U.S. Appl. No. 13/227,444, filed Sep. 7, 2011.

* cited by examiner

Figure 1A

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| 2,4-diamino-N-(1-hydroxy-1,3-dihydrobenzo[c][1,2]oxaborol-6-yl)benzenesulfonamide | 0.54 | 2.38 | 2.70 | 2 | 8 | 0.5 | 8 |
| 4-amino-N-(1-hydroxy-1,3-dihydrobenzo[c][1,2]oxaborol-6-yl)-3-(trifluoromethyl)benzenesulfonamide | 5.16 | 156.50 | >100 | NT | 32 | 4 | 64 |
| 4-amino-N-(1-hydroxy-1,3-dihydrobenzo[c][1,2]oxaborol-6-yl)-2-methoxybenzenesulfonamide | 1.86 | 15.22 | 18.76 | NT | 16 | 1 | 8 |
| 4-amino-2-hydroxy-N-(1-hydroxy-1,3-dihydrobenzo[c][1,2]oxaborol-6-yl)benzenesulfonamide | 0.61 | 1.18 | 2.08 | 4 | 4 | 0.75 | 4 |
| 4-amino-3-fluoro-N-(1-hydroxy-1,3-dihydrobenzo[c][1,2]oxaborol-6-yl)benzenesulfonamide | 0.52 | 3.40 | 3.79 | NT | 4 | 0.25 | 16 |
| N-(1-hydroxy-1,3-dihydrobenzo[c][1,2]oxaborol-6-yl)-2-oxoindoline-5-sulfonamide | 1.67 | 54.40 | 40.29 | NT | >64 | 8 | >64 |
| N-(1-hydroxy-1,3-dihydrobenzo[c][1,2]oxaborol-6-yl)-2-oxo-2,3-dihydrobenzo[d]oxazole-6-sulfonamide | 6.64 | 179.13 | 58.96 | NT | >64 | 4 | 64 |
| 4-amino-2-chloro-N-(1-hydroxy-1,3-dihydrobenzo[c][1,2]oxaborol-6-yl)benzenesulfonamide | 0.37 | 1.49 | 1.87 | NT | 2 | 1 | 8 |

Figure 1B

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| 1-acetyl-N-(1-hydroxy-1,3-dihydrobenzo[c][1,2]oxaborol-6-yl)indoline-5-sulfonamide | 197.46 | >300 | 134.04 | NT | >64 | 8 | >64 |
| N-(1-hydroxy-1,3-dihydrobenzo[c][1,2]oxaborol-6-yl)-2-oxo-2,3-dihydro-1H-benzo[d]imidazole-5-sulfonamide | 4.14 | 2.64 | 27.87 | NT | >64 | 32 | >64 |
| N-(1-hydroxy-1,3-dihydrobenzo[c][1,2]oxaborol-6-yl)-2,3-dioxo-1,2,3,4-tetrahydroquinoxaline-6-sulfonamide | 0.77 | 4.92 | 9.85 | NT | >64 | >64 | >64 |
| 4-amino-N-(1-hydroxy-1,3-dihydrobenzo[c][1,2]oxaborol-6-yl)-2-methylbenzenesulfonamide | 0.66 | 3.08 | 3.19 | NT | 2 | 1 | 8 |
| N-(1-hydroxy-1,3-dihydrobenzo[c][1,2]oxaborol-6-yl)-1H-indazole-5-sulfonamide | 0.76 | 10.06 | NT | NT | 16 | 4 | 32 |
| N-(1-hydroxy-1,3-dihydrobenzo[c][1,2]oxaborol-6-yl)-1-(2,2,2-trifluoroacetyl)indoline-5-sulfonamide | 5.50 | 161.36 | NT | NT | >64 | 8 | >64 |
| 4-amino-2-fluoro-N-(1-hydroxy-1,3-dihydrobenzo[c][1,2]oxaborol-6-yl)benzenesulfonamide | 0.72 | 3.56 | NT | NT | 2 | 0.5 | 8 |
| 4-amino-2-chloro-N-(5-fluoro-1-hydroxy-1,3-dihydrobenzo[c][1,2]oxaborol-6-yl)benzenesulfonamide | 1.04 | 3.08 | NT | NT | 2 | 0.5 | 8 |

Figure 1C

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| 4-amino-2-ethyl-N-(1-hydroxy-1,3-dihydrobenzo[c][1,2]oxaborol-6-yl)benzenesulfonamide | 0.69 | 3.33 | NT | 8 | 2 | 2 | 16 |
| N-(1-hydroxy-1,3-dihydrobenzo[c][1,2]oxaborol-6-yl)indoline-5-sulfonamide | 4.16 | 35.63 | 37.75 | >64 | 32 | 8 | 64 |
| 4-amino-2-(3-ethylureido)-N-(1-hydroxy-1,3-dihydrobenzo[c][1,2]oxaborol-6-yl)benzenesulfonamide | 0.44 | 0.83 | 0.33 | 2 | 32 | 0.25 | 2 |
| ethyl 2-(2-(N-(1-hydroxy-1,3-dihydrobenzo[c][1,2]oxaborol-6-yl)sulfamoyl)-5-(2,2,2-trifluoroacetamido)phenyl)acetate | 1.23 | 3.36 | 0.93 | 4 | 1 | 2 | 4 |
| 4-amino-2-fluoro-N-(5-fluoro-1-hydroxy-1,3-dihydrobenzo[c][1,2]oxaborol-6-yl)benzenesulfonamide | 0.41 | 2.32 | 1.01 | 2 | 2 | 0.25 | 4 |
| 4-amino-N-(1-hydroxy-1,3-dihydrobenzo[c][1,2]oxaborol-6-yl)-2-(3-hydroxypropyl)benzenesulfonamide | 0.44 | 1.75 | 0.91 | 0.5 | 16 | 0.25 | 8 |
| 4-amino-2-cyano-N-(1-hydroxy-1,3-dihydrobenzo[c][1,2]oxaborol-6-yl)benzenesulfonamide | 0.40 | 0.27 | 0.23 | 2 | 4 | 1 | 8 |

Figure 1D

| IUPAC Name | LeuRS_Ecoli IC50 [μM] | LeuRS_Saureus IC50 [μM] | LeuRS_Spneumoniae IC50 [μM] | H. influenzae ATCC 49766 MIC [μg/mL] | S. aureus ATCC 29213 MIC [μg/mL] | S. pneumoniae ATCC 6301 MIC [μg/mL] | S. pyogenes ATCC 19615 MIC [μg/mL] |
|---|---|---|---|---|---|---|---|
| methyl 2-(2-(N-(1-hydroxy-1,3-dihydrobenzo[c][1,2]oxaborol-6-yl)sulfamoyl)-5-(2,2,2-trifluoroacetamido)phenyl)acetate | 2.32 | 8.75 | 7.86 | 0.5 | 1 | 0.25 | 2 |
| N-(5-amino-2-(N-(1-hydroxy-1,3-dihydrobenzo[c][1,2]oxaborol-6-yl)sulfamoyl)benzyl)acetamide | 0.23 | 1.31 | 0.55 | 1 | 64 | 0.5 | 4 |
| Methyl 3-(methoxycarbonylamino)methyl)-4-(N-(1-hydroxy-1,3-dihydrobenzo[c][1,2]oxaborol-6-yl)sulfamoyl)phenylcarbamate | 0.80 | 5.10 | 19.04 | 32 | >64 | 4 | 32 |
| 4-amino-N-(1-hydroxy-1,3-dihydrobenzo[c][1,2]oxaborol-6-yl)-2-(2-hydroxyethyl)benzenesulfonamide | 0.36 | 0.52 | 0.23 | 0.25 | 4 | <=0.12 | 1 |
| ethyl 3-(2-(N-(1-hydroxy-1,3-dihydrobenzo[c][1,2]oxaborol-6-yl)sulfamoyl)-5-(2,2,2-trifluoroacetamido)phenyl)propanoate | 1.00 | 3.31 | 0.85 | 32 | 2 | 4 | 64 |
| 2-(5-amino-2-(N-(1-hydroxy-1,3-dihydrobenzo[c][1,2]oxaborol-6-yl)sulfamoyl)phenyl)acetamide | 0.55 | 1.16 | 0.38 | 2 | 32 | 0.25 | 4 |
| methyl 5-amino-2-(N-(1-hydroxy-1,3-dihydrobenzo[c][1,2]oxaborol-6-yl)sulfamoyl)benzylcarbamate | 0.30 | 0.51 | 0.36 | 1 | 4 | <=0.12 | 4 |

Figure 1E

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| methyl 2-(5-amino-2-(N-(5-fluoro-1-hydroxy-1,3-dihydrobenzo[c][1,2]oxaborol-6-yl)sulfamoyl)phenyl)acetate | 0.43 | 0.59 | 0.37 | 1 | 1 | 0.25 | 1 |
| ethyl 2-(2-(N-(5-fluoro-1-hydroxy-1,3-dihydrobenzo[c][1,2]oxaborol-6-yl)sulfamoyl)-5-(2,2,2-trifluoroacetamido)phenyl)acetate | 0.61 | 1.16 | 0.67 | 32 | 4 | 8 | 16 |
| 2-(5-amino-2-(N-(5-fluoro-1-hydroxy-1,3-dihydrobenzo[c][1,2]oxaborol-6-yl)sulfamoyl)phenyl)acetamide | 0.35 | 2.29 | 0.40 | 8 | 64 | 0.25 | 4 |
| methyl 2-(5-amino-2-(N-(1-hydroxy-1,3-dihydrobenzo[c][1,2]oxaborol-6-yl)sulfamoyl)phenyl)acetate | 0.47 | 0.99 | 0.39 | 0.25 | 1 | 0.5 | >2 |
| ethyl 2-(5-amino-2-(N-(5-fluoro-1-hydroxy-1,3-dihydrobenzo[c][1,2]oxaborol-6-yl)sulfamoyl)phenyl)acetate | 0.27 | 0.98 | 0.39 | 2 | 0.5 | 0.375 | 2 |
| ethyl 2-(5-amino-2-(N-(1-hydroxy-1,3-dihydrobenzo[c][1,2]oxaborol-6-yl)sulfamoyl)phenyl)acetate | 0.19 | 0.26 | 0.18 | 1 | 0.5 | 0.25 | 4 |
| 4-amino-N-(5-fluoro-1-hydroxy-1,3-dihydrobenzo[c][1,2]oxaborol-6-yl)-2-(2-hydroxyethyl)benzenesulfonamide | 0.34 | 0.56 | 0.24 | 0.5 | 4 | <=0.12 | 1.5 |

Figure 1F

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| 2-(5-amino-2-(N-(1-hydroxy-1,3-dihydrobenzo[c][1,2]oxaborol-6-yl)sulfamoyl)phenyl)acetic acid | 0.73 | 4.68 | 0.63 | >64 | >64 | 2 | 64 |
| 4-amino-2-(2-hydrazinyl-2-oxoethyl)-N-(1-hydroxy-1,3-dihydrobenzo[c][1,2]oxaborol-6-yl)benzenesulfonamide | 0.33 | 0.89 | 0.78 | 8 | 64 | 1 | 16 |
| N-(5-amino-2-(N-(5-fluoro-1-hydroxy-1,3-dihydrobenzo[c][1,2]oxaborol-6-yl)sulfamoyl)phenethyl)-2,2,2-trifluoroacetamide | 0.93 | 2.72 | 6.61 | 32 | 32 | 1 | 16 |
| 4-amino-2-(2-aminoethyl)-N-(1-hydroxy-1,3-dihydrobenzo[c][1,2]oxaborol-6-yl)benzenesulfonamide | 1.00 | 1.10 | 12.51 | >64 | 64 | 64 | 32 |
| 4-amino-N-(1-hydroxy-1,3-dihydrobenzo[c][1,2]oxaborol-6-yl)-2-(2-oxo-2-(pyrrolidin-1-yl)ethyl)benzenesulfonamide | 5.09 | 10.15 | 38.60 | 16 | 8 | 8 | 32 |
| 2-(5-amino-2-(N-(1-hydroxy-1,3-dihydrobenzo[c][1,2]oxaborol-6-yl)sulfamoyl)phenyl)-N-cyclopentylacetamide | 0.33 | 0.74 | 0.42 | 2 | 4 | 0.25 | 2 |
| N-(5-amino-2-(N-(1-hydroxy-1,3-dihydrobenzo[c][1,2]oxaborol-6-yl)sulfamoyl)phenethyl)-2,2,2-trifluoroacetamide | 0.84 | 3.49 | 15.54 | 8 | 64 | 1 | 16 |

Figure 1G

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| 4-amino-2-(cyanomethyl)-N-(1-hydroxy-1,3-dihydrobenzo[c][1,2]oxaborol-6-yl)benzenesulfonamide | 0.83 | 1.69 | 3.04 | 1 | 2 | 0.5 | 4 |
| 2-(5-amino-2-(N-(1-hydroxy-1,3-dihydrobenzo[c][1,2]oxaborol-6-yl)sulfamoyl)phenyl)-N-butylacetamide | 0.43 | 2.29 | 0.38 | 2 | 8 | <=0.12 | 2 |
| 2-(5-amino-2-(N-(1-hydroxy-1,3-dihydrobenzo[c][1,2]oxaborol-6-yl)sulfamoyl)phenyl)-N-butyl-N-methylacetamide | 1.17 | 3.92 | 10.99 | 64 | 4 | 4 | 32 |
| 2-(5-amino-2-(N-(1-hydroxy-1,3-dihydrobenzo[c][1,2]oxaborol-6-yl)sulfamoyl)phenyl)-N-propylacetamide | 0.53 | 2.12 | 0.31 | 1 | 16 | <=0.12 | 2 |
| 4-amino-2-(2-(azetidin-1-yl)-2-oxoethyl)-N-(1-hydroxy-1,3-dihydrobenzo[c][1,2]oxaborol-6-yl)benzenesulfonamide | 0.62 | 4.74 | 3.01 | 4 | 16 | 0.5 | 16 |
| 2-(5-amino-2-(N-(1-hydroxy-1,3-dihydrobenzo[c][1,2]oxaborol-6-yl)sulfamoyl)phenyl)-N-benzylacetamide | 0.36 | 1.21 | 0.61 | 2 | 8 | <=0.12 | 4 |
| 2-(5-amino-2-(N-(1-hydroxy-1,3-dihydrobenzo[c][1,2]oxaborol-6-yl)sulfamoyl)phenyl)-N-ethylacetamide | 0.41 | 1.67 | 0.36 | 0.5 | 16 | 0.5 | 2 |

Figure 1H

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| 2-(5-amino-2-(N-(1-hydroxy-1,3-dihydrobenzo[c][1,2]oxaborol-6-yl)sulfamoyl)phenyl)-N-cyclopropylacetamide | 0.30 | 1.18 | 0.50 | 1 | 16 | 0.25 | 4 |
| 2-(5-amino-2-(N-(1-hydroxy-1,3-dihydrobenzo[c][1,2]oxaborol-6-yl)sulfamoyl)phenyl)-N-methylacetamide | 0.72 | 2.62 | 0.87 | 0.5 | 16 | <=0.12 | 1.5 |
| 2-(5-amino-2-(N-(5-fluoro-1-hydroxy-1,3-dihydrobenzo[c][1,2]oxaborol-6-yl)sulfamoyl)phenyl)acetic acid | 0.19 | 1.62 | 0.16 | >64 | >64 | 2 | 32 |
| 2-(5-amino-2-(N-(1-hydroxy-1,3-dihydrobenzo[c][1,2]oxaborol-6-yl)sulfamoyl)phenyl)-N-isobutylacetamide | 0.18 | 1.39 | 0.35 | 4 | 8 | <=0.12 | 3 |
| 2,2,2-trifluoro-N-(4-(N-(1-hydroxy-1,3-dihydrobenzo[c][1,2]oxaborol-6-yl)sulfamoyl)-3-((5-methyl-1,3,4-oxadiazol-2-yl)methyl)phenyl)acetamide | 1.00 | 4.95 | 1.59 | <=0.12 | 8 | 0.5 | 4 |
| 4-amino-N-(1-hydroxy-1,3-dihydrobenzo[c][1,2]oxaborol-6-yl)-2-((5-methyl-1,3,4-oxadiazol-2-yl)methyl)benzenesulfonamide | 0.32 | 1.84 | 0.49 | <=0.12 | 8 | <=0.31 | 4 |

Figure 1I

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| 2-(5-amino-2-(N-(1-hydroxy-1,3-dihydrobenzo[c][1,2]oxaborol-6-yl)sulfamoyl)phenyl)-N-(prop-2-ynyl)acetamide | 0.39 | 1.10 | 0.40 | 0.5 | 8 | <=0.12 | 1.5 |
| isopropyl 2-(5-amino-2-(N-(1-hydroxy-1,3-dihydrobenzo[c][1,2]oxaborol-6-yl)sulfamoyl)phenyl)acetate | 0.27 | 1.05 | 0.58 | 2 | 0.5 | 0.25 | 1.5 |
| N-(3-((5-ethyl-1,3,4-oxadiazol-2-yl)methyl)-4-(N-(1-hydroxy-1,3-dihydrobenzo[c][1,2]oxaborol-6-yl)sulfamoyl)phenyl)-2,2,2-trifluoroacetamide | 3.35 | 12.34 | 3.40 | 8 | >64 | 4 | 64 |
| 2-(5-amino-2-(N-(1-hydroxy-1,3-dihydrobenzo[c][1,2]oxaborol-6-yl)sulfamoyl)phenyl)-N-cyclohexylacetamide | 0.31 | 1.26 | 0.41 | 4 | 4 | <=0.12 | 2 |
| 2-(5-amino-2-(N-(1-hydroxy-1,3-dihydrobenzo[c][1,2]oxaborol-6-yl)sulfamoyl)phenyl)-N-cyclobutylacetamide | 0.14 | 0.39 | 0.09 | 1 | 8 | <=0.12 | 0.75 |
| 4-amino-2-((5-ethyl-1,3,4-oxadiazol-2-yl)methyl)-N-(1-hydroxy-1,3-dihydrobenzo[c][1,2]oxaborol-6-yl)benzenesulfonamide | 0.17 | 1.98 | 0.43 | 0.25 | 8 | 0.25 | 4 |

Figure 1J

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| 2,2,2-trifluoro-N-(4-(N-(1-hydroxy-1,3-dihydrobenzo[c][1,2]oxaborol-6-yl)sulfamoyl)-3-((5-propyl-1,3,4-oxadiazol-2-yl)methyl)phenyl)acetamide | 12.97 | 18.30 | 7.81 | 0.5 | 8 | 0.25 | 8 |
| 4-amino-N-(1-hydroxy-1,3-dihydrobenzo[c][1,2]oxaborol-6-yl)-2-((5-propyl-1,3,4-oxadiazol-2-yl)methyl)benzenesulfonamide | 0.34 | 3.94 | 0.69 | 0.25 | 4 | 0.25 | 4 |
| 4-amino-N-(1-hydroxy-1,3-dihydrobenzo[c][1,2]oxaborol-6-yl)-2-((5-methyloxazol-2-yl)methyl)benzenesulfonamide | 0.42 | 2.55 | 0.78 | 0.5 | 2 | 0.5 | 4 |
| 2-(5-amino-2-(N-(1-hydroxy-1,3-dihydrobenzo[c][1,2]oxaborol-6-yl)sulfamoyl)phenyl)-N-sec-butylacetamide | 0.42 | 1.15 | 0.65 | 2 | 8 | 0.25 | 1.5 |
| 4-amino-N-(1-hydroxy-1,3-dihydrobenzo[c][1,2]oxaborol-6-yl)-2-((3-methyl-1,2,4-oxadiazol-5-yl)methyl)benzenesulfonamide | 0.38 | 4.97 | 2.68 | 0.5 | 4 | 0.5 | 8 |
| 6-Amino-2-(6-(1-hydroxy-1,3-dihydrobenzo[c][1,2]oxaborole))-1,1-dioxide-2H-1,2-benzothiazin-3(4H)-one | 33.53 | 126.99 | 73.93 | 16 | 32 | 4 | 32 |

Figure 1K

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| 4-amino-2-(aminomethyl)-N-(1-hydroxy-1,3-dihydrobenzo[c][1,2]oxaborol-6-yl)benzenesulfonamide | 0.53 | 0.74 | 2.75 | 8 | 8 | 16 | 0.75 |
| 4-amino-2-(2-ethoxyethyl)-N-(1-hydroxy-1,3-dihydrobenzo[c][1,2]oxaborol-6-yl)benzenesulfonamide | 0.54 | 8.69 | 3.78 | 4 | 4 | 0.5 | 16 |
| 4-amino-2-bromo-N-(1-hydroxy-1,3-dihydrobenzo[c][1,2]oxaborol-6-yl)benzenesulfonamide | 0.44 | 0.95 | 4.03 | 1 | 1 | 0.5 | 8 |
| 4-amino-2-(furan-2-yl)-N-(1-hydroxy-1,3-dihydrobenzo[c][1,2]oxaborol-6-yl)benzenesulfonamide | 3.60 | 15.52 | 41.48 | 32 | 8 | 2 | 32 |
| 4-amino-2-((3,3-dimethylureido)methyl)-N-(1-hydroxy-1,3-dihydrobenzo[c][1,2]oxaborol-6-yl)benzenesulfonamide | 0.66 | 8.19 | 0.67 | 2 | 64 | 0.25 | 8 |
| N-(5-amino-2-(N-(1-hydroxy-1,3-dihydrobenzo[c][1,2]oxaborol-6-yl)sulfamoyl)benzyl)-2,2,2-trifluoroacetamide | 0.80 | 4.15 | 0.81 | 0.5 | 16 | 0.25 | 2 |
| 2-(5-amino-2-(N-(1-hydroxy-1,3-dihydrobenzo[c][1,2]oxaborol-6-yl)sulfamoyl)phenyl)-N-methoxyacetamide | 0.87 | 4.13 | 0.81 | 1 | 64 | 0.25 | 4 |

Figure 1L

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| tert-butyl 2-(5-amino-2-(N-(1-hydroxy-1,3-dihydrobenzo[c][1,2]oxaborol-6-yl)sulfamoyl)phenyl)acetate | 0.88 | 3.15 | 1.72 | 4 | 1 | 0.25 | 2 |
| 4-amino-2-((3-ethyl-1,2,4-oxadiazol-5-yl)methyl)-N-(1-hydroxy-1,3-dihydrobenzo[c][1,2]oxaborol-6-yl)benzenesulfonamide | 1.52 | 10.11 | 2.98 | 2 | 4 | 0.5 | 8 |
| ethyl 5-amino-2-(N-(1-hydroxy-1,3-dihydrobenzo[c][1,2]oxaborol-6-yl)sulfamoyl)benzylcarbamate | 0.23 | 1.18 | 0.54 | 1 | 4 | 0.25 | 4 |
| propyl 5-amino-2-(N-(1-hydroxy-1,3-dihydrobenzo[c][1,2]oxaborol-6-yl)sulfamoyl)benzylcarbamate | 0.42 | 1.05 | 1.30 | 1 | 2 | 0.25 | 4 |
| isopropyl 5-amino-2-(N-(1-hydroxy-1,3-dihydrobenzo[c][1,2]oxaborol-6-yl)sulfamoyl)benzylcarbamate | 0.42 | 1.19 | 0.90 | 1 | 2 | 0.25 | 4 |
| isobutyl 5-amino-2-(N-(1-hydroxy-1,3-dihydrobenzo[c][1,2]oxaborol-6-yl)sulfamoyl)benzylcarbamate | 0.40 | 1.27 | 0.80 | 2 | 2 | 0.25 | 4 |
| pentan-3-yl 5-amino-2-(N-(1-hydroxy-1,3-dihydrobenzo[c][1,2]oxaborol-6-yl)sulfamoyl)benzylcarbamate | 0.54 | 4.28 | 2.07 | 8 | 2 | 0.5 | 8 |
| benzyl 5-amino-2-(N-(1-hydroxy-1,3-dihydrobenzo[c][1,2]oxaborol-6-yl)sulfamoyl)benzylcarbamate | 0.46 | 0.54 | 1.27 | 8 | 2 | 0.25 | 4 |

Figure 1M

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| 2-(5-amino-2-(N-(1-hydroxy-1,3-dihydrobenzo[c][1,2]oxaborol-6-yl)sulfamoyl)phenyl)-N-(3,3-difluorocyclobutyl)acetamide | 0.30 | 1.08 | 0.41 | 1 | 16 | 0.25 | 1 |
| (E)-2,2,2-trifluoro-N-(4-(N-(1-hydroxy-1,3-dihydrobenzo[c][1,2]oxaborol-6-yl)sulfamoyl)-3-((2-oxodihydrofuran-3(2H)-ylidene)methyl)phenyl)acetamide | NT | NT | NT | 1 | 16 | 0.25 | 4 |
| 2,2,2-trifluoro-N-(4-(N-(1-hydroxy-1,3-dihydrobenzo[c][1,2]oxaborol-6-yl)sulfamoyl)-3-((2-oxotetrahydrofuran-3-yl)methyl)phenyl)acetamide | NT | NT | NT | 32 | >64 | 16 | >64 |
| 4-amino-N-(1-hydroxy-1,3-dihydrobenzo[c][1,2]oxaborol-6-yl)-2-((2-oxotetrahydrofuran-3-yl)methyl)benzenesulfonamide | 0.28 | 1.88 | 0.53 | 0.5 | 16 | 0.5 | 4 |
| 4-amino-N-(1-hydroxy-1,3-dihydrobenzo[c][1,2]oxaborol-6-yl)-2-(3-oxobutyl)benzenesulfonamide | 0.16 | 0.39 | 0.33 | 0.25 | 20 | 0.5 | 1 |
| 4-amino-N-(1-hydroxy-1,3-dihydrobenzo[c][1,2]oxaborol-6-yl)-2-(3-hydroxybutyl)benzenesulfonamide | 0.48 | 3.62 | 3.08 | 8 | 16 | 8 | 32 |

Figure 1N

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| Trideuteromethyl 2-(5-amino-2-(N-(1-hydroxy-1,3-dihydrobenzo[c][1,2]oxaborol-6-yl)sulfamoyl)phenyl)acetate | 0.24 | 0.33 | 0.15 | <=0.185 | 1 | 0.5 | 1 |
| 2,2,2-trifluoro-N-(4-(N-(1-hydroxy-1,3-dihydrobenzo[c][1,2]oxaborol-6-yl)sulfamoyl)-3-((4-methyloxazol-2-yl)methyl)phenyl)acetamide | 1.23 | 7.22 | 5.85 | 1 | 4 | 0.5 | 8 |
| 4-amino-N-(1-hydroxy-1,3-dihydrobenzo[c][1,2]oxaborol-6-yl)-2-((4-methyloxazol-2-yl)methyl)benzenesulfonamide | 0.59 | 2.99 | 2.78 | 1 | 4 | 0.5 | 8 |
| 4-amino-2-(ethylsulfonylmethyl)-N-(1-hydroxy-1,3-dihydrobenzo[c][1,2]oxaborol-6-yl)benzenesulfonamide | 0.20 | 0.21 | 0.15 | 0.25 | 3 | <=0.185 | 1 |
| 4-amino-N-(1-hydroxy-1,3-dihydrobenzo[c][1,2]oxaborol-6-yl)-2-(2-(methylsulfonyl)ethyl)benzenesulfonamide | 0.23 | 0.27 | 0.19 | 0.50 | 16 | 0.25 | 2 |
| 4-amino-N-(1-hydroxy-1,3-dihydrobenzo[c][1,2]oxaborol-6-yl)-2-(2-methoxyethyl)benzenesulfonamide | 0.41 | 4.02 | 1.51 | 1.00 | 4 | 0.25 | 8 |
| 4-amino-N-(1-hydroxy-1,3-dihydrobenzo[c][1,2]oxaborol-6-yl)-2-((2-oxooxazolidin-3-yl)methyl)benzenesulfonamide | 0.31 | 1.03 | 1.19 | 1.00 | 16 | 0.5 | 8 |

Figure 10

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| methyl 5-amino-2-(N-(1-hydroxy-1,3-dihydrobenzo[c][1,2]oxaborol-6-yl)sulfamoyl)phenylcarbamate | 0.25 | 0.22 | 0.30 | 0.50 | 2 | 0.5 | 0.5 |
| 4-amino-2-(2-fluoroethyl)-N-(1-hydroxy-1,3-dihydrobenzo[c][1,2]oxaborol-6-yl)benzenesulfonamide | 0.29 | 0.88 | 0.93 | 0.50 | 0.5 | 0.25 | 4 |
| 4-amino-N-(1-hydroxy-1,3-dihydrobenzo[c][1,2]oxaborol-6-yl)-2-(2-(methylsulfinyl)ethyl)benzenesulfonamide | 0.38 | 4.08 | 1.80 | 4 | 32 | 2 | 8 |
| (E)-4-amino-N-(1-hydroxy-1,3-dihydrobenzo[c][1,2]oxaborol-6-yl)-2-((2-oxodihydrofuran-3(2H)-ylidene)methyl)benzenesulfonamide | 14.36 | 130.03 | 67.34 | 32 | >64 | 4 | >64 |
| 2,2,2-trifluoro-N-(4-(N-(1-hydroxy-1,3-dihydrobenzo[c][1,2]oxaborol-6-yl)sulfamoyl)-3-(oxazol-2-ylmethyl)phenyl)acetamide | 0.62 | 2.22 | 0.58 | 0.5 | 2 | 0.25 | 4 |
| 4-amino-N-(1-hydroxy-1,3-dihydrobenzo[c][1,2]oxaborol-6-yl)-2-(oxazol-2-ylmethyl)benzenesulfonamide | 0.34 | 1.52 | 0.70 | 0.25 | 1.5 | 0.375 | 2 |
| 4-amino-2-(cyclopropanesulfonamidomethyl)-N-(1-hydroxy-1,3-dihydrobenzo[c][1,2]oxaborol-6-yl)benzenesulfonamide | 0.23 | 0.52 | 0.19 | 1 | 32 | 0.5 | 4 |

Figure 1P

| IUPAC Name | LeuRS_Ecoli IC50 [μM] | LeuRS_Saureus IC50 [μM] | LeuRS_Spneumoniae IC50 [μM] | H. influenzae ATCC 49766 MIC [μg/mL] | S. aureus ATCC 29213 MIC [μg/mL] | S. pneumoniae ATCC 6301 MIC [μg/mL] | S. pyogenes ATCC 19615 MIC [μg/mL] |
|---|---|---|---|---|---|---|---|
| methyl 3-(5-amino-2-(N-(1-hydroxy-1,3-dihydrobenzo[c][1,2]oxaborol-6-yl)sulfamoyl)phenyl)propanoate | 0.42 | 1.96 | 0.47 | 0.50 | 2 | 8 | >64 |
| ethyl 3-(5-amino-2-(N-(1-hydroxy-1,3-dihydrobenzo[c][1,2]oxaborol-6-yl)sulfamoyl)phenyl)propanoate | 0.55 | 2.01 | 0.26 | 0.50 | 2 | 8 | >64 |
| 4-amino-N-(1-hydroxy-1,3-dihydrobenzo[c][1,2]oxaborol-6-yl)-2-(prop-1-ynyl)benzenesulfonamide | 18.33 | 56.70 | 35.30 | 16 | 8 | 2 | 16 |
| 4-amino-2-butyl-N-(1-hydroxy-1,3-dihydrobenzo[c][1,2]oxaborol-6-yl)benzenesulfonamide | 4.58 | >300 | >100 | 64.00 | 16 | 32 | >64 |
| 4-amino-2-(cyclohexanesulfonamidomethyl)-N-(1-hydroxy-1,3-dihydrobenzo[c][1,2]oxaborol-6-yl)benzenesulfonamide | 0.33 | 1.11 | 0.97 | 2 | 12 | <=0.185 | 2 |
| 2,2,2-trifluoro-N-(4-(N-(1-hydroxy-1,3-dihydrobenzo[c][1,2]oxaborol-6-yl)sulfamoyl)-3-((5-methyl-1,2,4-oxadiazol-3-yl)methyl)phenyl)acetamide | 3.05 | 11.08 | 8.05 | 0.5 | 2.5 | 0.25 | 1.5 |
| 4-amino-N-(1-hydroxy-1,3-dihydrobenzo[c][1,2]oxaborol-6-yl)-2-((5-methyl-1,2,4-oxadiazol-3-yl)methyl)benzenesulfonamide | 0.40 | 1.55 | 1.15 | 0.5 | 2 | 0.25 | 1 |

Figure 1Q

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| 4-amino-N-(1-hydroxy-1,3-dihydrobenzo[c][1,2]oxaborol-6-yl)-2-(hydroxymethyl)benzenesulfonamide | 0.68 | 2.69 | 6.10 | NT | 4 | 1 | 4 |
| ethyl 5-amino-2-(N-(1-hydroxy-1,3-dihydrobenzo[c][1,2]oxaborol-6-yl)sulfamoyl)phenylcarbamate | 0.44 | 1.94 | 1.86 | 2 | 3 | 0.625 | 1.5 |
| Trideuteromethyl 2-(5-amino-2-(N-(5-fluoro-1-hydroxy-1,3-dihydrobenzo[c][1,2]oxaborol-6-yl)sulfamoyl)phenyl)acetate | 0.47 | NT | NT | NT | 2 | 1 | 2 |
| isopropyl 5-amino-2-(N-(5-fluoro-1-hydroxy-1,3-dihydrobenzo[c][1,2]oxaborol-6-yl)sulfamoyl)phenylcarbamate | 0.39 | 3.53 | 1.47 | 4 | 2 | 0.25 | 1 |
| ethyl 5-amino-2-(N-(5-fluoro-1-hydroxy-1,3-dihydrobenzo[c][1,2]oxaborol-6-yl)sulfamoyl)phenylcarbamate | 0.39 | 4.58 | 1.52 | 4 | 3 | 0.375 | 1 |
| isopropyl 5-amino-2-(N-(1-hydroxy-1,3-dihydrobenzo[c][1,2]oxaborol-6-yl)sulfamoyl)phenylcarbamate | 0.34 | 2.28 | 1.70 | 2.00 | 2.5 | 0.625 | 1.5 |
| methyl 5-amino-2-(N-(5-fluoro-1-hydroxy-1,3-dihydrobenzo[c][1,2]oxaborol-6-yl)sulfamoyl)phenylcarbamate | 0.27 | NT | NT | 1 | 4 | 1 | 2 |

Figure 1R

| IUPAC Name | LeuRS_Ecoli IC50 [µM] | LeuRS_Saureus IC50 [µM] | LeuRS_Spneumoniae IC50 [µM] | H. influenzae ATCC 49766 MIC [µg/mL] | S. aureus ATCC 29213 MIC [µg/mL] | S. pneumoniae ATCC 6301 MIC [µg/mL] | S. pyogenes ATCC 19615 MIC [µg/mL] |
|---|---|---|---|---|---|---|---|
| 4-amino-N-(1-hydroxy-1,3-dihydrobenzo[c][1,2]oxaborol-6-yl)-2-(methylsulfonylmethyl)benzenesulfonamide | 0.39 | 0.49 | 0.15 | 0.25 | 4 | <=0.185 | 1.5 |
| 4-amino-N-(1-hydroxy-1,3-dihydrobenzo[c][1,2]oxaborol-6-yl)-2-(propylsulfonylmethyl)benzenesulfonamide | 0.51 | 0.57 | 0.26 | 0.5 | 1.5 | <=0.185 | 1 |

BORON-CONTAINING SMALL MOLECULES

CROSS-REFERENCE TO RELATED APPLICATIONS

This application claims the benefit of U.S. Provisional Pat. App. No. 61/260,384, filed Nov. 11, 2009, and U.S. Provisional Pat. App. No. 61/260,373, filed Nov. 11, 2009, each of which is incorporated by reference in its entirety for all purposes.

BACKGROUND OF THE INVENTION

The global rise of bacteria and other microorganisms resistant to antibiotics and antimicrobials in general, poses a major threat. Deployment of massive quantities of antimicrobial agents into the ecosphere during the past 60 years has introduced a powerful selective pressure for the emergence and spread of antimicrobial-resistant pathogens. Thus, there is a need to discover new broad spectrum antimicrobials, such as antibiotics, useful in combating microorganisms, especially those with multidrug-resistance.

Boron-containing molecules, such as 1-hydroxy-1,3-dihydro-benzo[c][1,2]oxaborole (also sometimes known as 1-hydroxy-benzo[c][1,2]oxaborole or oxaboroles or cyclic boronic esters), useful as antimicrobials have been described previously, such as in U.S. patent application Ser. Nos. 12/142,692; 11/505,591 and 11/357,687. Generally speaking, a 1-hydroxy-1,3-dihydro-benzo[c][1,2]oxaborole has the following structure and substituent numbering system:

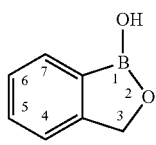

Surprisingly, it has now been discovered that certain classes of 1-hydroxy-1,3-dihydro-benzo[c][1,2]oxaboroles which are substituted with at least two moieties on an aryl or heteroaryl sulfonamide moiety at the 6-position are surprisingly effective antibacterials. This, and other uses of these 1-hydroxy-1,3-dihydro-benzo[c][1,2]oxaboroles are described herein.

SUMMARY OF THE INVENTION

In a first aspect, the invention provides a compound, or a salt thereof, having a structure which is

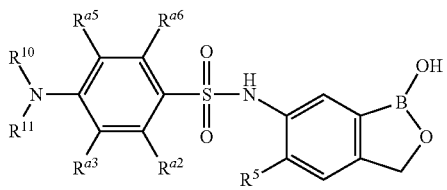

wherein $R^5$ is H or halogen, one of $R^{a2}$, $R^{a3}$, $R^{a5}$ and $R^{a6}$ is halogen or —NHC(O)OR$^{30}$ or alkyl substituted with —C(O)OR$^{30}$ or alkyl substituted with —S(O)$_2$R$^{30}$ or alkyl substituted with halogen or alkyl substituted with hydroxy or alkyl substituted with cyano or alkyl substituted with —NHC(O)OR$^{30}$ or alkyl substituted with unsubstituted oxazolyl or alkyl substituted with alkyl substituted oxazolyl or alkyl substituted with unsubstituted oxadiazolyl or alkyl substituted with alkyl substituted oxadiazolyl or alkyl substituted with —C(O)NHR$^{35}$, wherein R$^{30}$ is unsubstituted alkyl and R$^{35}$ is unsubstituted alkyl or unsubstituted cycloalkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In a second aspect, the invention provides a combination comprising: a) a compound of the invention, or a pharmaceutically acceptable salt thereof; and b) a therapeutically active agent.

In a third aspect, the invention provides a pharmaceutical formulation comprising: a) a compound of the invention, or a pharmaceutically acceptable salt thereof; and b) a pharmaceutically acceptable excipient.

In a fourth aspect, the invention provides a method of killing or inhibiting the growth of a bacteria, said method comprising: contacting said bacteria with an effective amount of a compound of the invention or a combination of the invention, or a pharmaceutically acceptable salt thereof, thereby killing or inhibiting the growth of the bacteria.

In a fifth aspect, the invention provides a method of treating a bacterial infection comprising: administering to an animal suffering from said infection an effective amount of a compound of the invention, or a pharmaceutically acceptable salt thereof, thereby treating the bacterial infection.

In a sixth aspect, the invention provides a method of inhibiting the editing domain of a t-RNA synthetase, comprising: contacting the synthetase with an effective amount of a compound of the invention, or a pharmaceutically acceptable salt thereof, thereby inhibiting the synthetase.

BRIEF DESCRIPTION OF THE DRAWINGS

FIG. 1 displays biological data for exemplary compounds of the invention.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; B$_2$pin$_2$ is bis(pinacolato) diboron; Bn is, in general, benzyl [see Cbz for one example of an exception]; (BnS)$_2$ is benzyl disulfide; BnSH is benzyl thiol or benzyl mercaptan; BnBr is benzyl bromide; Boc is tert-butoxy carbonyl; Boc$_2$O is di-tert-butyl dicarbonate; Bz is, in general, benzoyl; BzOOH is benzoyl peroxide; Cbz or Z is benzyloxycarbonyl or carboxybenzyl; Cs$_2$CO$_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino)pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; Et$_2$O is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; K$_2$CO$_3$ is potassium carbonate; LiAlH$_4$ or LAH is lithium aluminum hydride; LDA is lithium diisopropylamide; LHMDS is lithium bis(trimethylsilyl)amide; KHMDS is potassium bis(trimethylsilyl)amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; MgSO$_4$ is magnesium sulfate; mins or min is minutes; Mp or MP is melting point; NaCNBH$_3$ is sodium cyanoborohydride; NaOH is sodium hydroxide; Na$_2$SO$_4$ is sodium sulfate; NBS is N-bromosuccinimide; NH$_4$Cl is ammonium chloride; NIS is N-iodosuccinimide; N$_2$ is nitrogen; NMM is N-methylmorpholine; n-BuLi is n-butyllithium; overnight is O/N; PdCl$_2$ (pddf) is 1,1'-Bis(diphenylphosphino)ferrocene]dichloropalladium(II); Pd/C is the catalyst known as palladium on carbon; Pd$_2$(dba)$_3$ is an organometallic catalyst known as tris(dibenzylideneacetone)dipalladium(0); Ra Ni or Raney Ni is Raney nickel; Ph is phenyl; PMB is p-methoxybenzyl; PrOH is 1-propanol; iPrOH is 2-propanol; POCl$_3$ is phosphorus chloride oxide; PTSA is para-toluene sulfonic acid; Pyr. or Pyr or Py as used herein means Pyridine; RT or rt or r.t. is room temperature; sat. is saturated; Si-amine or Si—NH$_2$ is amino-functionalized silica, available from SiliCycle; Si-pyr is pyridyl-functionalized silica, available from SiliCycle; TEA or Et$_3$N is triethylamine; TFA is trifluoroacetic acid; Tf$_2$O is trifluoromethanesulfonic anhydride; THF is tetrahydrofuran; TFAA is trifluoroacetic anhydride; THP is tetrahydropyranyl; TMSI is trimethylsilyl iodide; H$_2$O is water; diNO$_2$PhSO$_2$Cl is dinitrophenyl sulfonyl chloride; 3-F-4-NO$_2$-PhSO$_2$Cl is 3-fluoro-4-nitrophenylsulfonyl chloride; 2-MeO-4-NO$_2$-PhSO$_2$Cl is 2-methoxy-4-nitrophenylsulfonyl chloride; and (EtO)$_2$POCH$_2$COOEt is a triethylester of phosphonoacetic acid known as triethyl phosphonoacetate.

"Compound of the invention," as used herein refers to the compounds discussed herein, salts (e.g. pharmaceutically acceptable salts), prodrugs, solvates and hydrates of these compounds.

MIC, or minimum inhibitory concentration, is the point where the compound stops more than 50% of cell growth, preferably 60% of cell growth, preferably 70% of cell growth, preferably 80% of cell growth, preferably 90% of cell growth, relative to an untreated control.

The term "poly" as used herein means at least 2. For example, a polyvalent metal ion is a metal ion having a valency of at least 2.

"Moiety" refers to a radical of a molecule that is attached to the remainder of the molecule.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkyl.

The term "heteroalkylene" by itself or as part of another substituent means a divalent radical derived from an heteroalkane.

The term "heterocycloalkylene" by itself or as part of another substituent means a divalent radical derived from an heteroalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$ —CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, 6-quinolyl, dioxaborolane, dioxaborinane and dioxaborepane. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes those radicals in which an aryl group is attached through the next moiety to the rest of the molecule. Thus, the term "arylalkyl" is meant to include those radicals in which an aryl group is attached to an alkyl group (e.g., benzyl, 1-(3-nitrophenyl)ethyl and the like). A substituent such as benzyl or 1-(3-nitrophenyl)ethyl can also be represented by 'substituted alkyl' wherein the ethyl radical is substituted with a 3-nitrophenyl moiety. The term "aryloxy" is meant to include those radicals in which an aryl group is attached to an oxygen atom. The term "aryloxyalkyl" is meant to include those radicals in which an aryl group is attached to an oxygen atom which is then attached to an alkyl group (e.g., phenoxymethyl, 3-(1-naphthyloxy)propyl, and the like).

For brevity, the term "heteroaryl" when used in combination with other terms (e.g., heteroaryloxy, heteroarylthioxy, heteroarylalkyl) includes those radicals in which a heteroaryl group is attached through the next moiety to the rest of the molecule. Thus, the term "heteroarylalkyl" is meant to include those radicals in which a heteroaryl group is attached to an alkyl group (e.g., pyridylmethyl and the like). The term "heteroaryloxy" is meant to include those radicals in which a heteroaryl group is attached to an oxygen atom. The term "heteroaryloxyalkyl" is meant to include those radicals in which an aryl group is attached to an oxygen atom which is then attached to an alkyl group. (e.g., 2-pyridyloxymethyl and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR""—C(NR'R"R"')=NR"", —NR""—C(NR'R")=NR"', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to (2 m'+1), where m' is the total number of carbon atoms in such radical. R', R", R"', R"" and R""' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"', R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"', —OC(O)R', —C(O)R', —CO$_2$R', —CONR'R", —OC(O)NR'R", —NR"C(O)R', —NR'—C(O)NR"R"', —NR"C(O)$_2$R', —NR""—C(NR'R"R"')=NR"", —NR""—C(NR'R") =NR"', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", R"" and R""" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R""" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), aluminum (Al) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of a active agent to provide the desired local or systemic effect. A "Topically effective," "Cosmetically effective," "pharmaceutically effective," or "therapeutically effective" amount refers to the amount of drug needed to effect the desired therapeutic result.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, *J. Chem. Ed.* 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and/isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H or T), iodine-125 ($^{125}$I) or carbon-14 ($^{14}$C). All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in *Remington: The Science and Practice of Pharmacy*, 21st Ed., Lippincott, Williams & Wilkins (2005) which is incorporated herein by reference.

The term "excipients" is conventionally known to mean carriers, diluents and/or vehicles used in formulating drug compositions effective for the desired use.

The term "microbial infection" or "infection by a microorganism" refers to any infection of a host tissue by an infectious agent including, but not limited to, bacteria or protozoa (see, e.g., Harrison's Principles of Internal Medicine, pp. 93-98 (Wilson et al., eds., 12th ed. 1991); Williams et al., J. of Medicinal Chem. 42:1481-1485 (1999), herein each incorporated by reference in their entirety).

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of enzyme. In an exemplary embodiment, the enzyme is an editing domain of a tRNA synthetase.

Boron is able to form dative bonds with oxygen, sulfur or nitrogen under some circumstances in this invention. Dative bonds are usually weaker than covalent bonds. In situations where a boron is covalently bonded to at least one oxygen, sulfur or nitrogen, and is at the same time datively bonded to an oxygen, sulfur or nitrogen, respectively, the dative bond and covalent bond between the boron and the two identical heteroatoms can interconvert or be in the form of a resonance hybrid. There is potential uncertainty surrounding the exact nature and extent of electron sharing in these situations. Generally, in boron compounds comprising both covalent and coordinate covalent (dative) bonds, the electrons in such bonds may be partially or fully delocalized.

Embodiments of the invention also encompass compounds that are poly- or multi-valent species, including, for example, species such as dimers, trimers, tetramers and higher homologs of the compounds of use in the invention or reactive analogues thereof.

"Salt counterion", as used herein, refers to positively charged ions that associate with a compound of the invention when the boron is fully negatively or partially negatively charged. Examples of salt counterions include $H^+$, $H_3O^+$, ammonium, potassium, calcium, magnesium and sodium.

The compounds comprising a boron bonded to a carbon and three heteroatoms (such as three oxygens described in this section) can optionally contain a fully negatively charged boron or partially negatively charged boron, due to the nature of the dative bond between the boron and one of the oxygens. Due to the negative charge, a positively charged counterion may associate with this compound, thus forming a salt. Examples of positively charged counterions include $H^+$, $H_3O^+$, calcium, sodium, ammonium and potassium. The salts of these compounds are implicitly contained in descriptions of these compounds.

II. Introduction

The invention provides novel boron compounds and methods for the preparation of these molecules. The invention further provides methods of treating bacterial infections, killing or inhibiting the growth of bacteria in part or wholly through the use of the compounds described herein. In another aspect, the invention is a combination of a compound of the invention and an antibiotic. In another aspect, the invention is a pharmaceutical formulation comprising a pharmaceutically acceptable excipient and a compound of the invention. In another aspect, the invention is a pharmaceutical formulation comprising a compound of the invention, an antibiotic, and a pharmaceutically acceptable excipient.

Embodiments of the invention include compounds having deuterium at positions that would otherwise have a protio. As is readily known, each element has a unique number of protons in the atom's nucleus. The number of protons is called the atomic number and in a neutral state is equal to the number of electrons that surround the nucleus. The mass number however is defined as the number of protons and neutrons contained within the nucleus of a given atom. The atomic weight of an atom is roughly equal to the number of protons and neutrons contained in that substance. Isotopes are defined as atoms that contain the same number of protons (which define the element) and different numbers of neutrons. Hydrogen or H has three naturally occurring isotopes—$^1$H, $^2$H, and $^3$H. $^1$H or protio contains only a single proton and no neutrons. Deuterium (D, $^2$H, deutero) is a stable isotope of hydrogen that contains 1 proton and 1 neutron having an atomic number of 1 and a mass number of 2. Deuterium is present in a natural abundance of 0.015%. Tritium (T, $^3$H) is a radioactive isotope of hydrogen that contains 1 proton and 2 neutrons.

Any carbon-hydrogen bond has a given energy resulting from vibrations in the molecule at a certain temperature. This energy is defined as the zero point energy. A corresponding carbon-deuterium bond also has a zero point energy under the same conditions, however because of the greater mass of the deuterium (resulting from the extra neutron) the vibrations contribute to give a lower zero point energy relative to the protio counterpart. The difference in the C—$^1$H and C-D bond energies results in a different activation energy requirement to reach a similar transition state. This difference in energy gives rise to what is called a kinetic isotope effect. This small but often significant energy difference can lead to retarded reaction rates in the deuterium analog when the bond is being broken in a rate limiting step during a chemical transformation. The approximate 1.2 kcal/mol energy difference that is often found when comparing the two isotope bonds (C—$^1$H or C-D) can lead to a several fold reduction in rate depending on the transition state dynamics. In some instances very little effect is noted between the bonds and the rate comparison is at or near 1. In other instances the rate of the protio containing reaction can be up to 7 times faster or even greater in certain circumstances than the deuterium analog. It is believed that this retardation of reaction rate can potentially affect the metabolism of drug molecules in an in vitro or in vivo setting, thus rendering an altered pharmacokinetic profile of a drug molecule.

Particular embodiments of the invention provide a compound where certain protio atoms, or potentially all protio atoms, are replaced with deuterium atoms. The steric environment is similar and the potency and pharmacologic profile of the compounds are generally expected to be the same when the molecular mechanism of action does not involve a carbon-hydrogen (for example, carbon-deuterium) bond breaking event.

III. a.) Compounds

In one aspect the invention provides a compound of the invention. In an exemplary embodiment, the invention provides a compound described herein, or a salt thereof. In an exemplary embodiment, the salt of a compound described herein is a pharmaceutically acceptable salt. In an exemplary embodiment, the invention provides a compound described herein, or a pharmaceutically acceptable salt thereof. In an exemplary embodiment, the invention provides a compound described in a formula provided herein. In an exemplary embodiment, the invention provides a compound described herein.

In an exemplary embodiment, the compound, or a salt thereof, has a structure which is

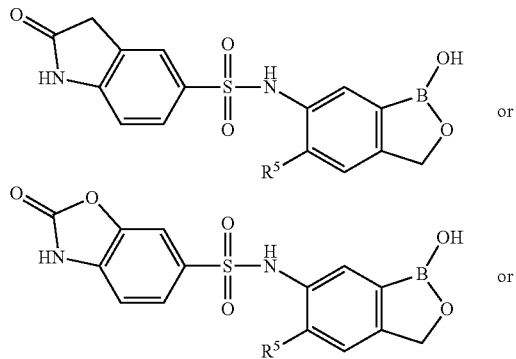

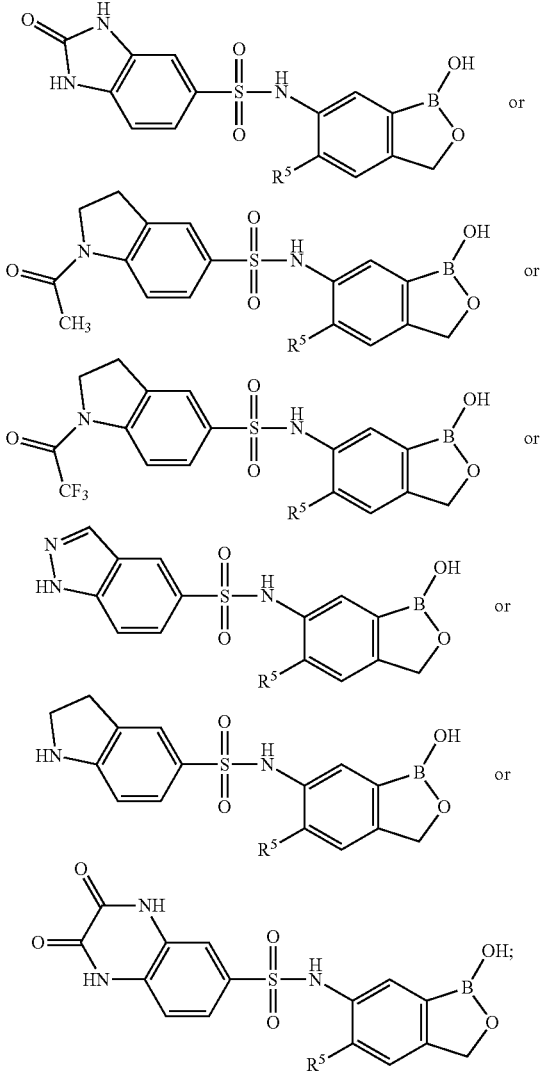

wherein $R^5$ is H or halogen. In an exemplary embodiment, $R^5$ is as described herein, and each hydrogen in said compound, or a salt thereof, is independently H or D. In an exemplary embodiment, $R^5$ is as described herein, and each hydrogen is optionally D. In an exemplary embodiment, $R^5$ is F. In an exemplary embodiment, $R^5$ is H.

In an exemplary embodiment, the compound, or a salt thereof, has a structure which is

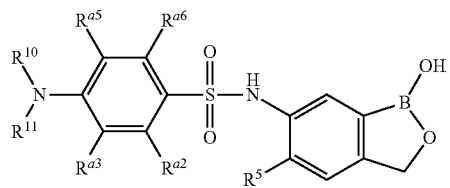

wherein $R^5$ is H or halogen, one of $R^{a2}$, $R^{a3}$, $R^{a5}$ and $R^{a6}$ is halogen and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, each hydrogen in said compound, or a salt thereof, is independently H or D. In an exemplary embodiment, each hydrogen is optionally D. In an exemplary embodiment, $R^5$ is halogen, one of $R^{a2}$, $R^{a3}$, $R^{a5}$ and $R^{a6}$ is F or Cl or Br and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is F or Cl or Br and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$ and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

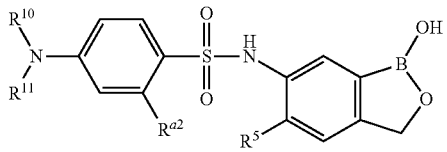

wherein $R^5$ is H or halogen, $R^{a2}$ is halogen, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$ and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is F, $R^{a2}$ is F or Cl or Br, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is F or Cl or Br, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$ and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

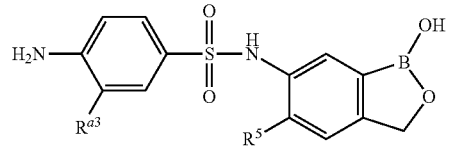

wherein $R^5$ is H or halogen, $R^{a3}$ is halogen. In an exemplary embodiment, $R^{a3}$ and $R^5$ are as described herein, and each hydrogen in said compound, or a salt thereof, is independently H or D. In an exemplary embodiment, $R^5$ is as described herein, and each hydrogen is optionally D. In an exemplary embodiment, $R^5$ is F, $R^{a3}$ is F. In an exemplary embodiment, $R^5$ is F, $R^{a3}$ is Cl. In an exemplary embodiment, $R^5$ is F, $R^{a3}$ is Br. In an exemplary embodiment, $R^5$ is F, $R^{a3}$ is I. In an exemplary embodiment, $R^5$ is H, $R^{a3}$ is F. In an exemplary embodiment, $R^5$ is H, $R^{a3}$ is Cl. In an exemplary embodiment, $R^5$ is H, $R^{a3}$ is Br. In an exemplary embodiment, $R^5$ is H, $R^{a3}$ is I.

In an exemplary embodiment, the compound, or a salt thereof, has a structure which is

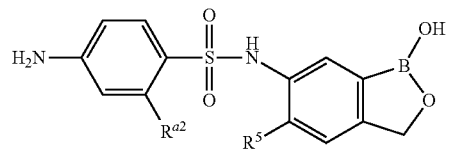

wherein $R^5$ is H or halogen, $R^{a2}$ is halogen. In an exemplary embodiment, $R^{a2}$ and $R^5$ are as described herein, and each hydrogen in said compound, or a salt thereof, is independently H or D. In an exemplary embodiment, $R^5$ is as described herein, and each hydrogen is optionally D. In an exemplary embodiment, $R^5$ is F, $R^{a2}$ is F. In an exemplary embodiment, $R^5$ is F, $R^{a2}$ is Cl. In an exemplary embodiment, $R^5$ is F, $R^{a2}$ is Br. In an exemplary embodiment, $R^5$ is F, $R^{a2}$ is I. In an exemplary embodiment, $R^5$ is H, $R^{a2}$ is F. In an exemplary embodiment, $R^5$ is H, $R^{a2}$ is Cl. In an exemplary embodiment, $R^5$ is H, $R^{a2}$ is Br. In an exemplary embodiment, $R^5$ is H, $R^{a2}$ is I.

In an exemplary embodiment, the compound, or a salt thereof, has a structure which is

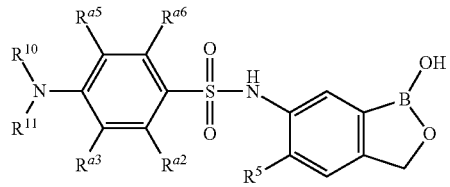

wherein $R^5$ is H or halogen, one of $R^{a2}$, $R^{a3}$, $R^{a5}$ and $R^{a6}$ is $OR^{20}$ and the remaining members of $R^{a2}$, $R^{a3}$, $R^{a5}$ and $R^{a6}$ are H, $R^{20}$ is H or unsubstituted alkyl, and $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, one of $R^{a2}$, $R^{a3}$, $R^{a5}$ and $R^{a6}$ is $OR^{20}$ and the remaining members of $R^{a2}$, $R^{a3}$, $R^{a5}$ and $R^{a6}$ are H, $R^{20}$ is H or unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is $OR^{20}$ and the remaining members of $R^{a2}$, $R^{a3}$, $R^{a5}$ and $R^{a6}$ are H, $R^{20}$ is H or unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

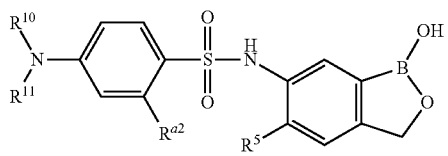

wherein $R^5$ is H or halogen, $R^{a2}$ is $OR^{20}$, $R^{20}$ is H or unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is F, $R^{a2}$ is $OR^{20}$, $R^{20}$ is H or unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is $OR^{20}$, $R^{20}$ is H or unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

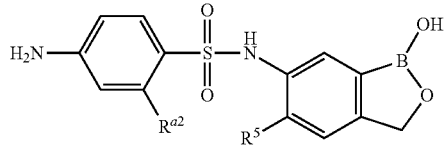

wherein $R^5$ is H or halogen, $R^{a2}$ is $OR^{20}$, $R^{20}$ is H or unsubstituted alkyl. In an exemplary embodiment, $R^{a2}$ and $R^5$ are as described herein, and each hydrogen in said compound, or a salt thereof, is independently H or D. In an exemplary embodiment, $R^5$ is as described herein, and each hydrogen is optionally D. In an exemplary embodiment, $R^5$ is F, $R^{a2}$ is OH. In an exemplary embodiment, $R^5$ is H, $R^{a2}$ is OH. In an exemplary embodiment, $R^5$ is F, $R^{a2}$ is $OCH_3$. In an exemplary embodiment, $R^5$ is H, $R^{a2}$ is $OCH_3$. In an exemplary embodiment, $R^5$ is F, $R^{a2}$ is $OCH_2CH_3$. In an exemplary embodiment, $R^5$ is H, $R^{a2}$ is $OCH_2CH_3$. In an exemplary embodiment, $R^5$ is F, $R^{a2}$ is $OR^{20}$, $R^{20}$ is unsubstituted $C_3$ alkyl. In an exemplary embodiment, $R^5$ is H, $R^{a2}$ is $OR^{20}$, $R^{20}$ is unsubstituted $C_3$ alkyl. In an exemplary embodiment, $R^5$ is F, $R^{a2}$ is $OR^{20}$, $R^{20}$ is unsubstituted $C_4$ alkyl. In an exemplary embodiment, $R^5$ is H, $R^{a2}$ is $OR^{20}$, $R^{20}$ is unsubstituted $C_4$ alkyl. In an exemplary embodiment, $R^5$ is F, $R^{a2}$ is $OR^{20}$, $R^{20}$ is unsubstituted $C_5$ alkyl. In an exemplary embodiment, $R^5$ is H, $R^{a2}$ is $OR^{20}$, $R^{20}$ is unsubstituted $C_5$ alkyl. In an exemplary embodiment, $R^5$ is F, $R^{a2}$ is $OR^{20}$, $R^{20}$ is unsubstituted $C_6$ alkyl. In an exemplary embodiment, $R^5$ is H, $R^{a2}$ is $OR^{20}$, $R^{20}$ is unsubstituted $C_6$ alkyl.

In an exemplary embodiment, the compound, or a salt thereof, has a structure which is

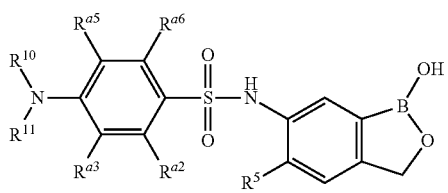

wherein $R^5$ is H or halogen, one of $R^{a2}$, $R^{a3}$, $R^{a5}$ and $R^{a6}$ is cyano and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, one of $R^{a2}$, $R^{a3}$, $R^{a5}$ and $R^{a6}$ is cyano and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is cyano and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

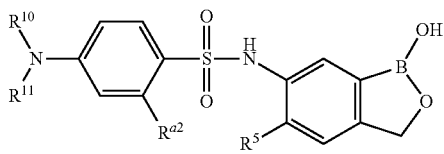

wherein $R^5$ is H or halogen, $R^{a2}$ is cyano, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is F, $R^{a2}$ is cyano, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is cyano, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

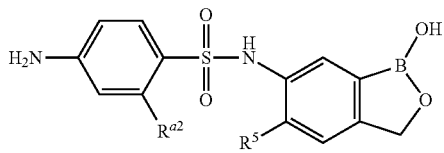

wherein $R^5$ is H or halogen, $R^{a2}$ is cyano. In an exemplary embodiment, $R^5$ is F, $R^{a2}$ is cyano. In an exemplary embodiment, $R^5$ is H, $R^{a2}$ is cyano.

In an exemplary embodiment, the compound, or a salt thereof, has a structure which is

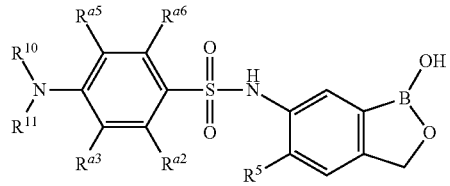

wherein $R^5$ is H or halogen, one of $R^{a2}$, $R^{a3}$, $R^{a5}$ and $R^{a6}$ is unsubstituted alkyl and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, one of $R^{a2}$, $R^{a3}$, $R^{a5}$ and $R^{a6}$ is methyl or ethyl or unsubstituted $C_3$ alkyl or unsubstituted $C_4$ alkyl or unsubstituted $C_5$ alkyl or unsubstituted $C_6$ alkyl and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl or ethyl or unsubstituted $C_3$ alkyl or unsubstituted $C_4$ alkyl or unsubstituted $C_5$ alkyl or unsubstituted $C_6$ alkyl and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$ and $R^5$ are as described herein, $R^{10}$ and $R^{11}$ are independently selected from the prodrug moieties described herein.

In an exemplary embodiment, the compound, or a salt thereof, has a structure which is

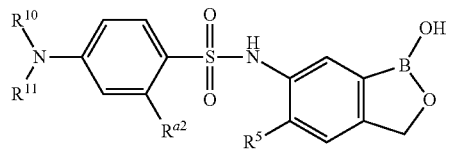

wherein $R^5$ is H or halogen, $R^{a2}$ is unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, $R^{a2}$ is methyl or ethyl or unsubstituted $C_3$ alkyl or unsubstituted $C_4$ alkyl or unsubstituted $C_5$ alkyl or unsubstituted $C_6$ alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl or ethyl or unsubstituted $C_3$ alkyl or unsubstituted $C_4$ alkyl or unsubstituted $C_5$ alkyl or unsubstituted $C_6$ alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

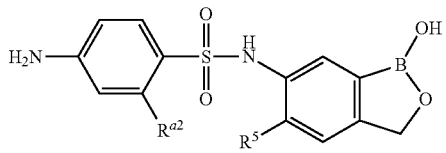

wherein $R^5$ is H or halogen, $R^{a2}$ is unsubstituted alkyl. In an exemplary embodiment, $R^{a2}$ and $R^5$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, $R^{a2}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is $CH_3$. In an exemplary embodiment, $R^5$ is H, $R^{a2}$ is $CH_3$. In an exemplary embodiment, $R^5$ is F, $R^{a2}$ is $CH_2CH_3$. In an exemplary embodiment, $R^5$ is H, $R^{a2}$ is $CH_2CH_3$. In an exemplary embodiment, $R^5$ is F, $R^{a2}$ is unsubstituted $C_3$ alkyl. In an exemplary embodiment, $R^5$ is H, $R^{a2}$ is unsubstituted $C_3$ alkyl. In an exemplary embodiment, $R^5$ is F, $R^{a2}$ is unsubstituted $C_4$ alkyl. In an exemplary embodiment, $R^5$ is H, $R^{a2}$ is unsubstituted $C_4$ alkyl. In an exemplary embodiment, $R^5$ is F, $R^{a2}$ is unsubstituted $C_5$ alkyl. In an exemplary embodiment, $R^5$ is H, $R^{a2}$ is unsubstituted $C_5$ alkyl. In an exemplary embodiment, $R^5$ is F, $R^{a2}$ is unsubstituted $C_6$ alkyl. In an exemplary embodiment, $R^5$ is H, $R^{a2}$ is unsubstituted $C_6$ alkyl.

In an exemplary embodiment, the compound, or a salt thereof, has a structure which is

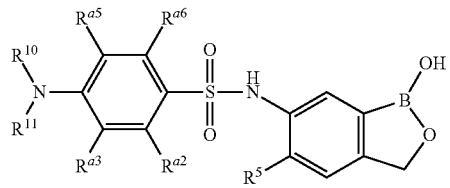

wherein $R^5$ is H or halogen, one of $R^{a2}$, $R^{a3}$, $R^{a5}$ and $R^{a6}$ is unsubstituted alkenyl or unsubstituted alkynyl and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$ and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, one of $R^{a2}$, $R^{a3}$, $R^{a5}$ and $R^{a6}$ is prop-1-ynyl or prop-1-enyl or prop-2-ynyl or prop-2-enyl or but-1-ynyl or but-1-enyl or but-2-ynyl or but-2-enyl or but-3-ynyl or but-3-enyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is prop-1-ynyl or prop-1-enyl or prop-2-ynyl or prop-2-enyl or but-1-ynyl or but-1-enyl or but-2-ynyl or but-2-enyl or but-3-ynyl or but-3-enyl and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound, or a salt thereof, has a structure which is

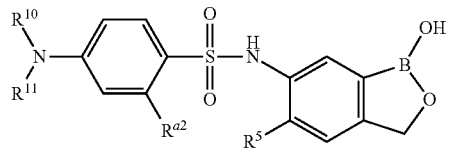

wherein $R^5$ is H or halogen, $R^{a2}$ is unsubstituted alkenyl or unsubstituted alkynyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, $R^{a2}$ is prop-1-ynyl or prop-1-enyl or prop-2-ynyl or prop-2-enyl or but-1-ynyl or but-1-enyl or but-2-ynyl or but-2-enyl or but-3-ynyl or but-3-enyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is prop-1-ynyl or prop-1-enyl or prop-2-ynyl or prop-2-enyl or but-1-ynyl or but-1-enyl or but-2-ynyl or but-2-enyl or but-3-ynyl or but-3-enyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound, or a salt thereof, has a structure which is

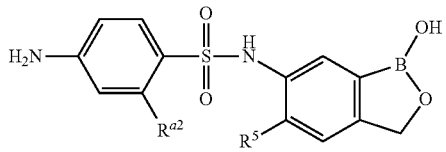

wherein $R^5$ is H or halogen, $R^{a2}$ is unsubstituted alkenyl or unsubstituted alkynyl. In an exemplary embodiment, $R^{a2}$ and $R^5$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, $R^{a2}$ is prop-1-ynyl or prop-1-enyl or prop-2-ynyl or prop-2-enyl or but-1-ynyl or but-1-enyl or but-2-ynyl or but-2-enyl or but-3-ynyl or but-3-enyl. In an exemplary embodiment, $R^5$ is F, $R^{a2}$ is prop-1-ynyl or prop-1-enyl or prop-2-ynyl or prop-2-enyl or but-1-ynyl or but-1-enyl or but-2-ynyl or but-2-enyl or but-3-ynyl or but-3-enyl. In an exemplary embodiment, $R^5$ is H, $R^{a2}$ is prop-1-ynyl or prop-1-enyl or prop-2-ynyl or prop-2-enyl or but-1-ynyl or but-1-enyl or but-2-ynyl or but-2-enyl or but-3-ynyl or but-3-enyl.

In an exemplary embodiment, the compound, or a salt thereof, has a structure which is

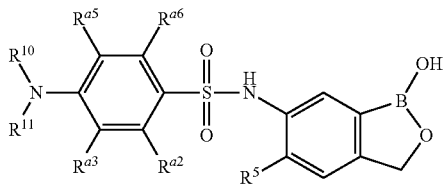

wherein $R^5$ is H or halogen, one of $R^{a2}$, $R^{a3}$, $R^{a5}$ and $R^{a6}$ is alkyl substituted with cyano and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, one of $R^{a2}$, $R^{a3}$, $R^{a5}$ and $R^{a6}$ is methyl substituted with cyano or ethyl substituted with cyano or $C_3$ alkyl substituted with cyano or $C_4$ alkyl substituted with cyano or $C_5$ alkyl substituted with cyano or $C_6$ alkyl substituted with cyano and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl substituted with cyano or ethyl substituted with cyano or $C_3$ alkyl substituted with cyano or $C_4$ alkyl substituted with cyano or $C_5$ alkyl substituted with cyano or $C_6$ alkyl substituted with cyano and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

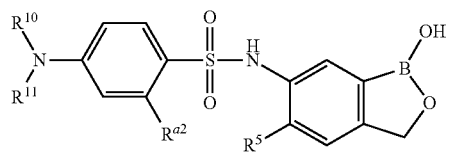

wherein $R^5$ is H or halogen, $R^{a2}$ is alkyl substituted with cyano, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, $R^{a2}$ is methyl substituted with cyano or ethyl substituted with cyano or $C_3$ alkyl substituted with cyano or $C_4$ alkyl substituted with cyano or $C_5$ alkyl substituted with cyano or $C_6$ alkyl substituted with cyano, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl substituted with cyano or ethyl substituted with cyano or $C_3$ alkyl substituted with cyano or $C_4$ alkyl substituted with cyano or $C_5$ alkyl substituted with cyano or $C_6$ alkyl substituted with cyano, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

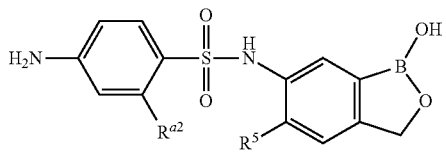

wherein $R^5$ is H or halogen, $R^{a2}$ is alkyl substituted with cyano. In an exemplary embodiment, $R^{a2}$ and $R^5$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, $R^{a2}$ is methyl substituted with cyano or ethyl substituted with cyano or $C_3$ alkyl substituted with cyano or $C_4$ alkyl substituted with cyano or $C_5$ alkyl substituted with cyano or $C_6$ alkyl substituted with cyano. In an exemplary embodiment, $R^5$ is H, $R^{a2}$ is methyl substituted with cyano or ethyl substituted with cyano or $C_3$ alkyl substituted with cyano or $C_4$ alkyl substituted with cyano or $C_5$ alkyl substituted with cyano or $C_6$ alkyl substituted with cyano. In an exemplary embodiment, $R^5$ is F, $R^{a2}$ is $CH_2CN$. In an exemplary embodiment, $R^5$ is H, $R^{a2}$ is $CH_2CN$. In an exemplary embodiment, $R^5$ is F, $R^{a2}$ is $CH_2CH_2CN$. In an exemplary embodiment, $R^5$ is H, $R^{a2}$ is $CH_2CH_2CN$. In an exemplary embodiment, $R^5$ is F, $R^{a2}$ is $CH_2CH_2CH_2CN$. In an exemplary embodiment, $R^5$ is H, $R^{a2}$ is $CH_2CH_2CH_2CN$. In an exemplary embodiment, $R^5$ is F, $R^{a2}$ is $CH_2CH_2CH_2CH_2CN$. In an exemplary embodiment, $R^5$ is H, $R^{a2}$ is $CH_2CH_2CH_2CH_2CN$. In an exemplary embodiment, $R^5$ is F, $R^{a2}$ is $CH_2CH_2CH_2CH_2CH_2CN$. In an exemplary embodiment, $R^5$ is H, $R^{a2}$ is $CH_2CH_2CH_2CH_2CH_2CN$. In an exemplary embodiment, $R^5$ is F, $R^{a2}$ is $CH_2CH_2CH_2CH_2CH_2CH_2CN$. In an exemplary embodiment, $R^5$ is H, $R^{a2}$ is $CH_2CH_2CH_2CH_2CH_2CH_2CN$.

In an exemplary embodiment, the compound, or a salt thereof, has a structure which is

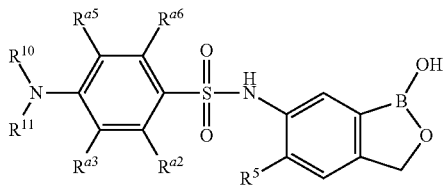

wherein $R^5$ is H or halogen, one of $R^{a2}$, $R^{a3}$, $R^{a5}$ and $R^{a6}$ is alkyl substituted with hydroxy and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, one of $R^{a2}$, $R^{a3}$, $R^{a5}$ and $R^{a6}$ is methyl substituted with hydroxy or ethyl substituted with hydroxy or $C_3$ alkyl substituted with hydroxy or $C_4$ alkyl substituted with hydroxy or $C_5$ alkyl substituted with hydroxy or $C_6$ alkyl substituted with hydroxy and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl substituted with hydroxy or ethyl substituted with hydroxy or $C_3$ alkyl substituted with hydroxy or $C_4$ alkyl substituted with hydroxy or $C_5$ alkyl substituted with hydroxy or $C_6$ alkyl substituted with hydroxy and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

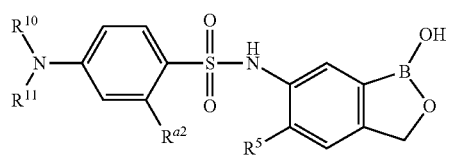

wherein $R^5$ is H or halogen, $R^{a2}$ is alkyl substituted with hydroxy, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, $R^5$ is as described herein, and each hydrogen is optionally D. In an exemplary embodiment, $R^5$ is halogen, $R^{a2}$ is methyl substituted with hydroxy or ethyl substituted with hydroxy or $C_3$ alkyl substituted with hydroxy or $C_4$ alkyl substituted with hydroxy or $C_5$ alkyl substituted with hydroxy or $C_6$ alkyl substituted with hydroxy, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl substituted with hydroxy or ethyl substituted with hydroxy or $C_3$ alkyl substituted with hydroxy or $C_4$ alkyl substituted with hydroxy or $C_5$ alkyl substituted with hydroxy or $C_6$ alkyl substituted with hydroxy, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

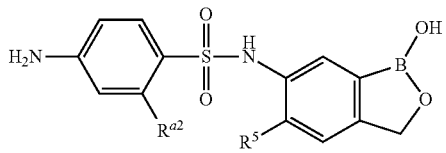

wherein $R^5$ is H or halogen, $R^{a2}$ is alkyl substituted with hydroxy. In an exemplary embodiment, $R^{a2}$ and $R^5$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, $R^{a2}$ is methyl substituted with hydroxy or ethyl substituted with hydroxy or $C_3$ alkyl substituted with hydroxy or $C_4$ alkyl substituted with hydroxy or $C_5$ alkyl substituted with hydroxy or $C_6$ alkyl substituted with hydroxy. In an exemplary embodiment, $R^5$ is H, $R^{a2}$ is methyl substituted with hydroxy or ethyl substituted with hydroxy or $C_3$ alkyl substituted with hydroxy or $C_4$ alkyl substituted with hydroxy or $C_5$ alkyl substituted with hydroxy or $C_6$ alkyl substituted with hydroxy. In an exemplary embodiment, $R^5$ is F, $R^{a2}$ is $CH_2OH$. In an exemplary embodiment, $R^5$ is H, $R^{a2}$ is $CH_2OH$. In an exemplary embodiment, $R^5$ is F, $R^{a2}$ is $CH_2CH_2OH$. In an exemplary embodiment, $R^5$ is H, $R^{a2}$ is $CH_2CH_2OH$. In an exemplary embodiment, $R^5$ is F, $R^{a2}$ is $CH_2CH_2CH_2OH$. In an exemplary embodiment, $R^5$ is H, $R^{a2}$ is $CH_2CH_2CH_2OH$. In an exemplary embodiment, $R^5$ is F, $R^{a2}$ is $CH_2CH_2CH_2CH_2OH$. In an exemplary embodiment, $R^5$ is H, $R^{a2}$ is $CH_2CH_2CH_2CH_2OH$. In an exemplary embodiment, $R^5$ is F, $R^{a2}$ is $CH_2CH_2CH_2CH_2CH_2OH$. In an exemplary embodiment, $R^5$ is H, $R^{a2}$ is $CH_2CH_2CH_2CH_2CH_2OH$. In an exemplary embodiment, $R^5$ is F, $R^{a2}$ is $CH_2CH_2CH_2CH_2CH_2CH_2OH$. In an exemplary embodiment, $R^5$ is H, $R^{a2}$ is $CH_2CH_2CH_2CH_2CH_2CH_2OH$.

In an exemplary embodiment, the compound, or a salt thereof, has a structure which is

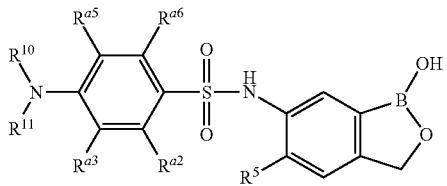

wherein $R^5$ is H or halogen, one of $R^{a2}$, $R^{a3}$, $R^{a5}$ and $R^{a6}$ is alkyl substituted with $OR^{30}$, wherein $R^{30}$ is unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, one of $R^{a2}$, $R^{a3}$, $R^{a5}$ and $R^{a6}$ is methyl substituted with $OR^{30}$ or ethyl substituted with $OR^{30}$ or $C_3$ alkyl substituted with $OR^{30}$ or $C_4$ alkyl substituted with $OR^{30}$ or $C_5$ alkyl substituted with $OR^{30}$ or $C_6$ alkyl substituted with $OR^{30}$, wherein $R^{30}$ is unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl substituted with $OR^{30}$ or ethyl substituted with $OR^{30}$ or $C_3$ alkyl substituted with $OR^{30}$ or $C_4$ alkyl substituted with $OR^{30}$ or $C_5$ alkyl substituted with $OR^{30}$ or $C_6$ alkyl substituted with $OR^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound, or a salt thereof, has a structure which is

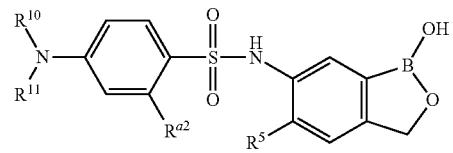

wherein $R^5$ is H or halogen, $R^{a2}$ is alkyl substituted with $OR^{30}$, wherein $R^{30}$ is unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, $R^{a2}$ is methyl substituted with $OR^{30}$ or ethyl substituted with $OR^{30}$ or $C_3$ alkyl substituted with $OR^{30}$ or $C_4$ alkyl substituted with $OR^{30}$ or $C_5$ alkyl substituted with $OR^{30}$ or $C_6$ alkyl substituted with $OR^{30}$, wherein $R^{30}$ is unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl substituted with $OR^{30}$ or ethyl substituted with $OR^{30}$ or $C_3$ alkyl substituted with $OR^{30}$ or $C_4$ alkyl substituted with $OR^{30}$ or $C_5$ alkyl substituted with $OR^{30}$ or $C_6$ alkyl substituted with $OR^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

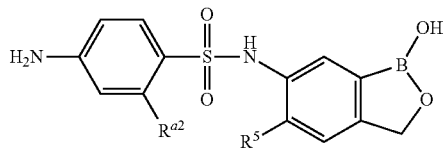

wherein $R^5$ is H or halogen, $R^{a2}$ is alkyl substituted with $OR^{30}$, wherein $R^{30}$ is unsubstituted alkyl. In an exemplary embodiment, $R^{a2}$ and $R^5$ are as described herein, and each hydrogen in said compound, or a salt thereof, is independently H or D. In an exemplary embodiment, each hydrogen in said compound, or a salt thereof, is optionally D. In an exemplary embodiment, $R^5$ is H or halogen, $R^{a2}$ is alkyl substituted with $OR^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is $CH_2OR^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is $CH_2OR^{30}$, wherein $R^{30}$ is methyl or ethyl or unsubstituted $C_3$ alkyl. In an exemplary embodiment, $R^5$ is F, $R^{a2}$ is $CH_2OR^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is $CH_2OR^{30}$, wherein $R^{30}$ is methyl or ethyl or unsubstituted $C_3$ alkyl. In an exemplary embodiment, $R^5$ is H, $R^{a2}$ is $CH_2CH_2OR^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is $CH_2CH_2OR^{30}$, wherein $R^{30}$ is methyl or ethyl or unsubstituted $C_3$ alkyl. In an exemplary embodiment, $R^5$ is F, $R^{a2}$ is $CH_2CH_2OR^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is $CH_2CH_2OR^{30}$, wherein $R^{30}$ is methyl or ethyl or unsubstituted $C_3$ alkyl. In an exemplary embodiment, $R^5$ is H, $R^{a2}$ is $CH_2CH_2CH_2OR^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is $CH_2CH_2CH_2OR^{30}$, wherein $R^{30}$ is methyl or ethyl or unsubstituted $C_3$ alkyl. In an exemplary embodiment, $R^5$ is F, $R^{a2}$ is $CH_2CH_2CH_2OR^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is $CH_2CH_2CH_2OR^{30}$, wherein $R^{30}$ is methyl or ethyl or unsubstituted $C_3$ alkyl.

In an exemplary embodiment, the compound, or a salt thereof, has a structure which is

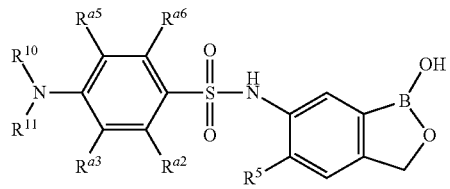

wherein $R^5$ is H or halogen, one of $R^{a2}$, $R^{a3}$, $R^{a5}$ and $R^{a6}$ is alkyl substituted with $NH_2$ and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, one of $R^{a2}$, $R^{a3}$, $R^{a5}$ and $R^{a6}$ is methyl substituted with $NH_2$ or ethyl substituted with $NH_2$ or $C_3$ alkyl substituted with $NH_2$ or $C_4$ alkyl substituted with $NH_2$ or $C_5$ alkyl substituted with $NH_2$ or $C_6$ alkyl substituted with $NH_2$ and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl substituted with $NH_2$ or ethyl substituted with $NH_2$ or $C_3$ alkyl substituted with $NH_2$ or $C_4$ alkyl substituted with $NH_2$ or $C_5$ alkyl substituted with $NH_2$ or $C_6$ alkyl substituted with $NH_2$ and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound, or a salt thereof, has a structure which is

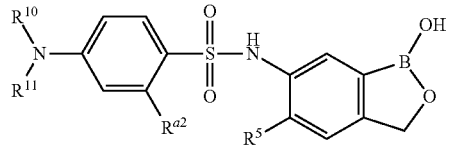

wherein $R^5$ is H or halogen, $R^{a2}$ is alkyl substituted with $NH_2$, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, $R^5$ is H or halogen, and $R^{a2}$ is alkyl substituted with $NH_2$ and at least one D. In an exemplary embodiment, each hydrogen in said compound, or a salt thereof, is optionally D. In an exemplary embodiment, $R^5$ is halogen, $R^{a2}$ is methyl substituted with $NH_2$ or ethyl substituted with $NH_2$ or $C_3$ alkyl substituted with $NH_2$ or $C_4$ alkyl substituted with $NH_2$ or $C_5$ alkyl substituted with $NH_2$ or $C_6$ alkyl substituted with $NH_2$, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl substituted with $NH_2$ or ethyl substituted with $NH_2$ or $C_3$ alkyl substituted with $NH_2$ or $C_4$ alkyl substituted with $NH_2$ or $C_5$ alkyl substituted with $NH_2$ or $C_6$ alkyl substituted with $NH_2$, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

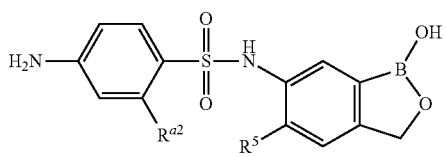

wherein $R^5$ is H or halogen, $R^{a2}$ is alkyl substituted with $NH_2$. In an exemplary embodiment, $R^{a2}$ and $R^5$ are as described herein, and each hydrogen in said compound, or a salt thereof, is independently H or D. In an exemplary embodiment, $R^5$ is H or halogen, and $R^{a2}$ is alkyl substituted with $NH_2$ and at least one D. In an exemplary embodiment, $R^5$ is H or halogen, and $R^{a2}$ is alkyl substituted with $NH_2$ and one D. In an exemplary embodiment, $R^5$ is H or halogen, and $R^{a2}$ is alkyl substituted with $NH_2$ and two D. In an exemplary embodiment, $R^5$ is H or halogen, and $R^{a2}$ is alkyl substituted with $NH_2$ and three D. In an exemplary embodiment, each hydrogen in said compound, or a salt thereof, is optionally D. In an exemplary embodiment, $R^5$ is halogen, $R^{a2}$ is methyl substituted with $NH_2$ or ethyl substituted with $NH_2$ or $C_3$ alkyl substituted with $NH_2$ or $C_4$ alkyl substituted with $NH_2$ or $C_5$ alkyl substituted with $NH_2$ or $C_6$ alkyl substituted with $NH_2$. In an exemplary embodiment, $R^5$ is H, $R^{a2}$ is methyl substituted with $NH_2$ or ethyl substituted with $NH_2$ or $C_3$ alkyl substituted with $NH_2$ or $C_4$ alkyl substituted with $NH_2$ or $C_5$ alkyl substituted with $NH_2$ or $C_6$ alkyl substituted with $NH_2$. In an exemplary embodiment, $R^5$ is F, $R^{a2}$ is $CH_2NH_2$. In an exemplary embodiment, $R^5$ is H, $R^{a2}$ is $CH_2NH_2$. In an exemplary embodiment, $R^5$ is F, $R^{a2}$ is $CH_2CH_2NH_2$. In an exemplary embodiment, $R^5$ is H, $R^{a2}$ is $CH_2CH_2NH_2$. In an exemplary embodiment, $R^5$ is F, $R^{a2}$ is $CH_2CH_2CH_2NH_2$. In an exemplary embodiment, $R^5$ is H, $R^{a2}$ is $CH_2CH_2CH_2NH_2$. In an exemplary embodiment, $R^5$ is F, $R^{a2}$ is $CH_2CH_2CH_2CH_2NH_2$. In an exemplary embodiment, $R^5$ is H, $R^{a2}$ is $CH_2CH_2CH_2CH_2NH_2$. In an exemplary embodiment, $R^5$ is F, $R^{a2}$ is $CH_2CH_2CH_2CH_2CH_2NH_2$. In an exemplary embodiment, $R^5$ is H, $R^{a2}$ is $CH_2CH_2CH_2CH_2CH_2NH_2$. In an exemplary embodiment, $R^5$ is F, $R^{a2}$ is $CH_2CH_2CH_2CH_2CH_2CH_2NH_2$. In an exemplary embodiment, $R^5$ is H, $R^{a2}$ is $CH_2CH_2CH_2CH_2CH_2CH_2NH_2$.

In an exemplary embodiment, the compound, or a salt thereof, has a structure which is

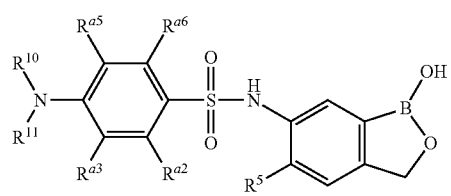

wherein $R^5$ is H or halogen, one of $R^{a2}$, $R^{a3}$, $R^{a5}$ and $R^{a6}$ is alkyl substituted with $R^{31}$, wherein $R^{31}$ is halogen, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$ and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, one of $R^{a2}$, $R^{a3}$, $R^{a5}$ and $R^{a6}$ is methyl substituted with $R^{31}$ or ethyl substituted with $R^{31}$ or $C_3$ alkyl substituted with $R^{31}$ or $C_4$ alkyl substituted with $R^{31}$ or $C_5$ alkyl substituted with $R^{31}$ or $C_6$ alkyl substituted with $R^{31}$, wherein $R^{31}$ is halogen, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl substituted with $R^{31}$ or ethyl substituted with $R^{31}$ or $C_3$ alkyl substituted with $R^{31}$ or $C_4$ alkyl substituted with $R^{31}$ or $C_5$ alkyl substituted with $R^{31}$ or $C_6$ alkyl substituted with $R^{31}$, wherein $R^{31}$ is F or Cl or Br, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound, or a salt thereof, has a structure which is

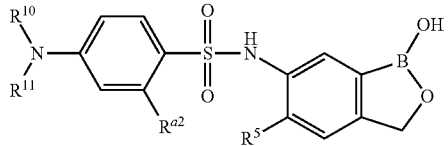

wherein $R^5$ is H or halogen, $R^{a2}$ is alkyl substituted with $R^{31}$, wherein $R^{31}$ is halogen, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, $R^5$ is H or halogen, and $R^{a3}$ is alkyl substituted with one $R^{31}$ and at least one D. In an exemplary embodiment, each hydrogen in said compound, or a salt thereof, is optionally D. In an exemplary embodiment, $R^5$ is halogen, $R^{a2}$ is methyl substituted with $R^{31}$ or ethyl substituted with $R^{31}$ or $C_3$ alkyl substituted with $R^{31}$ or $C_4$ alkyl substituted with $R^{31}$ or $C_5$ alkyl substituted with $R^{31}$ or $C_6$ alkyl substituted with $R^{31}$, wherein $R^{31}$ is halogen, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl substituted with $R^{31}$ or ethyl substituted with $R^{31}$ or $C_3$ alkyl substituted with $R^{31}$ or $C_4$ alkyl substituted with $R^{31}$ or $C_5$ alkyl substituted with $R^{31}$ or $C_6$ alkyl substituted with $R^{31}$, wherein $R^{31}$ is F or Cl or Br, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H or halogen, $R^{a2}$ is alkyl substituted with two $R^{31}$, wherein each $R^{31}$ is independently selected from F or Cl or Br or I, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H or halogen, $R^{a2}$ is alkyl substituted with three $R^{31}$, wherein each $R^{31}$ is independently selected from F or Cl or Br or I, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

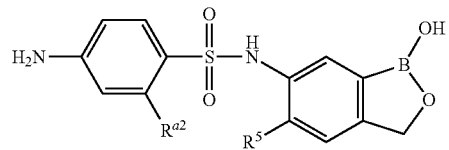

wherein $R^5$ is H or halogen, $R^{a2}$ is alkyl substituted with one $R^{31}$, wherein $R^{31}$ is F or Cl or Br or I. In an exemplary embodiment, $R^{a2}$ and $R^5$ are as described herein, and each hydrogen in said compound, or a salt thereof, is independently H or D. In an exemplary embodiment, $R^5$ is H or halogen, and $R^{a2}$ is alkyl substituted with one $R^{31}$ and at least one D. In an exemplary embodiment, $R^5$ is H or halogen, and $R^{a2}$ is alkyl substituted with one $R^{31}$ and one D. In an exemplary embodiment, $R^5$ is H or halogen, and $R^{a2}$ is alkyl substituted with one $R^{31}$ and two D. In an exemplary embodiment, $R^5$ is H or halogen, and $R^{a2}$ is alkyl substituted with one $R^{31}$ and three D. In an exemplary embodiment, each hydrogen in said compound, or a salt thereof, is optionally D. In an exemplary embodiment, $R^5$ is H or halogen, $R^{a2}$ is alkyl substituted with two $R^{31}$, wherein each $R^{31}$ is independently selected from F or Cl or Br or I. In an exemplary embodiment, $R^5$ is H or halogen, $R^{a2}$ is alkyl substituted with three $R^{31}$, wherein each $R^{31}$ is independently selected from F or Cl or Br or I. In an exemplary embodiment, $R^5$ is H or halogen, $R^{a2}$ is alkyl substituted with $R^{31}$, wherein $R^{31}$ is F or Cl or Br. In an exemplary embodiment, $R^5$ is H, $R^{a2}$ is $CH_2F$. In an exemplary embodiment, $R^5$ is F, $R^{a2}$ is $CH_2F$. In an exemplary embodiment, $R^5$ is H, $R^{a2}$ is $CHF_2$. In an exemplary embodiment, $R^5$ is F, $R^{a2}$ is $CHF_2$. In an exemplary embodiment, $R^5$ is H, $R^{a2}$ is $CF_3$. In an exemplary embodiment, $R^5$ is F, $R^{a2}$ is $CF_3$. In an exemplary embodiment, $R^5$ is H or halogen, $R^{a2}$ is ethyl substituted with $R^{31}$, wherein $R^{31}$ is F or Cl or Br. In an exemplary embodiment, $R^5$ is H or halogen, $R^{a2}$ is ethyl substituted with two $R^{31}$, wherein each $R^{31}$ is independently selected from F or Cl or Br. In an exemplary embodiment, $R^5$ is H or halogen, $R^{a2}$ is ethyl substituted with three $R^{31}$, wherein each $R^{31}$ is independently selected from F or Cl or Br. In an exemplary embodiment, $R^5$ is H, $R^{a2}$ is $CH_2CH_2F$. In an exemplary embodiment, $R^5$ is F, $R^{a2}$ is $CH_2CH_2F$. In an exemplary embodiment, $R^5$ is H, $R^{a2}$ is $CH_2CHF_2$. In an exemplary embodiment, $R^5$ is F, $R^{a2}$ is $CH_2CHF_2$. In an exemplary embodiment, $R^5$ is H, $R^{a2}$ is $CH_2CF_3$. In an exemplary embodiment, $R^5$ is F, $R^{a2}$ is $CH_2CF_3$. In an exemplary embodiment, $R^5$ is H or halogen, $R^{a2}$ is $C_3$ alkyl substituted with $R^{31}$, wherein $R^{31}$ is F or Cl or Br. In an exemplary embodiment, $R^5$ is H or halogen, $R^{a2}$ is $C_3$ alkyl substituted with two $R^{31}$, wherein each $R^{31}$ is independently selected from F or Cl or Br. In an exemplary embodiment, $R^5$ is H or halogen, $R^{a2}$ is $C_3$ alkyl substituted with three $R^{31}$, wherein each $R^{31}$ is independently selected from F or Cl or Br. In an exemplary embodiment, $R^5$ is H, $R^{a2}$ is $CH_2CH_2CH_2F$. In an exemplary embodiment, $R^5$ is F, $R^{a2}$ is $CH_2CH_2CH_2F$. In an exemplary embodiment, $R^5$ is H, $R^{a2}$ is $CH_2CH_2CHF_2$. In an exemplary embodiment, $R^5$ is F, $R^{a2}$ is $CH_2CH_2CHF_2$. In an exemplary embodiment, $R^5$ is H, $R^{a2}$ is $CH_2CH_2CF_3$. In an exemplary embodiment, $R^5$ is F, $R^{a2}$ is $CH_2CH_2CF_3$.

In an exemplary embodiment, the compound, or a salt thereof, has a structure which is

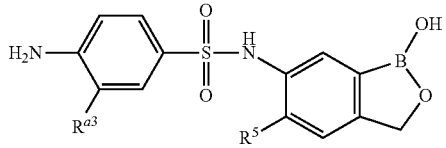

wherein $R^5$ is H or halogen, $R^{a3}$ is alkyl substituted with one $R^{31}$, wherein $R^{31}$ is F or Cl or Br or I. In an exemplary embodiment, $R^{a3}$ and $R^5$ are as described herein, and each hydrogen in said compound, or a salt thereof, is independently H or D. In an exemplary embodiment, $R^{a3}$ and $R^5$ are as described herein, and each hydrogen in said $R^{a3}$ is independently H or D. In an exemplary embodiment, $R^5$ is H or halogen, and $R^{a3}$ is alkyl substituted with one $R^{31}$ and at least one D. In an exemplary embodiment, $R^5$ is H or halogen, and $R^{a3}$ is alkyl substituted with one $R^{31}$ and one D. In an exemplary embodiment, $R^5$ is H or halogen, and $R^{a3}$ is alkyl substituted with one $R^{31}$ and two D. In an exemplary embodiment, $R^5$ is H or halogen, and $R^{a3}$ is alkyl substituted with one $R^{31}$ and three D. In an exemplary embodiment, each hydrogen in said compound, or a salt thereof, is optionally D. In an exemplary embodiment, $R^5$ is H or halogen, $R^{a3}$ is alkyl substituted with two $R^{31}$, wherein each $R^{31}$ is independently selected from F or Cl or Br or I. In an exemplary embodiment, $R^5$ is H or halogen, $R^{a3}$ is alkyl substituted with three $R^{31}$, wherein each $R^{31}$ is independently selected from F or Cl or Br or I. In an exemplary embodiment, $R^5$ is H or halogen, $R^{a3}$ is alkyl substituted with $R^{31}$, wherein $R^{31}$ is F or Cl or Br. In an exemplary embodiment, $R^5$ is H, $R^{a3}$ is $CH_2F$. In an exemplary embodiment, $R^5$ is F, $R^{a3}$ is $CH_2F$. In an exemplary embodiment, $R^5$ is H, $R^{a3}$ is $CHF_2$. In an exemplary embodiment, $R^5$ is F, $R^{a3}$ is $CHF_2$. In an exemplary embodiment, $R^5$ is H, $R^{a3}$ is $CF_3$. In an exemplary embodiment, $R^5$ is F, $R^{a3}$ is $CF_3$. In an exemplary embodiment, $R^5$ is H or halogen, $R^{a3}$ is ethyl substituted with $R^{31}$, wherein $R^{31}$ is F or Cl or Br. In an exemplary embodiment, $R^5$ is H or halogen, $R^{a3}$ is ethyl substituted with two $R^{31}$, wherein each $R^{31}$ is independently selected from F or Cl or Br. In an exemplary embodiment, $R^5$ is H or halogen, $R^{a3}$ is ethyl substituted with three $R^{31}$, wherein each $R^{31}$ is independently selected from F or Cl or Br. In an exemplary embodiment, $R^5$ is H, $R^{a3}$ is $CH_2CH_2F$. In an exemplary embodiment, $R^5$ is F, $R^{a3}$ is $CH_2CH_2F$. In an exemplary embodiment, $R^5$ is H, $R^{a3}$ is $CH_2CHF_2$. In an exemplary embodiment, $R^5$ is F, $R^{a3}$ is $CH_2CHF_2$. In an exemplary embodiment, $R^5$ is H, $R^{a3}$ is $CH_2CF_3$. In an exemplary embodiment, $R^5$ is F, $R^{a3}$ is $CH_2CF_3$. In an exemplary embodiment, $R^5$ is H or halogen, $R^{a3}$ is $C_3$ alkyl substituted with $R^{31}$, wherein $R^{31}$ is F or Cl or Br. In an exemplary embodiment, $R^5$ is H or halogen, $R^{a3}$ is $C_3$ alkyl substituted with two $R^{31}$, wherein each $R^{31}$ is independently selected from F or Cl or Br. In an exemplary embodiment, $R^5$ is H or halogen, $R^{a3}$ is $C_3$ alkyl substituted with three $R^{31}$, wherein each $R^{31}$ is independently selected from F or Cl or Br. In an exemplary embodiment, $R^5$ is H, $R^{a3}$ is $CH_2CH_2CH_2F$. In an exemplary embodiment, $R^5$ is F, $R^{a3}$ is $CH_2CH_2CH_2F$. In an exemplary embodiment, $R^5$ is H, $R^{a3}$ is $CH_2CH_2CHF_2$. In an exemplary embodiment, $R^5$ is F, $R^{a3}$ is $CH_2CH_2CHF_2$. In an exemplary embodiment, $R^5$ is H, $R^{a3}$ is $CH_2CH_2CF_3$. In an exemplary embodiment, $R^5$ is F, $R^{a3}$ is $CH_2CH_2CF_3$.

In an exemplary embodiment, the compound, or a salt thereof, has a structure which is

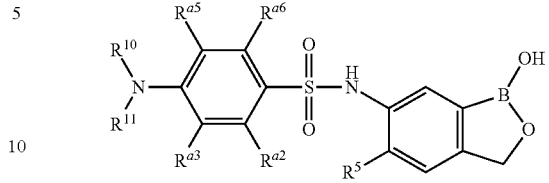

wherein $R^5$ is H or halogen, one of $R^{a2}$, $R^{a3}$, $R^{a5}$ and $R^{a6}$ is alkyl substituted with $-C(O)OR^{30}$, wherein $R^{30}$ is unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^{a2}$, $R^{a3}$, $R^{a5}$, $R^{a6}$, $R^5$, $R^{10}$, and $R^{11}$ are as described herein, and each hydrogen in said $R^{a2}$, $R^{a3}$, $R^{a5}$, $R^{a6}$, is independently H or D. In an exemplary embodiment, $R^5$ is halogen, one of $R^{a2}$, $R^{a3}$, $R^{a5}$ and $R^{a6}$ is methyl substituted with $-C(O)OR^{30}$ or ethyl substituted with $-C(O)OR^{30}$ or $C_3$ alkyl substituted with $-C(O)OR^{30}$ or $C_4$ alkyl substituted with $-C(O)OR^{30}$ or $C_5$ alkyl substituted with $-C(O)OR^{30}$ or $C_6$ alkyl substituted with $-C(O)OR^{30}$, wherein $R^{30}$ is unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H or halogen, one of $R^{a2}$, $R^{a3}$, $R^{a5}$ and $R^{a6}$ is alkyl substituted with $-C(O)OR^{30}$, wherein $R^{30}$ is $CD_3$, and the remaining members of $R^{a2}$, $R^{a3}$, $R^{a5}$ and $R^{a6}$ are H, $R^{10}$ and $R^{11}$ are as described herein. In an exemplary embodiment, $R^5$ is H or halogen, $R^{a2}$ is alkyl substituted with $-C(O)OCD_3$. In an exemplary embodiment, $R^5$ is H, $R^{a2}$ is alkyl substituted with $-C(O)OCD_3$. In an exemplary embodiment, $R^5$ is F, $R^{a2}$ is alkyl substituted with $-C(O)OCD_3$. In an exemplary embodiment, $R^5$ is H or halogen, $R^{a2}$ is alkyl substituted with $-C(O)OCH_2CD_3$. In an exemplary embodiment, $R^5$ is H, one of $R^{a2}$, $R^{a3}$, $R^{a5}$ and $R^{a6}$ is methyl substituted with $-C(O)OR^{30}$ or ethyl substituted with $-C(O)OR^{30}$ or $C_3$ alkyl substituted with $-C(O)OR^{30}$ or $C_4$ alkyl substituted with $-C(O)OR^{30}$ or $C_5$ alkyl substituted with $-C(O)OR^{30}$ or $C_6$ alkyl substituted with $-C(O)OR^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

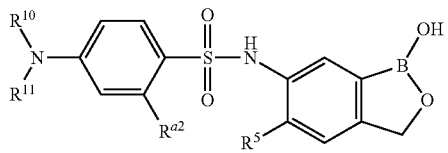

wherein $R^5$ is H or halogen, $R^{a2}$ is alkyl substituted with —C(O)OR$^{30}$, wherein R$^{30}$ is unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, $R^{a2}$, $R^5$, $R^{10}$, and $R^{11}$ are as described herein, and each hydrogen in said $R^{a2}$ is independently H or D. In an exemplary embodiment, each hydrogen in said compound, or a salt thereof, is optionally D. In an exemplary embodiment, $R^5$ is halogen, $R^{a2}$ is methyl substituted with —C(O)OR$^{30}$ or ethyl substituted with —C(O)OR$^{30}$ or $C_3$ alkyl substituted with —C(O)OR$^{30}$ or $C_4$ alkyl substituted with —C(O)OR$^{30}$ or $C_5$ alkyl substituted with —C(O)OR$^{30}$ or $C_6$ alkyl substituted with —C(O)OR$^{30}$, wherein R$^{30}$ is unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{10}$ and $R^{11}$ are as described herein, $R^5$ is H or halogen, $R^{a2}$ is alkyl substituted with —C(O)OCD$_3$. In an exemplary embodiment, $R^{10}$ and $R^{11}$ are as described herein, $R^5$ is H, $R^{a2}$ is alkyl substituted with —C(O)OCD$_3$. In an exemplary embodiment, $R^{10}$ and $R^{11}$ are as described herein, $R^5$ is F, $R^{a2}$ is alkyl substituted with —C(O)OCD$_3$. In an exemplary embodiment, $R^{10}$ and $R^{11}$ are as described herein, $R^5$ is H or halogen, $R^{a2}$ is alkyl substituted with —C(O)OCH$_2$CD$_3$. In an exemplary embodiment, $R^5$ is H, $R^{a2}$ is methyl substituted with —C(O)OR$^{30}$ or ethyl substituted with —C(O)OR$^{30}$ or $C_3$ alkyl substituted with —C(O)OR$^{30}$ or $C_4$ alkyl substituted with —C(O)OR$^{30}$ or $C_5$ alkyl substituted with —C(O)OR$^{30}$ or $C_6$ alkyl substituted with —C(O)OR$^{30}$, wherein R$^{30}$ is methyl or ethyl or unsubstituted $C_3$ alkyl or unsubstituted $C_4$ alkyl or unsubstituted $C_5$ alkyl or unsubstituted $C_6$ alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

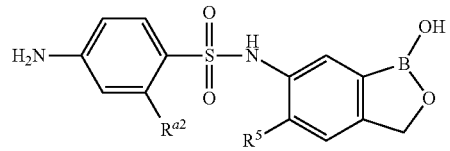

wherein $R^5$ is H or halogen, $R^{a2}$ is alkyl substituted with —C(O)OR$^{30}$, wherein R$^{30}$ is unsubstituted alkyl. In an exemplary embodiment, $R^{a2}$ and $R^5$ are as described herein, and each hydrogen in said compound, or a salt thereof, is independently H or D. In an exemplary embodiment, $R^{a2}$ and $R^5$ are as described herein, and each hydrogen in $R^{a2}$ is independently H or D. In an exemplary embodiment, $R^{a2}$ and $R^5$ are as described herein, and each hydrogen in $R^{30}$ is independently H or D. In an exemplary embodiment, each hydrogen in said compound, or a salt thereof, is optionally D. In an exemplary embodiment, $R^5$ is H or halogen, $R^{a2}$ is alkyl substituted with —C(O)OR$^{30}$, wherein R$^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H or halogen, $R^{a2}$ is alkyl substituted with —C(O)OCD$_3$. In an exemplary embodiment, $R^5$ is H, $R^{a2}$ is alkyl substituted with —C(O)OCD$_3$. In an exemplary embodiment, $R^5$ is F, $R^{a2}$ is alkyl substituted with —C(O)OCD$_3$. In an exemplary embodiment, $R^5$ is H or halogen, $R^{a2}$ is alkyl substituted with —C(O)OCH$_2$CD$_3$. In an exemplary embodiment, $R^5$ is H, $R^{a2}$ is CH$_2$C(O)OR$^{30}$, wherein R$^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$C(O)OR$^{30}$, wherein R$^{30}$ is CD$_3$ or CH$_2$CD$_3$. In an exemplary embodiment, $R^5$ is H, $R^{a2}$ is CH$_2$C(O)OR$^{30}$, wherein R$^{30}$ is methyl or ethyl or unsubstituted $C_3$ alkyl. In an exemplary embodiment, $R^5$ is F, $R^{a2}$ is CH$_2$C(O)OR$^{30}$, wherein R$^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is CH$_2$C(O)OR$^{30}$, wherein R$^{30}$ is methyl or ethyl or unsubstituted $C_3$ alkyl. In an exemplary embodiment, $R^5$ is H, $R^{a2}$ is CH$_2$CH$_2$C(O)OR$^{30}$, wherein R$^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$CH$_2$C(O)OR$^{30}$, wherein R$^{30}$ is methyl or ethyl or unsubstituted $C_3$ alkyl. In an exemplary embodiment, $R^5$ is F, $R^{a2}$ is CH$_2$CH$_2$C(O)OR$^{30}$, wherein R$^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is CH$_2$CH$_2$C(O)OR$^{30}$, wherein R$^{30}$ is methyl or ethyl or unsubstituted $C_3$ alkyl. In an exemplary embodiment, $R^5$ is H, $R^{a2}$ is CH$_2$CH$_2$CH$_2$C(O)OR$^{30}$, wherein R$^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$CH$_2$CH$_2$C(O)OR$^{30}$, wherein R$^{30}$ is methyl or ethyl or unsubstituted $C_3$ alkyl. In an exemplary embodiment, $R^5$ is F, $R^{a2}$ is CH$_2$CH$_2$CH$_2$C(O)OR$^{30}$, wherein R$^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is CH$_2$CH$_2$CH$_2$C(O)OR$^{30}$, wherein R$^{30}$ is methyl or ethyl or unsubstituted $C_3$ alkyl. In an exemplary embodiment, $R^5$ is H, $R^{a2}$ is $CH_2C(O)OCH(CH_3)_2$. In an exemplary embodiment, $R^5$ is F, $R^{a2}$ is $CH_2C(O)OCH(CH_3)_2$. In an exemplary embodiment, $R^5$ is H, $R^{a2}$ is $CH_2CH_2C(O)OCH(CH_3)_2$. In an exemplary embodiment, $R^5$ is F, $R^{a2}$ is $CH_2CH_2C(O)OCH(CH_3)_2$. In an exemplary embodiment, $R^5$ is H, $R^{a2}$ is $CH_2CH_2CH_2C(O)OCH(CH_3)_2$. In an exemplary embodiment, $R^5$ is F, $R^{a2}$ is $CH_2CH_2CH_2C(O)OCH(CH_3)_2$. In an exemplary embodiment, $R^5$ is H, $R^{a2}$ is $CH_2C(O)OC(CH_3)_3$. In an exemplary embodiment, $R^5$ is F, $R^{a2}$ is $CH_2C(O)OC(CH_3)_3$. In an exemplary embodiment, $R^5$ is H, $R^{a2}$ is $CH_2CH_2C(O)OC(CH_3)_3$. In an exemplary embodiment, $R^5$ is F, $R^{a2}$ is $CH_2CH_2C(O)OC(CH_3)_3$. In an exemplary embodiment, $R^5$ is H, $R^{a2}$ is $CH_2CH_2CH_2C(O)OC(CH_3)_3$. In an exemplary embodiment, $R^5$ is F, $R^{a2}$ is $CH_2CH_2CH_2C(O)OC(CH_3)_3$.

In an exemplary embodiment, the compound, or a salt thereof, has a structure which is

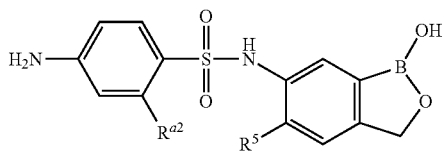

wherein $R^5$ is H or halogen, $R^{a2}$ is alkyl substituted with —C(O)OH. In an exemplary embodiment, $R^5$ is H, $R^{a2}$ is $CH_2C(O)OH$. In an exemplary embodiment, $R^{a2}$ and $R^5$ are as described herein, and each hydrogen in said compound, or a salt thereof, is independently H or D. In an exemplary embodiment, $R^{a2}$ and $R^5$ are as described herein, and each hydrogen in $R^{a2}$ is independently H or D. In an exemplary embodiment, each hydrogen in said compound, or a salt thereof, is optionally D. In an exemplary embodiment, $R^5$ is F, $R^{a2}$ is $CH_2C(O)OH$. In an exemplary embodiment, $R^5$ is H, $R^{a2}$ is $CH_2CH_2C(O)OH$. In an exemplary embodiment, $R^5$ is F, $R^{a2}$ is $CH_2CH_2C(O)OH$. In an exemplary embodiment, $R^5$ is H, $R^{a2}$ is $CH_2CH_2CH_2C(O)OH$. In an exemplary embodiment, $R^5$ is F, $R^{a2}$ is $CH_2CH_2CH_2C(O)OH$.

In an exemplary embodiment, the compound, or a salt thereof, has a structure which is

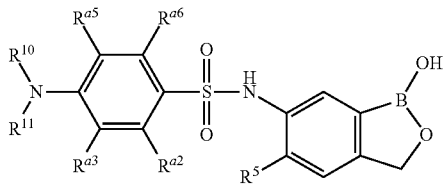

wherein $R^5$ is H or halogen, one of $R^{a2}$, $R^{a3}$, $R^{a5}$ and $R^{a6}$ is alkyl substituted with —C(O)NHR$^{35}$, wherein R$^{35}$ is unsubstituted alkyl or unsubstituted cyclobutyl or unsubstituted cyclopentyl or unsubstituted cyclohexyl or unsubstituted cycloheptyl or unsubstituted cyclooctyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, one of $R^{a2}$, $R^{a3}$, $R^{a5}$ and $R^{a6}$ is methyl substituted with —C(O)NHR$^{35}$ or ethyl substituted with —C(O)NHR$^{35}$ or $C_3$ alkyl substituted with —C(O)NHR$^{35}$ or $C_4$ alkyl substituted with —C(O)NHR$^{35}$ or $C_5$ alkyl substituted with —C(O)NHR$^{35}$ or $C_6$ alkyl substituted with —C(O)NHR$^{35}$, wherein R$^{35}$ is unsubstituted alkyl or unsubstituted cyclobutyl or unsubstituted cyclopentyl or unsubstituted cyclohexyl or unsubstituted cycloheptyl or unsubstituted cyclooctyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl substituted with —C(O)NHR$^{35}$ or ethyl substituted with —C(O)NHR$^{35}$ or $C_3$ alkyl substituted with —C(O)NHR$^{35}$ or $C_4$ alkyl substituted with —C(O)NHR$^{35}$, wherein R$^{35}$ is methyl or ethyl or unsubstituted $C_3$ alkyl or unsubstituted $C_4$ alkyl or unsubstituted cyclobutyl or unsubstituted cyclopentyl or unsubstituted cyclohexyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound, or a salt thereof, has a structure which is

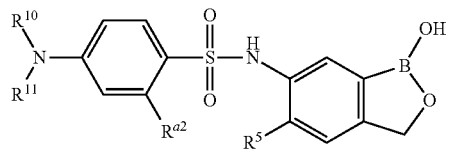

wherein $R^5$ is H or halogen, $R^{a2}$ is alkyl substituted with —C(O)NHR$^{35}$, wherein R$^{35}$ is unsubstituted alkyl or unsubstituted cyclobutyl or unsubstituted cyclopentyl or unsubstituted cyclohexyl or unsubstituted cycloheptyl or unsubstituted cyclooctyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, $R^{a2}$ is methyl substituted with —C(O)NHR$^{35}$ or ethyl substituted with —C(O)NHR$^{35}$ or $C_3$ alkyl substituted with —C(O)NHR$^{35}$ or $C_4$ alkyl substituted with —C(O)NHR$^{35}$ or $C_5$ alkyl substituted with —C(O)NHR$^{35}$ or $C_6$ alkyl substituted with —C(O)NHR$^{35}$, wherein R$^{35}$ is unsubstituted alkyl or unsubstituted cyclobutyl or unsubstituted cyclopentyl or unsubstituted cyclohexyl or unsubstituted cycloheptyl or unsubstituted cyclooctyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl substituted with —C(O)NHR$^{35}$ or ethyl substituted with —C(O)NHR$^{35}$ or $C_3$ alkyl substituted with —C(O)NHR$^{35}$ or $C_4$ alkyl substituted with —C(O)NHR$^{35}$ or $C_5$ alkyl substituted with —C(O)NHR$^{35}$ or $C_6$ alkyl substituted with —C(O)NHR$^{35}$, wherein $R^{35}$ is methyl or ethyl or unsubstituted $C_3$ alkyl or unsubstituted $C_4$ alkyl or unsubstituted $C_5$ alkyl or unsubstituted $C_6$ alkyl or unsubstituted cyclobutyl or unsubstituted cyclopentyl or unsubstituted cyclohexyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

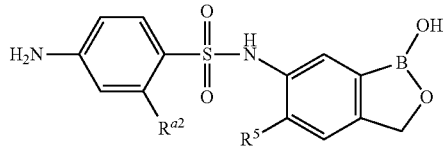

wherein $R^5$ is H or halogen, $R^{a2}$ is alkyl substituted with —C(O)NHR$^{35}$, wherein $R^{35}$ is unsubstituted alkyl. In an exemplary embodiment, $R^{a2}$ and $R^5$ are as described herein, and each hydrogen in said compound, or a salt thereof, is independently H or D. In an exemplary embodiment, $R^{a2}$ and $R^5$ are as described herein, and each hydrogen in $R^{35}$ of said compound or a salt thereof is independently H or D. In an exemplary embodiment, each hydrogen in said compound, or a salt thereof, is optionally D. In an exemplary embodiment, $R^5$ is H or halogen, $R^{a2}$ is alkyl substituted with —C(O)NHR$^{35}$, wherein $R^{35}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$C(O)NHR$^{35}$, wherein $R^{35}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$C(O)NHR$^{35}$, wherein $R^{35}$ is methyl or ethyl or unsubstituted $C_3$ alkyl. In an exemplary embodiment, $R^5$ is F, $R^{a2}$ is CH$_2$C(O)NHR$^{35}$, wherein $R^{35}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is CH$_2$C(O)NHR$^{35}$, wherein $R^{35}$ is methyl or ethyl or unsubstituted $C_3$ alkyl. In an exemplary embodiment, $R^5$ is H, $R^{a2}$ is CH$_2$CH$_2$C(O)NHR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$CH$_2$C(O)NHR$^{30}$, wherein $R^{30}$ is methyl or ethyl or unsubstituted $C_3$ alkyl. In an exemplary embodiment, $R^5$ is F, $R^{a2}$ is CH$_2$CH$_2$C(O)NHR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is CH$_2$CH$_2$C(O)NHR$^{30}$, wherein $R^{30}$ is methyl or ethyl or unsubstituted $C_3$ alkyl. In an exemplary embodiment, $R^5$ is H, $R^{a2}$ is CH$_2$CH$_2$CH$_2$C(O)NHR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$CH$_2$CH$_2$C(O)NHR$^{30}$, wherein $R^{30}$ is methyl or ethyl or unsubstituted $C_3$ alkyl. In an exemplary embodiment, $R^5$ is F, $R^{a2}$ is CH$_2$CH$_2$CH$_2$C(O)NHR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is CH$_2$CH$_2$CH$_2$C(O)NHR$^{30}$, wherein $R^{30}$ is methyl or ethyl or unsubstituted $C_3$ alkyl.

In an exemplary embodiment, the compound, or a salt thereof, has a structure which is

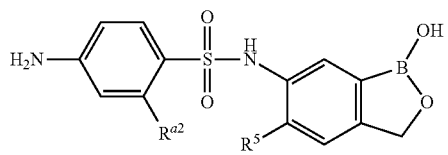

wherein $R^5$ is H or halogen, $R^{a2}$ is alkyl substituted with —C(O)NHR$^{35}$, wherein $R^{35}$ is unsubstituted cyclobutyl or unsubstituted cyclopentyl or unsubstituted cyclohexyl or unsubstituted cycloheptyl or unsubstituted cyclooctyl. In an exemplary embodiment, $R^{a2}$ and $R^5$ are as described herein, and each hydrogen in said compound, or a salt thereof, is independently H or D. In an exemplary embodiment, each hydrogen in said compound, or a salt thereof, is optionally D. In an exemplary embodiment, $R^5$ is H or halogen, $R^{a2}$ is alkyl substituted with —C(O)NHR$^{35}$, wherein $R^{35}$ is unsubstituted cyclobutyl or unsubstituted cyclopentyl or unsubstituted cyclohexyl or unsubstituted cycloheptyl or unsubstituted cyclooctyl. In an exemplary embodiment, $R^5$ is H or halogen, $R^{a2}$ is alkyl substituted with —C(O)NHR$^{35}$, wherein $R^{35}$ is unsubstituted cyclobutyl or unsubstituted cyclopentyl or unsubstituted cyclohexyl or unsubstituted cycloheptyl or unsubstituted cyclooctyl. In an exemplary embodiment, $R^5$ is H, $R^{a2}$ is CH$_2$C(O)NHR$^{35}$, wherein $R^{35}$ is unsubstituted cyclobutyl or unsubstituted cyclopentyl or unsubstituted cyclohexyl or unsubstituted cycloheptyl or unsubstituted cyclooctyl. In an exemplary embodiment, $R^5$ is H, $R^{a2}$ is CH$_2$C(O)NHR$^{35}$, wherein $R^{35}$ is unsubstituted cyclopropyl or unsubstituted cyclobutyl or unsubstituted cyclopentyl or unsubstituted cyclohexyl. In an exemplary embodiment, $R^5$ is F, $R^{a2}$ is CH$_2$C(O)NHR$^{35}$, wherein $R^{35}$ is unsubstituted cyclobutyl or unsubstituted cyclopentyl or unsubstituted cyclohexyl or unsubstituted cycloheptyl or unsubstituted cyclooctyl. In an exemplary embodiment, $R^5$ is F, $R^{a2}$ is CH$_2$C(O)NHR$^{35}$, wherein $R^{35}$ is unsubstituted cyclobutyl or unsubstituted cyclopentyl or unsubstituted cyclohexyl. In an exemplary embodiment, $R^5$ is H, $R^{a2}$ is CH$_2$CH$_2$C(O)NHR$^{35}$, wherein $R^{35}$ is unsubstituted cyclobutyl or unsubstituted cyclopentyl or unsubstituted cyclohexyl or unsubstituted cycloheptyl or unsubstituted cyclooctyl. In an exemplary embodiment, $R^5$ is H, $R^{a2}$ is CH$_2$CH$_2$C(O)NHR$^{35}$, wherein $R^{35}$ is unsubstituted cyclobutyl or unsubstituted cyclopentyl or unsubstituted cyclohexyl. In an exemplary embodiment, $R^5$ is F, $R^{a2}$ is CH$_2$CH$_2$C(O)NHR$^{35}$, wherein $R^{35}$ is unsubstituted cyclobutyl or unsubstituted cyclopentyl or unsubstituted cyclohexyl or unsubstituted cycloheptyl or unsubstituted cyclooctyl. In an exemplary embodiment, $R^5$ is F, $R^{a2}$ is CH$_2$CH$_2$C(O)NHR$^{35}$, wherein $R^{35}$ is unsubstituted cyclobutyl or unsubstituted cyclopentyl or unsubstituted cyclohexyl. In an exemplary embodiment, $R^5$ is H, $R^{a2}$ is CH$_2$CH$_2$CH$_2$C(O)NHR$^{35}$, wherein $R^{35}$ is unsubstituted cyclobutyl or unsubstituted cyclopentyl or unsubstituted cyclohexyl or unsubstituted cycloheptyl or unsubstituted cyclooctyl. In an exemplary embodiment, $R^5$ is H, $R^{a2}$ is $CH_2CH_2CH_2C(O)$ $NHR^{35}$, wherein $R^{35}$ is unsubstituted cyclobutyl or unsubstituted cyclopentyl or unsubstituted cyclohexyl. In an exemplary embodiment, $R^5$ is F, $R^{a2}$ is $CH_2CH_2CH_2C(O)NHR^{35}$, wherein $R^{35}$ is unsubstituted cyclobutyl or unsubstituted cyclopentyl or unsubstituted cyclohexyl or unsubstituted cycloheptyl or unsubstituted cyclooctyl. In an exemplary embodiment, $R^5$ is F, $R^{a2}$ is $CH_2CH_2CH_2C(O)NHR^{35}$, wherein $R^{35}$ is unsubstituted cyclobutyl or unsubstituted cyclopentyl or unsubstituted cyclohexyl.

In an exemplary embodiment, the compound, or a salt thereof, has a structure which is

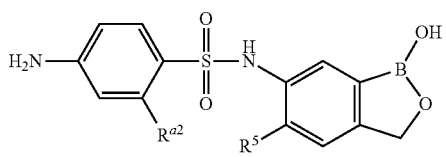

wherein $R^5$ is H or halogen, $R^{a2}$ is alkyl substituted with —C(O)NHR$^{30}$, wherein $R^{30}$ is alkyl substituted with alkenyl or alkynyl. In an exemplary embodiment, $R^{a2}$ and $R^5$ are as described herein, and each hydrogen in said compound, or a salt thereof, is independently H or D. In an exemplary embodiment, each hydrogen in said compound, or a salt thereof, is optionally D. In an exemplary embodiment, $R^5$ is H or halogen, $R^{a2}$ is alkyl substituted with —C(O)NHR$^{30}$, wherein $R^{30}$ is prop-1-ynyl or prop-1-enyl or prop-2-ynyl or prop-2-enyl or but-1-ynyl or but-1-enyl or but-2-ynyl or but-2-enyl or but-3-ynyl or but-3-enyl. In an exemplary embodiment, $R^5$ is H, $R^{a2}$ is $CH_2C(O)NHR^{30}$, wherein $R^{30}$ is prop-1-ynyl or prop-1-enyl or prop-2-ynyl or prop-2-enyl or but-1-ynyl or but-1-enyl or but-2-ynyl or but-2-enyl or but-3-ynyl or but-3-enyl. In an exemplary embodiment, $R^5$ is F, $R^{a2}$ is $CH_2C(O)NHR^{30}$, wherein $R^{30}$ is prop-1-ynyl or prop-1-enyl or prop-2-ynyl or prop-2-enyl or but-1-ynyl or but-1-enyl or but-2-ynyl or but-2-enyl or but-3-ynyl or but-3-enyl.

In an exemplary embodiment, the compound, or a salt thereof, has a structure which is

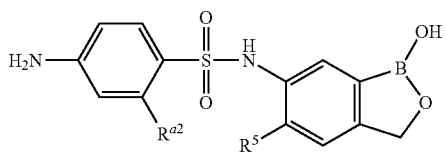

wherein $R^5$ is H or halogen, $R^{a2}$ is alkyl substituted with —C(O)NHR$^{30}$, wherein $R^{30}$ is benzyl. In an exemplary embodiment, $R^5$ is H, $R^{a2}$ is $CH_2C(O)NHR^{30}$, wherein $R^{30}$ is benzyl. In an exemplary embodiment, $R^5$ is F, $R^{a2}$ is $CH_2C(O)NHR^{30}$, wherein $R^{30}$ is benzyl.

In an exemplary embodiment, the compound, or a salt thereof, has a structure which is

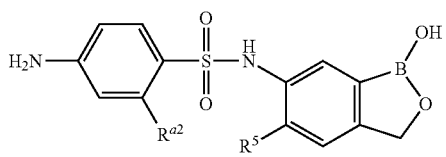

wherein $R^5$ is H or halogen, $R^{a2}$ is alkyl substituted with —C(O)NH$_2$. In an exemplary embodiment, $R^5$ is H, $R^{a2}$ is $CH_2C(O)NH_2$. In an exemplary embodiment, $R^5$ is F, $R^{a2}$ is $CH_2C(O)NH_2$. In an exemplary embodiment, $R^5$ is H, $R^{a2}$ is $CH_2CH_2C(O)NH_2$. In an exemplary embodiment, $R^5$ is F, $R^{a2}$ is $CH_2CH_2C(O)NH_2$. In an exemplary embodiment, $R^5$ is H, $R^{a2}$ is $CH_2CH_2CH_2C(O)NH_2$. In an exemplary embodiment, $R^5$ is F, $R^{a2}$ is $CH_2CH_2CH_2C(O)NH_2$.

In an exemplary embodiment, the compound, or a salt thereof, has a structure which is

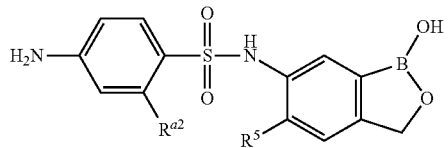

wherein $R^5$ is H or halogen, $R^{a2}$ is alkyl substituted with —C(O)NHNH$_2$. In an exemplary embodiment, $R^5$ is H, $R^{a2}$ is $CH_2C(O)NHNH_2$. In an exemplary embodiment, $R^5$ is F, $R^{a2}$ is $CH_2C(O)NHNH_2$. In an exemplary embodiment, $R^5$ is H, $R^{a2}$ is $CH_2CH_2C(O)NHNH_2$. In an exemplary embodiment, $R^5$ is F, $R^{a2}$ is $CH_2CH_2C(O)NHNH_2$. In an exemplary embodiment, $R^5$ is H, $R^{a2}$ is $CH_2CH_2CH_2C(O)NHNH_2$. In an exemplary embodiment, $R^5$ is F, $R^{a2}$ is $CH_2CH_2CH_2C(O)NHNH_2$.

In an exemplary embodiment, the compound, or a salt thereof, has a structure which is

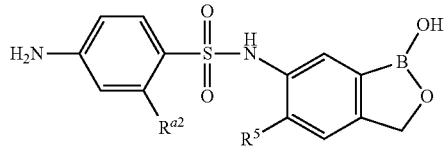

wherein $R^5$ is H or halogen, $R^{a2}$ is alkyl substituted with —C(O)NHOR$^{30}$ wherein $R^{30}$ is unsubstituted alkyl. In an exemplary embodiment, $R^5$ is H, $R^{a2}$ is $CH_2C(O)NHOR^{30}$ wherein $R^{30}$ is methyl or ethyl or unsubstituted $C_3$ alkyl. In an exemplary embodiment, $R^5$ is F, $R^{a2}$ is $CH_2C(O)NHOR^{30}$ wherein $R^{30}$ is methyl or ethyl or unsubstituted $C_3$ alkyl. In an exemplary embodiment, $R^5$ is H, $R^{a2}$ is $CH_2CH_2C(O)NHOR^{30}$ wherein $R^{30}$ is methyl or ethyl or unsubstituted $C_3$ alkyl. In an exemplary embodiment, $R^5$ is F, $R^{a2}$ is $CH_2CH_2C(O)NHOR^{30}$ wherein $R^{30}$ is methyl or ethyl or unsubstituted $C_3$ alkyl. In an exemplary embodiment, $R^5$ is H, $R^{a2}$ is $CH_2CH_2CH_2C(O)NHOR^{30}$ wherein $R^{30}$ is methyl or ethyl or unsubstituted $C_3$ alkyl. In an exemplary embodiment, $R^5$ is F, $R^{a2}$ is $CH_2CH_2CH_2C(O)NHOR^{30}$ wherein $R^{30}$ is methyl or ethyl or unsubstituted $C_3$ alkyl.

In an exemplary embodiment, the compound, or a salt thereof, has a structure which is

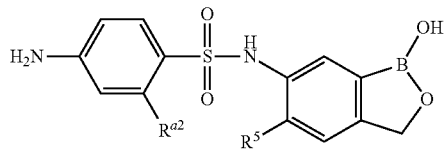

wherein $R^5$ is H or halogen, $R^{a2}$ is alkyl substituted with —C(O)NR$^{33}$R$^{34}$, wherein $R^{33}$ and $R^{34}$, along with the nitrogen to which they are attached, form a 4 or 5 or 6 or 7 or 8 membered ring. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is H, $R^{a2}$ is $CH_2C(O)NR^{33}R^{34}$, wherein $R^{33}$ and $R^{34}$, along with the nitrogen to which they are attached, form a 4 or 5 or 6 or 7 or 8 membered ring. In an exemplary embodiment, $R^5$ is F, $R^{a2}$ is $R^{a2}$ is $CH_2C(O)NR^{33}R^{34}$, wherein $R^{33}$ and $R^{34}$, along with the nitrogen to which they are attached, form a 4 or 5 or 6 or 7 or 8 membered ring. In an exemplary embodiment, $R^5$ is H, $R^{a2}$ is $CH_2CH_2C(O)NR^{33}R^{34}$, wherein $R^{33}$ and $R^{34}$, along with the nitrogen to which they are attached, form a 4 or 5 or 6 or 7 or 8 membered ring. In an exemplary embodiment, $R^5$ is F, $R^{a2}$ is $R^{a2}$ is $CH_2CH_2C(O)NR^{33}R^{34}$, wherein $R^{33}$ and $R^{34}$, along with the nitrogen to which they are attached, form a 4 or 5 or 6 or 7 or 8 membered ring.

In an exemplary embodiment, the compound, or a salt thereof, has a structure which is

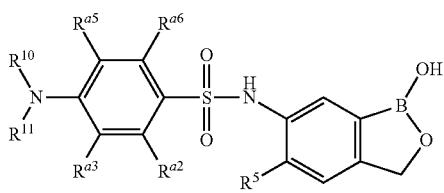

wherein $R^5$ is H or halogen, one of $R^{a2}$, $R^{a3}$, $R^{a5}$ and $R^{a6}$ is alkyl substituted with $-S(O)_2R^{30}$, wherein $R^{30}$ is unsubstituted alkyl or $C_3$-$C_8$ cycloalkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, one of $R^{a2}$, $R^{a3}$, $R^{a5}$ and $R^{a6}$ is methyl substituted with $-S(O)_2R^{30}$ or ethyl substituted with $-S(O)_2R^{30}$ or $C_3$ alkyl substituted with $-S(O)_2R^{30}$ or $C_4$ alkyl substituted with $-S(O)_2R^{30}$ or $C_5$ alkyl substituted with $-S(O)_2R^{30}$ or $C_6$ alkyl substituted with $-S(O)_2R^{30}$, wherein $R^{30}$ is unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl substituted with $-S(O)_2R^{30}$ or ethyl substituted with $-S(O)_2R^{30}$ or $C_3$ alkyl substituted with $-S(O)_2R^{30}$ or $C_4$ alkyl substituted with $-S(O)_2R^{30}$ or $C_5$ alkyl substituted with $-S(O)_2R^{30}$ or $C_6$ alkyl substituted with $-S(O)_2R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is halogen, one of $R^{a2}$, $R^{a3}$, $R^{a5}$ and $R^{a6}$ is methyl substituted with $-S(O)_2R^{30}$ or ethyl substituted with $-S(O)_2R^{30}$ or $C_3$ alkyl substituted with $-S(O)_2R^{30}$, wherein $R^{30}$ is unsubstituted cyclopropyl or unsubstituted cyclobutyl or unsubstituted cyclopentyl or unsubstituted cyclohexyl or unsubstituted cycloheptyl or unsubstituted cyclooctyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl substituted with $-S(O)_2R^{30}$ or ethyl substituted with $-S(O)_2R^{30}$ or $C_3$ alkyl substituted with $-S(O)_2R^{30}$, wherein $R^{30}$ is wherein $R^{30}$ is unsubstituted cyclopropyl or unsubstituted cyclobutyl or unsubstituted cyclopentyl or unsubstituted cyclohexyl or unsubstituted cycloheptyl or unsubstituted cyclooctyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a2}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

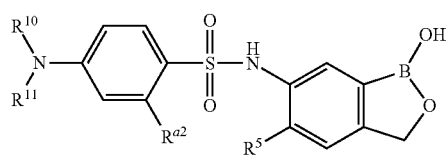

wherein $R^5$ is H or halogen, $R^{a2}$ is alkyl substituted with $-S(O)_2R^{30}$, wherein $R^{30}$ is unsubstituted alkyl or $C_3$-$C_8$ cycloalkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, $R^{a2}$ is methyl substituted with $-S(O)_2R^{30}$ or ethyl substituted with $-S(O)_2R^{30}$ or $C_3$ alkyl substituted with $-S(O)_2R^{30}$ or $C_4$ alkyl substituted with $-S(O)_2R^{30}$ or $C_5$ alkyl substituted with $-S(O)_2R^{30}$ or $C_6$ alkyl substituted with $-S(O)_2R^{30}$, wherein $R^{30}$ is unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl substituted with —S(O)$_2$R$^{30}$ or ethyl substituted with —S(O)$_2$R$^{30}$ or C$_3$ alkyl substituted with —S(O)$_2$R$^{30}$ or C$_4$ alkyl substituted with —S(O)$_2$R$^{30}$ or C$_5$ alkyl substituted with —S(O)$_2$R$^{30}$ or C$_6$ alkyl substituted with —S(O)$_2$R$^{30}$, wherein R$^{30}$ is methyl or ethyl or unsubstituted C$_3$ alkyl or unsubstituted C$_4$ alkyl or unsubstituted C$_5$ alkyl or unsubstituted C$_6$ alkyl, R$^{10}$ and R$^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is halogen, $R^{a2}$ is methyl substituted with —S(O)$_2$R$^{30}$ or ethyl substituted with —S(O)$_2$R$^{30}$ or C$_3$ alkyl substituted with —S(O)$_2$R$^{30}$, wherein R$^{30}$ is unsubstituted cyclopropyl or unsubstituted cyclobutyl or unsubstituted cyclopentyl or unsubstituted cyclohexyl or unsubstituted cycloheptyl or unsubstituted cyclooctyl, R$^{10}$ and R$^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl substituted with —S(O)$_2$R$^{30}$ or ethyl substituted with —S(O)$_2$R$^{30}$ or C$_3$ alkyl substituted with —S(O)$_2$R$^{30}$, wherein R$^{30}$ is unsubstituted cyclopropyl or unsubstituted cyclobutyl or unsubstituted cyclopentyl or unsubstituted cyclohexyl or unsubstituted cycloheptyl or unsubstituted cyclooctyl, R$^{10}$ and R$^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

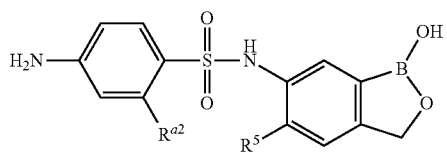

wherein $R^5$ is H or halogen, $R^{a2}$ is alkyl substituted with —S(O)$_2$R$^{30}$, wherein R$^{30}$ is unsubstituted alkyl. In an exemplary embodiment, $R^{a2}$ and $R^5$ are as described herein, and each hydrogen in said compound, or a salt thereof, is independently H or D. In an exemplary embodiment, $R^{a2}$ and $R^5$ are as described herein, and each hydrogen in $R^{a2}$ in said compound, or a salt thereof, is independently H or D. In an exemplary embodiment, $R^{30}$ and $R^5$ are as described herein, and each hydrogen in said alkyl of $R^{a2}$ is independently H or D. In an exemplary embodiment, $R^{a2}$ and $R^5$ are as described herein, and each hydrogen in R$^{30}$ in said compound, or a salt thereof, is independently H or D. In an exemplary embodiment, each hydrogen in said compound, or a salt thereof, is optionally D. In an exemplary embodiment, $R^5$ is H or halogen, $R^{a2}$ is alkyl substituted with —S(O)$_2$R$^{30}$, wherein R$^{30}$ is methyl or ethyl or unsubstituted C$_3$ alkyl or unsubstituted C$_4$ alkyl or unsubstituted C$_5$ alkyl or unsubstituted C$_6$ alkyl. In an exemplary embodiment, $R^5$ is H, $R^{a2}$ is CH$_2$S(O)$_2$R$^{30}$, wherein R$^{30}$ is methyl or ethyl or unsubstituted C$_3$ alkyl or unsubstituted C$_4$ alkyl or unsubstituted C$_5$ alkyl or unsubstituted C$_6$ alkyl. In an exemplary embodiment, $R^5$ is H, $R^{a2}$ is CH$_2$S(O)$_2$R$^{30}$, wherein R$^{30}$ is methyl or ethyl or unsubstituted C$_3$ alkyl. In an exemplary embodiment, $R^5$ is F, $R^{a2}$ is CH$_2$S(O)$_2$R$^{30}$, wherein R$^{30}$ is methyl or ethyl or unsubstituted C$_3$ alkyl or unsubstituted C$_4$ alkyl or unsubstituted C$_5$ alkyl or unsubstituted C$_6$ alkyl. In an exemplary embodiment, $R^5$ is F, $R^{a2}$ is CH$_2$S(O)$_2$R$^{30}$, wherein R$^{30}$ is methyl or ethyl or unsubstituted C$_3$ alkyl. In an exemplary embodiment, $R^5$ is H, $R^{a2}$ is CH$_2$CH$_2$S(O)$_2$R$^{30}$, wherein R$^{30}$ is methyl or ethyl or unsubstituted C$_3$ alkyl or unsubstituted C$_4$ alkyl or unsubstituted C$_5$ alkyl or unsubstituted C$_6$ alkyl. In an exemplary embodiment, $R^5$ is H, $R^{a2}$ is CH$_2$CH$_2$S(O)$_2$R$^{30}$, wherein R$^{30}$ is methyl or ethyl or unsubstituted C$_3$ alkyl. In an exemplary embodiment, $R^5$ is F, $R^{a2}$ is CH$_2$CH$_2$S(O)$_2$R$^{30}$, wherein R$^{30}$ is methyl or ethyl or unsubstituted C$_3$ alkyl or unsubstituted C$_4$ alkyl or unsubstituted C$_5$ alkyl or unsubstituted C$_6$ alkyl. In an exemplary embodiment, $R^5$ is F, $R^{a2}$ is CH$_2$CH$_2$S(O)$_2$R$^{30}$, wherein R$^{30}$ is methyl or ethyl or unsubstituted C$_3$ alkyl. In an exemplary embodiment, $R^5$ is H, $R^{a2}$ is CH$_2$CH$_2$CH$_2$S(O)$_2$R$^{30}$, wherein R$^{30}$ is methyl or ethyl or unsubstituted C$_3$ alkyl or unsubstituted C$_4$ alkyl or unsubstituted C$_5$ alkyl or unsubstituted C$_6$ alkyl. In an exemplary embodiment, $R^5$ is H, $R^{a2}$ is CH$_2$CH$_2$CH$_2$S(O)$_2$R$^{30}$, wherein R$^{30}$ is methyl or ethyl or unsubstituted C$_3$ alkyl. In an exemplary embodiment, $R^5$ is F, $R^{a2}$ is CH$_2$CH$_2$CH$_2$S(O)$_2$R$^{30}$, wherein R$^{30}$ is methyl or ethyl or unsubstituted C$_3$ alkyl or unsubstituted C$_4$ alkyl or unsubstituted C$_5$ alkyl or unsubstituted C$_6$ alkyl. In an exemplary embodiment, $R^5$ is F, $R^{a2}$ is CH$_2$CH$_2$CH$_2$S(O)$_2$R$^{30}$, wherein R$^{30}$ is methyl or ethyl or unsubstituted C$_3$ alkyl.

In an exemplary embodiment, the compound, or a salt thereof, has a structure which is

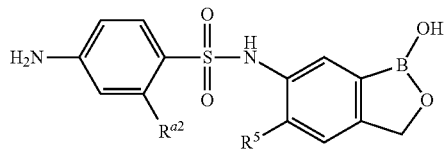

wherein $R^5$ is H or halogen, $R^{a2}$ is alkyl substituted with —S(O)$_2$R$^{30}$, wherein R$^{30}$ is unsubstituted C$_3$-C$_8$ cycloalkyl. In an exemplary embodiment, $R^{a2}$ and $R^5$ are as described herein, and each hydrogen in $R^{a2}$ in said compound, or a salt thereof, is independently H or D. In an exemplary embodiment, $R^{30}$ and $R^5$ are as described herein, and each hydrogen in said alkyl of $R^{a2}$ is independently H or D. In an exemplary embodiment, $R^{a2}$ and $R^5$ are as described herein, and each hydrogen in R$^{30}$ of said compound or a salt thereof, is independently H or D. In an exemplary embodiment, each hydrogen in said compound, or a salt thereof, is optionally D. In an exemplary embodiment, $R^5$ is H or halogen, $R^{a2}$ is alkyl substituted with —S(O)$_2$R$^{30}$, wherein R$^{30}$ is unsubstituted cyclopropyl or unsubstituted cyclobutyl or unsubstituted cyclopentyl or unsubstituted cyclohexyl or cycloheptyl or unsubstituted cyclooctyl. In an exemplary embodiment, $R^5$ is H, $R^{a2}$ is CH$_2$S(O)$_2$R$^{30}$, wherein R$^{30}$ is unsubstituted cyclopropyl or unsubstituted cyclobutyl or unsubstituted cyclopentyl or unsubstituted cyclohexyl or cycloheptyl or unsubstituted cyclooctyl. In an exemplary embodiment, $R^5$ is H, $R^{a2}$ is $CH_2S(O)_2R^{30}$, wherein $R^{30}$ is unsubstituted cyclopentyl or unsubstituted cyclohexyl. In an exemplary embodiment, $R^5$ is F, $R^{a2}$ is $CH_2S(O)_2R^{30}$, wherein $R^{30}$ is unsubstituted cyclopropyl or unsubstituted cyclobutyl or unsubstituted cyclopentyl or unsubstituted cyclohexyl or cycloheptyl or unsubstituted cyclooctyl. In an exemplary embodiment, $R^5$ is F, $R^{a2}$ is $CH_2S(O)_2R^{30}$, wherein $R^{30}$ is unsubstituted cyclopentyl or unsubstituted cyclohexyl. In an exemplary embodiment, $R^5$ is H, $R^{a2}$ is $CH_2CH_2S(O)_2R^{30}$, wherein $R^{30}$ is unsubstituted cyclopropyl or unsubstituted cyclobutyl or unsubstituted cyclopentyl or unsubstituted cyclohexyl or cycloheptyl or unsubstituted cyclooctyl. In an exemplary embodiment, $R^5$ is H, $R^{a2}$ is $CH_2CH_2S(O)_2R^{30}$, wherein $R^{30}$ is unsubstituted cyclopentyl or unsubstituted cyclohexyl. In an exemplary embodiment, $R^5$ is F, $R^{a2}$ is $CH_2CH_2S(O)_2R^{30}$, wherein $R^{30}$ is unsubstituted cyclopropyl or unsubstituted cyclobutyl or unsubstituted cyclopentyl or unsubstituted cyclohexyl or cycloheptyl or unsubstituted cyclooctyl. In an exemplary embodiment, $R^5$ is F, $R^{a2}$ is $CH_2CH_2S(O)_2R^{30}$, wherein $R^{30}$ is unsubstituted cyclopentyl or unsubstituted cyclohexyl.

In an exemplary embodiment, the compound, or a salt thereof, has a structure which is

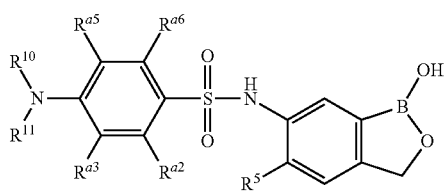

wherein $R^5$ is H or halogen, one of $R^{a2}$, $R^{a3}$, $R^{a5}$ and $R^{a6}$ is alkyl substituted with —S(O)$R^{30}$, wherein $R^{30}$ is unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, one of $R^{a2}$, $R^{a3}$, $R^{a5}$ and $R^{a6}$ is methyl substituted with —S(O)$R^{30}$ or ethyl substituted with —S(O)$R^{30}$ or $C_3$ alkyl substituted with —S(O)$R^{30}$ or $C_4$ alkyl substituted with —S(O)$R^{30}$ or $C_5$ alkyl substituted with —S(O)$R^{30}$ or $C_6$ alkyl substituted with —S(O)$R^{30}$, wherein $R^{30}$ is unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl substituted with —S(O)$R^{30}$ or ethyl substituted with —S(O)$R^{30}$ or $C_3$ alkyl substituted with —S(O)$R^{30}$ or $C_4$ alkyl substituted with —S(O)$R^{30}$ or $C_5$ alkyl substituted with —S(O)$R^{30}$ or $C_6$ alkyl substituted with —S(O)$R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound, or a salt thereof, has a structure which is

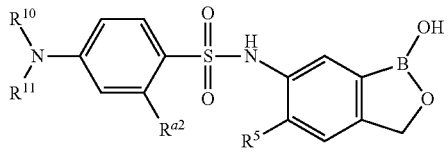

wherein $R^5$ is H or halogen, $R^{a2}$ is alkyl substituted with —S(O)$R^{30}$, wherein $R^{30}$ is unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, $R^{a2}$ is methyl substituted with —S(O)$R^{30}$ or ethyl substituted with —S(O)$R^{30}$ or $C_3$ alkyl substituted with —S(O)$R^{30}$ or $C_4$ alkyl substituted with —S(O)$R^{30}$ or $C_5$ alkyl substituted with —S(O)$R^{30}$ or $C_6$ alkyl substituted with —S(O)$R^{30}$, wherein $R^{30}$ is unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl substituted with —S(O)$R^{30}$ or ethyl substituted with —S(O)$R^{30}$ or $C_3$ alkyl substituted with —S(O)$R^{30}$ or $C_4$ alkyl substituted with —S(O)$R^{30}$ or $C_5$ alkyl substituted with —S(O)$R^{30}$ or $C_6$ alkyl substituted with —S(O)$R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

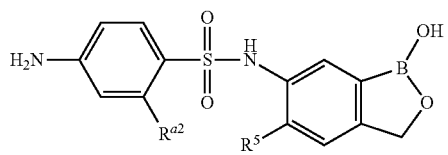

wherein $R^5$ is H or halogen, $R^{a2}$ is alkyl substituted with —S(O)$R^{30}$, wherein $R^{30}$ is unsubstituted alkyl. In an exemplary embodiment, $R^{a2}$ and $R^5$ are as described herein, and each hydrogen in said compound, or a salt thereof, is independently H or D. In an exemplary embodiment, $R^{a2}$ and $R^5$ are as described herein, and each hydrogen in $R^{30}$ of said compound or a salt thereof, is independently H or D. In an exemplary embodiment, each hydrogen in said compound, or a salt thereof, is optionally D. In an exemplary embodiment, $R^5$ is H or halogen, $R^{a2}$ is alkyl substituted with —S(O)$R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$S(O)$R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$S(O)$R^{30}$, wherein $R^{30}$ is methyl or ethyl or unsubstituted $C_3$ alkyl. In an exemplary embodiment, $R^5$ is F, $R^{a2}$ is CH$_2$S(O)$R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is CH$_2$S(O)$R^{30}$, wherein $R^{30}$ is methyl or ethyl or unsubstituted $C_3$ alkyl. In an exemplary embodiment, $R^5$ is H, $R^{a2}$ is CH$_2$CH$_2$S(O)$R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$CH$_2$S(O)$R^{30}$, wherein $R^{30}$ is methyl or ethyl or unsubstituted $C_3$ alkyl. In an exemplary embodiment, $R^5$ is F, $R^{a2}$ is CH$_2$CH$_2$S(O)$R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is CH$_2$CH$_2$S(O)$R^{30}$, wherein $R^{30}$ is methyl or ethyl or unsubstituted $C_3$ alkyl. In an exemplary embodiment, $R^5$ is H, $R^{a2}$ is CH$_2$CH$_2$CH$_2$S(O)$R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$CH$_2$CH$_2$S(O)$R^{30}$, wherein $R^{30}$ is methyl or ethyl or unsubstituted $C_3$ alkyl. In an exemplary embodiment, $R^5$ is F, $R^{a2}$ is CH$_2$CH$_2$CH$_2$S(O)$R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is CH$_2$CH$_2$CH$_2$S(O)$R^{30}$, wherein $R^{30}$ is methyl or ethyl or unsubstituted $C_3$ alkyl.

In an exemplary embodiment, the compound, or a salt thereof, has a structure which is

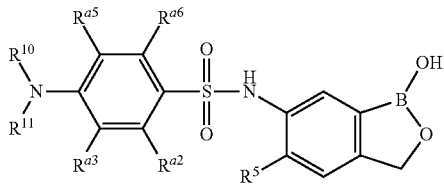

wherein $R^5$ is H or halogen, one of $R^{a2}$, $R^{a3}$, $R^{a5}$ and $R^{a6}$ is alkyl substituted with —NHS(O)$_2$$R^{30}$, wherein $R^{30}$ is unsubstituted alkyl or unsubstituted $C_3$-$C_8$ cycloalkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, one of $R^{a2}$, $R^{a3}$, $R^{a5}$ and $R^{a6}$ is methyl substituted with —NHS(O)$_2$$R^{30}$ or ethyl substituted with —NHS(O)$_2$$R^{30}$ or $C_3$ alkyl substituted with —NHS(O)$_2$$R^{30}$ or $C_4$ alkyl substituted with —NHS(O)$_2$$R^{30}$ or $C_5$ alkyl substituted with —NHS(O)$_2$$R^{30}$ or $C_6$ alkyl substituted with —NHS(O)$_2$$R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl or unsubstituted cyclopropyl or unsubstituted cyclobutyl or unsubstituted cyclopentyl or unsubstituted cyclohexyl or unsubstituted cycloheptyl or unsubstituted cyclooctyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl substituted with —NHS(O)$_2$$R^{30}$ or ethyl substituted with —NHS(O)$_2$$R^{30}$ or $C_3$ alkyl substituted with —NHS(O)$_2$$R^{30}$ or $C_4$ alkyl substituted with —NHS(O)$_2$$R^{30}$ or $C_5$ alkyl substituted with —NHS(O)$_2$$R^{30}$ or $C_6$ alkyl substituted with —NHS(O)$_2$$R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl or unsubstituted cyclopropyl or unsubstituted cyclobutyl or unsubstituted cyclopentyl or unsubstituted cyclohexyl or unsubstituted cycloheptyl or unsubstituted cyclooctyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound, or a salt thereof, has a structure which is

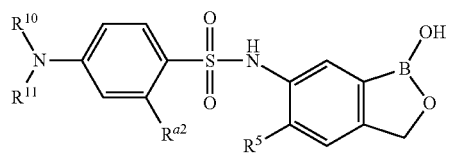

wherein $R^5$ is H or halogen, $R^{a2}$ is alkyl substituted with —NHS(O)$_2$$R^{30}$, wherein $R^{30}$ is unsubstituted alkyl or unsubstituted $C_3$-$C_8$ cycloalkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, $R^{a2}$ is methyl substituted with —NHS(O)$_2$$R^{30}$ or ethyl substituted with —NHS(O)$_2$$R^{30}$ or $C_3$ alkyl substituted with —NHS(O)$_2$$R^{30}$ or $C_4$ alkyl substituted with —NHS(O)$_2$$R^{30}$ or $C_5$ alkyl substituted with —NHS(O)$_2$$R^{30}$ or $C_6$ alkyl substituted with —NHS(O)$_2$$R^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl or unsubstituted cyclopropyl or unsubstituted cyclobutyl or unsubstituted cyclopentyl or unsubstituted cyclohexyl or unsubstituted cycloheptyl or unsubstituted cyclooctyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl substituted with —NHS(O)$_2$R$^{30}$ or ethyl substituted with —NHS(O)$_2$R$^{30}$ or $C_3$ alkyl substituted with —NHS(O)$_2$R$^{30}$ or $C_4$ alkyl substituted with —NHS(O)$_2$R$^{30}$ or $C_5$ alkyl substituted with —NHS(O)$_2$R$^{30}$ or $C_6$ alkyl substituted with —NHS(O)$_2$R$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl or unsubstituted cyclopropyl or unsubstituted cyclobutyl or unsubstituted cyclopentyl or unsubstituted cyclohexyl or unsubstituted cycloheptyl or unsubstituted cyclooctyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

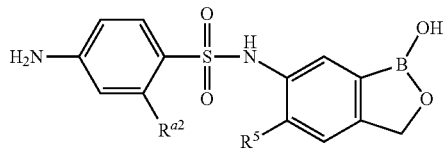

wherein $R^5$ is H or halogen, $R^{a2}$ is alkyl substituted with —NHS(O)$_2$R$^{30}$, wherein $R^{30}$ is unsubstituted alkyl or unsubstituted $C_3$-$C_8$ cycloalkyl. In an exemplary embodiment, $R^{a2}$ and $R^5$ are as described herein, and each hydrogen in said compound, or a salt thereof, is independently H or D. In an exemplary embodiment, $R^{a2}$ and $R^5$ are as described herein, and each hydrogen in said compound, or a salt thereof, is independently H or D. In an exemplary embodiment, each hydrogen in said compound, or a salt thereof, is optionally D. In an exemplary embodiment, $R^5$ is H or halogen, $R^{a2}$ is alkyl substituted with —NHS(O)$_2$R$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl or unsubstituted cyclopropyl or unsubstituted cyclobutyl or unsubstituted cyclopentyl or unsubstituted cyclohexyl or unsubstituted cycloheptyl or unsubstituted cyclooctyl. In an exemplary embodiment, $R^5$ is H, $R^{a2}$ is CH$_2$NHS(O)$_2$R$^{30}$, wherein $R^{30}$ is unsubstituted cyclopropyl or unsubstituted cyclobutyl or unsubstituted cyclopentyl or unsubstituted cyclohexyl or unsubstituted cycloheptyl or unsubstituted cyclooctyl. In an exemplary embodiment, $R^5$ is F, $R^{a2}$ is CH$_2$NHS(O)$_2$R$^{30}$, wherein $R^{30}$ is unsubstituted cyclopropyl or unsubstituted cyclobutyl or unsubstituted cyclopentyl or unsubstituted cyclohexyl or unsubstituted cycloheptyl or unsubstituted cyclooctyl. In an exemplary embodiment, $R^5$ is H, $R^{a2}$ is CH$_2$CH$_2$NHS(O)$_2$R$^{30}$, wherein $R^{30}$ is unsubstituted cyclopropyl or unsubstituted cyclobutyl or unsubstituted cyclopentyl or unsubstituted cyclohexyl or unsubstituted cycloheptyl or unsubstituted cyclooctyl. In an exemplary embodiment, $R^5$ is F, $R^{a2}$ is CH$_2$CH$_2$NHS(O)$_2$R$^{30}$, wherein $R^{30}$ is unsubstituted cyclopropyl or unsubstituted cyclobutyl or unsubstituted cyclopentyl or unsubstituted cyclohexyl or unsubstituted cycloheptyl or unsubstituted cyclooctyl. In an exemplary embodiment, $R^5$ is H, $R^{a2}$ is CH$_2$CH$_2$CH$_2$NHS(O)$_2$R$^{30}$, wherein $R^{30}$ is unsubstituted cyclopropyl or unsubstituted cyclobutyl or unsubstituted cyclopentyl or unsubstituted cyclohexyl or unsubstituted cycloheptyl or unsubstituted cyclooctyl. In an exemplary embodiment, $R^5$ is F, $R^{a2}$ is CH$_2$CH$_2$CH$_2$NHS(O)$_2$R$^{30}$, wherein $R^{30}$ is unsubstituted cyclopropyl or unsubstituted cyclobutyl or unsubstituted cyclopentyl or unsubstituted cyclohexyl or unsubstituted cycloheptyl or unsubstituted cyclooctyl.

In an exemplary embodiment, the compound, or a salt thereof, has a structure which is

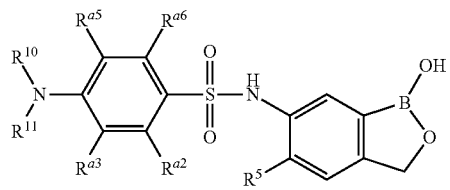

wherein $R^5$ is H or halogen, one of $R^{a2}$, $R^{a3}$, $R^{a5}$ and $R^{a6}$ is alkyl substituted with —NHC(O)OR$^{30}$, wherein $R^{30}$ is unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, one of $R^{a2}$, $R^{a3}$, $R^{a5}$ and $R^{a6}$ is methyl substituted with —NHC(O)OR$^{30}$ or ethyl substituted with —NHC(O)OR$^{30}$ or $C_3$ alkyl substituted with —NHC(O)OR$^{30}$ or $C_4$ alkyl substituted with —NHC(O)OR$^{30}$ or $C_5$ alkyl substituted with —NHC(O)OR$^{30}$ or $C_6$ alkyl substituted with —NHC(O)OR$^{30}$, wherein $R^{30}$ is unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl substituted with —NHC(O)OR$^{30}$ or ethyl substituted with —NHC(O)OR$^{30}$ or $C_3$ alkyl substituted with —NHC(O)OR$^{30}$ or $C_4$ alkyl substituted with —NHC(O)OR$^{30}$ or $C_5$ alkyl substituted with —NHC(O)OR$^{30}$ or $C_6$ alkyl substituted with —NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

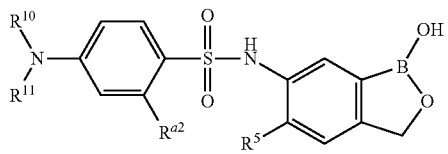

wherein $R^5$ is H or halogen, $R^{a2}$ is alkyl substituted with —NHC(O)OR$^{30}$, wherein $R^{30}$ is unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, $R^{a2}$ is methyl substituted with —NHC(O)OR$^{30}$ or ethyl substituted with —NHC(O)OR$^{30}$ or $C_3$ alkyl substituted with —NHC(O)OR$^{30}$ or $C_4$ alkyl substituted with —NHC(O)OR$^{30}$ or $C_5$ alkyl substituted with —NHC(O)OR$^{30}$ or $C_6$ alkyl substituted with —NHC(O)OR$^{30}$, wherein $R^{30}$ is unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl substituted with —NHC(O)OR$^{30}$ or ethyl substituted with —NHC(O)OR$^{30}$ or $C_3$ alkyl substituted with —NHC(O)OR$^{30}$ or $C_4$ alkyl substituted with —NHC(O)OR$^{30}$ or $C_5$ alkyl substituted with —NHC(O)OR$^{30}$ or $C_6$ alkyl substituted with —NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

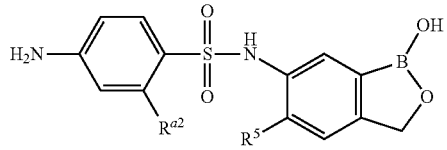

wherein $R^5$ is H or halogen, $R^{a2}$ is alkyl substituted with —NHC(O)OR$^{30}$, wherein $R^{30}$ is unsubstituted alkyl. In an exemplary embodiment, $R^{a2}$ and $R^5$ are as described herein, and each hydrogen in said compound, or a salt thereof, is independently H or D. In an exemplary embodiment, $R^{a2}$ and $R^5$ are as described herein, and each hydrogen in $R^{30}$ of said compound or a salt thereof, is independently H or D. In an exemplary embodiment, each hydrogen in said compound, or a salt thereof, is optionally D. In an exemplary embodiment, $R^5$ is H or halogen, $R^{a2}$ is alkyl substituted with —NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$NHC(O)OR$^{30}$, wherein $R^{30}$ is methyl or ethyl or unsubstituted $C_3$ alkyl. In an exemplary embodiment, $R^5$ is F, $R^{a2}$ is CH$_2$NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is CH$_2$NHC(O)OR$^{30}$, wherein $R^{30}$ is methyl or ethyl or unsubstituted $C_3$ alkyl. In an exemplary embodiment, $R^5$ is H, $R^{a2}$ is CH$_2$CH$_2$NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$CH$_2$NHC(O)OR$^{30}$, wherein $R^{30}$ is methyl or ethyl or unsubstituted $C_3$ alkyl. In an exemplary embodiment, $R^5$ is F, $R^{a2}$ is CH$_2$CH$_2$NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is CH$_2$CH$_2$NHC(O)OR$^{30}$, wherein $R^{30}$ is methyl or ethyl or unsubstituted $C_3$ alkyl. In an exemplary embodiment, $R^5$ is H, $R^{a2}$ is CH$_2$CH$_2$CH$_2$NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is CH$_2$CH$_2$CH$_2$NHC(O)OR$^{30}$, wherein $R^{30}$ is methyl or ethyl or unsubstituted $C_3$ alkyl. In an exemplary embodiment, $R^5$ is F, $R^{a2}$ is CH$_2$CH$_2$CH$_2$NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is CH$_2$CH$_2$CH$_2$NHC(O)OR$^{30}$, wherein $R^{30}$ is methyl or ethyl or unsubstituted $C_3$ alkyl. In an exemplary embodiment, $R^5$ is H, $R^{a2}$ is CH$_2$NHC(O)OCH(CH$_3$)$_2$. In an exemplary embodiment, $R^5$ is F, $R^{a2}$ is CH$_2$NHC(O)OCH(CH$_3$)$_2$. In an exemplary embodiment, $R^5$ is H, $R^{a2}$ is CH$_2$NHC(O)OCH$_2$CH(CH$_3$)$_2$. In an exemplary embodiment, $R^5$ is F, $R^{a2}$ is CH$_2$NHC(O)OCH$_2$CH(CH$_3$)$_2$. In an exemplary embodiment, $R^5$ is H, $R^{a2}$ is CH$_2$NHC(O)OCH(CH$_2$CH$_3$)$_2$. In an exemplary embodiment, $R^5$ is F, $R^{a2}$ is CH$_2$NHC(O)OCH(CH$_2$CH$_3$)$_2$.

In an exemplary embodiment, the compound, or a salt thereof, has a structure which is

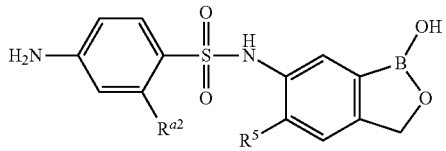

wherein $R^5$ is H or halogen, $R^{a2}$ is alkyl substituted with —NHC(O)OR$^{30}$, wherein $R^{30}$ is benzyl. In an exemplary embodiment, $R^5$ is H, $R^{a2}$ is CH$_2$NHC(O)OR$^{30}$, wherein $R^{30}$ is benzyl. In an exemplary embodiment, $R^5$ is F, $R^{a2}$ is CH$_2$NHC(O)OR$^{30}$, wherein $R^{30}$ is benzyl. In an exemplary embodiment, $R^5$ is H, $R^{a2}$ is CH$_2$CH$_2$NHC(O)OR$^{30}$, wherein $R^{30}$ is benzyl. In an exemplary embodiment, $R^5$ is F, $R^{a2}$ is CH$_2$CH$_2$NHC(O)OR$^{30}$, wherein $R^{30}$ is benzyl. In an exemplary embodiment, $R^5$ is H, $R^{a2}$ is CH$_2$CH$_2$CH$_2$NHC(O)OR$^{30}$, wherein $R^{30}$ is benzyl. In an exemplary embodiment, $R^5$ is F, $R^{a2}$ is CH$_2$CH$_2$CH$_2$NHC(O)OR$^{30}$, wherein $R^{30}$ is benzyl.

In an exemplary embodiment, the compound, or a salt thereof, has a structure which is

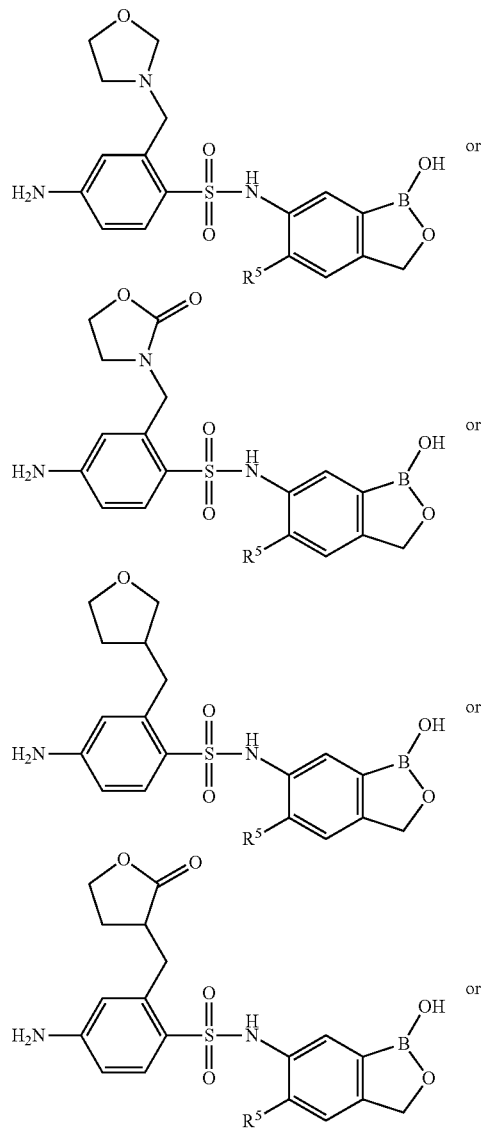

or

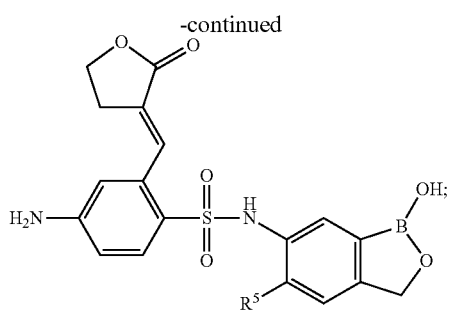

wherein $R^5$ is H or halogen. In an exemplary embodiment, each hydrogen in said compound or a salt thereof, is independently H or D. In an exemplary embodiment, each hydrogen in said compound, or a salt thereof, is optionally D. In an exemplary embodiment, $R^5$ is F. In an exemplary embodiment, $R^5$ is H.

In an exemplary embodiment, the compound, or a salt thereof, has a structure which is

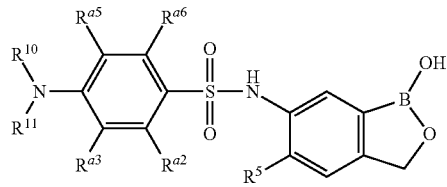

wherein $R^5$ is H or halogen, one of $R^{a2}$, $R^{a3}$, $R^{a5}$ and $R^{a6}$ is alkyl substituted with $R^{32}$, wherein $R^{32}$ is unsubstituted oxazolyl or oxazolyl substituted with unsubstituted alkyl or unsubstituted oxadiazolyl or oxadiazolyl substituted with unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound or a salt thereof, is independently H or D. In an exemplary embodiment, each hydrogen in said compound, or a salt thereof, is optionally D. In an exemplary embodiment, $R^5$ is halogen, one of $R^{a2}$, $R^{a3}$, $R^{a5}$ and $R^{a6}$ is methyl substituted with $R^{32}$ or ethyl substituted with $R^{32}$ or C$_3$ alkyl substituted with $R^{32}$ or C$_4$ alkyl substituted with $R^{32}$ or C$_5$ alkyl substituted with $R^{32}$ or C$_6$ alkyl substituted with $R^{32}$, wherein $R^{32}$ is unsubstituted oxazolyl or oxazolyl substituted with unsubstituted alkyl or unsubstituted oxadiazolyl or oxadiazolyl or substituted with unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is methyl substituted with $R^{32}$ or ethyl substituted with $R^{32}$ or C$_3$ alkyl substituted with $R^{32}$ or C$_4$ alkyl substituted with $R^{32}$ or C$_5$ alkyl substituted with $R^{32}$ or C$_6$ alkyl substituted with $R^{32}$, wherein $R^{32}$ is unsubstituted oxazolyl or oxazolyl substituted with unsubstituted alkyl or unsubstituted oxadiazolyl or oxadiazolyl or substituted with unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound, or a salt thereof, has a structure which is

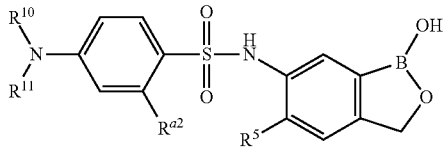

wherein $R^5$ is H or halogen, $R^{a2}$ is alkyl substituted with $R^{32}$, wherein $R^{32}$ is unsubstituted oxazolyl or oxazolyl substituted with unsubstituted alkyl or unsubstituted oxadiazolyl or oxadiazolyl or substituted with unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, $R^{a2}$ is methyl substituted with $R^{32}$ or ethyl substituted with $R^{32}$ or $C_3$ alkyl substituted with $R^{32}$ or $C_4$ alkyl substituted with $R^{32}$ or $C_5$ alkyl substituted with $R^{32}$ or $C_6$ alkyl substituted with $R^{32}$, wherein $R^{32}$ is unsubstituted oxazolyl or oxazolyl substituted with unsubstituted alkyl or unsubstituted oxadiazolyl or oxadiazolyl or substituted with unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is methyl substituted with $R^{32}$ or ethyl substituted with $R^{32}$ or $C_3$ alkyl substituted with $R^{32}$ or $C_4$ alkyl substituted with $R^{32}$ or $C_5$ alkyl substituted with $R^{32}$ or $C_6$ alkyl substituted with $R^{32}$, wherein $R^{32}$ is unsubstituted oxazolyl or oxazolyl substituted with unsubstituted alkyl or unsubstituted oxadiazolyl or oxadiazolyl or substituted with unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

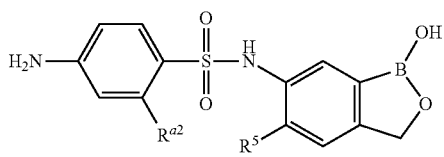

wherein $R^5$ is H or halogen, $R^{a2}$ is alkyl substituted with $R^{32}$, wherein $R^{32}$ is unsubstituted oxazolyl or oxazolyl substituted with unsubstituted alkyl or unsubstituted oxadiazolyl or oxadiazolyl or substituted with unsubstituted alkyl. In an exemplary embodiment, $R^{a2}$ and $R^5$ are as described herein, and each hydrogen in said compound, or a salt thereof, is independently H or D. In an exemplary embodiment, each hydrogen in said compound, or a salt thereof, is optionally D. In an exemplary embodiment, $R^5$ is H or F, $R^{a2}$ is methyl substituted with unsubstituted oxazolyl. In an exemplary embodiment, $R^5$ is H or F, $R^{a2}$ is methyl substituted with unsubstituted oxazol-2-yl. In an exemplary embodiment, $R^5$ is H or F, $R^{a2}$ is methyl substituted with 4-methyl oxazol-2-yl. In an exemplary embodiment, $R^5$ is H or F, $R^{a2}$ is methyl substituted with 5-methyl oxazol-2-yl. In an exemplary embodiment, $R^5$ is H or F, $R^{a2}$ is methyl substituted with 4-ethyl oxazol-2-yl. In an exemplary embodiment, $R^5$ is H or F, $R^{a2}$ is methyl substituted with 5-ethyl oxazol-2-yl. In an exemplary embodiment, $R^5$ is H or F, $R^{a2}$ is methyl substituted with 4-unsubstituted $C_3$ alkyl oxazol-2-yl. In an exemplary embodiment, $R^5$ is H or F, $R^{a2}$ is methyl substituted with 5-unsubstituted $C_3$ alkyl oxazol-2-yl. In an exemplary embodiment, $R^5$ is H or F, $R^{a2}$ is methyl substituted with 4-unsubstituted $C_4$ alkyl oxazol-2-yl. In an exemplary embodiment, $R^5$ is H or F, $R^{a2}$ is methyl substituted with 5-unsubstituted $C_4$ alkyl oxazol-2-yl. In an exemplary embodiment, $R^5$ is H or F, $R^{a2}$ is methyl substituted with 4-unsubstituted $C_5$ alkyl oxazol-2-yl. In an exemplary embodiment, $R^5$ is H or F, $R^{a2}$ is methyl substituted with 5-unsubstituted $C_5$ alkyl oxazol-2-yl. In an exemplary embodiment, $R^5$ is H or F, $R^{a2}$ is methyl substituted with 4-unsubstituted $C_6$ alkyl oxazol-2-yl. In an exemplary embodiment, $R^5$ is H or F, $R^{a2}$ is methyl substituted with 5-unsubstituted $C_6$ alkyl oxazol-2-yl. In an exemplary embodiment, $R^5$ is H or F, $R^{a2}$ is ethyl substituted with unsubstituted oxazol-2-yl. In an exemplary embodiment, $R^5$ is H or F, $R^{a2}$ is ethyl substituted with 4-methyl oxazol-2-yl. In an exemplary embodiment, $R^5$ is H or F, $R^{a2}$ is ethyl substituted with 5-methyl oxazol-2-yl. In an exemplary embodiment, $R^5$ is H or F, $R^{a2}$ is ethyl substituted with 4-ethyl oxazol-2-yl. In an exemplary embodiment, $R^5$ is H or F, $R^{a2}$ is ethyl substituted with 5-ethyl oxazol-2-yl. In an exemplary embodiment, $R^5$ is H or F, $R^{a2}$ is ethyl substituted with 4-unsubstituted $C_3$ alkyl oxazol-2-yl. In an exemplary embodiment, $R^5$ is H or F, $R^{a2}$ is ethyl substituted with 5-unsubstituted $C_3$ alkyl oxazol-2-yl. In an exemplary embodiment, $R^5$ is H or F, $R^{a2}$ is ethyl substituted with 4-unsubstituted $C_4$ alkyl oxazol-2-yl. In an exemplary embodiment, $R^5$ is H or F, $R^{a2}$ is ethyl substituted with 5-unsubstituted $C_4$ alkyl oxazol-2-yl. In an exemplary embodiment, $R^5$ is H or F, $R^{a2}$ is ethyl substituted with 4-unsubstituted $C_5$ alkyl oxazol-2-yl. In an exemplary embodiment, $R^5$ is H or F, $R^{a2}$ is ethyl substituted with 5-unsubstituted $C_5$ alkyl oxazol-2-yl. In an exemplary embodiment, $R^5$ is H or F, $R^{a2}$ is ethyl substituted with 4-unsubstituted $C_6$ alkyl oxazol-2-yl. In an exemplary embodiment, $R^5$ is H or F, $R^{a2}$ is ethyl substituted with 5-unsubstituted $C_6$ alkyl oxazol-2-yl. In an exemplary embodiment, $R^5$ is H or F, $R^{a2}$ is $C_3$ alkyl substituted with unsubstituted oxazol-2-yl. In an exemplary embodiment, $R^5$ is H or F, $R^{a2}$ is $C_3$ alkyl substituted with 4-methyl oxazol-2-yl. In an exemplary embodiment, $R^5$ is H or F, $R^{a2}$ is $C_3$ alkyl substituted with 5-methyl oxazol-2-yl. In an exemplary embodiment, $R^5$ is H or F, $R^{a2}$ is $C_3$ alkyl substituted with 4-ethyl oxazol-2-yl. In an exemplary embodiment, $R^5$ is H or F, $R^{a2}$ is $C_3$ alkyl substituted with 5-ethyl oxazol-2-yl. In an exemplary embodiment, $R^5$ is H or F, $R^{a2}$ is $C_3$ alkyl substituted with 4-unsubstituted $C_3$ alkyl oxazol-2-yl. In an exemplary embodiment, $R^5$ is H or F, $R^{a2}$ is $C_3$ alkyl substituted with 5-unsubstituted $C_3$ alkyl oxazol-2-yl. In an exemplary embodiment, $R^5$ is H or F, $R^{a2}$ is $C_3$ alkyl substituted with 4-unsubstituted $C_4$ alkyl oxazol-2-yl. In an exemplary embodiment, $R^5$ is H or F, $R^{a2}$ is $C_3$ alkyl substituted with 5-unsubstituted $C_4$ alkyl oxazol-2-yl. In an exemplary embodiment, $R^5$ is H or F, $R^{a2}$ is $C_3$ alkyl substituted with 4-unsubstituted $C_5$ alkyl oxazol-2-yl. In an exemplary embodiment, $R^5$ is H or F, $R^{a2}$ is $C_3$ alkyl substituted with 5-unsubstituted $C_5$ alkyl oxazol-2-yl. In an exemplary embodiment, $R^5$ is H or F, $R^{a2}$ is $C_3$ alkyl substituted with 4-unsubstituted $C_6$ alkyl oxazol-2-yl. In an exemplary embodiment, $R^5$ is H or F, $R^{a2}$ is $C_3$ alkyl substituted with 5-unsubstituted $C_6$ alkyl oxazol-2-yl.

In an exemplary embodiment, the compound, or a salt thereof, has a structure which is

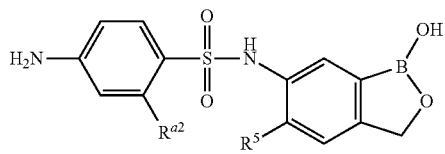

wherein $R^5$ is H or halogen, $R^{a2}$ is alkyl substituted with $R^{32}$, wherein $R^{32}$ is unsubstituted oxadiazolyl or oxadiazolyl or substituted with unsubstituted alkyl. In an exemplary embodiment, $R^5$ is H or F, $R^{a2}$ is methyl substituted with unsubstituted oxadiazolyl. In an exemplary embodiment, $R^5$ is H or F, $R^{a2}$ is methyl substituted with unsubstituted oxadiazol-2-yl. In an exemplary embodiment, $R^5$ is H or F, $R^{a2}$ is methyl substituted with unsubstituted 1,2,4 oxadiazol-2-yl. In an exemplary embodiment, $R^5$ is H or F, $R^{a2}$ is methyl substituted with unsubstituted 1,3,4 oxadiazol-2-yl. In an exemplary embodiment, $R^5$ is H or F, $R^{a2}$ is methyl substituted with 4-methyl oxadiazol-2-yl. In an exemplary embodiment, $R^5$ is H or F, $R^{a2}$ is methyl substituted with 5-methyl oxadiazol-2-yl. In an exemplary embodiment, $R^5$ is H or F, $R^{a2}$ is methyl substituted with 4-methyl 1,2,4 oxadiazol-2-yl. In an exemplary embodiment, $R^5$ is H or F, $R^{a2}$ is methyl substituted with 5-methyl 1,2,4 oxadiazol-2-yl. In an exemplary embodiment, $R^5$ is H or F, $R^{a2}$ is methyl substituted with 4-methyl 1,3,4 oxadiazol-2-yl. In an exemplary embodiment, $R^5$ is H or F, $R^{a2}$ is methyl substituted with 5-methyl 1,3,4 oxadiazol-2-yl. In an exemplary embodiment, $R^5$ is H or F, $R^{a2}$ is methyl substituted with 4-ethyl oxadiazol-2-yl. In an exemplary embodiment, $R^5$ is H or F, $R^{a2}$ is methyl substituted with 5-ethyl oxadiazol-2-yl. In an exemplary embodiment, $R^5$ is H or F, $R^{a2}$ is methyl substituted with 4-ethyl 1,2,4 oxadiazol-2-yl. In an exemplary embodiment, $R^5$ is H or F, $R^{a2}$ is methyl substituted with 5-ethyl 1,2,4 oxadiazol-2-yl. In an exemplary embodiment, $R^5$ is H or F, $R^{a2}$ is methyl substituted with 4-ethyl 1,3,4 oxadiazol-2-yl. In an exemplary embodiment, $R^5$ is H or F, $R^{a2}$ is methyl substituted with 5-ethyl 1,3,4 oxadiazol-2-yl. In an exemplary embodiment, $R^5$ is H or F, $R^{a2}$ is methyl substituted with 4-unsubstituted $C_3$ alkyl oxadiazol-2-yl. In an exemplary embodiment, $R^5$ is H or F, $R^{a2}$ is methyl substituted with 5-unsubstituted $C_3$ alkyl oxadiazol-2-yl. In an exemplary embodiment, $R^5$ is H or F, $R^{a2}$ is methyl substituted with 4-unsubstituted $C_3$ alkyl 1,2,4 oxadiazol-2-yl. In an exemplary embodiment, $R^5$ is H or F, $R^{a2}$ is methyl substituted with 5-unsubstituted $C_3$ alkyl 1,2,4 oxadiazol-2-yl. In an exemplary embodiment, $R^5$ is H or F, $R^{a2}$ is methyl substituted with 4-unsubstituted $C_3$ alkyl 1,3,4 oxadiazol-2-yl. In an exemplary embodiment, $R^5$ is H or F, $R^{a2}$ is methyl substituted with 5-unsubstituted $C_3$ alkyl 1,3,4 oxadiazol-2-yl. In an exemplary embodiment, $R^5$ is H or F, $R^{a2}$ is methyl substituted with 4-unsubstituted $C_4$ alkyl oxadiazol-2-yl. In an exemplary embodiment, $R^5$ is H or F, $R^{a2}$ is methyl substituted with 5-unsubstituted $C_4$ alkyl oxadiazol-2-yl. In an exemplary embodiment, $R^5$ is H or F, $R^{a2}$ is methyl substituted with 4-unsubstituted $C_4$ alkyl 1,2,4 oxadiazol-2-yl. In an exemplary embodiment, $R^5$ is H or F, $R^{a2}$ is methyl substituted with 5-unsubstituted $C_4$ alkyl 1,2,4 oxadiazol-2-yl. In an exemplary embodiment, $R^5$ is H or F, $R^{a2}$ is methyl substituted with 4-unsubstituted $C_4$ alkyl 1,3,4 oxadiazol-2-yl. In an exemplary embodiment, $R^5$ is H or F, $R^{a2}$ is methyl substituted with 5-unsubstituted $C_4$ alkyl 1,3,4 oxadiazol-2-yl. In an exemplary embodiment, $R^5$ is H or F, $R^{a2}$ is methyl substituted with 4-unsubstituted $C_5$ alkyl oxadiazol-2-yl. In an exemplary embodiment, $R^5$ is H or F, $R^{a2}$ is methyl substituted with 5-unsubstituted $C_5$ alkyl oxadiazol-2-yl. In an exemplary embodiment, $R^5$ is H or F, $R^{a2}$ is methyl substituted with 4-unsubstituted $C_5$ alkyl 1,2,4 oxadiazol-2-yl. In an exemplary embodiment, $R^5$ is H or F, $R^{a2}$ is methyl substituted with 5-unsubstituted $C_5$ alkyl 1,2,4 oxadiazol-2-yl. In an exemplary embodiment, $R^5$ is H or F, $R^{a2}$ is methyl substituted with 4-unsubstituted $C_5$ alkyl 1,3,4 oxadiazol-2-yl. In an exemplary embodiment, $R^5$ is H or F, $R^{a2}$ is methyl substituted with 5-unsubstituted $C_5$ alkyl 1,3,4 oxadiazol-2-yl. In an exemplary embodiment, $R^5$ is H or F, $R^{a2}$ is methyl substituted with 4-unsubstituted $C_6$ alkyl oxadiazol-2-yl. In an exemplary embodiment, $R^5$ is H or F, $R^{a2}$ is methyl substituted with 5-unsubstituted $C_6$ alkyl oxadiazol-2-yl. In an exemplary embodiment, $R^5$ is H or F, $R^{a2}$ is methyl substituted with 4-unsubstituted $C_6$ alkyl 1,2,4 oxadiazol-2-yl. In an exemplary embodiment, $R^5$ is H or F, $R^{a2}$ is methyl substituted with 5-unsubstituted $C_6$ alkyl 1,2,4 oxadiazol-2-yl. In an exemplary embodiment, $R^5$ is H or F, $R^{a2}$ is methyl substituted with 4-unsubstituted $C_6$ alkyl 1,3,4 oxadiazol-2-yl. In an exemplary embodiment, $R^5$ is H or F, $R^{a2}$ is methyl substituted with 5-unsubstituted $C_6$ alkyl 1,3,4 oxadiazol-2-yl. In an exemplary embodiment, $R^5$ is H or F, $R^{a2}$ is ethyl substituted with unsubstituted oxadiazol-2-yl. In an exemplary embodiment, $R^5$ is H or F, $R^{a2}$ is ethyl substituted with unsubstituted 1,2,4 oxadiazol-2-yl. In an exemplary embodiment, $R^5$ is H or F, $R^{a2}$ is ethyl substituted with unsubstituted 1,3,4 oxadiazol-2-yl. In an exemplary embodiment, $R^5$ is H or F, $R^{a2}$ is ethyl substituted with 4-methyl oxadiazol-2-yl. In an exemplary embodiment, $R^5$ is H or F, $R^{a2}$ is ethyl substituted with 5-methyl oxadiazol-2-yl. In an exemplary embodiment, $R^5$ is H or F, $R^{a2}$ is ethyl substituted with 4-methyl 1,2,4 oxadiazol-2-yl. In an exemplary embodiment, $R^5$ is H or F, $R^{a2}$ is ethyl substituted with 5-methyl 1,2,4 oxadiazol-2-yl. In an exemplary embodiment, $R^5$ is H or F, $R^{a2}$ is ethyl substituted with 4-methyl 1,3,4 oxadiazol-2-yl. In an exemplary embodiment, $R^5$ is H or F, $R^{a2}$ is ethyl substituted with 5-methyl 1,3,4 oxadiazol-2-yl. In an exemplary embodiment, $R^5$ is H or F, $R^{a2}$ is ethyl substituted with 4-ethyl oxadiazol-2-yl. In an exemplary embodiment, $R^5$ is H or F, $R^{a2}$ is ethyl substituted with 5-ethyl oxadiazol-2-yl. In an exemplary embodiment, $R^5$ is H or F, $R^{a2}$ is ethyl substituted with 5-ethyl oxadiazol-2-yl. In an exemplary embodiment, $R^5$ is H or F, $R^{a2}$ is ethyl substituted with 4-ethyl 1,2,4 oxadiazol-2-yl. In an exemplary embodiment, $R^5$ is H or F, $R^{a2}$ is ethyl substituted with 5-ethyl 1,2,4 oxadiazol-2-yl. In an exemplary embodiment, $R^5$ is H or F, $R^{a2}$ is ethyl substituted with 4-ethyl 1,3,4 oxadiazol-2-yl. In an exemplary embodiment, $R^5$ is H or F, $R^{a2}$ is ethyl substituted with 5-ethyl 1,3,4 oxadiazol-2-yl. In an exemplary embodiment, $R^5$ is H or F, $R^{a2}$ is ethyl substituted with 4-unsubstituted $C_3$ alkyl oxadiazol-2-yl. In an exemplary embodiment, $R^5$ is H or F, $R^{a2}$ is ethyl substituted with 5-unsubstituted $C_3$ alkyl oxadiazol-2-yl. In an exemplary embodiment, $R^5$ is H or F, $R^{a2}$ is ethyl substituted with 4-unsubstituted $C_3$ alkyl 1,2,4 oxadiazol-2-yl. In an exemplary embodiment, $R^5$ is H or F, $R^{a2}$ is ethyl substituted with 5-unsubstituted $C_3$ alkyl 1,2,4 oxadiazol-2-yl. In an exemplary embodiment, $R^5$ is H or F, $R^{a2}$ is ethyl substituted with 4-unsubstituted $C_3$ alkyl 1,3,4 oxadiazol-2-yl. In an exemplary embodiment, $R^5$ is H or F, $R^{a2}$ is ethyl substituted with 5-unsubstituted $C_3$ alkyl 1,3,4 oxadiazol-2-yl. In an exemplary embodiment, $R^5$ is H or F, $R^{a2}$ is ethyl substituted with 4-unsubstituted $C_4$ alkyl oxadiazol-2-yl. In an exemplary embodiment, $R^5$ is H or F, $R^{a2}$ is ethyl substituted with 5-unsubstituted $C_4$ alkyl oxadiazol-2-yl. In an exemplary embodiment, $R^5$ is H or F, $R^{a2}$ is ethyl substituted with 4-unsubstituted $C_4$ alkyl 1,2,4 oxadiazol-2-yl. In an exemplary embodiment, $R^5$ is H or F, $R^{a2}$ is ethyl substituted with 5-unsubstituted $C_4$ alkyl 1,2,4 oxadiazol-2-yl. In an exemplary embodiment, $R^5$ is H or F, $R^{a2}$ is ethyl substituted with 4-unsubstituted $C_4$ alkyl 1,3,4 oxadiazol-2-yl. In an exemplary embodiment, $R^5$ is H or F, $R^{a2}$ is ethyl substituted with 5-unsubstituted $C_4$ alkyl 1,3,4 oxadiazol-2-yl. In an exemplary embodiment, $R^5$ is H or F, $R^{a2}$ is ethyl substituted with 4-unsubstituted $C_5$ alkyl oxadiazol-2-yl. In an exemplary embodiment, $R^5$ is H or F, $R^{a2}$ is ethyl substituted with 5-unsubstituted $C_5$ alkyl oxadiazol-2-yl. In an exemplary embodiment, $R^5$ is H or F, $R^{a2}$ is ethyl substituted with 4-unsubstituted $C_5$ alkyl 1,2,4-oxadiazol-2-yl. In an exemplary embodiment, $R^5$ is H or F, $R^{a2}$ is ethyl substituted with 5-unsubstituted $C_5$ alkyl 1,2,4 oxadiazol-2-yl. In an exemplary embodiment, $R^5$ is H or F, $R^{a2}$ is ethyl substituted with 4-unsubstituted $C_5$ alkyl 1,3,4 oxadiazol-2-yl. In an exemplary embodiment, $R^5$ is H or F, $R^{a2}$ is ethyl substituted with 5-unsubstituted $C_5$ alkyl 1,3,4 oxadiazol-2-yl. In an exemplary embodiment, $R^5$ is H or F, $R^{a2}$ is ethyl substituted with 4-unsubstituted $C_6$ alkyl oxadiazol-2-yl. In an exemplary embodiment, $R^5$ is H or F, $R^{a2}$ is ethyl substituted with 5-unsubstituted $C_6$ alkyl oxadiazol-2-yl. In an exemplary embodiment, $R^5$ is H or F, $R^{a2}$ is ethyl substituted with 4-unsubstituted $C_6$ alkyl 1,2,4 oxadiazol-2-yl. In an exemplary embodiment, $R^5$ is H or F, $R^{a2}$ is ethyl substituted with 5-unsubstituted $C_6$ alkyl 1,2,4 oxadiazol-2-yl. In an exemplary embodiment, $R^5$ is H or F, $R^{a2}$ is ethyl substituted with 4-unsubstituted $C_6$ alkyl 1,3,4 oxadiazol-2-yl. In an exemplary embodiment, $R^5$ is H or F, $R^{a2}$ is ethyl substituted with 5-unsubstituted $C_6$ alkyl 1,3,4 oxadiazol-2-yl. In an exemplary embodiment, $R^5$ is H or F, $R^{a2}$ is $C_3$ alkyl substituted with unsubstituted oxadiazol-2-yl. In an exemplary embodiment, $R^5$ is H or F, $R^{a2}$ is $C_3$ alkyl substituted with unsubstituted 1,2,4 oxadiazol-2-yl. In an exemplary embodiment, $R^5$ is H or F, $R^{a2}$ is $C_3$ alkyl substituted with unsubstituted 1,3,4 oxadiazol-2-yl. In an exemplary embodiment, $R^5$ is H or F, $R^{a2}$ is $C_3$ alkyl substituted with 4-methyl oxadiazol-2-yl. In an exemplary embodiment, $R^5$ is H or F, $R^{a2}$ is $C_3$ alkyl substituted with 5-methyl oxadiazol-2-yl. In an exemplary embodiment, $R^5$ is H or F, $R^{a2}$ is $C_3$ alkyl substituted with 4-methyl 1,2,4 oxadiazol-2-yl. In an exemplary embodiment, $R^5$ is H or F, $R^{a2}$ is $C_3$ alkyl substituted with 5-methyl 1,2,4 oxadiazol-2-yl. In an exemplary embodiment, $R^5$ is H or F, $R^{a2}$ is $C_3$ alkyl substituted with 4-methyl 1,3,4 oxadiazol-2-yl. In an exemplary embodiment, $R^5$ is H or F, $R^{a2}$ is $C_3$ alkyl substituted with 5-methyl 1,3,4 oxadiazol-2-yl. In an exemplary embodiment, $R^5$ is H or F, $R^{a2}$ is $C_3$ alkyl substituted with 4-ethyl oxadiazol-2-yl. In an exemplary embodiment, $R^5$ is H or F, $R^{a2}$ is $C_3$ alkyl substituted with 5-ethyl oxadiazol-2-yl. In an exemplary embodiment, $R^5$ is H or F, $R^{a2}$ is $C_3$ alkyl substituted with 4-ethyl 1,2,4 oxadiazol-2-yl. In an exemplary embodiment, $R^5$ is H or F, $R^{a2}$ is $C_3$ alkyl substituted with 5-ethyl 1,2,4 oxadiazol-2-yl. In an exemplary embodiment, $R^5$ is H or F, $R^{a2}$ is $C_3$ alkyl substituted with 4-ethyl 1,3,4 oxadiazol-2-yl. In an exemplary embodiment, $R^5$ is H or F, $R^{a2}$ is $C_3$ alkyl substituted with 5-ethyl 1,3,4 oxadiazol-2-yl. In an exemplary embodiment, $R^5$ is H or F, $R^{a2}$ is $C_3$ alkyl substituted with 4-unsubstituted $C_3$ alkyl oxadiazol-2-yl. In an exemplary embodiment, $R^5$ is H or F, $R^{a2}$ is $C_3$ alkyl substituted with 5-unsubstituted $C_3$ alkyl oxadiazol-2-yl. In an exemplary embodiment, $R^5$ is H or F, $R^{a2}$ is $C_3$ alkyl substituted with 4-unsubstituted $C_3$ alkyl 1,2,4 oxadiazol-2-yl. In an exemplary embodiment, $R^5$ is H or F, $R^{a2}$ is $C_3$ alkyl substituted with 5-unsubstituted $C_3$ alkyl 1,2,4 oxadiazol-2-yl. In an exemplary embodiment, $R^5$ is H or F, $R^{a2}$ is $C_3$ alkyl substituted with 4-unsubstituted $C_3$ alkyl 1,3,4 oxadiazol-2-yl. In an exemplary embodiment, $R^5$ is H or F, $R^{a2}$ is $C_3$ alkyl substituted with 5-unsubstituted $C_3$ alkyl 1,3,4 oxadiazol-2-yl. In an exemplary embodiment, $R^5$ is H or F, $R^{a2}$ is $C_3$ alkyl substituted with 4-unsubstituted $C_4$ alkyl oxadiazol-2-yl. In an exemplary embodiment, $R^5$ is H or F, $R^{a2}$ is $C_3$ alkyl substituted with 5-unsubstituted $C_4$ alkyl oxadiazol-2-yl. In an exemplary embodiment, $R^5$ is H or F, $R^{a2}$ is $C_3$ alkyl substituted with 4-unsubstituted $C_4$ alkyl 1,2,4 oxadiazol-2-yl. In an exemplary embodiment, $R^5$ is H or F, $R^{a2}$ is $C_3$ alkyl substituted with 5-unsubstituted $C_4$ alkyl 1,2,4 oxadiazol-2-yl. In an exemplary embodiment, $R^5$ is H or F, $R^{a2}$ is $C_3$ alkyl substituted with 4-unsubstituted $C_4$ alkyl 1,3,4 oxadiazol-2-yl. In an exemplary embodiment, $R^5$ is H or F, $R^{a2}$ is $C_3$ alkyl substituted with 5-unsubstituted $C_4$ alkyl 1,3,4 oxadiazol-2-yl. In an exemplary embodiment, $R^5$ is H or F, $R^{a2}$ is $C_3$ alkyl substituted with 4-unsubstituted $C_5$ alkyl oxadiazol-2-yl. In an exemplary embodiment, $R^5$ is H or F, $R^{a2}$ is $C_3$ alkyl substituted with 5-unsubstituted $C_5$ alkyl oxadiazol-2-yl. In an exemplary embodiment, $R^5$ is H or F, $R^{a2}$ is $C_3$ alkyl substituted with 4-unsubstituted $C_5$ alkyl 1,2,4 oxadiazol-2-yl. In an exemplary embodiment, $R^5$ is H or F, $R^{a2}$ is $C_3$ alkyl substituted with 5-unsubstituted $C_5$ alkyl 1,2,4 oxadiazol-2-yl. In an exemplary embodiment, $R^5$ is H or F, $R^{a2}$ is $C_3$ alkyl substituted with 4-unsubstituted $C_5$ alkyl 1,3,4 oxadiazol-2-yl. In an exemplary embodiment, $R^5$ is H or F, $R^{a2}$ is $C_3$ alkyl substituted with 5-unsubstituted $C_5$ alkyl 1,3,4 oxadiazol-2-yl. In an exemplary embodiment, $R^5$ is H or F, $R^{a2}$ is $C_3$ alkyl substituted with 4-unsubstituted $C_6$ alkyl oxadiazol-2-yl. In an exemplary embodiment, $R^5$ is H or F, $R^{a2}$ is $C_3$ alkyl substituted with 5-unsubstituted $C_6$ alkyl oxadiazol-2-yl. In an exemplary embodiment, $R^5$ is H or F, $R^{a2}$ is $C_3$ alkyl substituted with 4-unsubstituted $C_6$ alkyl 1,2,4 oxadiazol-2-yl. In an exemplary embodiment, $R^5$ is H or F, $R^{a2}$ is $C_3$ alkyl substituted with 5-unsubstituted $C_6$ alkyl 1,2,4 oxadiazol-2-yl. In an exemplary embodiment, $R^5$ is H or F, $R^{a2}$ is $C_3$ alkyl substituted with 4-unsubstituted $C_6$ alkyl 1,3,4 oxadiazol-2-yl. In an exemplary embodiment, $R^5$ is H or F, $R^{a2}$ is $C_3$ alkyl substituted with 5-unsubstituted $C_6$ alkyl 1,3,4 oxadiazol-2-yl.

In an exemplary embodiment, the compound, or a salt thereof, has a structure which is

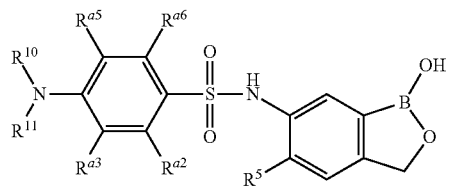

wherein $R^5$ is H or halogen, one of $R^{a2}$, $R^{a3}$, $R^{a5}$ and $R^{a6}$ is unsubstituted furan, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is H, $R^{a2}$ is unsubstituted furan. In an exemplary embodiment, $R^5$ is F, $R^{a2}$ is unsubstituted furan.

In an exemplary embodiment, the compound, or a salt thereof, has a structure which is

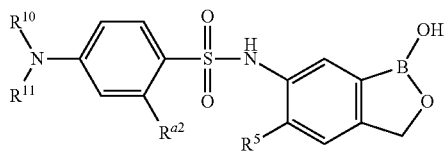

wherein $R^5$ is H or halogen, $R^{a2}$ is unsubstituted furan, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D.

In an exemplary embodiment, the compound, or a salt thereof, has a structure which is

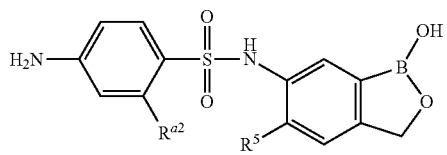

wherein $R^5$ is H or halogen, $R^{a2}$ is unsubstituted furan. In an exemplary embodiment, $R^{a2}$ and $R^5$ are as described herein, and each hydrogen in said compound, or a salt thereof, is independently H or D. In an exemplary embodiment, each hydrogen in said compound, or a salt thereof, is optionally D. In an exemplary embodiment, $R^5$ is H, $R^{a2}$ is unsubstituted furan. In an exemplary embodiment, $R^5$ is H, $R^{a2}$ is unsubstituted furan-2-yl. In an exemplary embodiment, $R^5$ is F, $R^{a2}$ is unsubstituted furan. In an exemplary embodiment, $R^5$ is F, $R^{a2}$ is unsubstituted furan-2-yl.

In an exemplary embodiment, the compound, or a salt thereof, has a structure which is

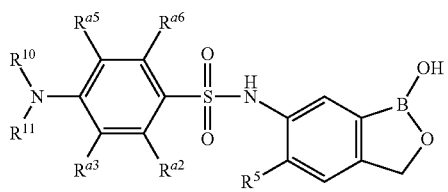

wherein $R^5$ is H or halogen, one of $R^{a2}$, $R^{a3}$, $R^{a5}$ and $R^{a6}$ is —NHC(O)OR$^{30}$, wherein $R^{30}$ is unsubstituted alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, one of $R^{a2}$, $R^{a3}$, $R^{a5}$ and $R^{a6}$ is —NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, one of $R^{a2}$, $R^{a3}$, $R^{a5}$ and $R^{a6}$ is —NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl, and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

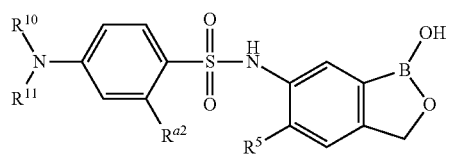

wherein $R^5$ is H or halogen, $R^{a2}$ is —NHC(O)OR$^{30}$, wherein $R^{30}$ is unsubstituted alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^5$, $R^{10}$, and $R^{11}$ are as described herein, and each hydrogen in said compound, or a salt thereof, is independently H or D. In an exemplary embodiment, each hydrogen in said compound, or a salt thereof, is optionally D. In an exemplary embodiment, $R^5$ is halogen, $R^{a2}$ is —NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^5$ is H, $R^{a2}$ is —NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, $R^{a2}$, $R^{a3}$, $R^{a5}$, $R^{a6}$, and $R^5$ are as described herein, $R^{10}$ is H and $R^{11}$ is a prodrug moiety. In an exemplary embodiment, $R^{a2}$, $R^{a3}$, $R^{a5}$, $R^{a6}$, and $R^5$ are as described herein, $R^{10}$ is H and $R^{11}$ is a prodrug moiety described herein. In an exemplary embodiment, $R^{a2}$, $R^{a3}$, $R^{a5}$, $R^{a6}$, and $R^5$ are as described herein, $R^{10}$ and $R^{11}$ are independently selected from the prodrug moieties described herein.

In an exemplary embodiment, the compound, or a salt thereof, has a structure which is

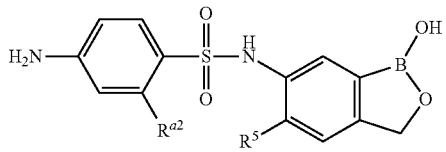

wherein $R^5$ is H or halogen, $R^{a2}$ is —NHC(O)OR$^{30}$, wherein $R^{30}$ is unsubstituted alkyl. In an exemplary embodiment, $R^{a2}$ and $R^5$ are as described herein, and each hydrogen in said compound, or a salt thereof, is independently H or D. In an exemplary embodiment, $R^{a2}$ and $R^5$ are as described herein, and each hydrogen in $R^{30}$ of said compound or a salt thereof, is independently H or D. In an exemplary embodiment, each hydrogen in said compound, or a salt thereof, is optionally D. In an exemplary embodiment, $R^5$ is H or halogen, $R^{a2}$ is —NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is —NHC(O)OR$^{30}$, wherein $R^{30}$ is methyl or ethyl or unsubstituted $C_3$ alkyl. In an exemplary embodiment, $R^5$ is F, $R^{a2}$ is —NHC(O)OR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is —NHC(O)OR$^{30}$, wherein $R^{30}$ is methyl or ethyl or unsubstituted $C_3$ alkyl. In an exemplary embodiment, $R^5$ is H, $R^{a2}$ is —NHC(O)OCH(CH$_3$)$_2$. In an exemplary embodiment, $R^5$ is F, $R^{a2}$ is —NHC(O)OCH(CH$_3$)$_2$.

In an exemplary embodiment, the compound, or a salt thereof, has a structure which is

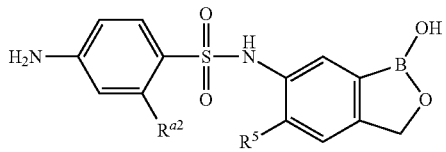

wherein $R^5$ is H or halogen, $R^{a2}$ is —NHC(O)OR$^{30}$, wherein $R^{30}$ is unsubstituted cyclopropyl or unsubstituted cyclobutyl or unsubstituted cyclopentyl or unsubstituted cyclohexyl or unsubstituted cycloheptyl or unsubstituted cyclooctyl. In an exemplary embodiment, $R^{a2}$ and $R^5$ are as described herein, and each hydrogen in said compound, or a salt thereof, is independently H or D. In an exemplary embodiment, $R^{a2}$ and $R^5$ are as described herein, and each hydrogen in said compound, or a salt thereof, is independently H or D. In an exemplary embodiment, each hydrogen in said compound, or a salt thereof, is optionally D.

In an exemplary embodiment, the compound, or a salt thereof, has a structure which is

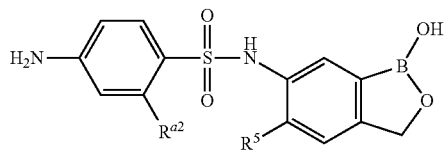

wherein $R^5$ is H or halogen, $R^{a2}$ is —NHC(O)NHR$^{30}$, wherein $R^{30}$ is unsubstituted alkyl. In an exemplary embodiment, $R^5$ is H or halogen, $R^{a2}$ is —NHC(O)NHR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is H, $R^{a2}$ is —NHC(O)NHR$^{30}$, wherein $R^{30}$ is methyl or ethyl or unsubstituted $C_3$ alkyl. In an exemplary embodiment, $R^5$ is F, $R^{a2}$ is —NHC(O)NHR$^{30}$, wherein $R^{30}$ is methyl or ethyl or unsubstituted $C_3$ alkyl or unsubstituted $C_4$ alkyl or unsubstituted $C_5$ alkyl or unsubstituted $C_6$ alkyl. In an exemplary embodiment, $R^5$ is F, $R^{a2}$ is —NHC(O)NHR$^{30}$, wherein $R^{30}$ is methyl or ethyl or unsubstituted $C_3$ alkyl.

In an exemplary embodiment, the compound, or a salt thereof, has a structure which is

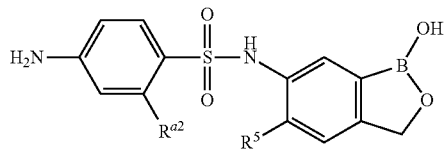

wherein $R^5$ is H or halogen, $R^{a2}$ is —NHC(O)NH$_2$. In an exemplary embodiment, $R^5$ is H, $R^{a2}$ is —NHC(O)NH$_2$. In an exemplary embodiment, $R^5$ is F, $R^{a2}$ is —NHC(O)NH$_2$.

In various embodiments of the invention, $R^{10}$ and/or $R^{11}$ can be a prodrug moiety. Prodrugs of amines are known in the art. See Krise et al., "Prodrugs of Amines" in *Prodrugs*; Springer: 2007; Vol. V, Part III, 801-831. Examples of prodrugs for amines include, but are not limited to, N-acyl derivatives, carbamates, N-acyloxyalkyl derivatives, quaternary ammonium derivatives, N-oxides, N-Mannich bases, Schiff bases, enaminones, azo derivatives, oxazolidines, and 4-imidazolidinones. One of skill in the art will be able to select a suitable prodrug moiety.

In an exemplary embodiment, the prodrug moiety is an acyl derivative. In an exemplary embodiment, at least one of $R^{10}$ and $R^{11}$ is

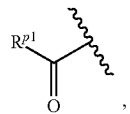

wherein $R^{p1}$ is a member selected from substituted or unsubstituted alkyl, substituted or unsubstituted arylalkyl, substituted or unsubstituted cycloalkyl, substituted or unsubstituted heterocycloalkyl, substituted or unsubstituted aryl and substituted or unsubstituted heteroaryl. In an exemplary embodiment, $R^{p1}$ is unsubstituted alkyl. In an exemplary embodiment, $R^{p1}$ is unsubstituted alkyl. In an exemplary embodiment, $R^{p1}$ is unsubstituted arylalkyl. In an exemplary embodiment, $R^{p1}$ is methyl. In another exemplary embodiment $R^{p1}$ is $CF_3$.

In an exemplary embodiment, the prodrug moiety is an ester. In an exemplary embodiment, at least one of $R^{10}$ and $R^{11}$ is

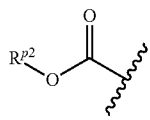

wherein $R^{p2}$ is a member selected from substituted or unsubstituted alkyl, substituted or unsubstituted arylalkyl, substituted or unsubstituted cycloalkyl, substituted or unsubstituted heterocycloalkyl, substituted or unsubstituted aryl and substituted or unsubstituted heteroaryl. In an exemplary embodiment, $R^{p2}$ is unsubstituted alkyl. In an exemplary embodiment, $R^{p2}$ is methyl. In another exemplary embodiment $R^{p2}$ is ethyl. In another exemplary embodiment $R^{p2}$ is n-propyl. In another exemplary embodiment $R^{p2}$ is isopropyl. In another exemplary embodiment $R^{p2}$ is iso-butyl. In another exemplary embodiment $R^{p2}$ is benzyl.

In an exemplary embodiment, the prodrug moiety is an ester. In an exemplary embodiment, at least one of $R^{10}$ and $R^{11}$ is

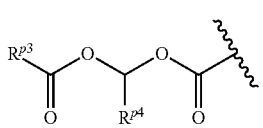

wherein $R^{p3}$ and $R^{p4}$ are members independently selected from substituted or unsubstituted alkyl, substituted or unsubstituted arylalkyl, substituted or unsubstituted cycloalkyl, substituted or unsubstituted heterocycloalkyl, substituted or unsubstituted aryl and substituted or unsubstituted heteroaryl.

In an exemplary embodiment, the invention provides poly- or multi-valent species of the compounds of the invention, including a dimer or a trimer. Another exemplary embodiment of the invention provides an anhydride of the compounds of the invention. In another exemplary embodiment, the invention provides poly- or multi-valent species of the compounds of the invention. In an exemplary embodiment, the invention provides a dimer of the compounds described herein. In an exemplary embodiment, the invention provides a dimer of the compounds described herein.

In an exemplary embodiment, the invention provides a trimer of the compounds described herein. In an exemplary embodiment, the invention provides a trimer of the compounds described herein.

The compounds of the invention can form a hydrate with water, solvates with alcohols such as methanol, ethanol, propanol, and the like; adducts with amino compounds, such as ammonia, methylamine, ethylamine, and the like; adducts with acids, such as formic acid, acetic acid and the like; complexes with ethanolamine, quinoline, amino acids, and the like.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein. In an exemplary embodiment, the invention provides a compound as described in FIG. 1, or a salt thereof. In an exemplary embodiment, the invention provides a compound as described in FIG. 1, or a pharmaceutically acceptable salt thereof.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

III. b) Combinations Comprising Additional Therapeutic Agents

The compounds of the invention may also be used in combination with additional therapeutic agents. The invention thus provides, in a further aspect, a combination comprising a compound of the invention together with at least one additional therapeutic agent, or a salt, prodrug, hydrate or solvate thereof. In an exemplary embodiment, the compound of the invention is a compound described herein, or a salt thereof. In an exemplary embodiment, the additional therapeutic agent is a compound of the invention. In an exemplary embodiment, the additional therapeutic agent includes a boron atom. In an exemplary embodiment, the additional therapeutic agent does not contain a boron atom. In an exemplary embodiment, the additional therapeutic agent is a compound described in section III a).

In an exemplary embodiment, the additional therapeutic agent is an antibacterial. In an exemplary embodiment, the additional therapeutic agent is a macrolide antibiotic. In an exemplary embodiment, the additional therapeutic agent is azithromycin. In an exemplary embodiment, the additional therapeutic agent is a ketolide antibiotic. In an exemplary embodiment, the additional therapeutic agent is telithromycin. In an exemplary embodiment, the additional therapeutic agent is a fluoroquinolone. In an exemplary embodiment, the additional therapeutic agent is levofloxacin. In an exemplary embodiment, the additional therapeutic agent is moxifloxacin. In an exemplary embodiment, the additional therapeutic agent is amoxicillin. In an exemplary embodiment, the additional therapeutic agent is clavulanate or clavulanic acid.

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the animal (for example, a human) ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a single unit dosage form which includes a compound of the invention; an antibiotic and a pharmaceutically acceptable excipient. In an exemplary embodiment, the pharmaceutical formulation is a single unit dosage form which includes a compound of the invention; an antibiotic and at least one pharmaceutically acceptable excipient. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an antibiotic and d) a second pharmaceutically acceptable excipient.

III. c) Preparation of Boron-Containing Compounds

Compounds of use in the invention can be prepared using commercially available starting materials, known intermediates, or by using the synthetic methods published in references described and incorporated by reference herein, such as U.S. patent application Ser. No. 12/142,692 and U.S. Pat. Pubs. US20060234981, US20070155699 and US20070293457.

The following general procedures were used as indicated in generating the examples and can be applied, using the knowledge of one of skill in the art, to other appropriate compounds to obtain additional analogues.

General Procedure 1: Sulfonylation of Amino 3H-benzo[c][1,2]oxaborol-1-ols

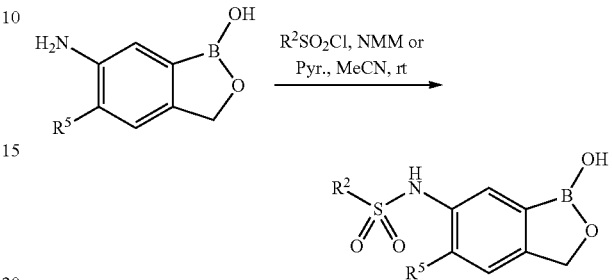

The sulfonyl chloride (1-1.2 equiv) and a base (either NMM, $K_2CO_3$, or pyridine 3-4 equiv) were added sequentially to a solution of the amine in MeCN (20 mL/g) at rt or cooled in an ice bath. After completion (typical duration O/N) the volatiles were removed in vacuo. $H_2O$ was added to the residue and the mixture adjusted to ~pH 6 with dilute HCl. The aqueous layer was then extracted with organic solvent (typically EtOAc), and the combined organic fractions dried (either $Na_2SO_4$ or $MgSO_4$), filtered, and concentrated in vacuo. The product was typically purified by either recrystallization from $H_2O$, trituration with $CH_2Cl_2$ or EtOAc, or flash chromatography.

General procedure 2: Deprotection of Substituted N-(4-(N-(1-hydroxy-1,3-dihydrobenzo[c][1,2]oxaborol-6-yl)sulfamoyl)phenyl)acetamide

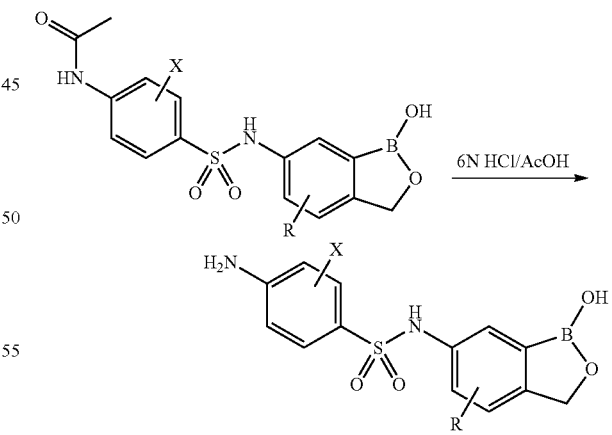

The acetamide and 1:1 6N HCl: AcOH (5 equiv) were heated to 40° C. for 2 days. Purification involved removal of solvent, work up with EtOAc and 1N HCl, washed with brine, dry on $Na_2SO_4$ and removal of solvent. The product was recrystallized in EtOAc or purified by flash chromatography or preparative TLC when required.

General Procedure 3: Deprotection of Cbz Protected Amines/Reduction of Aromatic Nitro

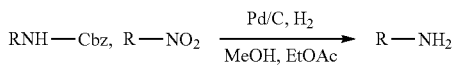

A mixture of starting material, Pd/C (10% wet, 0.2 equiv) in methanol was placed under a hydrogen atmosphere at 50 psi. The reaction was monitored by LC/MS. The catalyst was filtered off through a pad of Celite® and the solvent was evaporated to give the amine. The product was purified by flash chromatography or preparative when required.

General Procedure 4: Deprotection of 2,2,2-Trifluoroacetyl Protected Amines

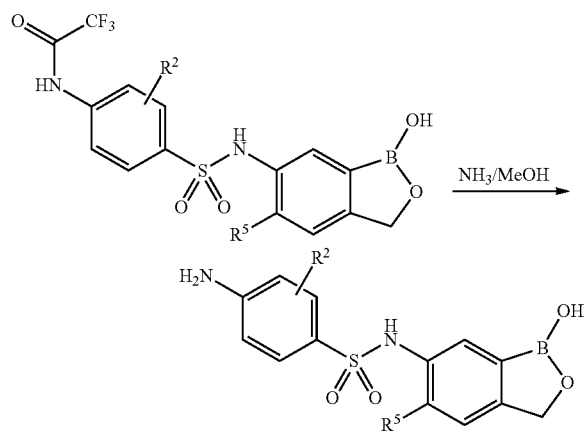

The acetamide and $NH_3$ (7M in MeOH, 5 equiv) was heated to 80° C. for 2 hrs. The reaction was monitored by LC/MS. Purification: remove solvent. The product was recrystallized in EtOAc/MeOH or purified by flash chromatography or preparative HPLC when required.

IV. Assays

Art-recognized techniques of genetics and molecular biology are of use to identify compounds that bind to and/or inhibit an enzyme, such as a tRNA synthetase. Moreover, these techniques are of use to distinguish whether a compound binds to and/or inhibits a particular domain of the enzyme. For example, for LeuRS, these techniques can distinguish whether a compound binds to and/or inhibits the synthetic domain, the editing domain, or both the editing and synthetic domains. LeuRS can be obtained from Genscript (Piscataway, N.J.) and also obtained from Prof. Susan Martinez (University of Illinois, Champaign, Ill.).

IV. a) LeuRS

In an exemplary assay, activity of a representative compound against the editing domain was confirmed. To identify the target of a novel boron-containing antibacterial compound, mutants in *E. coli* showing resistance to the compound were isolated. Characterization of mutants showed that they have an 32-256 fold increase in resistance to the compound over wildtype. The mutants were furthermore shown to be sensitive to various antibacterial agents with known modes of action, suggesting that the cellular target of the compound is distinct from the target of the other antibacterial agents. The leuS gene from the mutants was cloned onto a plasmid and their resistance was confirmed by MIC. The editing domain from these mutants were sequenced and the mutations were all located in the editing domain of this enzyme.

Assays to determine whether, and how effectively, a particular compound binds to and/or inhibits the editing domain of a selected tRNA synthetase are also set forth herein, and additional assays are readily available to those of skill in the art. Briefly, in an exemplary assay, an improperly charged tRNA and a tRNA synthetase that is capable of editing the improperly charged tRNA are combined. The resulting mixture is contacted with the putative inhibitor and the degree of editing inhibition is observed.

Another assay uses genetics to show that a drug works via the editing domain. In this assay, the compound is first tested against a strain of cells over-expressing copies of the tRNA synthetase gene. The compound's effect on the over-expressing strain is compared with a control strain to determine whether the compound is active against the synthetase. If the minimum inhibitory concentration (MIC) is 2-fold higher in the strain with extra copies of the synthetase gene than the MIC of the inhibitor against a wild type cell, a further genetic screen is conducted to determine whether the increased resistance is due to mutations in the editing domain. In this second screen, the control strain is challenged against a high concentration of the inhibitor. The colonies surviving the challenge are isolated and DNA from these cells is isolated. The editing domain is amplified using a proof-reading PCR enzyme and the appropriate primers. The PCR product can be purified using standard procedures. The sequence amplified mutant DNA is compared to wild-type. If the mutant DNA bears mutations in the editing domain, such results would suggest that the compound binds to the editing domain and affects the editing function of the molecule through this domain.

Generally, the compounds to be tested are present in the assays in ranges from about 1 pM to about 100 mM, preferably from about 1 pM to about 1 µM. Other compounds range from about 1 nM to about 100 nM, preferably from about 1 nM to about 1 µM.

The effects of the test compounds upon the function of the enzymes can also be measured by any suitable physiological change. When the functional consequences are determined using intact cells or animals, one can also measure a variety of effects such as transmitter release, hormone release, transcriptional changes to both known and uncharacterized genetic markers, changes in cell metabolism such as cell growth or pH changes, and changes in intracellular second messengers such as $Ca^{2+}$, or cyclic nucleotides.

Utilizing the assays set forth herein and others readily available in the art, those of skill in the art will be able to readily and routinely determine other compounds and classes of compounds that operate to bind to and/or inhibit the editing domain of tRNA synthetases.

In another aspect, the invention provides a method for identifying a compound which binds to an editing domain of a tRNA synthetase comprising: a) contacting said editing domain with a test compound under conditions suitable for binding; and b) detecting binding of said test compound to said editing domain. In an exemplary embodiment, detecting binding of said compound comprises use of at least one detectable element, isotope, or chemical label attached to said compound. In an exemplary embodiment, the element, isotope or chemical label is detected by a fluorescent, luminescent, radioactive, or absorbance readout. In an exemplary embodiment, the contacting of said test compound with said editing domain also includes further contacting said test compound and said editing domain with a member selected from AMP and a molecule with a terminal adenosine. In an exemplary embodiment, the tRNA synthetase is derived from leucyl tRNA synthetase. In an exemplary embodiment, the tRNA synthetase is derived from a mutated tRNA synthetase, wherein said mutated tRNA synthetase comprises amino acid mutations in an editing domain. In another exemplary embodiment, wherein said editing domain of a tRNA synthetase comprises the amino acid sequence of a peptide sequence described herein.

In another aspect, the invention provides a method for identifying a compound which binds to an editing domain of a tRNA synthetase, said assay comprising: a) contacting said editing domain of a tRNA synthetase with said compound under conditions suitable for binding of said compound with said editing domain of a tRNA synthetase; b) comparing a biological activity of said editing domain of a tRNA synthetase contacting said compound to said biological activity when not contacting said compound; and c) identifying said compound as binding to said editing domain of a tRNA synthetase if said biological activity of said editing domain of a tRNA synthetase is reduced when contacting said compound. In an exemplary embodiment, the biological activity is hydrolysis of noncognate amino acid. In another exemplary embodiment, the hydrolysis of said noncognate amino acid is detected through the use of one or more labels. In another exemplary embodiment, the labels include a radiolabel, a fluorescent marker, an antibody, or a combination thereof. In another exemplary embodiment, said labels can be detected using spectroscopy. In another exemplary embodiment, said editing domain of a tRNA synthetase is derived from leucyl tRNA synthetase.

In another aspect, the invention provides a method of generating a tRNA molecule with a noncognate amino acid comprising: a) creating or isolating a mutated tRNA synthetase with altered amino acid editing domains; and b) contacting a tRNA molecule with said mutated tRNA synthetase and a noncognate amino acid. In another exemplary embodiment, the mutated tRNA synthetase contains one or more amino acid mutations in an editing domain. In another exemplary embodiment, the mutated tRNA synthetase is unable to bind with a compound of the invention. In another exemplary embodiment, the mutated tRNA synthetase is unable to bind with a compound described herein, or a pharmaceutically acceptable salt thereof. In another exemplary embodiment, the mutated tRNA synthetase is unable to bind with a compound according to a formula described herein, or a pharmaceutically acceptable salt thereof.

In another aspect, the invention provides a composition that comprises one or more tRNA molecules attached to noncognate amino acids, wherein said tRNA molecules are synthesized using one or more mutated tRNA synthetases isolated from a microorganism or a cell line derived from a microorganism. In an exemplary embodiment, the microorganism is a bacteria. In an exemplary embodiment, wherein said mutated tRNA synthetases contain amino acid mutations in their editing domains.

V. Amino Acid and Nucleotide Sequences Used in Assays

Amino acid and nucleotide sequences of use in the invention are published in references described and incorporated by reference herein, such as U.S. patent application Ser. No. 12/142,692 and U.S. Pat. Pubs. US20060234981, US20070155699 and US20070293457.

VI. Methods

In another aspect, the compounds of the invention can be utilized to inhibit an enzyme. In another aspect, the compounds of the invention and/or combinations of the invention exhibit potency against microorganisms, such as bacteria, and therefore have the potential to kill and/or inhibit the growth of microorganisms. In another aspect, the compounds of the invention and/or combinations of the invention exhibit potency against microorganisms, such as bacteria, and therefore have the potential to achieve therapeutic efficacy in the animals described herein.

VI. LeuRS—

In an exemplary embodiment, the compounds of the invention exhibit the ability of inhibiting the editing domain of tRNA synthetases, such as leucyl tRNA synthetase, of microorganisms, such as bacteria, and therefore have the potential to be used as editing domain inhibitors of microorganism tRNA synthetases.

According to another aspect of the invention, a method for binding to and/or inhibiting the editing domain of a tRNA synthetase is provided which comprises contacting a tRNA synthetase with a compound of the invention that inhibits the editing domain under conditions in which the tRNA synthetase interacts with its substrate to form an aminoacyl adenylate intermediate and, preferably, to form a charged tRNA. Such conditions are known to those skilled in the art. In an exemplary embodiment, the compound has a structure according to a formula described herein. In an exemplary embodiment, the compound is described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the invention provides a compound described herein, or a salt thereof. The tRNA synthetase is contacted with an amount of compound of the invention sufficient to result in a detectable amount of tRNA synthetase inhibition. This method can be performed on a tRNA synthetase that is contained within an organism or which is outside an organism. In an exemplary embodiment, the method is performed on a tRNA synthetase that is contained within a microorganism or a microbial cell that is in, or on the surface of, an animal. In an exemplary embodiment, the animal is a human. The method results in a decrease in the amount of charged tRNA produced by the tRNA synthetase that has an inhibited editing domain. In an exemplary embodiment, the inhibition takes place in a cell, such as a microorganism cell. In another exemplary embodiment, the microorganism cell is a bacteria. In another exemplary embodiment, the tRNA synthetase is leucyl tRNA synthetase.

In an exemplary embodiment, the invention provides a method of inhibiting conversion of a tRNA molecule into a charged tRNA molecule. The method involves contacting a tRNA synthetase with a compound of the invention effective to inhibit activity of an editing domain of said tRNA synthetase, under conditions sufficient to inhibit said activity, thereby inhibiting said conversion. In an exemplary embodiment, the compound of the invention is a compound described herein, or a pharmaceutically acceptable salt thereof. In an exemplary embodiment, the inhibition occurs within a cell, and the cell is a microorganism cell. In another exemplary embodiment, the microorganism cell is a bacteria. In another exemplary embodiment, the microorganism cell is a bacteria which is described herein. In another exemplary embodiment, the enzyme is a leucyl tRNA synthetase of a bacteria described herein. In another exemplary embodiment, the tRNA synthetase is leucyl tRNA synthetase. In another exemplary embodiment, the compound has a $K_{D,\ synthesis}$ of greater than 100 μM against a synthetic domain of said tRNA synthetase.

In certain embodiments, the mechanism of action of a compound of the invention is to inhibit the conversion of a tRNA molecule into a charged tRNA molecule by binding to and/or inhibiting at least the editing domain of the synthetase. The compounds of use in this method may also inhibit or otherwise interact with the synthetic domain (e.g., the active site of the synthetic domain). In a presently preferred embodiment, the editing domain is inhibited selectively in the presence of the synthetic domain. In a preferred embodiment, the synthetic domain is essentially uninhibited, while the editing domain is inhibited at least 50%, preferably at least 60%, more preferably at least 70%, still more preferably, at least 80% and even still more preferably at least 90% of the activity of the tRNA synthetase. In another preferred embodiment, the synthetic domain is inhibited by at most 50%, preferably at most 30%, preferably at most 20%, 10%, preferably at most 8%, more preferably at most 5%, still more preferably, at most 3% and even still more preferably at most 1%. Inhibition of the editing domain produces a decrease in the amount of the properly charged tRNA which results in retardation or cessation of cell growth and division.

In another exemplary embodiment, the ratio of a minimum concentration of said compound inhibiting said editing domain to a minimum concentration of said compound inhibiting said synthetic domain of said tRNA synthetase, represented as $K_{D,\ edit}/K_{D,\ synthesis}$, is less than one. In another exemplary embodiment, the $K_{D,\ edit}/K_{D,\ synthesis}$ of the compound is a member selected from less than 0.5, less than 0.1 and less than 0.05.

VI. a) Inhibiting Microorganism Growth or Killing Microorganisms

The compounds of the invention and/or combinations of the invention exhibit potency against microorganisms, such as bacteria, and therefore have the potential to treat, and/or prevent a microorganism infection, or kill and/or inhibit the growth of microorganisms.

In a further aspect, the invention provides a method of treating and/or preventing a microorganism infection, or a method of killing and/or inhibiting the growth of a microorganism, said method comprising: contacting said microorganism with an effective amount of a compound of the invention, thereby killing and/or inhibiting the growth of the microorganism. In a further aspect, the invention provides a method of treating and/or preventing a microorganism infection, or a method of killing and/or inhibiting the growth of a microorganism, said method comprising: contacting said microorganism with an effective amount of a combination of the invention, thereby killing and/or inhibiting the growth of the microorganism.

In a further aspect, the invention provides a method of treating a bacterial infection comprising adminstering to an animal suffering from the infection an effective amount of a compound of the invention or a combination of the invention, or a pharmaceutically acceptable salt thereof, thereby treating the bacterial infection. In an exemplary embodiment, the invention provides a method of treating a bacterial infection comprising adminstering to an animal suffering from the infection an effective amount of a compound of the invention, or a pharmaceutically acceptable salt thereof, and an effective amount of an antibiotic, or a pharmaceutically acceptable salt thereof, thereby treating the bacterial infection.

In a further aspect, the invention provides a method of preventing a bacterial infection comprising adminstering to an animal a prophylactic amount of a compound of the invention or a combination of the invention, or a pharmaceutically acceptable salt thereof, thereby treating the bacterial infection. In an exemplary embodiment, the invention provides a method of preventing a bacterial infection comprising administering to an animal a prophylactic amount of a compound of the invention, or a pharmaceutically acceptable salt thereof.

In an exemplary embodiment, the microorganism is a bacteria. In an exemplary embodiment, the compound or combination is described herein, or a salt, prodrug, hydrate or solvate thereof, or a combination thereof. In an exemplary embodiment, the invention provides a compound or combination described herein, or a salt, hydrate or solvate thereof. In an exemplary embodiment, the invention provides a compound or combination described herein, or a prodrug thereof. In an exemplary embodiment, the invention provides a compound or combination described herein, or a salt thereof. In another exemplary embodiment, the compound or combination of the invention is a compound or combination described herein, or a pharmaceutically acceptable salt thereof. In another exemplary embodiment, the compound or compound of the combination is described by a formula listed herein, or a pharmaceutically acceptable salt thereof. In an exemplary embodiment, the compound is part of a combination described herein. In an exemplary embodiment, the compound is part of a pharmaceutical formulation described herein. In another exemplary embodiment, the contacting occurs under conditions which permit entry of the compound into the organism. Such conditions are known to one skilled in the art and are described herein.

In another aspect, the microorganism is inside, or on the surface of an animal. In an exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism infection is treated and or prevented, or the microorganism is killed or its growth is inhibited, through oral administration of the compound of the invention and/or the combination of the invention. In an exemplary embodiment, the microorganism infection is treated and or prevented, or the microorganism is killed or its growth is inhibited through intravenous administration of the compound of the invention and/or the combination of the invention.

In an exemplary embodiment, the microorganism is a bacterium. In an exemplary embodiment, an infection is caused by and/or associated with a microorganism, particularly a bacterium. In an exemplary embodiment, the bacterium is a gram-positive bacteria. In another exemplary embodiment, the gram-positive bacterium is selected from the group consisting of *Staphylococcus* species, *Streptococcus* species, *Bacillus species, Mycobacterium species, Corynebacterium* species (*Propionibacterium* species), *Clostridium* species, *Actinomyces* species, *Enterococcus* species and *Streptomyces* species. In another exemplary embodiment, the gram-positive bacterium is selected from the group consisting of *Pro-*

*pionibacterium acnes, Staphylococcus aureus, Staphylococcus epidermidis, Staphylococcus saprophyticus, Staphylococcus haemolyticus, Streptococcus pyogenes, Streptococcus agalactiae, Streptococcus pneumoniae, Enterococcus faecalis, Enterococcus faecium, Bacillus anthracis, Mycobacterium avium-intracellulare, Mycobacterium tuberculosis, Acinetobacter baumanii, Corynebacterium diphtheria, Clostridium perfringens, Clostridium botulinum, Clostridium tetani*, and *Clostridium difficile*. In another exemplary embodiment, the gram-positive bacterium is selected from the group consisting of *Staphylococcus aureus, Staphylococcus epidermidis, Streptococcus pneumoniae, Streptococcus pyogenes, Enterococcus faecalis, Enterococcus faecium, Clostridium difficile* and *Propionibacter acnes*. In another exemplary embodiment, the bacterium is a gram-negative bacterium. In another exemplary embodiment, the gram-negative bacterium is selected from the group consisting of *Acinetobacter* species, *Neisseria* species, *Pseudomonas* species, *Brucella* species, *Agrobacterium* species, *Bordetella* species, *Escherichia* species, *Shigelia* species, *Yersinia* species, *Salmonella* species, *Klebsiella* species, *Enterobacter* species, *Haemophilus* species, *Pasteurella* species, *Streptobacillus* species, *spirochetal* species, *Campylobacter* species, *Vibrio* species, *Helicobacter* species, *Bacteroides* species, *Citrobacter* species, *Proteus* species, *Providencia* species, *Serratia* species, *Stenotrophomonas* species and *Burkholderia* species. In another exemplary embodiment, the gram-negative bacterium is selected from the group consisting of *Acinetobacter* species, *Pseudomonas* species, *Escherichia* species, *Klebsiella* species, *Enterobacter* species, *Bacteroides* species, *Citrobacter* species, *Proteus* species, *Providencia* species, *Serratia* species, *Stenotrophomonas* species and *Burkholderia* species. In another exemplary embodiment, the gram-negative bacterium is selected from the group consisting of *Neisseria gonorrhoeae, Neisseria meningitidis, Pseudomonas aeruginosa, Legionella pneumophila, Escherichia coli, Yersinia pestis, Haemophilus influenzae, Helicobacter pylori, Campylobacter fetus, Campylobacter jejuni, Vibrio cholerae, Vibrio parahemolyticus, Trepomena pallidum, Actinomyces israelii, Rickettsia prowazekii, Rickettsia rickettsii, Chlamydia trachomatis, Chlamydia psittaci, Brucella abortus, Agrobacterium tumefaciens, Francisella tularensis, Klebsiella pneumoniae, Enterobacter cloacae, Acinetobacter baumannii, Bacteroides fragilis, Citrobacter freundii, Proteus mirabilis, Providencia stuartii, Serratia marcescens, Stenotrophomonas maltophilia* and *Burkholderia cepacia*. In another exemplary embodiment, the gram-negative bacterium is selected from the group consisting of *Pseudomonas aeruginosa, Escherichia coli, Haemophilus influenzae, Klebsiella pneumoniae, Enterobacter cloacae, Acinetobacter baumannii, Bacteroides fragilis, Citrobacter freundii, Proteus mirabilis, Providencia stuartii, Serratia marcescens, Stenotrophomonas maltophilia* and *Burkholderia cepacia*. In another exemplary embodiment, the gram-negative bacterium is selected from the group consisting of *Enterobacter aerogenes, Enterobacter cloacae, Enterobacter sakazakii, Escherichia coli, Klebsiella pneumoniae, Proteus mirabilis, Serratia marcescens* and *Citrobacter freundii*. In another exemplary embodiment, the gram-negative bacterium is a *Providencia* spp. In another exemplary embodiment, the gram-negative bacterium is an *Enterobacter* spp.

In another exemplary embodiment, the bacterium is a *Pseudomonas* species. In another exemplary embodiment, the bacterium is *Pseudomonas aeruginosa*. In another exemplary embodiment, the bacterium is selected from the group consisting of *Pseudomonas aeruginosa, Acinetobacter baumannii, Stenotrophomonas maltophilia* and *Burkholderia cepacia*. In another exemplary embodiment, the bacterium is *Acinetobacter baumannii*. In another exemplary embodiment, the bacterium is *Stenotrophomonas maltophilia*. In another exemplary embodiment, the bacterium is *Burkholderia cepacia*. In another exemplary embodiment, the bacterium is *Acinetobacter* species. In another exemplary embodiment, the bacterium is *Acinetobacter anitratus*. In another exemplary embodiment, the bacterium is selected from the group consisting of *Enterobacter aerogenes, Enterobacter cloacae, Enterobacter sakazakii, E. coli, K. pneumoniae, P. mirabilis, Serratia marcescens, Citrobacter freundii* and *Providencia* spp. In another exemplary embodiment, the bacterium is selected from the group consisting of *Enterobacter aerogenes, Enterobacter cloacae, Enterobacter sakazakii, E. coli, K. pneumoniae, P. mirabilis, Serratia marcescens, Citrobacter freundii, Providencia* spp., *S. aureus, S. pneumonia, S. pyogenes, E. faecalis,* and *E. faecium*. In another exemplary embodiment, the bacterium is selected from the group consisting of *Pseudomonas aeruginosa, Acinetobacter baumannii, Stenotrophomonas maltophilia, Burkholderia cepacia*. In another exemplary embodiment, the bacterium is selected from the group consisting of *S. aureus, S. pneumonia, S. pyogenes, E. faecalis,* and *E. faecium*. In another exemplary embodiment, the bacterium is selected from the group consisting of Viridans group Strep. In another exemplary embodiment, the bacterium is selected from the group consisting of Strep. mitis, Strep. mutans, Strep. oxalis, Strep. sanguis, Strep. sobrinus and Strep. millari. In another exemplary embodiment, the bacterium is *S. pneumonia*. In another exemplary embodiment, the bacterium is *H. influenzae*. In another exemplary embodiment, the bacterium is *S. aureus*. In another exemplary embodiment, the bacterium is *M. catarrhalis*. In another exemplary embodiment, the bacterium is *M. pneumoniae*. In another exemplary embodiment, the bacterium is *L. pneumoniae*. In another exemplary embodiment, the bacterium is *C. pneumoniae*. In another exemplary embodiment, the bacterium is *S. pyogenes*. In another exemplary embodiment, the bacterium is an anaerobe. In another exemplary embodiment, the bacterium is an *Alcaligenes* species. In another exemplary embodiment, the bacterium is a *B. cepacia*. In another exemplary embodiment, the bacterium is selected from the group consisting of *Enterobacter cloacae, Escherichia coli, Klebsiella pneumoniae, Proteus mirabilis, Providencia stuartii, Serratia marcescens,* and *Citrobacter freundii*. In another exemplary embodiment, the bacterium is resistant to methicillin. In another exemplary embodiment, the bacterium is methicillin-resistant *staphylococcus aureus*. In another exemplary embodiment, the bacterium is selected from the group consisting of *Streptococcus pneumoniae, Haemophilus influenzae, Staphylococcus aureus, Mycobacterium catarrhalis, Mycobacterium pneumoniae, Legionella pneumophila* and *Chlamydia pneumoniae*. In another exemplary embodiment, the bacterium is selected from the group consisting of *Enterobacter cloacae, Escherichia coli, Klebsiella pneumoniae, Proteus mirabilis, Serratia marcescens, Citrobacter freundii, Providencia stuartii, Pseudomonas aeruginosa, Acinetobacter baumannii, Stenotrophomonas maltophilia, Burkholderia cepacia, Staphylococcus aureus, Streptococcus pneumoniae, Streptococcus pyogenes, Enterococcus faecalis,* and *Enterococcus faecium*. In another exemplary embodiment, the bacterium is selected from the group consisting of *Staphylococcus aureus, Staphylococcus epidermidis, Staphylococcus haemolyticus, Streptococcus pyogenes, Streptococcus agalactiae* and *Streptococcus pneumoniae*.

In an exemplary embodiment, the microorganism is a bacterium, which is selected from the group consisting of acid-fast bacteria, including *Mycobacterium* species; bacilli, including *Bacillus* species, *Corynebacterium* species (also *Propionibacterium*) and *Clostridium* species; filamentous bacteria, including *Actinomyces species* and *Streptomyces* species; bacilli, such as *Pseudomonas* species, *Brucella* species, *Agrobacterium* species, *Bordetella* species, *Escherichia* species, *Shigella* species, *Yersinia* species, *Salmonella* species, *Klebsiella* species, *Enterobacter* species, *Haemophilus* species, *Pasteurella* species, and *Streptobacillus* species; spirochetal species, *Campylobacter* species, *Vibrio* species; and intracellular bacteria including *Rickettsiae* species and *Chlamydia* species.

VI. b) Microorganism Infection

The compounds of the invention and/or combinations of the invention exhibit potency against microorganisms, such as bacteria, and therefore have the potential to be used to treat and/or prevent a micororganism infection, such as a bacterial infection.

In a further aspect, the invention provides a method of treating a bacterial infection comprising adminstering to an animal suffering from the infection an effective amount of a compound of the invention, or a pharmaceutically acceptable salt thereof, thereby treating the bacterial infection. In an exemplary embodiment, the invention provides a method of treating a bacterial infection comprising adminstering to an animal suffering from the infection an effective amount of a compound of the invention, or a pharmaceutically acceptable salt thereof, and an effective amount of an antibiotic, or a pharmaceutically acceptable salt thereof, thereby treating the bacterial infection.

In a further aspect, the invention provides a method of preventing a bacterial infection comprising adminstering to an animal a prophylactic amount of a compound of the invention, or a pharmaceutically acceptable salt thereof, thereby treating the bacterial infection. In an exemplary embodiment, the invention provides a method of preventing a bacterial infection comprising adminstering to an animal a prophylactic amount of a compound of the invention, or a pharmaceutically acceptable salt thereof, and an effective amount of an antibiotic, or a pharmaceutically acceptable salt thereof, thereby treating the bacterial infection.

VI. c) Diseases

The compounds of the invention and/or combinations of the invention exhibit potency against microorganisms, such as bacteria, and therefore have the potential to achieve therapeutic efficacy in the animals described herein.

In another aspect, the invention provides a method of treating and/or preventing a disease. In an exemplary embodiment, the method includes administering to the animal a therapeutically effective amount of a compound of the invention, sufficient to treat and/or prevent the disease. In an exemplary embodiment, the method includes administering to the animal a therapeutically effective amount of a combination of the invention, sufficient to treat and/or prevent the disease. In an exemplary embodiment, the compound of the invention or the combination of the invention can be used in human or veterinary medical therapy, particularly in the treatment or prophylaxis of bacterial-associated disease. In an exemplary embodiment, the compound is described herein, or a salt, prodrug, hydrate or solvate thereof, or a combination thereof. In an exemplary embodiment, the invention provides a compound described herein, or a prodrug thereof. In an exemplary embodiment, the invention provides a compound described herein, or a salt, hydrate or solvate thereof. In an exemplary embodiment, the invention provides a compound described herein, or a salt thereof. In another exemplary embodiment, the compound of the invention is a compound described herein, or a pharmaceutically acceptable salt thereof. In an exemplary embodiment, the compound is a compound described herein, or a pharmaceutically acceptable salt thereof. In an exemplary embodiment, the compound is according to a formula described herein, or a pharmaceutically acceptable salt thereof. In an exemplary embodiment, the compound is part of a combination described herein. In an exemplary embodiment, the compound is part of a pharmaceutical formulation described herein. In another exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is selected from the group consisting of a human, cattle, goat, pig, sheep, horse, cow, bull, dog, guinea pig, gerbil, rabbit, cat, chicken and turkey. In another exemplary embodiment, the disease is a systemic disease. In another exemplary embodiment, the disease is a topical disease.

In an exemplary embodiment, the disease is treated through oral administration of a compound of the invention and/or a combination of the invention. In an exemplary embodiment, the disease is treated through intravenous administration of a compound of the invention and/or a combination of the invention.

Systemic Diseases

In another aspect, the invention provides a method of treating a systemic disease. The method involves contacting an animal with a compound of the invention and/or a combination of the invention.

In an exemplary embodiment, the disease is selected from the group consisting of candidiasis, aspergillosis, coccidioidomycosis, cryptococcosis, histoplasmosis, blastomycosis, paracoccidioidomycosis, zygomycosis, phaeohyphomycosis and rhinosporidiosis.

In another exemplary embodiment, the disease is associated with infection by a Gram-positive bacteria. In an exemplary embodiment, the disease is associated with a *Staphylococcus* species. In another exemplary embodiment, the disease is selected from the group consisting of pneumonia, gastroenteritis, toxic shock syndrome, community acquired pneumonia (CAP), meningitis, septic arthritis, urinary tract infection, bacteremia, endocarditis, osteomylitis, skin and skin-structure infection. In an exemplary embodiment, the disease is associated with a *Streptococcus* species. In another exemplary embodiment, the disease is selected from the group consisting of strep throat, skin infections, necrotizing fasciitis, toxic shock syndrome, pneumonia, otitis media and sinusitis. In an exemplary embodiment, the disease is associated with an *Actinomyces* species. In another exemplary embodiment, the disease is actinomycosis. In an exemplary embodiment, the disease is associated with a *Norcardia* species. In another exemplary embodiment, the disease is pneumonia. In an exemplary embodiment, the disease is associated with a *Corynebacterium* species. In another exemplary embodiment, the disease is diphtheria. In an exemplary embodiment, the disease is associated with a *Listeria* species. In another exemplary embodiment, the disease is meningitis. In an exemplary embodiment, the disease is associated with a

*Bacillus* species. In another exemplary embodiment, the disease is anthrax or food poisoning. In an exemplary embodiment, the disease is associated with a *Clostridium* species. In another exemplary embodiment, the disease is selected from the group consisting of botulism, tetanus, gas gangrene and diarrhea. In an exemplary embodiment, the disease is associated with a *Mycobacterium* species. In another exemplary embodiment, the disease is tuberculosis or leprosy.

In another exemplary embodiment, the disease is associated with infection by a Gram-negative bacteria. In an exemplary embodiment, the disease is associated with a *Neisseria* species. In another exemplary embodiment, the disease is selected from the group consisting of meningitis, gonorrhea, otitis extema and folliculitis. In an exemplary embodiment, the disease is associated with an *Escherichia* species. In another exemplary embodiment, the disease is selected from the group consisting of diarrhea, urinary tract infections, meningitis, sepsis and HAP. In an exemplary embodiment, the disease is associated with a *Shigella* species. In another exemplary embodiment, the disease is selected from the group consisting of diarrhea, bacteremia, endocarditis, meningitis and gastroenteritis. In an exemplary embodiment, the disease is associated with a *Salmonella* species. In another exemplary embodiment, the disease is selected from the group consisting of typhoid fever, supsis, gastroenteritis, endocarditis, sinusitis and meningitis. In an exemplary embodiment, the disease is associated with a *Yersinia* species. In another exemplary embodiment, the disease is selected from the group consisting of typhoid fever, bubonic plague, enteric fever and gastroenteritis. In an exemplary embodiment, the disease is associated with a *Klebsiella* species. In another exemplary embodiment, the disease is sepsis or urinary tract infection. In an exemplary embodiment, the disease is associated with a *Proteus* species. In another exemplary embodiment, the disease is an urinary tract infection. In an exemplary embodiment, the disease is associated with an *Enterobacter* species. In another exemplary embodiment, the disease is a hospital-acquired infection. In an exemplary embodiment, the disease is associated with a *Serratia* species. In another exemplary embodiment, the disease is selected from the group consisting of a urinary tract infection, skin and skin-structure infection and pneumonia. In an exemplary embodiment, the disease is associated with a *Vibrio* species. In another exemplary embodiment, the disease is cholera or gastroenteritis. In an exemplary embodiment, the disease is associated with a *Campylobacter* species. In another exemplary embodiment, the disease is gastroenteritis. In an exemplary embodiment, the disease is associated with a *Helicobacter* species. In another exemplary embodiment, the disease is chronic gastritis. In an exemplary embodiment, the disease is associated with a *Pseudomonas* species. In another exemplary embodiment, the disease is selected from the group consisting of pneumonia, osteomylitis, burn-wound infections, sepsis, UTIs, endocarditis, otitis and corneal infections. In an exemplary embodiment, the disease is associated with a *Bacteroides* species. In another exemplary embodiment, the disease is periodontal disease or aspriation pneumonia. In an exemplary embodiment, the disease is associated with a *Haemophilus* species. In another exemplary embodiment, the disease is selected from the group consisting of meningitis, epiglottitis, septic arthritis, sepsis, chancroid and vaginitis. In an exemplary embodiment, the disease is associated with a *Bordetella* species. In another exemplary embodiment, the disease is Whooping cough. In an exemplary embodiment, the disease is associated with a *Legionella* species. In another exemplary embodiment, the disease is pneumonia or pontiac fever. In an exemplary embodiment, the disease is associated with a *Francisella* species. In another exemplary embodiment, the disease is tularemia. In an exemplary embodiment, the disease is associated with a *Brucella* species. In another exemplary embodiment, the disease is brucellosis. In an exemplary embodiment, the disease is associated with a *Pasteurella* species. In another exemplary embodiment, the disease is a skin infection. In an exemplary embodiment, the disease is associated with a *Gardnerella* species. In another exemplary embodiment, the disease is vaginitis. In an exemplary embodiment, the disease is associated with a *Spirochetes* species. In another exemplary embodiment, the disease is syphilis or Lyme disease. In an exemplary embodiment, the disease is associated with a *Chlamydia* species. In another exemplary embodiment, the disease is chlamydia. In an exemplary embodiment, the disease is associated with a *Rickettsiae* species. In another exemplary embodiment, the disease is Rocky Mountain spotted fever or typhus.

In an exemplary embodiment, the disease is associated with *Mycoplasma pneumoniae*. In another exemplary embodiment, the disease is tracheobronchitis or walking pneumonia. In an exemplary embodiment, the disease is associated with *Ureaplasma urealyticum*. In another exemplary embodiment, the disease is urethritis. In another exemplary embodiment, the disease is pyelonephritis. In another exemplary embodiment, the disease is an intra-abdominal infection. In another exemplary embodiment, the disease is febrile neutropenia. In another exemplary embodiment, the disease is a pelvic infection. In another exemplary embodiment, the disease is bacteraemia. In another exemplary embodiment, the disease is septicaemia.

In another exemplary embodiment, the disease is community acquired pneumonia (CAP). In another exemplary embodiment, the disease is sinusitis. In another exemplary embodiment, the disease is a urinary tract infection. In another exemplary embodiment, the disease is a skin and skin-structure infection. In another exemplary embodiment, the disease is pyelonephritis. In another exemplary embodiment, the disease is intra-abdominal infection. In another exemplary embodiment, the disease is an acute pelvic infection. In another exemplary embodiment, the disease is tonsillitis.

In another exemplary embodiment, the disease is chronic obstructive pulmonary disease. In an exemplary embodiment, the disease is an acute exacerbaton of chronic obstructive pulmonary disease. In an exemplary embodiment, the disease is chronic obstructive pulmonary disease. In an exemplary embodiment, the disease is pharyngitis. In an exemplary embodiment, the disease is tonsillitis. In an exemplary embodiment, the disease is Acute Exacerbation of Chronic Bronchitis (AECB). In an exemplary embodiment, the disease is cervicitis. In an exemplary embodiment, the disease is genital ulcer disease.

In an exemplary embodiment, for any of the methods described herein, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, for any of the methods described herein, the animal is selected from the group consisting of a human, cattle, goat, pig, sheep, horse, cow, bull, dog, guinea pig, gerbil, rabbit, cat, chicken and turkey. In another exemplary embodiment, for any of the methods described herein, the animal is a human.

In an exemplary embodiment, for any of the methods described herein, a compound of the invention, a combination of the invention, a compound described herein or a pharmaceutically acceptable salt thereof, or combination described herein, and/or a pharmaceutical formulation described herein can be used.

VII. Pharmaceutical Formulation

In another aspect, the invention provides a pharmaceutical formulation comprising: a) a compound of the invention; and b) a pharmaceutically acceptable excipient. In another aspect, the invention provides a pharmaceutical formulation comprising: a) a combination of the invention; and b) a pharmaceutically acceptable excipient. In an exemplary embodiment, the compound is according to a formula described herein. In an exemplary embodiment, the compound is according to an example described herein. In an exemplary embodiment, the compound of the invention in the pharmaceutical formulation is a compound described herein. In an exemplary embodiment, the compound of the invention in the pharmaceutical formulation is a pharmaceutically acceptable salt of a compound described herein.

In an exemplary embodiment, the compound of the invention is present in the pharmaceutical formulation in an amount of between about 0.0001% to about 60% (w/w). In an exemplary embodiment, the amount is between about 0.01% to about 10% (w/w). In an exemplary embodiment, the amount is between about 0.1% to about 10% (w/w). In an exemplary embodiment, the amount is between about 0.25% to about 6% (w/w). In an exemplary embodiment, the amount is between about 0.5% to about 5% (w/w). In an exemplary embodiment, the amount is between about 0.1% and about 1.0% (w/w). In an exemplary embodiment, the amount is between about 1.0% and about 2.0% (w/w). In an exemplary embodiment, the amount is between about 2.0% and about 3.0% (w/w). In an exemplary embodiment, the amount is between about 3.0% and about 4.0% (w/w). In an exemplary embodiment, the amount is between about 4.0% and about 5.0% (w/w).

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethylsulfoxide (DMSO).

The pharmaceutical formulation of the invention may be administered orally, topically, intraperitoneally, parenterally, by inhalation or spray or rectally in unit dosage forms containing conventional non-toxic pharmaceutically acceptable carriers, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In an exemplary embodiment, the pharmaceutical formulation is administered orally. In an exemplary embodiment, the pharmaceutical formulation is administered intravenously. In an exemplary embodiment, the pharmaceutical formulation is administered topically. In an exemplary embodiment, the pharmaceutical formulation is administered in a topically effective dose. In an exemplary embodiment, the pharmaceutical formulation is administered in a cosmetically effective dose. In an exemplary embodiment, the pharmaceutical formulation is administered in an orally effective dose.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition of the invention may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a unit dosage form will vary depending upon the condition being treated and the particular mode of administration. Unit dosage forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

In an exemplary embodiment, the unit dosage form contains from about 1 mg to about 800 mg of a compound of the invention. In an exemplary embodiment, the unit dosage form contains from about 1 mg to about 500 mg of an active ingredient. In an exemplary embodiment, the unit dosage form contains from about 100 mg to about 800 mg of a compound of the invention. In an exemplary embodiment, the unit dosage form contains from about 200 mg to about 500 mg of a compound of the invention. In an exemplary embodiment, the unit dosage form contains from about 500 mg to about 800 mg of a compound of the invention. In an exemplary embodiment, the unit dosage form contains from about 1 mg to about 100 mg of a compound of the invention. In an exemplary embodiment, the unit dosage form contains from about 10 mg to about 100 mg of a compound of the invention. In an exemplary embodiment, the unit dosage form contains from about 50 mg to about 100 mg of a compound of the invention. In an exemplary embodiment, the unit dosage form contains from about 25 mg to about 75 mg of a compound of the invention. In an exemplary embodiment, the unit dosage form contains from about 40 mg to about 60 mg of a compound of the invention. In an exemplary embodiment, the unit dosage form contains from about 75 mg to about 200 mg of a compound of the invention. In an exemplary embodiment, the unit dosage form contains from about 1 mg to about 5 mg of a compound of the invention. In an exemplary embodiment, the unit dosage form contains from about 10 mg to about 25 mg of a compound of the invention. In an exemplary embodiment, the unit dosage form contains from about 50 mg to about 350 mg of a compound of the invention. In an exemplary embodiment, the unit dosage form contains from about 200 mg to about 400 mg of a compound of the invention.

In an exemplary embodiment, the daily dosage contains from about 1 mg to about 800 mg of a compound of the invention. In an exemplary embodiment, the daily dosage contains from about 1 mg to about 500 mg of an active ingredient. In an exemplary embodiment, the daily dosage contains from about 100 mg to about 800 mg of a compound of the invention. In an exemplary embodiment, the daily dosage contains from about 200 mg to about 500 mg of a compound of the invention. In an exemplary embodiment, the daily dosage contains from about 500 mg to about 800 mg of a compound of the invention. In an exemplary embodiment, the daily dosage contains from about 1 mg to about 100 mg of a compound of the invention. In an exemplary embodiment, the daily dosage contains from about 10 mg to about 100 mg of a compound of the invention. In an exemplary embodiment, the daily dosage contains from about 50 mg to about 100 mg of a compound of the invention. In an exemplary embodiment, the daily dosage contains from about 75 mg to about 200 mg of a compound of the invention. In an exemplary embodiment, the daily dosage contains from about 1 mg to about 5 mg of a compound of the invention. In an exemplary embodiment, the daily dosage contains from about 10 mg to about 25 mg of a compound of the invention. In an exemplary embodiment, the daily dosage contains from about 50 mg to about 350 mg of a compound of the invention. In an exemplary embodiment, the daily dosage contains from about 200 mg to about 400 mg of a compound of the invention.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

The amount of the composition required for use in treatment will vary not only with the particular compound selected but also with the route of administration, the nature of the condition being treated and the age and condition of the patient and will ultimately be at the discretion of the attendant physician or clinician.

VII. a) Testing

Preferred compounds for use in the pharmaceutical formulations described herein will have certain pharmacological properties. Such properties include, but are not limited to, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcova et al. (1996, *J. Chromat. B*677: 1-27).

Toxicity and therapeutic efficacy of such compounds can be determined by standard pharmaceutical procedures in cell cultures or experimental animals, e.g., for determining the LD50 (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the unit dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

VII. b) Administration

In general, the compounds prepared by the methods, and from the intermediates, described herein will be administered in a therapeutically or cosmetically effective amount by any of the accepted modes of administration for agents that serve similar utilities. It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician. The drug can be administered from once or twice a day, or up to 3 or 4 times a day.

Usual patient dosages for systemic administration range from 0.1 to 1000 mg/day, preferably, 1-500 mg/day, more preferably 10-200 mg/day, even more preferably 100-200 mg/day. Stated in terms of patient body surface areas, usual dosages range from 50-91 mg/m$^2$/day.

The amount of the compound in a pharmaceutical formulation can vary within the full range employed by those skilled in the art. Typically, the pharmaceutical formulation will contain, on a weight percent (wt %) basis, from about 0.01-10 wt % of the drug based on the total formulation, with the balance being one or more suitable pharmaceutical excipients. Preferably, the compound is present at a level of about 0.1-3.0 wt %, more preferably, about 1.0 wt %.

Exemplary embodiments are summarized herein below.

In an exemplary embodiment, the invention is a compound, or a salt thereof, having a structure which is

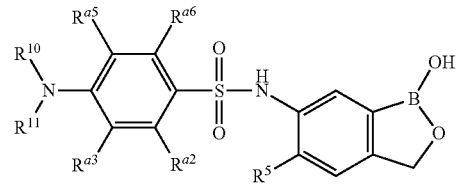

wherein $R^5$ is H or halogen, one of $R^{a2}$, $R^{a3}$, $R^{a5}$ and $R^{a6}$ is halogen or —NHC(O)OR$^{30}$ or alkyl substituted with —C(O)OR$^{30}$ or alkyl substituted with —S(O)$_2$R$^{30}$ or alkyl substituted with halogen or alkyl substituted with hydroxy or alkyl substituted with cyano or alkyl substituted with —NHC(O)OR$^{30}$ or alkyl substituted with unsubstituted oxazolyl or alkyl substituted with alkyl substituted oxazolyl or alkyl substituted with unsubstituted oxadiazolyl or alkyl substituted with alkyl substituted oxadiazolyl or alkyl substituted with —C(O)NHR$^{35}$, wherein R$^{30}$ is unsubstituted alkyl and R$^{35}$ is unsubstituted alkyl or unsubstituted cycloalkyl, and the remaining members of $R^{a2}$, $R^{a3}$, $R^{a5}$ and $R^{a6}$ are H, R$^{10}$ and R$^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to the above paragraph, wherein each hydrogen in said compound, or a salt thereof, is independently H or D.

In an exemplary embodiment, according to either of the above paragraphs, wherein each hydrogen in said compound, or a salt thereof, is independently H or D.

In an exemplary embodiment, according to any of the above paragraphs, having a structure which is

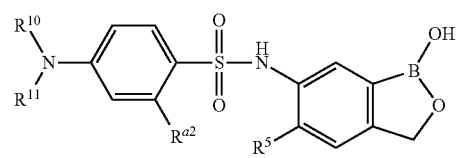

wherein $R^5$ is H or halogen, $R^{a2}$ is halogen or —NHC(O)OR$^{30}$ or alkyl substituted with —C(O)OR$^{30}$ or alkyl substituted with —S(O)$_2$R$^{30}$ or alkyl substituted with halogen or alkyl substituted with hydroxy or alkyl substituted with cyano or alkyl substituted with —NHC(O)OR$^{30}$ or alkyl substituted with unsubstituted oxazolyl or alkyl substituted with alkyl substituted oxazolyl or alkyl substituted with unsubstituted oxadiazolyl or alkyl substituted with alkyl substituted oxadiazolyl or alkyl substituted with —C(O)NHR$^{35}$, wherein R$^{30}$ is unsubstituted alkyl and R$^{35}$ is unsubstituted alkyl or unsubstituted cycloalkyl, R$^{10}$ and R$^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, wherein each hydrogen in said R$^{a2}$ or said R$^5$ is independently H or D.

In an exemplary embodiment, according to any of the above paragraphs, wherein R$^5$ is H.

In an exemplary embodiment, according to any of the above paragraphs, wherein R$^5$ is F.

In an exemplary embodiment, according to any of the above paragraphs, having a structure which is

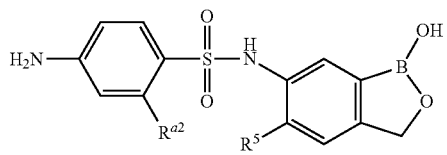

In an exemplary embodiment, according to any of the above paragraphs, R$^{a2}$ is CH$_2$NHC(O)OR$^{30}$ or CH$_2$C(O)OR$^{30}$ or CH$_2$S(O)$_2$R$^{30}$ or CH$_2$CN or CH$_2$C(O)NHR$^{35}$ or methyl substituted with unsubstituted oxazolyl or methyl substituted with alkyl substituted oxazolyl or methyl substituted with unsubstituted oxadiazolyl or methyl substituted with alkyl substituted oxadiazolyl, wherein R$^{30}$ is unsubstituted alkyl and R$^{35}$ is unsubstituted alkyl or unsubstituted cycloalkyl.

In an exemplary embodiment, according to any of the above paragraphs, wherein each hydrogen in said R$^{a2}$ is independently H or D.

In an exemplary embodiment, according to any of the above paragraphs, wherein each hydrogen in said R$^{30}$ is independently H or D.

In an exemplary embodiment, according to any of the above paragraphs, wherein each hydrogen in said R$^{35}$ is independently H or D.

In an exemplary embodiment, according to any of the above paragraphs, wherein R$^{a2}$ is CH$_2$NHC(O)OR$^{30}$ or CH$_2$C(O)OR$^{30}$ or CH$_2$S(O)$_2$R$^{30}$, and R$^{30}$ is CH$_3$ or CH$_2$CH$_3$ or CH$_2$CH$_2$CH$_3$ or CH(CH$_3$)$_2$ or CH$_2$CH$_2$CH$_2$CH$_3$ or C(CH$_3$)$_3$ or C(CH$_3$)(CH$_2$CH$_3$), wherein each hydrogen in said R$^{a2}$ is independently H or D.

In an exemplary embodiment, according to any of the above paragraphs, wherein R$^{a2}$ is CH$_2$NHC(O)OR$^{30}$ or CH$_2$C(O)OR$^{30}$ or CH$_2$S(O)$_2$R$^{30}$, and R$^{30}$ is CH$_3$ or CH$_2$CH$_3$ or CH$_2$CH$_2$CH$_3$ or CH(CH$_3$)$_2$ or CH$_2$CH$_2$CH$_2$CH$_3$ or C(CH$_3$)$_3$ or C(CH$_3$)(CH$_2$CH$_3$), wherein each hydrogen in said R$^{30}$ is independently H or D.

In an exemplary embodiment, according to any of the above paragraphs, R$^{a2}$ is CH$_2$NHC(O)OR$^{30}$ or CH$_2$C(O)OR$^{30}$ or CH$_2$S(O)$_2$R$^{30}$, and R$^{30}$ is CH$_3$ or CD$_3$ or CD$_2$H or CDH$_2$ or CH$_2$CH$_3$ or CH$_2$CD$_3$ or CH$_2$CD$_2$H or CH$_2$CDH$_2$ or CH$_2$CH$_2$CH$_3$ or CH$_2$CH$_2$CD$_3$ or CH$_2$CH$_2$CD$_2$H or CH$_2$CH$_2$CDH$_2$ or CH(CH$_3$)$_2$ or CH(CD$_3$)$_2$ or CH(CD$_3$)(CH$_3$) or CH$_2$CH$_2$CH$_2$CH$_3$ or CH$_2$CH$_2$CH$_2$CD$_3$ or CH$_2$CH$_2$CH$_2$CD$_2$H or CH$_2$CH$_2$CH$_2$CDH$_2$ or C(CH$_3$)$_3$ or C(CD$_3$)$_3$ or C(CD$_3$)(CH$_3$)$_2$ or C(CD$_3$)$_2$(CH$_3$) or CH(CH$_3$)(CH$_2$CH$_3$) or CH(CD$_3$)(CH$_2$CH$_3$) or CH(CH$_3$)(CH$_2$CD$_3$) or CH(CD$_3$)(CH$_2$CD$_3$).

In an exemplary embodiment, according to any of the above paragraphs, R$^{a2}$ is CH$_2$NHC(O)OR$^{30}$ or CH$_2$C(O)OR$^{30}$ or CH$_2$S(O)$_2$R$^{30}$, and R$^{30}$ is CH$_3$ or CD$_3$ or CD$_2$H or CDH$_2$ or CH$_2$CH$_3$ or CH$_2$CD$_3$ or CH$_2$CD$_2$H or CH$_2$CDH$_2$ or CH$_2$CH$_2$CH$_3$ or CH$_2$CH$_2$CD$_3$ or CH$_2$CH$_2$CD$_2$H or CH$_2$CH$_2$CDH$_2$ or CH(CH$_3$)$_2$ or CH(CD$_3$)$_2$ or CH(CD$_3$)(CH$_3$) or CH$_2$CH$_2$CH$_2$CH$_3$ or CH$_2$CH$_2$CH$_2$CD$_3$ or CH$_2$CH$_2$CH$_2$CD$_2$H or CH$_2$CH$_2$CH$_2$CDH$_2$ or C(CH$_3$)$_3$ or C(CD$_3$)$_3$ or C(CD$_3$)(CH$_3$)$_2$ or C(CD$_3$)$_2$(CH$_3$) or CH(CH$_3$)(CH$_2$CH$_3$) or CH(CD$_3$)(CH$_2$CH$_3$) or CH(CH$_3$)(CH$_2$CD$_3$) or CH(CD$_3$)(CH$_2$CD$_3$).

In an exemplary embodiment, according to any of the above paragraphs, R$^{a2}$ is CH$_2$NHC(O)OR$^{30}$ or CH$_2$C(O)OR$^{30}$ or CH$_2$S(O)$_2$R$^{30}$, and R$^{30}$ is CH$_3$ or CD$_3$ or CD$_2$H or CDH$_2$ or CH$_2$CH$_3$ or CH$_2$CD$_3$ or CH$_2$CD$_2$H or CH$_2$CDH$_2$.

In an exemplary embodiment, according to any of the above paragraphs, R$^{a2}$ is CH$_2$NHC(O)OR$^{30}$ or CH$_2$C(O)OR$^{30}$ or CH$_2$S(O)$_2$R$^{30}$, and R$^{30}$ is CH$_3$ or CD$_3$ or CD$_2$H or CDH$_2$.

In an exemplary embodiment, according to any of the above paragraphs, R$^{a2}$ is CH$_2$C(O)OR$^{30}$, and R$^{30}$ is CH$_3$ or CD$_3$ or CD$_2$H or CDH$_2$.

In an exemplary embodiment, according to any of the above paragraphs, wherein R$^{a2}$ is CH$_2$NHC(O)OCH$_3$ or CH$_2$C(O)OCH$_3$ or CH$_2$S(O)$_2$CH$_3$.

In an exemplary embodiment, according to any of the above paragraphs, wherein R$^5$ is H and R$^{a2}$ is CH$_2$C(O)OR$^{30}$, and R$^{30}$ is CH$_3$ or CH$_2$CH$_3$ or CH$_2$CH$_2$CH$_3$ or CH(CH$_3$)$_2$ or CH$_2$CH$_2$CH$_2$CH$_3$ or C(CH$_3$)$_3$ or CH(CH$_3$)(CH$_2$CH$_3$), wherein each hydrogen in said R$^{a2}$ is independently H or D.

In an exemplary embodiment, according to any of the above paragraphs, wherein R$^5$ is H and R$^{a2}$ is CH$_2$C(O)OR$^{30}$, and R$^{30}$ is CH$_3$ or CD$_3$ or CD$_2$H or CDH$_2$ or CH$_2$CH$_3$ or CH$_2$CD$_3$ or CH$_2$CD$_2$H or CH$_2$CDH$_2$.

In an exemplary embodiment, according to any of the above paragraphs, wherein R$^{a2}$ is CH$_2$C(O)NHR$^{35}$, wherein R$^{35}$ is cyclobutyl or cyclopentyl or cyclohexyl.

In an exemplary embodiment, according to any of the above paragraphs, R$^{a2}$ is F or Cl or Br or CH$_2$CH$_2$F or CH$_2$CH$_2$OH or —NHC(O)OR$^{30}$, wherein R$^{30}$ is methyl or ethyl or propyl or isopropyl or butyl or t-butyl or isobutyl.

In an exemplary embodiment, according to any of the above paragraphs, R$^{a2}$ is methyl substituted with 4-methyloxazol-2-yl or methyl substituted with 5-methyloxazol-2-yl or methyl substituted with 5-propyl-1,3,4 oxadiazol-2-yl or methyl substituted with 5-methyl-1,2,4 oxadiazol-2-yl.

In an exemplary embodiment, the invention is a combination comprising a) a compound according to any of the above paragraphs, or a pharmaceutically acceptable salt thereof; and b) at least one therapeutic agent.

In an exemplary embodiment, the invention is a pharmaceutical formulation comprising a) a compound according to any of the above paragraphs or a combination according to any of the above paragraphs, or a pharmaceutically acceptable salt thereof; and b) a pharmaceutically acceptable excipient.

In an exemplary embodiment, according to any of the above paragraphs, the formulation is a unit dosage form.

In an exemplary embodiment, according to any of the above paragraphs, the formulation is an oral unit dosage form or a topical unit dosage form.

In an exemplary embodiment, the invention is a method of killing or inhibiting the growth of a bacteria comprising: contacting said bacteria with an effective amount of a compound or a combination according to any of the above paragraphs, or a pharmaceutically acceptable salt thereof, thereby killing or inhibiting the growth of the bacteria.

In an exemplary embodiment, the invention is a method of treating a bacterial infection comprising: administering to an animal suffering from said infection an effective amount of a compound or a combination according to any of the above paragraphs, or a pharmaceutically acceptable salt thereof, thereby treating the bacterial infection.

In an exemplary embodiment, according to any of the above paragraphs, the animal is a human.

In an exemplary embodiment, the invention is a use of a compound or a combination according to any of the above paragraphs, or a pharmaceutically acceptable salt thereof, in the manufacture of a medicament for the treatment and/or prophylaxis of bacterial infection.

In an exemplary embodiment, the invention is a method of inhibiting the editing domain of a t-RNA synthetase, comprising: contacting the synthetase with an effective amount of a compound described herein, or a pharmaceutically acceptable salt thereof, thereby inhibiting the synthetase.

In an exemplary embodiment, according to any of the above paragraphs, the synthetase is a leucyl t-RNA synthetase.

The invention is further illustrated by the Examples that follow. The Examples are not intended to define or limit the scope of the invention.

EXAMPLES

Proton NMR were recorded on Varian AS 300 spectrometer and chemical shifts are reported as δ (ppm) down field from tetramethylsilane. Mass spectra were determined on Micromass Quattro II.

Example 1

4-Amino-N-(1-hydroxy-1,3-dihydro-benzo[c][1,2]oxaborol-6-yl)-3-trifluoromethyl-benzenesulfonamide

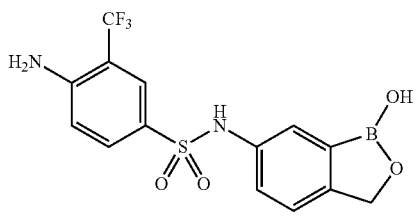 [SMILES: Nc1ccc(S(=O)(=O)Nc2ccc3c(c2)B(O)OC3)cc1C(F)(F)F]

N-(1-Hydroxy-1,3-dihydro-benzo[c][1,2]oxaborol-6-yl)-4-nitro-3-trifluoromethyl-benzenesulfonamide General Procedure 1: 6-amino-3H-benzo[c][1,2]oxaborol-1-ol (250 mg, 1.7 mmol), 4-nitro-3-(trifluoromethyl)benzenesulfonyl chloride (578 mg, 2.0 mmol), Si-pyridine (4.7 g, 6.8 mmol), and MeCN (20 mL) at rt O/N. Si-amine (1.0 g, 1.79 mmol) was added and the mixture stirred at rt for 1.5 h. The mixture was filtered through a pad of celite and the filtrate was concentrated in vacuo at 40° C. The residue was recrystallization from MeCN/H$_2$O to give a white solid (410 mg). Purification by prep HPLC, followed by lyophilization gave the title compound as a white solid: yield; 284 mg (42%). $^1$H NMR (400 MHz, DMSO-d$_6$) δ (ppm): 10.65 (s, 1H), 9.26 (s, 1H), 8.34-8.33 (m, 1H), 8.21-8.18 (m, 2H), 7.51-7.50 (m, 1H), 7.35-7.33 (m, 1H), 7.20-7.17 (m, 1H), 4.91 (s, 2H); $^{19}$F NMR (376 MHz, DMSO-d$_6$) δ (ppm): −59.7 (s); MS (ESI) m/z=401 (M−1, negative); HPLC purity: 97.66% (MaxPlot 200-400 nm), 98.45% (220 nm).

4-Amino-N-(1-hydroxy-1,3-dihydro-benzo[c][1,2]oxaborol-6-yl)-3-trifluoromethyl-benzenesulfonamide A suspension of N-(1-hydroxy-1,3-dihydro-benzo[c][1,2]oxaborol-6-yl)-4-nitro-3-trifluoromethyl-benzenesulfonamide (212 mg, 0.53 mmol), 10% Pd/C (50 mg), and abs. EtOH (100 mL) was shaken in a Parr apparatus at rt under an atmosphere of H$_2$ (50 psi) for 2 h. The mixture was filtered through Celite (washing with EtOH) and then a 0.2 μM filter. The filtrate was concentrated in vacuo at 40° C. and the residue was recrystallized (MeCN/H$_2$O) to give the title compound as a white solid; yield 122 mg (62%). mp 178-179° C.; $^1$H NMR (400 MHz, DMSO-d$_6$) δ (ppm): 9.98 (s, 1H), 9.22 (s, 1H), 7.65-7.64 (m, 1H), 7.54-7.51 (m, 1H), 7.48-7.47 (m, 1H), 7.28-7.26 (m, 1H), 7.16-7.14 (m, 1H), 6.82-6.79 (m, 1H), 6.49 (s, 2H), 4.88 (s, 2H); $^{19}$F NMR (376 MHz, DMSO-d$_6$) δ (ppm): −63.0 (s); MS (ESI) m/z=371 (M−1, negative); HPLC purity: 98.02% (MaxPlot 200-400 nm), 98.34% (220 nm).

4-Amino-3-fluoro-N-(1-hydroxy-1,3-dihydro-benzo[c][1,2]oxaborol-6-yl)-benzenesulfonamide

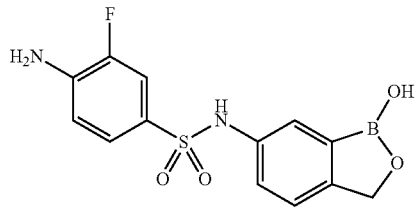 [SMILES: Nc1ccc(S(=O)(=O)Nc2ccc3c(c2)B(O)OC3)cc1F]

3-Fluoro-N-(1-hydroxy-1,3-dihydro-benzo[c][1,2]oxaborol-6-yl)-4-nitro-benzenesulfonamide General Procedure 1: 6-amino-3H-benzo[c][1,2]oxaborol-1-ol (500 mg, 3.35 mmol), 3-fluoro-4-nitrobenzenesulfonyl chloride (0.96 g, 4.0 mmol), pyridine (1.10 mL, 13.4 mmol), and MeCN (10 mL) at rt O/N. The mixture was concentrated in vacuo and H$_2$O (7.5 mL) and EtOAc (20 mL) were added. The mixture was stirred until a clear biphasic solution was observed. The aqueous layer was loaded onto an Isolute HM-N column and left to stand for 10 min. The organic layer was then eluted through the column. The column was then further washed with EtOAc (30 mL). The organic fractions were concentrated in vacuo and the residue was dissolved in EtOAc and loaded onto a pre-column (silica, 12 g). Purification by flash chromatography (silica, 40 g; 30-100% EtOAc/hexane) gave a yellow oil which was dissolved in MeCN/H$_2$O. Concentration in vacuo gave the title compound as a white solid: yield; 160 mg (14%). $^1$H NMR (400 MHz, DMSO-d$_6$) δ (ppm): 10.56 (bs, 1H), 9.22 (s, 1H), 8.32-8.28 (m, 1H), 7.87-7.84 (m, 1H), 7.71-7.69 (m, 1H), 7.48-7.47 (m, 1H), 7.31-7.29 (m, 1H), 7.19-7.17 (m, 1H), 4.88 (s, 2H); $^{19}$F NMR (376 MHz, DMSO-d$_6$) δ (ppm): −155.85 (s); MS (ESI) m/z=351 (M−1, negative); HPLC purity: 90.38% (MaxPlot 200-400 nm), 89.75% (220 nm).

4-Amino-3-fluoro-N-(1-hydroxy-1,3-dihydro-benzo[c][1,2]oxaborol-6-yl)-benzenesulfonamide A suspension of N-(1-hydroxy-1,3-dihydro-benzo[c][1,2]oxaborol-6-yl)-2-hydroxy-4-nitro-benzenesulfonamide (112 mg, 0.32 mmol), 10% Pd/C (40 mg), and abs. EtOH (50 mL) was shaken in a Parr apparatus at rt under an atmosphere of $H_2$ (50 psi) for 3 h. The mixture was filtered through Celite (washing with EtOH) and then a 0.2 μM filter. The filtrate was concentrated in vacuo at 40° C. The residue was purified by prep HPLC [MeCN/0.1% $HCO_2H$ (aq)]. The major fraction was concentrated in vacuo at 40° C. and lyophilization from 1 M HCl gave the title compound as a yellow solid; yield 65 mg (63%). $^1$H NMR (400 MHz, DMSO-$d_6$) δ (ppm): 9.92 (s, 1H), 7.45-7.44 (m, 1H), 7.29-7.24 (m, 2H), 7.23 (s, 2H), 7.20-7.19 (m, 1H), 7.15-7.12 (m, 1H), 6.73-6.69 (m, 1H), 4.86 (s, 2H); $^{19}$F NMR (376 MHz, DMSO-$d_6$) δ (ppm): −134.73 (t); MS (ESI) m/z=321 (M−1, negative); HPLC purity: 98.69% (MaxPlot 200-400 nm), 98.83% (220 nm).

2-Oxo-2,3-dihydro-1H-indole-5-sulfonic acid (1-hydroxy-1,3-dihydro-benzo[c][1,2]oxaborol-6-yl)-amide

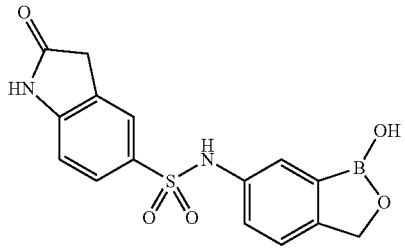 [SMILES: O=C1Cc2cc(S(=O)(=O)Nc3ccc4c(c3)B(O)OC4)ccc2N1]

General Procedure 1: 6-Amino-3H-benzo[c][1,2]oxaborol-1-ol (138 mg, 0.9 mmol), 2-oxoindoline-5-sulfonyl chloride (250 mg, 1.1 mmol), pyridine (0.4 mL, 5.2 mmol), DMSO (2 mL), and MeCN (10 mL) at rt O/N. The mixture was concentrated in vacuo at 40° C. and the remaining DMSO solution was partitioned by RP-Biotage (10-100% MeOH/0.1% aq TFA). The major fraction was concentrated in vacuo at 40° C. and then lyophilized to give the title compound as a yellow solid: yield; 195 mg (63%). $^1$H NMR (400 MHz, DMSO-$d_6$) δ (ppm): 10.74 (s, 1H), 10.12 (s, 1H), 9.21 (s, 1H), 7.59-7.57 (m, 3H), 7.48-7.47 (m, 1H), 7.26-7.25 (m, 1H), 7.19-7.18 (m, 1H), 6.89-6.87 (m, 1H), 4.87 (s, 2H), 3.53 (s, 2H); MS (ESI) m/z=343 (M−1, negative); HPLC purity: 96.974% (MaxPlot 200-400 nm), 97.18% (220 nm).

2-Oxo-2,3-dihydro-benzooxazole-6-sulfonic acid (1-hydroxy-1,3-dihydro-benzo[c][1,2]oxaborol-6-yl)-amide

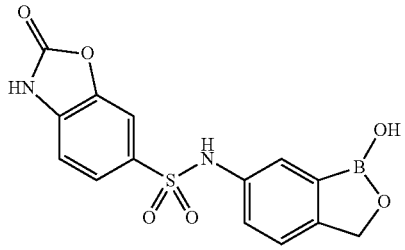 [SMILES: O=c1[nH]c2ccc(S(=O)(=O)Nc3ccc4c(c3)B(O)OC4)cc2o1]

General Procedure 1: 6-Amino-3H-benzo[c][1,2]oxaborol-1-ol (200 mg, 1.3 mmol), 2-oxo-2,3-dihydrobenzooxazole-6-sulfonyl chloride (373 mg, 1.6 mmol), pyridine (0.4 mL, 5.2 mmol), DMSO (2 mL), and MeCN (10 mL) at rt O/N. The mixture was concentrated in vacuo at 40° C. and the remaining DMSO solution was partitioned by RP-Biotage (10-100% MeOH/0.1% aq TFA). The major fraction was concentrated in vacuo at 40° C. and then lyophilized to give the title compound as a white solid: yield; 249 mg (55%). $^1$H NMR (400 MHz, DMSO-$d_6$) δ (ppm): 12.11 (s, 1H), 10.21 (s, 1H), 9.21 (bs, 1H), 7.62-7.61 (m, 1H), 7.54-7.51 (m, 1H), 7.49-7.48 (m, 1H), 7.28-7.25 (m, 1H), 7.20-7.17 (m, 2H), 4.88 (s, 2H); MS (ESI) m/z=345 (M−1, negative); HPLC purity: 98.51% (MaxPlot 200-400 nm), 98.46% (220 nm).

2-Oxo-2,3-dihydro-benzooxazole-6-sulfonic acid (1-hydroxy-1,3-dihydro-benzo[c][1,2]oxaborol-6-yl)-amide

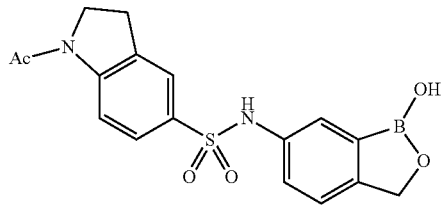 [SMILES: CC(=O)N1CCc2cc(S(=O)(=O)Nc3ccc4c(c3)B(O)OC4)ccc21]

1-Acetyl-2,3-dihydro-1H-indole-5-sulfonyl chloride

Chlorosulfonic acid (3 mL, 45 mmol) was added slowly to N-acetylindoline (1.0 g, 6.2 mmol), resulting in a strongly exothermic reaction. The mixture was then heated to 70° C. for 2 h. The mixture was allowed to cool to rt and was then poured onto crushed ice resulting in the formation of a cream precipitate that was isolated by filtration to give the title compound as a cream solid: yield; 1.34 g (52%). $^1$H NMR (400 MHz, DMSO-$d_6$) δ (ppm): 7.93-7.91 (m, 1H), 7.41-7.40 (m, 1H), 7.40-7.38 (m, 1H), 4.06 (t, J=7.8 Hz, 2H), 3.09 (t, J=7.8 Hz, 2H), 2.13 (s, 3H).

2-Oxo-2,3-dihydro-benzooxazole-6-sulfonic acid (1-hydroxy-1,3-dihydro-benzo[c][1,2]oxaborol-6-yl)-amide General Procedure 1: 6-amino-3H-benzo[c][1,2]oxaborol-1-ol (607 mg, 4.1 mmol), 1-acetyl-2,3-dihydro-1H-indole-5-sulfonyl chloride (1.27 g, 4.9 mmol), pyridine (1.3 mL, 16.4 mmol), and MeCN (20 mL) at rt O/N. The mixture was concentrated in vacuo at 40° C. The residue was purified by RP-Biotage (10-100% MeOH/0.1% aq TFA). The major fraction was concentrated in vacuo at 50° C. and then lyophilized to give the title compound as a white solid: yield; 520 mg (35%). mp 208-209° C.; $^1$H NMR (400 MHz, DMSO-d6) δ (ppm): 10.10 (s, 1H), 9.19 (s, 1H), 8.05-8.03 (m, 1H), 7.55-7.53 (m, 2H), 7.46-7.45 (m, 1H), 7.24-7.23 (m, 1H), 7.16-7.14 (m, 1H), 4.85 (s, 2H), 4.11 (t, J=7.8 Hz, 2H), 3.12 (t, J=7.8 Hz, 2H), 2.13 (s, 3H); MS (ESI) m/z=373 (M+H, positive); HPLC purity: 94.58% (MaxPlot 200-400 nm), 94.82% (220 nm).

2-Oxo-2,3-dihydro-1H-benzoimidazole-5-sulfonic acid (1-hydroxy-1,3-dihydro-benzo[c][1,2]oxaborol-6-yl)-amide

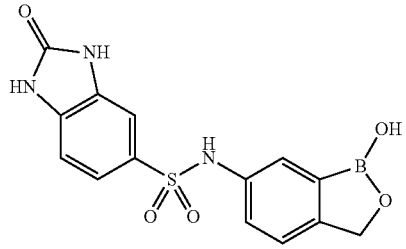 [SMILES: O=c1[nH]c2ccc(S(=O)(=O)Nc3ccc4c(c3)B(O)OC4)cc2[nH]1]

General Procedure 1: 6-amino-3H-benzo[c][1,2]oxaborol-1-ol (0.426 g, 2.86 mmol), MeCN (10 mL), pyridine (0.694 mL, 8.58 mmol), and 2-oxo-2,3-dihydro-1H-benzoimidazole-5-sulfonyl chloride (0.634 g, 2.72 mmol). Purification: precipitation from acidic H$_2$O upon THF removal. The title compound was isolated as a light-orange solid: yield 410 mg (44%). mp>300° C.; $^1$H NMR (400 MHz, DMSO-d$_6$) δ (ppm): 11.07 (s, 1H), 10.95 (s, 1H), 10.07 (s, 1H), 9.20 (s, 1H), 7.47 (d, J=2.0 Hz, 1H), 7.35 (dd, J=8.2, 1.6 Hz, 1H), 7.26-7.24 (m, 2H), 7.16 (dd, J=8.2, 2.0 Hz, 1H), 7.00 (d, J=8.2 Hz, 1H), 4.87 (s, 2H); MS (ESI) m/z=346 (M+1, positive); HPLC purity: 92.46% (MaxPlot 200-400 nm), 94.23% (220 nm); Anal. Calcd for C$_{14}$H$_{12}$BN$_3$O$_5$S: C, 48.72%; H, 3.50%; N, 12.17%. Found: C, 48.93%; H, 3.70%; N, 11.97%.

2,3-Dioxo-1,2,3,4-tetrahydro-quinoxaline-6-sulfonic acid (1-hydroxy-1,3-dihydro-benzo[c][1,2]oxaborol-6-yl)-amide

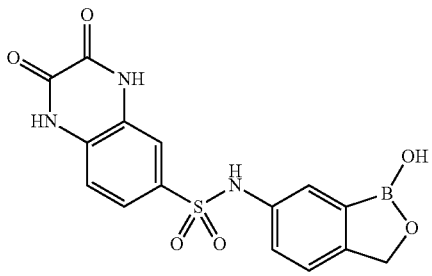 [SMILES: O=c1[nH]c2ccc(S(=O)(=O)Nc3ccc4c(c3)B(O)OC4)cc2[nH]c1=O]

General Procedure 1: 6-amino-3H-benzo[c][1,2]oxaborol-1-ol (0.432 g, 2.90 mmol), MeCN (10 mL), pyridine (0.704 mL, 8.70 mmol), and 2,3-dioxo-1,2,3,4-tetrahydro-quinoxaline-6-sulfonyl chloride (0.719 g, 2.76 mmol). Purification: precipitation from acidic H$_2$O upon THF removal. The title compound was isolated as a light-orange solid: yield 605 mg (59%). mp>300° C.; $^1$H NMR (400 MHz, DMSO-d$_6$) δ (ppm): 12.13 (s, 1H), 12.06 (s, 1H), 10.26 (s, 1H), 9.21 (br.s, 1H), 7.50-7.47 (m, 2H), 7.42 (dd, J=8.2, 1.6 Hz, 1H), 7.27 (d, J=8.2 Hz, 1H), 7.19-7.15 (m, 2H), 4.89 (s, 2H); MS (ESI) m/z=374 (M+1, positive); HPLC purity: 96.47% (MaxPlot 200-400 nm), 98.01% (220 nm); Anal. Calcd for C$_{15}$H$_{12}$BN$_3$O$_6$S.1H$_2$O: C, 46.06%; H, 3.61%; N, 10.74%. Found: C, 46.15%; H, 3.62%; N, 10.90%.

N-(1-hydroxy-1,3-dihydrobenzo[c][1,2]oxaborol-6-yl)-1-(2,2,2-trifluoroacetyl)indoline-5-sulfonamide

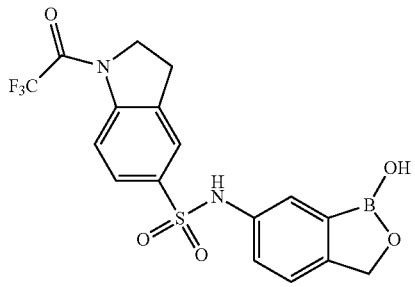 [SMILES: O=C(N1CCc2cc(S(=O)(=O)Nc3ccc4c(c3)B(O)OC4)ccc21)C(F)(F)F]

2,2,2-Trifluoro-1-(indolin-1-yl)ethanone

Indoline (5 g, 42 mmol) was dissolved in pyridine (50 mL) and cooled to 0° C. Trifluoroacetic anhydride (7 mL, 1.2 eq) was added dropwise and the solution was allowed to warm to rt and stirred for an additional 2 hrs. All solvent was removed under vacuum and the residue partitioned between EtOAc and 1M HCl. Evaporated to 8.59 g of the title compound as a red colored solid.

1-(2,2,2-Trifluoroacetyl)indoline-5-sulfonyl chloride 2,2,2-trifluoro-1-(indolin-1-yl)ethanone (5 g, 16 mmol) was added to neat chlorosulfonic acid at 0° C. and then the solution was allowed to warm to rt and stirred for an additional 2 hrs. Reaction mixture was slowly added to ice chips and stirred for 10 min then filtered off 4.2 g of the title compound as a dark red colored solid.

N-(1-Hydroxy-1,3-dihydrobenzo[c][1,2]oxaborol-6-yl)-1-(2,2,2-trifluoroacetyl)indoline-5-sulfonamide General Procedure 1: 6-amino-3H-benzo[c][1,2]oxaborol-1-ol (1 g, 6.7 mmol), pyridine (25 mL), and 1-(2,2,2-trifluoroacetyl)indoline-5-sulfonyl chloride (2.1 g, 1 eq). The title compound that was obtained as an orange solid. $^1$H NMR (400 MHz, DMSO-d$_6$) δ (ppm): 10.36 (s, 1H), 9.23 (s, 1H), 7.67 (t, J=8.8 Hz, 1H), 7.46 (s, 1H), 7.24 (d, J=8.2 Hz, 1H), 7.17 (dd, J=8.2, 1.6 Hz, 1H), 6.97 (dd, J=12.1, 2.3 Hz, 1H), 6.84 (dd, J=8.6, 2.3 Hz, 1H), 4.85 (s, 2H), 3.77 (s, 3H) MS (ESI) m/z=336 (M−1, negative); HPLC purity: 96.86% (MaxPlot 200-400 nm), 96.51% (220 nm).

1H-Indazole-5-sulfonic acid (1-hydroxy-1,3-dihydro-benzo[c][1,2]oxaborol-6-yl)-amide

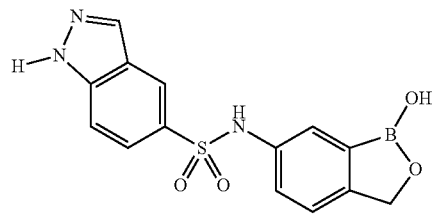 [SMILES: O=S(=O)(Nc1ccc2c(c1)B(O)OC2)c1ccc2[nH]ncc2c1]

To a solution of 6-amino-3H-benzo[c][1,2]oxaborol-1-ol (0.385 g, 2.07 mmol) in anhydrous pyridine (30 mL) at 5° C. was added 1H-indazole-5-sulfonyl chloride (0.45 g, 2.07 mmol) and the resulting orange solution stirred at room temperature for 0.5 h. The reaction was warmed to 50° C. for 2 h and then the pyridine was removed under reduced pressure to afford a sticky residue. This was treated with water (40 mL) and sonicated for 5 h at 70° C. The fine precipitate that formed was collected by filtration, washed with water and dried in vacuo generating 0.402 g (59%) of the title compound as a yellowish orange solid. mp 222° C.; $^1$H NMR (400 MHz, DMSO-d$_6$) δ (ppm): 10.21 (s, 1H), 9.19 (s, 1H), 8.24 (s, 2H), 7.67 (s, 2H), 7.48 (d, J=1.2 Hz, 1H), 7.22 (d, J=8.0 Hz, 1H), 7.17 (dd, J=8.2, 2.0 Hz, 1H), 4.84 (s, 2H); MS (ESI) m/z=330 (M+1, positive); HPLC purity: 97.30% (MaxPlot 200-400 nm), 97.30% (220 nm).

N-(1-hydroxy-1,3-dihydrobenzo[c][1,2]oxaborol-6-yl)indoline-5-sulfonamide

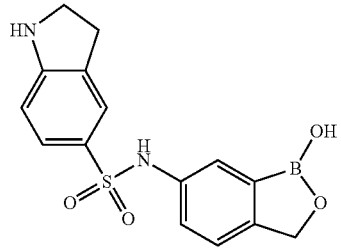 [SMILES: O=S(=O)(Nc1ccc2c(c1)B(O)OC2)c1ccc2c(c1)CCN2]

General Procedure 6: Starting material —N-(1-hydroxy-1,3-dihydrobenzo[c][1,2]oxaborol-6-yl)-1-(2,2,2-trifluoroacetyl)indoline-5-sulfonamide (1.58 g, 3.7 mmol). $^1$H NMR (400 MHz, DMSO-$d_6$) δ ppm 10.69 (br.s., 1H), 9.23 (s, 1H), 8.75 (s, 1H), 7.53 (s, 1H), 7.30-7.25 (m, 2H), 4.90 (s, 2H); MS (ESI) m/z=279 (M−1, negative); HPLC purity: 98.32% (MaxPlot 200-400 nm), 98.94% (220 nm).

4-Amino-2-fluoro-N-(1-hydroxy-1,3-dihydrobenzo[c][1,2]oxaborol-6-yl)benzenesulfonamide

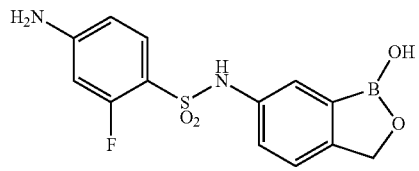 [SMILES: Nc1ccc(S(=O)(=O)Nc2ccc3c(c2)B(O)OC3)c(F)c1]

N-(3-fluoro-4-(N-(1-hydroxy-1,3-dihydrobenzo[c][1,2]oxaborol-6-yl)sulfamoyl)phenyl)acetamide Neat N-(3-fluorophenyl)acetamide (5 g, 32.65 mmol) was put on an ice-water bath and had chlorosulfonic acid added drop-wise. The solution was stirred at 0° C. for one hour, and was then stirred at room temperature overnight. The reaction was then stirred at 50° C. for four hours. The solution was then cooled to room temperature and added to a beaker of ice water. The ice was allowed to melt and then the solution was extracted with ethyl ether. The organic layer was washed with brine, then dried over sodium sulfate, and filtered. The solvent was removed under slightly reduced pressure to give 4-acetamido-2-fluorobenzene-1-sulfonyl chloride (1.50 g, 18% yield).

A solution of 4-acetamido-2-fluorobenzene-1-sulfonyl chloride (1.47 g, 5.84 mmol) and 6-aminobenzo[c][1,2]oxaborol-1(3H)-ol (0.870 g, 5.84 mmol), triethylamine (8.2 mL, 58.4 mmol), and N,N-dimethylformamide (30 mL) was stirred for one hour at room temperature. The solution was then made to pH 5 using 6 N hydrochloric acid. The solution was then extracted using ethyl acetate and water. The organic layer was washed five times with water, and then washed with brine. The organic layer was dried over sodium sulfate and filtered. The solvent was removed under reduced pressure to give N-(3-fluoro-4-(N-(1-hydroxy-1,3-dihydrobenzo[c][1,2]oxaborol-6-yl)sulfamoyl)phenyl)acetamide (1.57 g, 74% yield). $^1$H NMR (400 MHz, DMSO-$d_6$) δ (ppm) 2.04 (s, 3H), 4.85 (s, 2H), 7.17 (dd, J=2.1 Hz, J=8.2 Hz, 1H), 7.24 (d, J=8.2 Hz, 1H), 7.30 (dd, J=1.8 Hz, J=8.7 Hz, 1H), 7.45 (d, J=1.7 Hz, 1H), 7.65-7.70 (m, 2H), 9.19 (s, 1H), 10.41 (s, 1H), 10.44 (s, 1H)

4-Amino-2-fluoro-N-(1-hydroxy-1,3-dihydrobenzo[c][1,2]oxaborol-6-yl)benzenesulfonamide A solution of N-(3-fluoro-4-(N-(1-hydroxy-1,3-dihydrobenzo[c][1,2]oxaborol-6-yl)sulfamoyl)phenyl)acetamide (1.45 g, 3.98 mmol) in 1,4-dioxane (8 mL) and concentrated hydrochloric acid (2 mL) was refluxed at 100° C. for three hours. The solution was cooled to room temperature and neutralized to pH 5 using 3 N sodium hydroxide. The solution was extracted using ethyl acetate and water. The organic layer was washed three times with water, than washed with brine, dried over sodium sulfate, and filtered. The solvent was removed under reduced pressure. The residue was purified by silica column via CombiFlash using dichloromethane and methanol. The desired fractions were collected and the solvent was removed under reduced pressure. Water and toluene were added and removed under reduced pressure. Diisopropyl ether was used to transfer powder from round bottom flask to Buckner funnel to give 4-amino-2-fluoro-N-(1-hydroxy-1,3-dihydrobenzo[c][1,2]oxaborol-6-yl)benzenesulfonamide (0.176 g, 14% yield). $^1$H NMR (400 MHz, DMSO-$d_6$) δ (ppm) 4.85 (s, 2H), 6.23-6.31 (m, 4H), 7.16 (dd, J=2.1 Hz, J=8.1 Hz, 1H), 7.22 (d, J=8.3 Hz, 1H), 7.36 (t, J=8.6 Hz, 1H), 7.43 (d, J=1.8 Hz, 1H), 9.17 (s, 1H), 10.06 (s, 1H).

4-Amino-2-fluoro-N-(5-fluoro-1-hydroxy-1,3-dihydrobenzo[c][1,2]oxaborol-6-yl)benzenesulfonamide

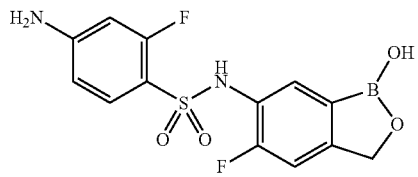 [SMILES: Nc1ccc(S(=O)(=O)Nc2cc3c(cc2F)COB3O)c(F)c1]

2-Fluoro-N-(5-fluoro-1-hydroxy-1,3-dihydrobenzo[c][1,2]oxaborol-6-yl)-4-nitrobenzenesulfonamide To a stirred solution of 2-fluoro-4-nitrobenzene-1-sulfonyl chloride (1.336 g, 5.57 mmol) and 6-amino-5-fluorobenzo[c][1,2]oxaborol-1(3H)-ol (0.93 g, 5.57 mmol) in 20 mL of ACN was added pyridine (900 uL, 11.14 mmol) dropwise. The reaction mixture was stirred at room temperature for 16 hours. After quenched with water, the solvent was removed in vacuo. The residue was extracted with ethyl acetate three times, and washed with water and brine. The organic layer was dried over $Na_2SO_4$, and concentrated to give 1.84 g of the title compound as a yellow residue. MS calcd for ($C_{13}H_9BF_2N_2O_6S$): 370.0. MS found (ESI negative): (M−H)$^-$=368.9

4-Amino-2-fluoro-N-(5-fluoro-1-hydroxy-1,3-dihydrobenzo[c][1,2]oxaborol-6-yl)benzenesulfonamide To a solution of 2-fluoro-N-(5-fluoro-1-hydroxy-1,3-dihydrobenzo[c][1,2]oxaborol-6-yl)-4-nitrobenzenesulfonamide (1.84 g, 4.97 mmol) in 50 mL of dioxane was added Pd/C (10 wt. % on activated carbon, 500 mg). The reaction mixture was hydrogenated at room temperature under 50 psi of hydrogen for 16 hours. After Pd/C was filtered through a pad of Celite, the solution was concentrated under reduced pressure to give a yellow residue. The crude residue was purified by prep HPLC (SunFire Prep C18 OBD 5 uM 30×50 mm column) to give 0.88 g of the title compound as a white solid. MS calcd for ($C_{13}H_{11}BF_2N_2O_4S$): 340.1. MS found (ESI negative): (M−H)⁻=339.1. $^1$H NMR (DMSO-$d_6$) δ (ppm): 9.69 (s, 1H), 9.23 (bs, 1H), 7.58 (d, 1H), 7.10-7.21 (m, 3H), 6.67 (t, 1H), 4.83 (s, 2H).

4-Amino-2-chloro-N-(1-hydroxy-1,3-dihydro-benzo[c][1,2]oxaborol-6-yl)-benzenesulfonamide

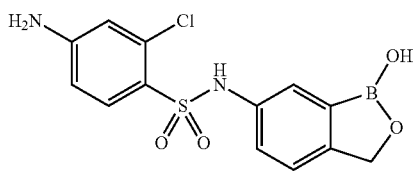 [SMILES: Nc1ccc(S(=O)(=O)Nc2ccc3c(c2)B(O)OC3)c(Cl)c1]

2-Chloro-N-(1-hydroxy-1,3-dihydro-benzo[c][1,2]oxaborol-6-yl)-4-nitro-benzenesulfonamide General Procedure 1: 6-amino-3H-benzo[c][1,2]oxaborol-1-ol (0.20 g, 1.30 mmol), acetonitrile (8 mL), 2-chloro-4-nitro-benzenesulfonyl chloride (0.34 g, 1.30 mmol), pyridine (0.212 g 2.6 mmol). Purification was accomplished by flash chromatography (3% methanol in dichloromethane) providing 0.40 g (80%) of the title compound as light yellow solid. mp 143-145° C. (dec.); $^1$H NMR (400 MHz, DMSO-$d_6$) δ (ppm): 10.91 (s, 1H), 9.23 (s, 1H), 8.43 (d, J=2.0 Hz, 1H), 8.29 (dd, J=9.0, 2.3 Hz, 1H), 8.23 (d, J=9.0 Hz, 1H), 7.50 (d, J=1.6 Hz, 1H), 7.30 (d, J=8.6 Hz, 1H), 7.24 (dd, J=8.2, 2.0 Hz, 1H), 4.87 (s, 2H); MS (ESI) m/z=367 (M−1, negative); HPLC purity: 99.41% (MaxPlot 200-400 nm), 98.31% (220 nm); Anal. Calcd for $C_{13}H_{10}BClN_2O_6S$: C, 42.37%; H, 2.73%; N, 7.60%. Found: C, 42.75%; H, 2.84%; N, 7.86%.

4-Amino-2-chloro-N-(1-hydroxy-1,3-dihydro-benzo[c][1,2]oxaborol-6-yl)-benzenesulfonamide Iron powder (0.19 g, 3.30 mmol) was added to a solution of 2-chloro-N-(1-hydroxy-1,3-dihydro-benzo[c][1,2]oxaborol-6-yl)-4-nitro-benzenesulfonamide (0.25 g, 0.67 mmol) in acetic acid (10 mL). The reaction mixture was stirred at 80° C. (bath temp) for 2 h. The mixture was then cooled to rt, and the acetic acid was removed under reduced pressure. The residue was diluted with ethyl acetate (50 mL), the undissolved particulates were removed by filtration through a pad of Celite. The filtrate was washed with water, brine and dried over $Na_2SO_4$, decanted and concentrated in vacuo. Purification was accomplished by flash silica gel column chromatography (3% methanol in dichloromethane) followed by dissolving in acidic water (with dilute HCl) and lyophilized provided 48.0 mg (21%) of the title compound as light yellow solid. $^1$H NMR (400 MHz, DMSO-$d_6$) δ (ppm): 10.10 (s, 1H), 7.63 (d, J=8.9 Hz, 1H), 7.45 (d, J=1.6 Hz, 1H), 7.23 (d, J=8.2 Hz, 1H), 7.19 (dd, J=8.2, 1.9 Hz, 1H), 6.59 (d, J=2.2 Hz, 1H), 6.46 (dd, J=8.6, 2.2 Hz, 1H), 4.85 (s, 2H); MS (ESI) m/z=339 (M+1, positive); HPLC purity: 97.48% (MaxPlot 200-400 nm), 97.96% (220 nm).

4-Amino-2-chloro-N-(5-fluoro-1-hydroxy-1,3-dihydrobenzo[c][1,2]oxaborol-6-yl)benzenesulfonamide

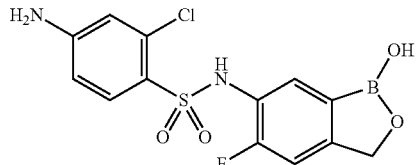

A mixture of 2-chloro-N-(5-fluoro-1-hydroxy-1,3-dihydrobenzo[c][1,2]oxaborol-6-yl)-4-nitrobenzenesulfonamide (0.5 g, 1.3 mmol), iron powder (0.36 g, 6.5 mmol) in AcOH (10 mL) was heated to 50° C. over night and monitored by LC/MS. The mixture was filtered, washed with EtOAc then AcOH, and evaporated under vacuum. Preparative HPLC was applied for the purification and give title product as yellow powder yield 36.3 mg (2%). $^1$H NMR (400 MHz, DMSO-$d_6$) δ (ppm): 9.71 (s, 1H), 7.64 (d, J=8 Hz, 1H), 7.44 (d, J=8.8 Hz, 1H), 7.20 (d, J=10 Hz, 1H), 6.65 (d, J=2 Hz, 1H), 6.41 (dd, J=8.8, 2.4 Hz, 1H), 4.88 (s, 2H); MS (ESI): m/z=355.0 (M−H, negative).

4-Amino-N-(1-hydroxy-1,3-dihydro-benzo[c][1,2]oxaborol-6-yl)-2-methoxy-benzenesulfonamide hydrochloride

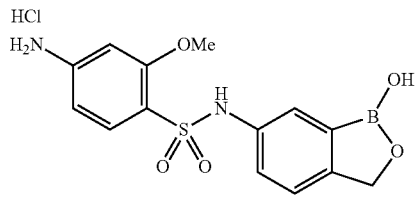 [SMILES: Cl ; COc1cc(N)ccc1S(=O)(=O)Nc1ccc2c(c1)B(O)OC2]

N-(1-Hydroxy-1,3-dihydro-benzo[c][1,2]oxaborol-6-yl)-2-methoxy-4-nitro-benzenesulfonamide General Procedure 1: 6-amino-3H-benzo[c][1,2]oxaborol-1-ol (1.0 g, 6.7 mmol), 2-methoxy-4-nitrobenzenesulfonyl chloride (2.0 g, 8.0 mmol), pyridine (2.2 mL, 26.8 mmol), and MeCN (15 mL) at rt O/N. The mixture was concentrated in vacuo and $H_2O$ (10 mL) and EtOAc (20 mL) were added. The mixture was stirred until a clear biphasic solution was observed. The aqueous layer was loaded onto an Isolute HM-N column and left to stand for 10 min. The organic layer was then eluted through the column. The column was then further washed with EtOAc (60 mL). The organic fractions were concentrated in vacuo and the residue was dissolved in MeOH and loaded onto a pre-column (silica, 12 g). Purification by flash chromatography (silica, 40 g; 30-100% EtOAc/hexane) gave a yellow oil. Recrystallization from MeCN/$H_2O$ gave the title compound as a white solid: yield; 589 mg (24%). $^1$H NMR (400 MHz, DMSO-$d_6$) δ (ppm): 10.32 (s, 1H), 9.22 (s, 1H), 7.98-7.96 (m, 1H), 7.90-7.89 (m, 1H), 7.85-7.83 (m, 1H), 7.48-7.47 (m, 1H), 7.26-7.24 (m, 1H), 7.21-7.18 (m, 1H), 4.86 (s, 2H), 4.04 (s, 3H); MS (ESI) m/z=362 (M−1, negative); HPLC purity: 97.28% (MaxPlot 200-400 nm), 97.01% (220 nm).

4-Amino-N-(1-hydroxy-1,3-dihydro-benzo[c][1,2]oxaborol-6-yl)-2-methoxy-benzenesulfonamide hydrochloride A suspension of N-(1-hydroxy-1,3-dihydro-benzo[c][1,2]oxaborol-6-yl)-2-methoxy-4-nitro-benzenesulfonamide (200 mg, 0.60 mmol), 10% Pd/C (75 mg), and abs. EtOH (100 mL) was shaken in a Parr apparatus at rt under an atmosphere of $H_2$ (50 psi) for 2 h. The mixture was filtered through Celite (washing with EtOH) and then a 0.2 μM filter. The filtrate was concentrated in vacuo at 40° C. The residue was purified by prep HPLC (MeCN/0.1% $HCO_2H$ (aq)). The major fraction was concentrated in vacuo at 40° C. followed by addition of 1 M HCl and lyophilization to give the title compound as a yellow solid; yield 30 mg (13%). $^1$H NMR (400 MHz, DMSO-$d_6$) δ (ppm): 9.48 (s, 1H), 7.41-7.40 (m, 1H), 7.32-7.29 (m, 1H), 7.18-7.12 (m, 2H), 6.11-6.10 (m, 1H), 6.04-6.01 (m, 1H), 4.82 (s, 2H), 3.73 (s, 3H); MS (ESI) m/z=335 (M+H, positive); HPLC purity: 97.53% (MaxPlot 200-400 nm), 97.30% (220 nm).

4-Amino-2-hydroxy-N-(1-hydroxy-1,3-dihydro-benzo[c][1,2]oxaborol-6-yl)-benzenesulfonamide hydrochloride

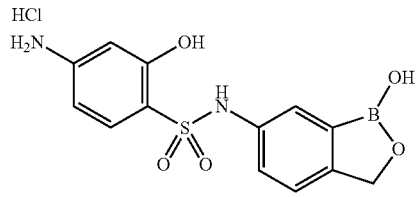

2-Hydroxy-N-(1-hydroxy-1,3-dihydro-benzo[c][1,2]oxaborol-6-yl)-4-nitro-benzenesulfonamide N-(1-Hydroxy-1,3-dihydro-benzo[c][1,2]oxaborol-6-yl)-2-methoxy-4-nitro-benzenesulfonamide (200 mg, 0.55 mmol) was dissolved in 1 M $BBr_3$ in $CH_2Cl_2$ (5.0 mL, 5.0 mmol) and the resulting soln was stirred at rt O/N. $H_2O$ was the resulting precipitate was isolated by filtration to give the title compound as a white solid: yield: 160 mg (83%). mp 198-199° C.; $^1$H NMR (400 MHz, DMSO-$d_6$) δ (ppm): 11.98 (s, 1H), 10.22 (s, 1H), 9.18 (s, 1H), 7.89-7.87 (m, 1H), 7.67-7.63 (m, 2H), 7.48 (s, 1H), 7.23-7.18 (m, 2H), 4.84 (s, 2H); MS (ESI) m/z=349 (M−1, negative); HPLC purity: 95.49% (MaxPlot 200-400 nm), 95.48% (220 nm).

4-Amino-2-hydroxy-N-(1-hydroxy-1,3-dihydro-benzo[c][1,2]oxaborol-6-yl)-benzenesulfonamide hydrochloride A suspension of N-(1-hydroxy-1,3-dihydro-benzo[c][1,2]oxaborol-6-yl)-2-hydroxy-4-nitro-benzenesulfonamide (130 mg, 0.37 mmol), 10% Pd/C (50 mg), and abs. EtOH (50 mL) was shaken in a Parr apparatus at rt under an atmosphere of $H_2$ (50 psi) for 3 h. The mixture was filtered through Celite® (washing with EtOH) and then a 0.2 μM filter. The filtrate was concentrated in vacuo at 50° C. The residue was purified by prep HPLC [MeCN/0.1% $HCO_2H$ (aq)]. The major fraction was concentrated in vacuo at 40° C. and lyophilized from 1 M HCl to give the title compound as a yellow solid; yield 14 mg (12%). $^1$H NMR (400 MHz, DMSO-$d_6$) δ (ppm): 10.17 (s, 1H), 9.49 (s, 1H), 7.44 (s, 1H), 7.30-7.27 (m, 1H), 7.18-7.17 (m, 2H), 6.00-5.99 (m, 1H), 5.98-5.96 (m, 1H), 4.85 (s, 2H); MS (ESI) m/z=319 (M−1, negative); HPLC purity: 93.88% (MaxPlot 200-400 nm), 94.37% (220 nm).

4-Amino-2-cyano-N-(1-hydroxy-1,3-dihydrobenzo[c][1,2]oxaborol-6-yl)benzenesulfonamide

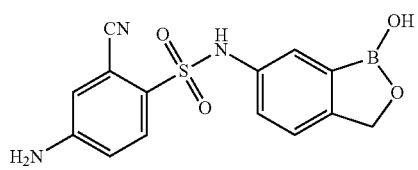 [SMILES: N#Cc1cc(N)ccc1S(=O)(=O)Nc1ccc2c(c1)B(O)OC2]

2-(Benzylthio)-5-nitrobenzonitrile

To a solution of 2-chloro-5-nitrobenzonitrile (27.375 g, 0.15 mol) in MeCN (500 ml) was added $K_2CO_3$ (24.84 g, 0.18 mol) and phenylmethanethiol (17.71 ml, 0.15 mol). The solution was stirred at room temperature for overnight. The mixture was filtered through the celite pad and the filtrate was concentrated in vacuo to give 2-(benzylthio)-5-nitrobenzonitrile (40.5 g, 100%) as a yellow solid. $^1$H NMR: $CDCl_3$ 400 MHz δ8.43 (s, 1H), 8.27-8.25 (m, 1H), 7.44-7.31 (m, 6H), 4.35 (s, 2H).

2-Cyano-4-nitrobenzene-1-sulfonyl chloride

To a solution of 2-(benzylthio)-5-nitrobenzonitrile (20.25 g, 75 mmol) in $AcOH/H_2O$ (500 ml/50 ml) was vigorously bubbled chlorine (gas) for 2 hours at 15° C. The mixture was poured into ice-water and extracted with DCM. The extracts was washed with water, twice with saturated aqueous $NaHCO_3$ and then again with water. The organic layer was dried over $Na_2SO_4$ and evaporated at less than 40° C. in vacuo to yield the crude solid, which washed with 1M HCl and water to give 2-cyano-4-nitrobenzene-1-sulfonyl chloride (12 g, 64.90%) as a yellow solid. $^1$H NMR: $CDCl_3$ 400 MHz δ8.80 (s, 1H), 8.67 (d, J=11.6 Hz, 1H), 8.46 (d, J=8.8 Hz, 1H).

2-Cyano-N-(1-hydroxy-1,3-dihydrobenzo[c][1,2]oxaborol-6-yl)-4-nitrobenzenesulfonamide To a solution of 6-amino-3H-benzo[c][1,2]oxaborol-1-ol (2.98 g, 20 mmol) and NMM in MeCN (150 ml) was added 2-cyano-4-nitrobenzene-1-sulfonyl chloride (5.423 g, 22 mmol) at 0° C., then the solution was stirred at room temperature for overnight. The mixture was concentrated in vacuo at room temperature, and DCM and water was added to the residue. The organic layer was dried over $Na_2SO_4$ and concentrated to give the crude product. It was purified by prep. HPLC (column: Luna 300×50.0 mm, 10 u; liquid phase: [A-$H_2O$+0.025% TFA; B-MeCN] B %: 25%-50%, 25 min) to give the title compound (2.0 g, 27.86%) as a yellow solid. $^1$H NMR: DMSO 400 MHz. δ11.05 (s, 1H), 9.22 (s, 1H), 8.88 (s, 1H), 8.62 (d, J=11.2 Hz, 1H), 8.17 (d, J=8.8 Hz, 1H), 7.45 (s, 1H), 7.31 (d, J=8.0 Hz, 1H), 7.18 (d, J=10.0 Hz, 1H), 4.89 (s, 2H). ESI-MS m/z 360 (M+H, positive); HPLC purity: 93.07% (MaxPlot 190-370 nm), 98.72% (220 nm).

4-Amino-2-cyano-N-(1-hydroxy-1,3-dihydrobenzo [c][1,2]oxaborol-6-yl)benzenesulfonamide

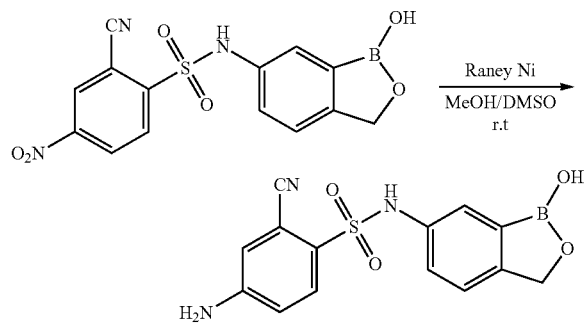

To a solution of 2-cyano-N-(1-hydroxy-1,3-dihydrobenzo [c][1,2]oxaborol-6-yl)-4-nitrobenzenesulfonamide (400 mg, 1.1 mmol) in MeOH/DMSO (40 ml/1 ml) was added Raney Ni (100 mg) under nitrogen, then the solution was stirred under hydrogen atmosphere at room temperature for 2 hours. The mixture was filtered and the filtrate was concentrated. The residue was purified by prep. HPLC (column: YMC AQ 150×30.0 mm, 5 u; liquid phase: [A-H$_2$O+0.075% TFA; B-MeCN+0.075% TFA] B %: 18%-48%, 10 min) to give the title compound (100 mg, 27.62%) as a yellow solid. $^1$H NMR: DMSO 400 MHz δ10.25 (s, 1H), 9.21 (s, 1H), 7.60 (d, J=9.6 Hz, 1H), 7.43 (s, 1H), 7.26 (d, J=8.4 Hz, 1H), 7.17 (d, J=9.2 Hz, 1H), 6.92 (s, 1H), 6.77 (d, J=10.4 Hz, 1H), 6.44 (brs, 2H), 4.89 (s, 2H). ESI-MS m/z 330 (M+H, positive); HPLC purity: 97.31% (MaxPlot 190-370 nm), 99.89% (220 nm).

4-Amino-N-(1-hydroxy-1,3-dihydro-benzo[c][1,2] oxaborol-6-yl)-2-methyl-benzenesulfonamide

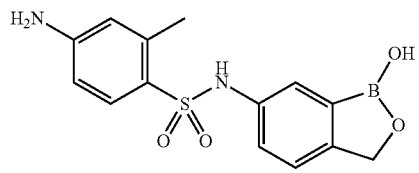 [SMILES: Cc1cc(N)ccc1S(=O)(=O)Nc1ccc2c(c1)B(O)OC2]

N-(1-Hydroxy-1,3-dihydro-benzo[c][1, 2]oxaborol-6-yl)-2-methyl-4-nitro-benzenesulfonamide General Procedure 1: 6-amino-3H-benzo[c][1,2]oxaborol-1-ol (0.500 g, 3.35 mmol), pyridine (10 mL), and 2-methyl-4-nitro-benzenesulfonyl chloride (0.790 g, 3.35 mmol). Purification: Recrystallization from hot water. The title compound was isolated as orange solid; yield 400 mg (34%). mp. 104-105° C. $^1$H NMR (400 MHz, DMSO-d$_6$) δ ppm 10.69 (s, 1H), 9.22 (s, 1H), 8.25 (d, J=2.0 Hz, 1H), 8.18-8.12 (m, 1H), 8.08-8.03 (m, 1H), 7.46 (d, J=1.6 Hz, 1H), 7.31-7.26 (m, 1H), 7.21-7.15 (m, 1H), 4.87 (s, 2H), 2.71 (s, 3H); MS (ESI) m/z=347 (M−1, negative); HPLC purity: 95.54% (MaxPlot 200-400 nm), 95.60% (220 nm).

4-Amino-N-(1-hydroxy-1,3-dihydro-benzo[c][1,2] oxaborol-6-yl)-2-methyl-benzenesulfonamide A mixture of N-[1-(2-hydroxy-[1,2]oxaborolan-3-ylidenemethyl)-vinyl]-2-methyl-4-nitro-benzenesulfonamide (300 mg, 0.86 mmol) and Pd/C (300 mg, 10% wet) in MeOH (20.0 mL) was placed under a hydrogen atmosphere at 50 psi at rt for 1 h. The solid catalyst was filtered off through a pad of Celite. The filtrate was then concentrated in vacuo and the residue was suspended in hot water. The solid product was filtered and dried to affording 40 mg (15%) of the title compound as a white solid. mp. 174-175° C.; $^1$H NMR (400 MHz, DMSO-d$_6$) δ ppm 9.90 (br. s., 1H), 9.15 (s, 1H), 7.51 (d, J=8.2 Hz, 1H), 7.40 (d, J=1.6 Hz, 1H), 7.21-7.16 (m, 1H), 7.14-7.09 (m, 1H), 6.34-6.28 (m, 2H), 5.81 (s, 2H), 4.83 (s, 2H), 2.38 (s, 3H); (ESI) m/z=317 (M−1, negative); HPLC purity: 96.23% (MaxPlot 200-400 nm), 97.5% (220 nm).

4-Amino-2-ethyl-N-(5-fluoro-1-hydroxy-1,3-dihydrobenzo[c][1,2]oxaborol-6-yl)benzenesulfonamide

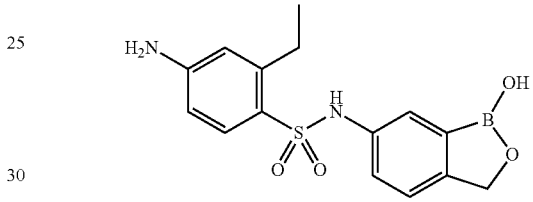

3-Ethylaniline (2 g, 0.016 mol) was added slowly in portion into neat Ac$_2$O (8 ml) at 0° C. After removed ice bath and the reaction was stirred at room temperature for 2 hour. The solvent was removed in vacuo and extracted with EtOAc, washed with water and brine, dried over Na$_2$SO$_4$. Concentrated to get crude N-(3-ethylphenyl)acetamide as light yellow solid.

N-(3-ethylphenyl)acetamide (2.5 g, 16 mmol) was mixed with chlorosulfonic acid (8 mL) at 0° C., and the mixture was stirred at room temperature for 3 hours. As the starting material was consumed as indicated by LC/MS, the mixture was added dropwise to ice-water. After filtered, the resulting residue was dried in vacuo to give the desired compound as a yellow residue (2 g).

To a stirred solution of 6-amino-3H-benzo[c][1,2]oxaborol-1-ol (0.57 g, 3.8 mmol) and pyridine (2 mL) in 10 mL of DCM was added 4-acetamido-2-ethylbenzene-1-sulfonyl chloride (1 g, 3.8 mmol) in portion. The reaction mixture was stirred at room temperature for 3 hours. After the mixture was concentrated, the residue was extracted with ethyl acetate and washed with water, 1N HCl and brine. The organic layer was dried over Na$_2$SO$_4$ and concentrated to give the desired compound as a yellow solid (520 mg, yield 82%).

The N-(3-ethyl-4-(N-(1-hydroxy-1,3-dihydrobenzo[c][1, 2]oxaborol-6-yl)sulfamoyl)phenyl)acetamide (0.52 g, 1.3 mmol) and 1:1 6N HCl: AcOH (5 equiv) mixture was heated to 40° C. for 2 days. Purification: remove solvent, work up with EtOAc and 1N HCl, washed with brine, dry on Na$_2$SO$_4$, remove solvent. The product was purified by preparative HPLC to give the desired product 4-amino-2-ethyl-N-(1-hydroxy-1,3-dihydrobenzo[c][1,2]oxaborol-6-yl)benzenesulfonamide as a white powder (80 mg).

MS calcd for (C$_{15}$H$_{17}$BN$_2$O$_4$S): 332.2. MS found (ESI negative): (M−H)$^-$=331.1. $^1$H NMR (400 MHz, DMSO-d$_6$) δ (ppm): 9.98 (s, 1H), 7.55 (d, J=8.8 Hz, 1H), 7.41 (d, J=1.6 Hz, 1H), 7.20 (d, J=8 Hz, 1H), 7.12 (dd, J=8.4, 2 Hz, 1H), 6.44 (d, J=2 Hz, 1H), 6.36 (dd, J=8.8, 2.4 Hz, 1H), 5.5 (b, 3H), 4.85 (s, 2H), 2.84 (q, J=7.6 Hz, 2H), 1.12 (t, J=7.6 Hz, 3H).

4-Amino-N-(1-hydroxy-1,3-dihydrobenzo[c][1,2]oxaborol-6-yl)-2-(prop-1-ynyl)benzenesulfonamide; and 4-Amino-2-butyl-N-(1-hydroxy-1,3-dihydrobenzo[c][1,2]oxaborol-6-yl)benzenesulfonamide

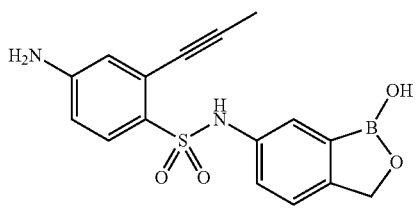

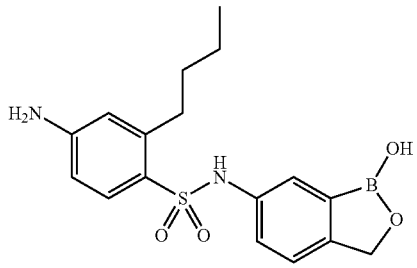

The mix of compound N-(3-bromo-4-(N-(1-hydroxy-1,3-dihydrobenzo[c][1,2]oxaborol-6-yl)sulfamoyl)phenyl)-2,2,2-trifluoroacetamide (87 mg, 0.182 mmol), tributyl(prop-1-ynyl)stannane (75.8 mg, 0.2 mmol), dimethylamino ethanol (17.9 mg, 0.2 mmol) and Pd(dppf)$_2$Cl$_2$ in NMP (2 ml) was degassed and heated to 100° C. overnight. The reaction mixture was washed with H$_2$O, 1N NaOH and brine, dried over MgSO$_4$, filtered and evaporated in reduced pressure to dryness. The residue was dissolved in 7N NH$_3$/MeOH and stirred at 40° C. for 12 hrs. Evaporated to dryness and purified by prep-HPLC to give the desired compound 4-amino-N-(1-hydroxy-1,3-dihydrobenzo[c][1,2]oxaborol-6-yl)-2-(prop-1-ynyl)benzenesulfonamide and 4-amino-2-butyl-N-(1-hydroxy-1,3-dihydrobenzo[c][1,2]oxaborol-6-yl)benzenesulfonamide.

4-Amino-N-(1-hydroxy-1,3-dihydrobenzo[c][1,2]oxaborol-6-yl)-2-(prop-1-ynyl)benzenesulfonamide: $^1$H NMR (400 MHz, DMSO-d$_6$) δ (ppm): 9.61 (s, 1H), 7.53 (d, J=8.8 Hz, 1H), 7.40 (d, J=2.0 Hz, 1H), 7.19 (d, J=2.0 Hz, 1H), 7.13 (dd, J=8.8, 2.0 Hz, 1H), 6.54 (d, J=2.4 Hz, 1H), 6.44 (dd, J=2.4, 8.8 Hz, 1H), 4.84 (s, 2H), 2.09 (s, 3H). MS (ESI) m/z=341 (M−1).

4-Amino-2-butyl-N-(1-hydroxy-1,3-dihydrobenzo[c][1,2]oxaborol-6-yl)benzenesulfonamide: $^1$H NMR (400 MHz, DMSO-d$_6$) δ (ppm): 9.93 (s, 1H), 9.20 (brs, 1H), 7.53 (d, J=8.6 Hz, 1H), 7.39 (d, J=1.7 Hz, 1H), 7.19 (d, J=8.2 Hz, 1H), 7.09 (dd, J=8.2, 2.0 Hz, 1H), 6.39 (d, J=2.2 Hz, 1H), 6.33 (dd, J=2.4, 8.6 Hz, 1H), 4.84 (s, 2H), 2.76 (t, J=7.2 Hz, 2H), 1.31-1.45 (m, 4H), 0.86 (t, J=7.2 Hz, 3H). MS (ESI) m/z=341 (M−1).

4-Amino-2-(cyanomethyl)-N-(1-hydroxy-1,3-dihydrobenzo[c][1,2]oxaborol-6-yl)benzenesulfonamide

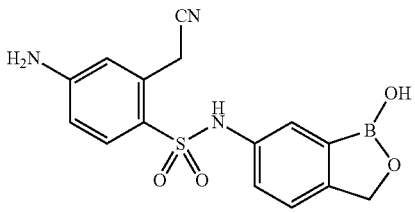

To the mixture of solution of 3-nitrophenylacetonitrile (16.2 g, 0.1 mol) and ion powder (56 g, 1 mol) in ethanol (160 ml) and water (40 ml), added hydrochloride (25 ml, 6N), heated to reflux for 4 hours. Filtered through celite, concentrated, extracted with EtOAc, washed with water and brine, dried over sodium sulfate. Removed solvent, got crude product as oil.

To the mixture of crude 2-(3-aminophenyl)acetonitrile and triethyl amine (14 ml, 100 mmol) in DCM (200 ml) at 0° C., added trifluoroacetic acid anhydride (14 ml, 100 mmol) slowly, stirred for 2 hours at rt after addition. Removed solvent, diluted with EtOAc, washed with water and brine, dried over Na$_2$SO$_4$. Concentrated to give light yellow solid used for next step without further purification.

The crude N-(3-(cyanomethyl)phenyl)-2,2,2-trifluoroacetamide was added to chlorosulphonyl acid (40 ml) at 0° C. in portion, stirred at rt after addition overnight. The reaction mixture was slowly poured onto ice/water under stirring, the result suspension was filtered and washed with cold water, dried under high vacuum. Got 2-(cyanomethyl)-4-(2,2,2-trifluoroacetamido)benzenesulfonic acid as off white solid.

The mixture of crude 2-(cyanomethyl)-4-(2,2,2-trifluoroacetamido)benzenesulfonic acid (9.24 g, 30 mmol) with added to PCl$_5$ (6.3 g, 30 mmol) was added CCl$_4$ (50 ml), heated to reflux for 4 hours, removed solvent, the residue was used without further purification.

General procedure 1: 6-aminobenzo[c][1,2]oxaborol-1(3H)-ol (1.5 g, 10 mmol), methyl 2-(cyanomethyl)-4-(2,2,2-trifluoroacetamido)benzene-1-sulfonyl chloride (3.3 g, 10 mmol), pyridine (0.9, 1 lmmol), rt, 3 hour. Removed solvent, the crude (450 mg) was dissolved in MeOH (50 ml), treated with NaOH (15 ml, 1N), stirred at 40° C. for 3 hours. Then adjusted pH to neutral with 1N HCl, concentrated, the result solid was purified by prep HPLC (SunFire Prep C18 OBD 5 uM 30×50 mm column). The title compound was obtained as light yellow powder. MS calcd for (C$_{15}$H$_{14}$BN$_3$O$_4$S): 343.08. MS found (ESI negative): (M−H)$^−$=342.0. $^1$H NMR (400 MHz, DMSO-d$_6$) δ (ppm): 9.95 (s, 1H), 7.45 (d, J=8.4 Hz, 1H), 7.37 (s, 1H), 7.19 (d, J=8.4 Hz, 1H), 7.07 (dd, J=8 Hz, 1H), 6.61 (s, 1H), 6.38 (dd, J=8.4 Hz, 1H), 4.81 (s, 2H), 4.12 (s, 2H).

Methyl 2-(2-(N-(1-hydroxy-1,3-dihydrobenzo[c][1,2]oxaborol-6-yl)sulfamoyl)-5-(2,2,2-trifluoroacetamido)phenyl)acetate

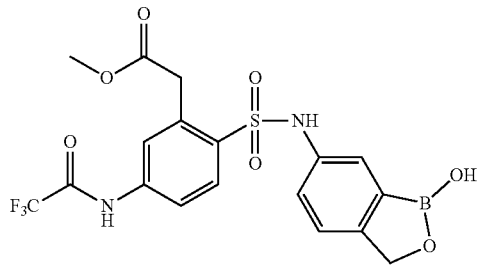 [SMILES: COC(=O)Cc1cc(NC(=O)C(F)(F)F)ccc1S(=O)(=O)Nc1ccc2c(c1)B(O)OC2]

2-(3-Nitrophenyl)acetonitrile

A solution of 1-(bromomethyl)-3-nitrobenzene (30 g, 0.139 mol) and NaCN (10.21 g, 0.208 mol) in DMF (150 mL) was stirred at 50° C. for 5 hrs. The mixture was poured into water and extracted with ethyl acetate. The combined organic layer were dried, concentrated and purified by silica-gel column chromatography (PE:EA 20:1~6:1) to give compound 2-(3-nitrophenyl)acetonitrile (9.9 g, yield 44%).

Methyl 2-(3-nitrophenyl)acetate

A suspension of 2-(3-nitrophenyl)acetonitrile (9.5 g, 0.059 mol) in MeOH (400 mL) saturated with HCl was stirred at r.t. over night. The solution was concentrated and aq. NaHCO$_3$ was added. The mixture was extracted with ethyl acetate. The combined organic layer were dried and concentrated to give crude product of methyl 2-(3-nitrophenyl)acetate (7.3 g, yield 63%). $^1$H NMR: CDCl$_3$ 400 MHz. δ 8.15-8.14 (m, 2H), 7.64-7.50 (m, 2H), 3.74 (s, 2H), 3.72-3.71 (s, 3H).

Methyl 2-(3-aminophenyl)acetate

To a stirred solution of methyl 2-(3-nitrophenyl)acetate (7.3 g, 0.038 mol) and Fe (6.3 g, 0.113 mol) in MeOH (200 mL) was added concentrated HCl (20 mL). Then the mixture was stirred at room temperature over night. The mixture was filtered, the solvent was concentrated and the residue was dissolved in ethyl acetate and washed with brine, dried and concentrated to give the crude product of methyl 2-(3-aminophenyl)acetate (8.0 g, yield 97%).

Methyl 2-(3-(2,2,2-trifluoroacetamido)phenyl)acetate

To a stirred solution of methyl 2-(3-aminophenyl)acetate (8.0 g, 0.048 mol) and 2,6-dimethylpyridine (7.8 g, 0.073 mol) in DCM (200 mL) at 0° C. was slowly added TFAA (12.2 g, 0.058 mol). Then the mixture was stirred at room temperature for two hrs. The mixture was washed with sat. NaHCO$_3$ and brine. The combined organic layer were dried, concentrated and purified by column chromatography (PE:EA 30:1~5:1) to give methyl 2-(3-(2,2,2-trifluoroacetamido)phenyl)acetate (12.2 g, yield 96%).

Methyl 2-(2-(chlorosulfonyl)-5-(2,2,2-trifluoroacetamido)phenyl)acetate

To methyl 2-(3-(2,2,2-trifluoroacetamido)phenyl)acetate (1.0 g, 3.8 mmol) at 0° C. was added ClSO$_2$OH (2.3 g, 19.2 mmol). Then the mixture was stirred at room temperature for 2 hr. The mixture was poured into ice water and extracted with DCM. The combined organic layer were dried and concentrated to give the crude product methyl 2-(2-(chlorosulfonyl)-5-(2,2,2-trifluoroacetamido)phenyl)acetate. The product used directly to next reaction.

Methyl 2-(2-(N-(1-hydroxy-1,3-dihydrobenzo[c][1,2]oxaborol-6-yl)sulfamoyl)-5-(2,2,2-trifluoroacetamido)phenyl)acetate To a stirred solution of 6-amino-3H-benzo[c][1,2]oxaborol-1-ol (3.5 g, 0.024 mol, 0.9 eq) and NMM (7.9 g, 0.079 mol, 3 eq) in acetonitrile (50 mL) was added a solution of methyl 2-(2-(chlorosulfonyl)-5-(2,2,2-trifluoroacetamido)phenyl)acetate (9.4 g, 0.026 mol) in anhydrous acetonitrile (50 mL) at 0-5° C. Then the mixture was stirred at r.t overnight, the mixture was concentrated and dissolved in DCM and then washed with brine, dried and concentrated, purified by column chromatography (PE:EA 10:1~1.5:1) to give the title compound (7.4 g, yield 60%). $^1$H NMR DMSO-d6 400 MHz δ 11.54 (s, 1H), 10.36 (s, 1H), 9.21 (s, 1H), 7.87-7.10 (m, 6H), 4.87 (s, 2H), 4.08 (s, 2H), 3.58 (s, 3H). ESI-MS m/z 495 (M+Na$^+$, positive); HPLC purity: 98.23% (220 nm), 99.55% (254 nm).

4-Amino-N-(1-hydroxy-1,3-dihydrobenzo[c][1,2]oxaborol-6-yl)-2-(hydroxymethyl)benzenesulfonamide

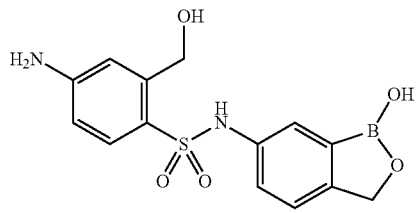 [SMILES: Nc1ccc(S(=O)(=O)Nc2ccc3c(c2)B(O)OC3)c(CO)c1]

To a solution of (3-aminophenyl)methanol (12.3 g, 0.1 mol) in DCM (150 ml) and TEA (30.3 g, 0.3 mol) was added TFAA (42 g, 0.2 mmol) dropwise at 0° C. over 20 min. The mixture was stirred at 0° C.-rt for 2 hrs. The reaction mixture was washed with H$_2$O, brine and dried over MgSO$_4$. Filtered, concentrated in reduced pressure to dryness to give the crude 3-(2,2,2-trifluoroacetamido)benzyl 2,2,2-trifluoroacetate which can be used without further purification.

The crude 3-(2,2,2-trifluoroacetamido)benzyl 2,2,2-trifluoroacetate (1.57 g, 10 mmol) was cooled to 0° C., then chlorosulfonic acid (100 mmol) was added dropwise at 0° C. over 10 min. The rxn mix was stirred at 0° C. to rt for 3 hrs. LC/MS monitored the rxn. The mix was poured into ice-H$_2$O (100 g) to quench the rxn. The sticky gum was washed with H$_2$O and dried in vacuum to give the crude compound 2-(chloromethyl)-4-(2,2,2-trifluoroacetamido)benzene-1-sulfonyl chloride.

The mix of crude 2-(chloromethyl)-4-(2,2,2-trifluoroacetamido)benzene-1-sulfonyl chloride and 6-amino-3H-benzo[c][1,2]oxaborol-1-ol (12 mmol) in acetonitrile (50 ml) was cooled to 0° C., followed by the addition of pyridine (15 mmol) dropwise. The mix was stirred at 0-rt for 1 hr. Filtered and washed with ethyl acetate. The ethyl acetate phase was washed with H$_2$O, 1N HCl and brine, dried over MgSO$_4$, filtered and concentrated in reduced pressure to dryness. The residue was dissolved in 7N NH$_3$/MeOH and stirred at 40° C. over night. The solvent was removed in reduced pressure to dryness and purified by prep-HPLC to give the title compound. $^1$H NMR (400 MHz, CD$_3$OD) δ (ppm): 9.8 (brs, 1H), 9.11 (s, 1H), 7.42 (d, J=8.4 Hz, 1H), 7.35 (d, J=1.8 Hz, 1H), 7.14 (d, J=8.2 Hz, 1H), 7.05 (dd, J=2.1, 8.2 Hz, 1H), 6.79 (d, J=1.9 Hz, 1H), 6.27 (dd, J=2.3, 8.6 Hz, 1H), 5.87 (s, 2H), 5.19 (t, J=6.1 Hz, 1H), 4.79 (s, 2H), 4.69 (d, J=5.5 Hz, 1H, 2H). MS (ESI) m/z=333 (M−1).

4-Amino-N-(1-hydroxy-1,3-dihydrobenzo[c][1,2] oxaborol-6-yl)-2-(2-hydroxyethyl)benzenesulfonamide

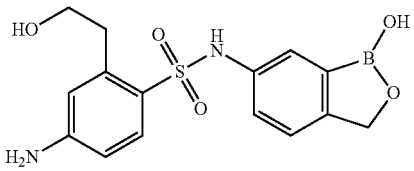 [SMILES: Nc1ccc(S(=O)(=O)Nc2ccc3c(c2)B(O)OC3)c(CCO)c1]

A solution of methyl 2-(2-(N-(1-hydroxy-1,3-dihydrobenzo[c][1,2]oxaborol-6-yl)sulfamoyl)-5-(2,2,2-trifluoroacetamido)phenyl)acetate (1.0 g, 0.002 mol) and NaBH$_4$ (0.2 g, 0.005 mol) in anhydrous THF (50 mL) was cooled to 0° C., and then CH$_3$OH (1 Ml) was added slowly. Then the reaction was stirred at r.t for 5 hrs. The solvent was removed and the residue dissolved in ethyl acetate and washed with brine, dried and concentrated, purified by silica-gel column chromatography (PE:EA 8:1~1:1.5) to give product compound, which was dissolved in MeCN, acidified with aq. HCl and freeze-dried to give the product as hydrochloride salt. (200 mg, yield 54%). $^1$HNMR: DMSO-d6 400 MHz. δ9.90 (s, 1H), 9.15 (s, 1H), 7.52-6.32 (m, 6H), 5.81 (s, 2H), 4.84 (s, 2H), 3.58-3.54 (t, 3H), 3.00-2.96 (t, 3H). ESI-MS m/z 371 (M+Na, positive); HPLC purity: 98.55% (220 nm), 100% (254 nm).

4-Amino-N-(5-fluoro-1-hydroxy-1,3-dihydrobenzo[c][1,2]oxaborol-6-yl)-2-(2-hydroxyethyl)benzenesulfonamide

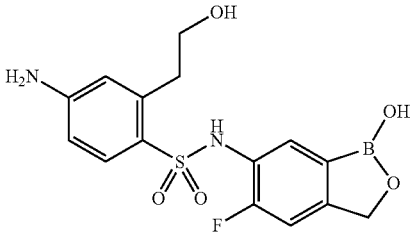 [SMILES: Nc1ccc(S(=O)(=O)Nc2cc3c(cc2F)COB3O)c(CCO)c1]

General Procedure 1: 6-amino-5-fluorobenzo[c][1,2]oxaborol-1(3H)-ol (2.34 g, 14 mmol), methyl 2-(2-(chlorosulfonyl)-5-(2,2,2-trifluoroacetamido)phenyl)acetate (5.15 g, 14 mmol), pyridine (1.12 ml, 17 mmol), rt, 0.5 hour. Removed solvent and got the crude product as solid. The crude (450 mg, 0.9 mmol) was dissolved in THF (15 ml), treated with LiBH$_4$ (2 ml, 0.5N in THF) at 0° C., then stirred for 2 hours at room temperature. Adjusted the pH to neutral, removed most solvent. The residue was purified by prep HPLC (SunFire Prep C18 OBD 5 uM 30×50 mm column). The title compound was obtained as off white powder. MS calcd for (C$_{15}$H$_{16}$BFN$_2$O$_5$S): 366.09. MS found (ESI negative): (M−H)$^−$=365.1. $^1$H NMR (400 MHz, DMSO-d$_6$) δ (ppm): 9.54 (s, 1H), 7.58 (d, J=8.4 Hz, 1H), 7.30 (d, J=8.8 Hz, 1H), 7.12 (d, J=10.4 Hz, 1H), 6.42 (d, J=2 Hz, 1H), 6.24 (dd, J=8.8 Hz, 1H), 4.81 (s, 2H), 3.53 (t, J=6.8 Hz, 2H), 2.93 (t, J=6.8 Hz, 2H).

Ethyl 3-(2-(N-(1-hydroxy-1,3-dihydrobenzo[c][1,2] oxaborol-6-yl)sulfamoyl)-5-(2,2,2-trifluoroacetamido)phenyl)propanoate

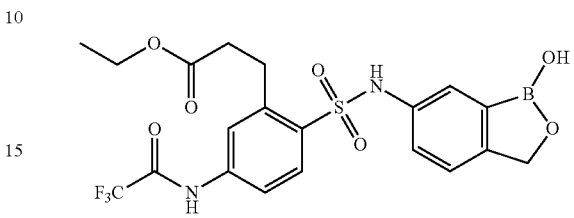

Ethyl 3-(3-nitrophenyl)acrylate

To a solution of 3-nitrobenzaldehyde (49 g, 295 mmol) and (diethoxy-phosphoryl)-acetic acid ethyl ester (72.74 g, 325 mmol) in DMF (300 ml) at 0° C. was added NaH (14.2 g, 354 mmol) portionwise and stirred for 1.5 hrs at r.t. The reaction mixture was poured into water to give colorless crystals, which were collected by filtration and washed with water and hexane to give the product ethyl 3-(3-nitrophenyl)acrylate (63 g, yield 96.6%). $^1$H NMR MeOD 400 MHz. δ 8.42-7.62 (m, 4H), 7.74-7.70 (d, 1H), 6.68-6.64 (d, 1H), 4.28-4.22 (m, 2H), 1.34-1.30 (m, 3H).

Ethyl 3-(3-aminophenyl)propanoate

A mixture of ethyl 3-(3-nitrophenyl)acrylate (63 g, 284 mmol) and Pd/C (6.3 g) in MeOH (800 ml) were stirred under 40 psi of H$_2$ at room temperature for 2 hr, then filtered through celite to give the product ethyl 3-(3-aminophenyl)propanoate (48 g, yield 89%). $^1$H NMR MeOD 400 MHz. δ 7.00-6.51 (m, 4H), 4.10-4.04 (m, 2H), 2.79-2.76 (m, 2H), 2.56-2.52 (m, 2H), 1.20-1.17 (m, 3H).

Ethyl 3-(3-(2,2,2-trifluoroacetamido)phenyl)propanoate

A mixture of ethyl 3-(3-aminophenyl)propanoate (20 g, 103 mmol), and N-methylmorpholine (NMM) (16.64 g, 164 mmol) were added to CH$_2$Cl$_2$ (200 mL) at 0° C. Then TFAA (26.1 g, 124 mmol) was added to the mixture and stirred at 0° C. overnight. The residue was washed with saturated NaHCO$_3$ and brine to give the product ethyl 3-(3-(2,2,2-trifluoroacetamido)phenyl) propanoate (21 g, yield 72%). $^1$H NMR MeOD 400 MHz. δ7.50-7.04 (m, 4H), 4.10-4.05 (m, 2H), 2.92-2.88 (m, 2H), 2.62-2.58 (m, 2H), 1.20-1.16 (m, 3H).

Ethyl 3-(2-(chlorosulfonyl)-5-(2,2,2-trifluoroacetamido)phenyl)propanoate

ClSO$_3$H (2 g, 17.3 mmol) was cooled to 0° C. and ethyl 3-(3-(2,2,2-trifluoroacetamido) phenyl)propanoate (1 g, 3.46 mmol) was added portionwise with vigorous stirring keeping the temperature below 5° C. The reaction mixture was stirred at room temperature overnight, and cautious poured onto ice. The solid produced was dissolved in CH$_2$Cl$_2$. The combined organic phase was washed with saturated NaHCO$_3$ and saturated brine, dried over MgSO₄ to give the product ethyl 3-(2-(chlorosulfonyl)-5-(2,2,2-trifluoroacetamido)phenyl)propanoate (0.41 g, yield 31%).

Ethyl 3-(2-(N-(1-hydroxy-1,3-dihydrobenzo[c][1,2]oxaborol-6-yl)sulfamoyl)-5-(2,2,2-trifluoroacetamido)phenyl)propanoate A solution of 6-amino-3H-benzo[c][1,2]oxaborol-1-ol (1.15 g, 7.7 mmol), NMM (2.93 g, 29 mmol) in CH₃CN (50 ml) was cooled to 0° C. Then ethyl 3-(2-(chlorosulfonyl)-5-(2,2,2-trifluoroacetamido)phenyl) propanoate (3.74 g, 9.7 mmol) was added to the above solution and stirred at room temperature overnight. Then the solvent was evaporated and the residue was washed with saturated NaHCO₃ and saturated brine. The crude product was purified by column chromatography on silica gel (PE:EA 10:1~3:1) to give the title compound (1.94 g, yield 40%). ¹H NMR: (400 MHz, DMSO): δ11.47 (s, 1H), 10.46 (s, 1H), 9.19 (s, 1H), 7.88-7.11 (m, 6H), 4.85 (s, 2H), 4.08-4.03 (m, 2H), 3.24-3.20 (m, 2H), 2.59-2.55 (m, 2H), 1.17-1.13 (m, 3H).

4-Amino-N-(1-hydroxy-1,3-dihydrobenzo[c][1,2]oxaborol-6-yl)-2-(3-hydroxypropyl)benzenesulfonamide

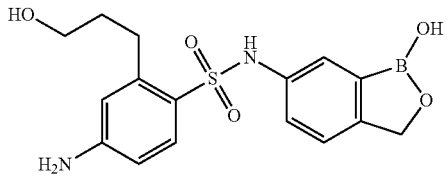 [SMILES: Nc1ccc(S(=O)(=O)Nc2ccc3c(c2)B(O)OC3)c(CCCO)c1]

A mixture of ethyl 3-(2-(N-(1-hydroxy-1,3-dihydrobenzo[c][1,2]oxaborol-6-yl)sulfamoyl)-5-(2,2,2-trifluoroacetamido)phenyl)propanoate (1.6 g, 3.2 mmol), and NaBH₄ (0.48 g, 12.8 mmol) in THF (30 mL) was stirred at 0° C. Then CH₃OH (1 ml) was added dropwise into the mixture and stirred at r.t. overnight. The solvent was evaporated and the residue was extracted with EtOAc, washed with brine, dried over Na₂SO₄ and concentrated to give the crude product. The residue was purified by prep-HPLC (column: YMC 150×30.0 mm, 20µ; liquid phase: [A-H₂O; B-MeCN+0.1% TFA] B %: 12%-42%, 10 min) to give the title compound, which was dissolved in MeCN, acidified with aq. HCl and freeze-dried to give the product as hydrochloride salt (280 mg, yield 70%). ¹H NMR (400 MHz, DMSO-d6): δ9.97 (s, 1H), 7.57-7.09 (m, 6H), 4.83 (s, 2H), 3.46-3.42 (m, 2H), 2.83-2.79 (m, 2H), 1.66-1.62 (m, 2H); ESI-MS m/z 385 (M+Na, positive); HPLC purity: 94.25% (MaxPlot 190-370 nm), 94.25% (220 nm).

4-Amino-N-(1-hydroxy-1,3-dihydrobenzo[c][1,2]oxaborol-6-yl)-2-(3-oxobutyl)benzenesulfonamide and

4-Amino-N-(1-hydroxy-1,3-dihydrobenzo[c][1,2]oxaborol-6-yl)-2-(3-hydroxybutyl)benzenesulfonamide The mixture of 3-nitrobenzaldehyde (15.1 g, 0.1 mol), acetone (20 mL) and water (40 mL) was slowly added 5% aqueous NaOH (8 mL) from a dropping funnel at 40° C. After the reactant disappeared in TLC monitoring, acetone was removed under reduced pressure. The residue was extracted with ethyl acetate. The organic layer was separated, washed with brine, dried (Na₂SO₄) and concentrated to give the (E)-4-(3-nitrophenyl)but-3-en-2-one (15 g, 78% yield) as a yellow oil. ¹H NMR: (400 MHz, CDCl₃) δ 8.31 (t, 1H), 8.15 (t, 1H), 7.83 (d, 1H), 7.52 (t, 1H), 7.44 (d, 1H), 6.70 (d, 1H), 2.33 (s, 3H).

A solution of (E)-4-(3-nitrophenyl)but-3-en-2-one (15 g, 78 mmol) in EtOAc (150 mL) was added Pd/C (1.7 g), H₂ was bubbled in, the reaction mixture was stirred at 40 psi H₂ for 4 hrs. The mixture was filtrated, and the filtrate was concentrated to give 4-(3-aminophenyl)butan-2-one (12 g, 94% yield). ¹H NMR: (400 MHz, CDCl₃) δ 7.08 (t, 1H), 6.63 (s, 1H), 6.54 (d, 1H), 6.42 (d, 1H), 2.76 (t, 2H), 2.71 (t, 2H), 2.1 (s, 3H).

To a stirred solution of 4-(3-aminophenyl)butan-2-one (16.5 g, 0.1 mol) in DCM (50 mL) was added pyridine (11.9 g, 0.15 mol). TFAA (31.5 g, 0.15 mol) was added dropwise to the solution at 0° C. The reaction mixture was stirred at r.t. for 3 hrs, then water was added, the organic layer was separated and washed with brine, dried over Na₂SO₄, concentrated and purified by silica gel chromatography (petroleum ether:EtOAc=1:0 to 10:1) to give 2,2,2-trifluoro-N-(3-(3-oxobutyl)phenyl)acetamide (21.3 g, 81% yield) as a yellow solid. ¹H NMR: (400 MHz, CDCl₃) δ 8.26 (s, 1H), 7.43 (t, 1H), 7.39 (d, 1H), 7.22 (t, 1H), 7.05 (d, 1H), 2.90-2.86 (m, 2H), 2.79-2.73 (m, 2H), 2.12 (s, 3H).

To 2,2,2-trifluoro-N-(3-(3-oxobutyl)phenyl)acetamide (2 g, 8 mmol) was added HOSO₂Cl (9 g, 77 mmol) dropwise at 0° C. The mixture was stirred at r.t. for 3 hrs. The reaction mixture was diluted with DCM and washed with water, the organics was dried over Na₂SO₄ and concentrated to give 2-(3-oxobutyl)-4-(2,2,2-trifluoroacetamido)benzene-1-sulfonyl chloride (1.5 g, yield 54%). ¹H NMR: (400 MHz, CDCl₃) δ 8.05 (s, 1H), 7.76 (d, 1H), 7.70 (t, 1H), 7.63 (d, 1H), 3.31 (t, 2H), 2.82 (t, 2H), 2.14 (s, 3H).

To a solution of 6-amino-3H-benzo[c][1,2]oxaborol-1-ol (0.37 g, 2 mmol) and NMM (0.76 g, 7 mmol) in CH₃CN (50 mL) was added a solution of 2-(3-oxobutyl)-4-(2,2,2-trifluoroacetamido)benzene-1-sulfonyl chloride (0.9 g, 2 mmol) in CH₃CN (30 mL) dropwise at 0° C. The reaction mixture was stirred at room temperature for 2 hrs, then the reaction mixture was concentrated in vacuo, the residue was diluted with water and extracted with EtOAc, the organics was dried over Na₂SO₄, concentrated to give the crude product, the crude was purified by pre-HPLC (column: Luna 300×50.0 mm, 10 um; liquid phase: [A-H₂O+0.05% TFA; B-MeCN] B %: 24%-51%, 23 min) to give 2,2,2-trifluoro-N-(4-(N-(1-hydroxy-1,3-dihydrobenzo[c][1,2]oxaborol-6-yl)sulfamoyl)-3-(3-oxobutyl)phenyl)acetamide (0.5 g, yield 42%) as yellow solid.

To a solution of 2,2,2-trifluoro-N-(4-(N-(1-hydroxy-1,3-dihydrobenzo[c][1,2]oxaborol-6-yl)sulfamoyl)-3-(3-oxobutyl)phenyl)acetamide (2 g, 4 mmol) in MeOH (15 mL) and water (15 mL) was added LiOH.H₂O (0.93 g, 22 mmol). The mixture was stirred at r.t. overnight. The reaction mixture was concentrated, the residue was purified by pre-HPLC (column: Luna 300×50.0 mm, 10 um; liquid phase: [A-H₂O+0.05% TFA; B-MeCN] B %: 12%-42%, 24 min), concentrated, acidified with HCl and freeze-dried to give 4-amino-N-(1-hydroxy-1,3-dihydrobenzo[c][1,2]oxaborol-6-yl)-2-(3-oxobutyl)benzenesulfonamide (650 mg, yield 40%) as HCl salt. ¹H NMR: (400 MHz, DMSO-d6). δ 10.00 (s, 1H), 7.40 (d, 1H), 7.21 (d, 1H), 7.11 (d, 1H), 7.09 (d, 1H), 6.36-6.33 (m, 2H), 4.84 (s, 2H), 2.97 (t, 2H), 2.61 (t, 2H), 2.06 (s, 3H).

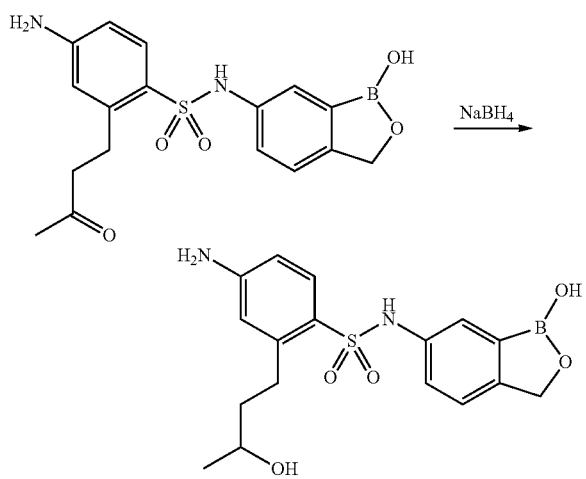

To a solution of 4-amino-N-(1-hydroxy-1,3-dihydrobenzo[c][1,2]oxaborol-6-yl)-2-(3-oxobutyl)benzenesulfonamide (0.42 g, 1 mmol) in MeOH (15 mL) was added NaBH$_4$ (0.13 g, 3 mmol). The mixture was stirred at r.t. for 2 hrs. The reaction mixture was concentrated, the residue was purified by pre-HPLC (column: Luna 300×50.0 mm, 10 um; liquid phase: [A-H$_2$O+0.05% TFA; B-MeCN] B %: 5%-33%, 23 min), concentrated, acidified with HCl and freeze-dried to give 4-amino-N-(1-hydroxy-1,3-dihydrobenzo[c][1,2]oxaborol-6-yl)-2-(3-hydroxybutyl)benzenesulfonamide (230 mg, yield 55%) as HCl salt. $^1$H NMR: (400 MHz, DMSO-d6): δ 9.90 (s, 1H), 7.56 (d, 1H), 7.42 (d, 1H), 7.22 (d, 1H), 7.13-7.10 (m, 1H), 6.42 (d, 1H), 6.36-6.33 (m, 1H), 4.85 (s, 2H), 3.69-3.65 (m, 1H), 2.87-2.80 (m, 2H), 1.55-1.49 (m, 2H), 1.08 (d, 3H).

4-Amino-N-(1-hydroxy-1,3-dihydrobenzo[c][1,2]oxaborol-6-yl)-2-(2-ethoxyethyl)benzenesulfonamide 4-Amino-2-bromo-N-(1-hydroxy-1,3-dihydrobenzo[c][1,2]oxaborol-6-yl)benzenesulfonamide

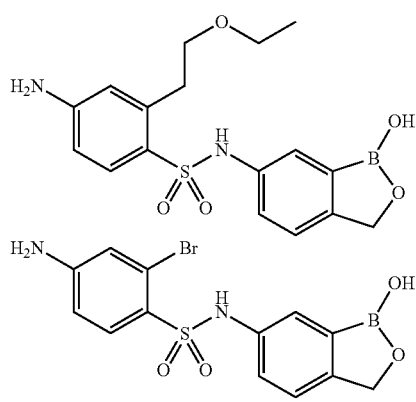

To a solution of 3-bromoaniline (21.7 g, 0.126 mol) and TEA (20 ml, 0.178 mol) in DCM (300 ml) was added trifluoroacetic anhydride (31.8 g, 0.151 mol) dropwise at) 0° C. over 30 min. The reaction mixture was stirred at 0° C. to room temperature for 3 hrs. The rxn mix was washed with H$_2$O, brine and dried over MgSO$_4$. Filtered, concentrated in reduced pressure to dryness to give crude N-(3-bromophenyl)-2,2,2-trifluoroacetamide.

The crude N-(3-bromophenyl)-2,2,2-trifluoroacetamide was cooled to 0° C., then chlorosulfonic acid was added dropwise at 0° C. over 10 min. The rxn mix was stirred at 0° C. to rt overnight. LC/MS monitored the rxn. The rxn mix poured into ice-H$_2$O (100 g) to quench the rxn. The sticky gum was washed with H$_2$O and dried in vacuum to give the crude 2-bromo-4-(2,2,2-trifluoroacetamido)benzene-1-sulfonyl chloride.

Pyridine (1.5 equiv) was added dropwise to the cooled suspension of the crude 2-bromo-4-(2,2,2-trifluoroacetamido)benzene-1-sulfonyl chloride (24 g, 0.06 mol) and 6-aminobenzo[c][1,2]oxaborol-1(3H)-ol (1.2 eq) in acetonitrile (300 ml) at 0° C. over 10 min. The rxn mix was stirred overnight. The solid was filtered and washed with EtOAc. The filtrate was washed with, H$_2$O, brine, dried over MgSO$_4$, filtered, and concentrated to dryness to give crude N-(3-bromo-4-(N-(1-hydroxy-1,3-dihydrobenzo[c][1,2]oxaborol-6-yl)sulfamoyl)phenyl)-2,2,2-trifluoroacetamide which was purified by flash chromatography on silica gel. $^1$H NMR (400 MHz, DMSO-d$_6$) δ (ppm): 11.6 (s, 1H), 10.56 (s, 1H), 9.20 (s, 1H), 8.12 (d, J=1.9 Hz, 1H), 8.06 (d, J=8.8 Hz, 1H), 7.79 (dd, J=2.0, 8.6 Hz, 1H), 7.47 (d, J=1.8 Hz, 1H), 7.24 (d, J=8.4 Hz, 1H), 7.20 (dd, J=1.9, 8.3 Hz, 1H), 4.85 (s, 2H). MS (ESI) m/z=479 (M+1).

N-(3-bromo-4-(N-(1-hydroxy-1,3-dihydrobenzo[c][1,2]oxaborol-6-yl)sulfamoyl)phenyl)-2,2,2-trifluoroacetamide (200 mg) was dissolved in 7N NH$_3$ in methanol and stirred at rt overnight. Evaporated to remove the solvent and purified by prep-HPLC to give 4-amino-2-bromo-N-(1-hydroxy-1,3-dihydrobenzo[c][1,2]oxaborol-6-yl)benzenesulfonamide (110 mg). $^1$H NMR (400 MHz, DMSO-d$_6$) δ (ppm): 10.06 (s, 1H), 9.10 (brs, 1H), 7.65 (d, J=8.8 Hz, 1H), 7.44 (d, J=2.0 Hz, 1H), 7.21 (d, J=8.4 Hz, 1H), 7.17 (dd, J=2.0, 8.4 Hz, 1H), 6.79 (d, J=2.0 Hz, 1H), 6.48 (dd, J=2.0, 8.4 Hz, 1H), 4.84 (s, 2H). MS (ESI) m/z=381 (M−1).

The mix of N-(3-bromo-4-(N-(1-hydroxy-1,3-dihydrobenzo[c][1,2]oxaborol-6-yl)sulfamoyl)phenyl)-2,2,2-trifluoroacetamide (87 mg, 0.182 mmol), (E)-tributyl(2-ethoxyvinyl) stannane (71 mg, 0.196 mmol), dimethylamino ethanol (17.9 mg, 0.2 mmol) and Pd(dppf)$_2$Cl$_2$ in NMP (2 ml) was degassed and heated to 100° C. overnight. The crude product was purified by prep-HPLC to give (E)-N-(3-(2-ethoxyvinyl)-4-(N-(1-hydroxy-1,3-dihydrobenzo[c][1,2]oxaborol-6-yl)sulfamoyl)phenyl)-2,2,2-trifluoroacetamide.

(E)-N-(3-(2-ethoxyvinyl)-4-(N-(1-hydroxy-1,3-dihydrobenzo[c][1,2]oxaborol-6-yl)sulfamoyl)phenyl)-2,2,2-trifluoroacetamide (47 mg) was hydrogenated with Pd/C (10%, 20 mg) in 7N NH$_3$ in methanol (6 ml) at 50 psi for 4 hrs. The catalyst was filtered and filtrate was concentrated to dryness. The crude product was purified by prep-HPLC to give 4-amino-N-(1-hydroxy-1,3-dihydrobenzo[c][1,2]oxaborol-6-yl)-2-(2-ethoxyethyl)benzenesulfonamide (18 mg). $^1$H NMR (400 MHz, DMSO-d$_6$) δ (ppm): 9.97 (s, 1H), 9.15 (s, 1H), 7.52 (d, J=8.8 Hz, 1H), 7.39 (d, J=1.9 Hz, 1H), 7.21 (d, J=8.4 Hz, 1H), 7.10 (dd, J=2.2, 8.2 Hz, 1H), 6.42 (d, J=2.2 Hz, 1H), 6.34 (dd, J=2.0, 8.4 Hz, 1H), 5.84 (brs, 2H), 4.84 (s, 2H), 3.50 (t, J=7.2 Hz, 2H), 3.40 (q, J=7.1 Hz, 2H), 3.03 (t, J=7.1 Hz, 2H), 1.08 (t, J=7.0 Hz, 3H). MS (ESI) m/z=375 (M−1).

4-Amino-N-(1-hydroxy-1,3-dihydrobenzo[c][1,2]oxaborol-6-yl)-2-(2-methoxyethyl)benzenesulfonamide

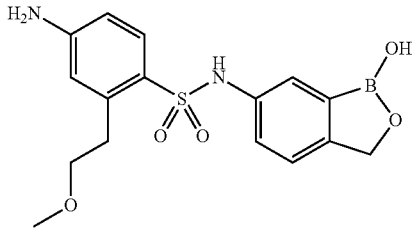 [SMILES: COCCc1cc(N)ccc1S(=O)(=O)Nc1ccc2c(c1)B(O)OC2]

A mixture of 1-bromo-2-methyl-4-nitrobenzene (15 g, 79 mmol), benzoyl peroxide (2 g, 8 mmol) and NBS (17 g, 95 mmol) in CCl$_4$ (150 mL) was stirred at reflux overnight. The mixture was cooled to room temperature and filtered, the filtrate was washed with water twice, dried over Na$_2$SO$_4$ and concentrated to give 1-bromo-2-(bromomethyl)-4-nitrobenzene as light yellow oil (17 g, 69%). $^1$H NMR: 400 MHz CDCl$_3$ δ 8.37-8.34 (m, 1H), 8.05-8.02 (m, 1H), 7.77-7.75 (m, 1H), 3.87 (s, 2H).

A solution of 1-bromo-2-(bromomethyl)-4-nitrobenzene (54 g, 183 mmol) in toluene (200 mL) and water (100 mL) was heated to 60° C., then NaCN (27.2 g, 555 mmol) was added, followed by stirring at reflux overnight. Water was added to the mixture, the aqueous layer was extracted with ethyl acetate 3 times. The combined organic phase was washed with brine, dried over sodium sulfate. The crude product was purified by silica gel column chromatography (petroleum ether/ethyl acetate=100:1 to 5:1) to give 2-(2-bromo-5-nitrophenyl)acetonitrile (15 g, yield 34%).

A solution of 2-(2-bromo-5-nitrophenyl)acetonitrile (15 g, 62.2 mmol) in MeOH/HCl (1000 mL, 4M) was stirred at room temperature overnight. The solvent was evaporated, saturated sodium bicarbonate was added, and the aqueous layer was extracted with ethyl acetate 3 times. The combined organic phase was washed with brine, dried over sodium sulfate and concentrated to give methyl 2-(2-bromo-5-nitrophenyl)acetate (14 g, yield 82%). $^1$H NMR: 400 MHz CDCl$_3$ δ 8.18-8.17 (m, 1H), 8.02-8.00 (m, 1H), 7.77-7.75 (m, 1H), 3.80 (s, 2H), 3.65 (s, 3H).

A solution of methyl 2-(2-bromo-5-nitrophenyl)acetate (14 g, 51 mmol) in THF (150 mL) was cooled to 0° C., then MeOH (15 ml) was added slowly, followed by stirring at room temperature overnight. Water was added to terminate the reaction. The aqueous layer was extracted with ethyl acetate 3 times. The combined organic phase was washed with brine, dried over sodium sulfate and concentrated to give 2-(2-bromo-5-nitrophenyl)ethanol (12 g, yield 96%). $^1$H NMR: 400 MHz CDCl$_3$ δ 8.18-8.17 (m, 1H), 8.18-8.17 (m, 1H), 7.96-7.93 (m, 1H), 7.74-7.72 (m, 1H), 3.97-3.94 (m, 2H), 3.13-3.10 (m, 2H).

A solution of 2-(2-bromo-5-nitrophenyl)ethanol (12 g, 48.7 mmol) in THF (100 mL) was cooled to 0° C., then NaH (2.53 g, 60%) was added slowly, followed by stirring at 0° C. for half an hour. Then MeI (33 mL, 487 mmol) was dropwise added, followed by stirring at room temperature overnight. The solvent was evaporated, water was added. The aqueous layer was extracted with ethyl acetate 3 times. The combined organic phase was washed with brine, dried over sodium sulfate and concentrated to give 1-bromo-2-(2-methoxyethyl)-4-nitrobenzene (10 g, yield 80%). $^1$H NMR: 400 MHz CDCl$_3$ δ 8.15 (s, 1H), 7.95-7.92 (m, 1H), 7.72-7.70 (m, 1H), 3.68-3.65 (m, 2H), 3.37 (s, 3H), 3.12-3.09 (m, 2H).

To a solution of 1-bromo-2-(2-methoxyethyl)-4-nitrobenzene (7.8 g, 30 mmol) and Cs$_2$CO$_3$ (14.66 g, 45 mmol) in DMF (100 mL) was added BnSH (4.1 g, 33 mmol) slowly, followed by stirring at room temperature for three hours. Water was added, the precipitate was filtered, washed by water and petroleum to give benzyl(2-(2-methoxyethyl)-4-nitrophenyl)sulfane (8 g, yield 88%). $^1$H NMR: 400 MHz CDCl$_3$ δ 8.05 (s, 1H), 8.01-7.98 (m, 1H), 7.38-7.28 (m, 6H), 4.23 (s, 2H), 3.64-3.61 (m, 2H), 3.34 (s, 3H), 3.03-2.99 (m, 2H).

A solution of benzyl(2-(2-methoxyethyl)-4-nitrophenyl)sulfane (3 g, 9.9 mmol) in DCM (40 mL) and water (10 mL) was cooled to 0° C., then chlorine was bubbled to reaction for 5 mins. The aqueous was extracted by DCM 3 times, washed with brine, dried over Na$_2$SO$_4$ and concentrated to give crude product 2-(2-methoxyethyl)-4-nitrobenzene-1-sulfonyl chloride (2 g, yield 76%). $^1$H NMR: 400 MHz CDCl$_3$ δ 8.45-8.44 (m, 1H), 8.32-8.27 (m, 1H), 7.38-7.28 (m, 6H), 3.81-3.78 (m, 2H), 3.54-2.51 (m, 2H), 3.40 (s, 3H).

To a solution of 6-amino-3H-benzo[c][1,2]oxaborol-1-ol (0.59 g, 3.9 mmol) and N-methylmorpholine (2.53 g, 25 mmol) in MeCN (70 mL) was added 2-(2-methoxyethyl)-4-nitrobenzene-1-sulfonyl chloride (1.4 g, 5 mmol) in MeCN (20 mL) at 0° C., then the solution was stirred at room temperature overnight. The mixture was concentrated in vacuo, and ethyl acetate and water was added to the residue. The organic layer was dried over Na$_2$SO$_4$ and concentrated to give the crude product. The crude product was purified by silica gel column chromatography (petroleum ether/ethyl acetate=10:1 to 0:1) to give N-(1-hydroxy-1,3-dihydrobenzo[c][1,2]oxaborol-6-yl)-2-(2-methoxyethyl)-4-nitrobenzenesulfonamide (1 g, yield 50%).

A mixture of N-(1-hydroxy-1,3-dihydrobenzo[c][1,2]oxaborol-6-yl)-2-(2-methoxyethyl)-4-nitrobenzenesulfonamide (1 g, crude, 2.5 mmol) and Pd/C (0.2 g, 10%) in MeOH (50 mL) was stirred under 50 PSI H$_2$ at room temperature for 2 hrs. The mixture was filtered and the filtrate was concentrated. The residue was purified by prep-HPLC (column: Luna 300×50.0 mm, 10 um; liquid phase: [A-H$_2$O+0.05% TFA; B-MeCN] B %: 5%-35%, 23 min), concentrated, acidified with HCl and freeze-dried to give the title compound (0.3 g, yield 32%) as HCl salt. $^1$H NMR: 400 MHz DMSO-d6 δ10.01 (s, 1H), 7.56-7.54 (m, 1H), 7.40-7.39 (m, 1H), 7.21-7.18 (m, 1H), 7.11-7.09 (m, 1H), 6.48-6.40 (m, 2H), 4.83 (s, 2H), 3.49-3.45 (m, 2H), 3.21 (s, 3H), 3.06-3.03 (m, 2H).

4-Amino-2-(aminomethyl)-N-(1-hydroxy-1,3-dihydrobenzo[c][1,2]oxaborol-6-yl)benzenesulfonamide To a solution of 2-chloro-5-nitrobenzonitrile (50 g, 0.15 mol) in MeCN (1000 mL) was added K$_2$CO$_3$ (45.5 g, 0.33 mol) and phenylmethanethiol (34 g, 0.27 mol). The mixture was stirred at room temperature overnight. The mixture was filtered through the celite pad and the filtrate was concentrated in vacuo to give 2-(benzylthio)-5-nitrobenzonitrile (54 g, 73%) as a yellow solid. $^1$H NMR CDCl$_3$ 400 MHz δ 8.43 (s, 1H), 8.27-8.25 (m, 1H), 7.44-7.31 (m, 6H), 4.35 (s, 2H).

To a solution of 2-(benzylthio)-5-nitrobenzonitrile (5 g, 18.5 mmol) in DCM/H$_2$O (100 mL/25 mL) was vigorously bubbled chlorine (gas) for 0.5 hr at 0° C. The organics was separated and washed with brine. The organic layer was dried over Na$_2$SO$_4$ and evaporated at less than 40° C. in vacuo to yield the crude solid, which washed with 1M HCl and water to give 2-cyano-4-nitrobenzene-1-sulfonyl chloride (12 g, 64.90%) as a yellow solid. ¹H NMR: CDCl₃ 400 MHz δ 8.80 (s, 1H), 8.67 (d, J=11.6 Hz, 1H), 8.46 (d, J=8.8 Hz, 1H).

2-Cyano-N-(1-hydroxy-1,3-dihydrobenzo[c][1,2]oxaborol-6-yl)-4-nitrobenzenesulfonamide To a solution of 6-aminobenzo[c][1,2]oxaborol-1(3H)-ol (16.4 g, 0.11 mol) and pyridine (10.3 g, 0.13 mol) in MeCN/DMF (400 mL/100 mL) was added 2-cyano-4-nitrobenzene-1-sulfonyl chloride (24.7 g, 0.1 mol) at 0° C., then the solution was stirred at room temperature overnight. The mixture was concentrated in vacuo, and DCM and water was added to the residue. The organic layer was dried over Na₂SO₄ and concentrated to give the crude product.

4-Amino-2-(aminomethyl)-N-(1-hydroxy-1,3-dihydrobenzo[c][1,2]oxaborol-6-yl)benzenesulfonamide A mixture of 2-cyano-N-(1-hydroxy-1,3-dihydrobenzo[c][1,2]oxaborol-6-yl)-4-nitrobenzenesulfonamide (3.6 g, crude, 10 mmol), NH₃H₂O (50 mL) and Raney Ni (3 g) in MeOH (500 mL) was stirred under 50 PSI H₂ at room temperature for 20 hrs. The mixture was filtered and the filtrate was concentrated. The residue was purified by prep-HPLC (column: Luna 300×50.0 mm, 10 u; liquid phase: [A-H₂O+ 0.025% TFA; B-MeCN] B %: 10%-45%, 25 min) to give 4-amino-2-(aminomethyl)-N-(1-hydroxy-1,3-dihydrobenzo[c][1,2]oxaborol-6-yl)benzenesulfonamide (2.5 g, 55%) as TFA salt. ¹H NMR DMSO 400 MHz δ10.05 (s, 1H), 8.16 (s, 3H), 7.47 (d, J=4.8 Hz, 1H), 7.42 (d, J=5.6 Hz, 1H), 7.23 (d, J=8.4 Hz, 1H), 7.10 (q, 1H), 6.54 (s, 1H), 6.47 (q, 1H), 4.86 (s, 2H), 4.12 (d, J=5.6 Hz, 1H).

4-Amino-2-(2-aminoethyl)-N-(1-hydroxy-1,3-dihydrobenzo[c][1,2]oxaborol-6-yl)benzenesulfonamide

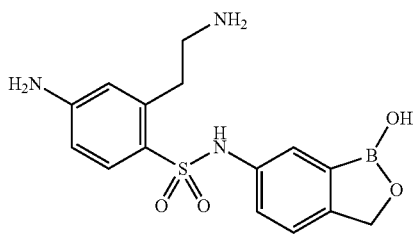 [SMILES: NCCc1cc(N)ccc1S(=O)(=O)Nc1ccc2c(c1)B(O)OC2]

General procedure 1: 6-aminobenzo[c][1,2]oxaborol-1(3H)-ol (600 mg, 4 mmol), 4-(2,2,2-trifluoroacetamido)-2-(2-(2,2,2-trifluoroacetamido)ethyl)benzene-1-sulfonyl chloride (1.7 g, 4 mmol), pyridine (0.4 ml, 5 mmol), rt, 1 hour. Removed solvent, the crude was dissolved in MeOH (50 ml), treated with NaOH (15 ml, 1N), stirred at 40° C. for 4 hours. Then adjusted the pH to neutral, concentrated, the result solid was purified by prep HPLC (SunFire Prep C18 OBD 5 uM 30×50 mm column). The title compound was obtained as light yellow power. MS calcd for (C₁₅H₁₈BN₃O₄S): 347.11. MS found (ESI negative): (M−H)⁻=346.1. ¹H NMR (400 MHz, DMSO-d₆) δ (ppm): 9.88 (s, 1H), 9.15 (br, 1H), 7.72 (s, 1H), 7.46 (d, J=8.4 Hz, 1H), 7.35 (d, J=1.6 Hz, 1H), 7.19 (d, J=8 Hz, 1H), 7.08 (dd, J=8 Hz, 1H), 6.37 (d, J=2 Hz, 1H), 6.35 (s, 1H), 4.81 (s, 2H), 3.03 (m, 2H), 2.89 (m, 2H).

4-Amino-2-(2-fluoroethyl)-N-(1-hydroxy-1,3-dihydrobenzo[c][1,2]oxaborol-6-yl)benzenesulfonamide

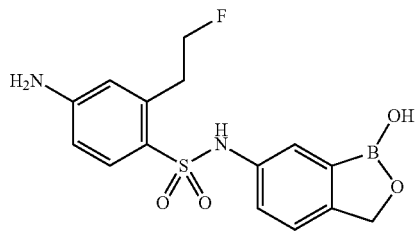 [SMILES: Nc1ccc(S(=O)(=O)Nc2ccc3c(c2)B(O)OC3)c(CCF)c1]

To a solution of 2-(3-nitrophenyl)acetic acid (1.8 g, 0.01 mol) in THF (20 ml) at 0° C., was added BH₃THF dropwise (1 M, 22 ml, 0.022 mol), removed ice bath and stirred at room temperature over night. The reaction was quenched with water and extracted with EtOAc, washed with water and brine, dried over Na₂SO₄. Concentrated to get crude 2-(3-nitrophenyl)ethanol as light yellow solid (0.9 g).

To a solution of 2-(3-nitrophenyl)ethanol (0.9 g, 5.38 mmol) in DCM (20 ml) at 0° C., was added DAST drop-wise (1.06 mL, 8.1 mmol), removed ice bath after 30 min and stirred at room temperature for 4 h. The reaction was quenched with water and extracted with DCM, washed with water and brine, dried over Na₂SO₄. The crude residue was purified by ISCO CombiFlash Rf silica chromatography eluted with 20:80 EtOAc:Hexane to give the desired product 1-(2-fluoroethyl)-3-nitrobenzene as yellow solid (0.68 g).

To a stirred solution of 1-(2-fluoroethyl)-3-nitrobenzene (0.68 g, 4 mmol) in 20 mL of MeOH: EtOAc was added Pd/C (10 wt. % on activated carbon, 100 mg). The flask was evacuated quickly and filled with hydrogen three times. A hydrogen balloon was then placed on the reaction flask. The reaction mixture was allowed to stir at room temperature under hydrogen overnight. After the mixture was filtered through a pad of Celite, the reaction was concentrated in vacuo to give the desired compound that was used directly for the next step.

To a stirred ice cold solution of 3-(2-fluoroethyl)aniline (0.42 g, 3.2 mmol) and TEA (1.5 mL, 10 mmol) in 10 mL of CH₂Cl₂ was added 2,2,2-trifluoroacetic anhydride (2 mL, 9.1 mmol) drop-wise. The reaction mixture was stirred at room temperature for 2 hours. After the mixture was concentrated, the residue was extracted with EtOAc, washed with water, NaHCO₃ solution and brine, dried over Na₂SO₄ to give the desired crude compound as a yellow solid (0.53 g).

The 2,2,2-trifluoro-N-(3-(2-fluoroethyl)phenyl)acetamide (0.53 g, 2.2 mmol) was mixed with chlorosulfonic acid (3 mL) at 0° C., and the mixture was stirred at room temperature for 2 hours. As the starting material was consumed as indicated by LC/MS, the mixture was added dropwise to ice-water. After filtered, the resulting residue was dried in vacuo to give the crude product as a yellow residue (0.6 g).

To a stirred solution of 6-aminobenzo[c][1,2]oxaborol-1(3H)-ol (0.5 g, 3.8 mmol) and pyridine (2 mL) in 10 mL of DCM was added 2-(2-fluoroethyl)-4-(2,2,2-trifluoroacetamido)benzene-1-sulfonyl chloride (0.6 g, 2 mmol) in portion. The reaction mixture was stirred at room temperature for 3 hours. After the mixture was concentrated, the residue was extracted with ethyl acetate and washed with water, 1N HCl and brine. The organic layer was dried over $Na_2SO_4$ and concentrated to give the crude product as a yellow solid (210 mg).

A solution of 2,2,2-trifluoro-N-(3-(2-fluoroethyl)-4-(N-(1-hydroxy-1,3-dihydrobenzo[c][1,2]oxaborol-6-yl)sulfamoyl)phenyl)acetamide (210 mg, 0.47 mmol) and 7M ammonium in MeOH (10 mL) in 10 mL of MeOH was stirred in a sealed tube at 60° C. for 2 hours. After concentrated, the crude mixture was purified by prep HPLC (SunFire Prep C18 OBD 5 uM 30×50 mm column) to give the title compound as a yellow solid (87 mg). MS calcd for ($C_{15}H_{16}BFN_2O_4S$): 350.1. MS found (ESI negative): (M–H)⁻=349.1. ¹H NMR (400 MHz, DMSO-$d_6$) δ (ppm): 10.05 (s, 1H), 9.2 (bs, 1H), 7.57 (d, J=8.4 Hz, 1H), 7.42 (d, J=2 Hz, 2H), 7.22 (d, J=8 Hz, 1H), 7.12 (dd, J=8, 2 Hz, 1H), 6.46 (d, J=2 Hz, 1H), 6.40 (dd, J=8.4, 2 Hz, 1H), 5.5 (bs, 2H), 4.86 (s, 2H), 4.59 (dt, J=48, 6.4 Hz, 2H), 4.23 (dt, J=23, 6 Hz, 2H).

2-(5-Amino-2-(N-(1-hydroxy-1,3-dihydrobenzo[c][1,2]oxaborol-6-yl)sulfamoyl)phenyl)acetic acid

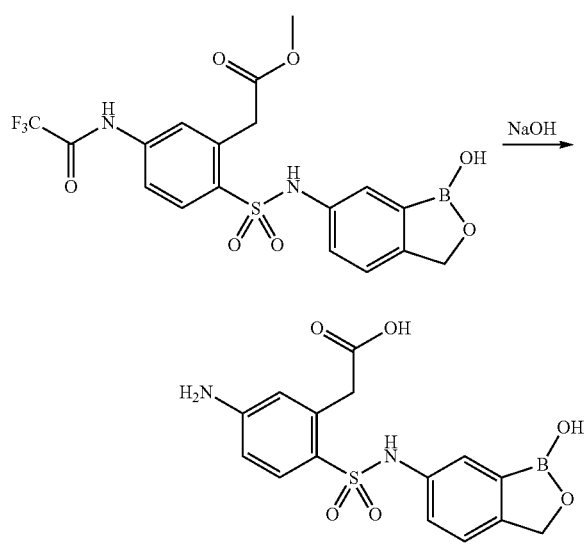

To a stirred solution of methyl 2-(2-(N-(1-hydroxy-1,3-dihydrobenzo[c][1,2]oxaborol-6-yl)sulfamoyl)-5-(2,2,2-trifluoroacetamido)phenyl)acetate (134 mg, 0.28 mmol) in 2 mL of MeOH and water (1:1, v/v) was added NaOH (34 mg, 0.85 mmol). The reaction mixture was stirred at room temperature for 16 hours. After MeOH was removed in vacuo, the residue was dissolved in water and acidified with 0.5N HCl. The mixture was extracted with ethyl acetate three times, and washed with water and brine. The organic layer was dried over $Na_2SO_4$, filtered and concentrated. The crude residue was purified by prep HPLC (SunFire Prep C18 OBD 5 uM 30×50 mm column) to give the title compound as an off-white solid (51 mg, yield 50%). MS calcd for ($C_{15}H_{15}BN_2O_6S$): 362.1. MS found (ESI negative): (M–H)⁻=361.1. ¹H NMR (DMSO-$d_6$) δ (ppm): 9.78 (s, 1H), 9.10 (bs, 1H), 7.41 (d, J=8.4 Hz, 1H), 7.35 (s, 1H), 7.14 (d, J=8.4 Hz, 1H), 7.04 (d, J=8.0 Hz, 1H), 6.34 (s, 1H), 6.32 (d, J=8.8 Hz, 1H), 4.79 (s, 2H), 3.73 (s, 2H).

2-(5-Amino-2-(N-(5-fluoro-1-hydroxy-1,3-dihydrobenzo[c][1,2]oxaborol-6-yl)sulfamoyl)phenyl)acetic acid

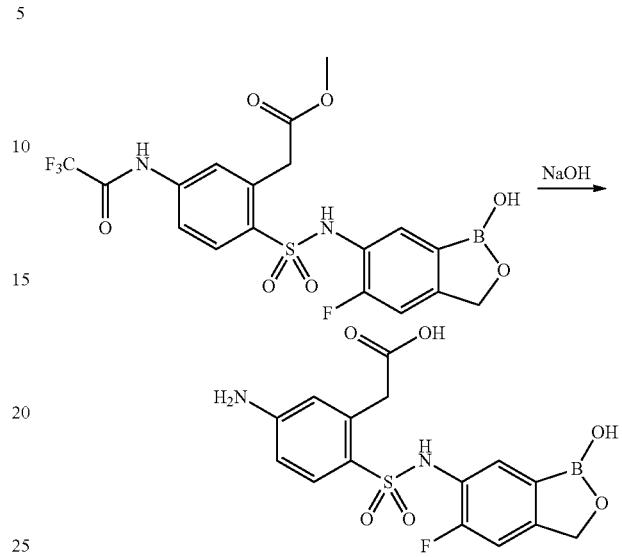

To a stirred solution of methyl 2-(2-(N-(5-fluoro-1-hydroxy-1,3-dihydrobenzo[c][1,2]oxaborol-6-yl)sulfamoyl)-5-(2,2,2-trifluoroacetamido)phenyl)acetate (250 mg, 0.51 mmol) in 10 mL of MeOH and water (1:1, v/v) was added NaOH (1N solution, 2 mL, 2.0 mmol). The reaction mixture was stirred at room temperature for 16 hours. After MeOH was removed in vacuo, the residue was dissolved in water and acidified with 0.5N HCl. The mixture was extracted with ethyl acetate three times, and washed with water and brine. The organic layer was dried over $Na_2SO_4$, filtered and concentrated. The crude residue was purified by prep HPLC (SunFire Prep C18 OBD 5 uM 30×50 mm column) to give the title compound as a white powder (142 mg, yield 75%). MS calcd for ($C_{15}H_{14}BFN_2O_6S$): 380.1. MS found (ESI negative): (M–H)⁻=379.1. ¹H NMR (400 MHz, DMSO-$d_6$) δ (ppm): 9.58 (s, 1H), 7.65 (d, J=8 Hz, 1H), 7.32 (d, J=8.8 Hz, 1H), 7.17 (d, J=10.4 Hz, 1H), 6.44 (d, J=2 Hz, 2H), 6.36 (dd, J=8.8, 2 Hz, 1H), 4.88 (s, 2H), 3.89 (s, 2H).

Methyl 2-(5-amino-2-((1-hydroxy-1,3-dihydrobenzo[c][1,2]oxaborol-6-yl)methylsulfonyl)phenyl)acetate To the mixture of methyl 2-(3-aminophenyl)acetate (8 g, 50 mmol) and triethyl amine (7 ml, 50 mmol) in DCM (50 ml) at 0° C., added trifluoroacetic acid anhydride (6.95 ml, 50 mmol) slowly, stirred for 2 hours at rt after addition. Removed solvent, diluted with EtOAc, washed with water and brine, dried over Na$_2$SO$_4$. Concentrated to give light yellow solid used for next step without further purification.

The crude methyl 2-(3-(2,2,2-trifluoroacetamido)phenyl) acetate (8.1 g, 31 mmol) was added to chlorosulphonyl acid (40 ml) at 0° C. in portion, stirred at rt after addition overnight. The reaction mixture was slowly poured onto ice/water under stirring, the result suspension was filtered and washed with cold water. Leave it for air dry. Got 6.7 g off white solid (methyl 2-(2-(chlorosulfonyl)-5-(2,2,2-trifluoroacetamido) phenyl)acetate) as product.

General procedure 1: 6-aminobenzo[c][1,2]oxaborol-1 (3H)-ol (1.5 g, 10 mmol), methyl 2-(2-(chlorosulfonyl)-5-(2, 2,2-trifluoroacetamido)phenyl)acetate (3.6 g, 10 mmol), pyridine (0.9 ml, 11mmol), rt, 0.5 hour. Removed solvent, the crude (450 mg) was dissolved in MeOH (5 ml), treated with ammonia (2 ml, 7N in MeOH), heated at 100° C. for 2 hours in a sealed tube. After cooled down to rt, concentrated, the result solid was purified by prep HPLC (SunFire Prep C18 OBD 5 uM 30×50 mm column). The title compound was obtained as light yellow powder.

MS calcd for (C$_{16}$H$_{17}$BN$_2$O$_6$S): 376.19. MS found (ESI negative): (M–H)$^-$=375.0. $^1$H NMR (400 MHz, DMSO-d$_6$) δ (ppm): 9.87 (s, 1H), 7.47 (d, J=8.4 Hz, 1H), 7.39 (d, J=2 Hz, 1H), 7.19 (d, J=8.4 Hz, 1H), 7.08 (dd, J=8 Hz, 1H), 6.40 (d, J=2.4 Hz, 1H), 6.38 (s, 1H), 4.84 (s, 2H), 3.86 (s, 2H), 3.54 (s, 3H).

Methyl 2-(5-amino-2-(N-(5-fluoro-1-hydroxy-1,3-dihydrobenzo[c][1,2]oxaborol-6-yl)sulfamoyl)phenyl)acetate

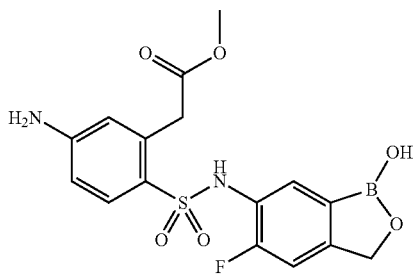 [SMILES: COC(=O)Cc1cc(N)ccc1S(=O)(=O)Nc1cc2c(cc1F)COB2O]

General Procedure 1: 6-amino-5-fluorobenzo[c][1,2]oxaborol-1(3H)-ol) (2.34 g, 14 mmol), methyl 2-(2-(chlorosulfonyl)-5-(2,2,2-trifluoroacetamido)phenyl)acetate (5.15 g, 14 mmol), pyridine (1.12, 17 mmol), rt, 0.5 hour. Removed solvent, the crude (380 mg, 0.77 mmol) was dissolved in MeOH (5 ml), treated with ammonia (2 ml, 7N in MeOH), heated at 100° C. for 2 hours in a sealed tube. After cooled down to rt, concentrated, and the resulting solid was purified by prep HPLC (SunFire Prep C18 OBD 5 uM 30×50 mm column). The title compound was obtained as light yellow powder. MS calcd for (C$_{16}$H$_{16}$BN$_2$O$_6$FS): 394.18. MS found (ESI negative): (M–H)$^-$=393.1. $^1$H NMR (400 MHz, DMSO-d$_6$) δ (ppm): 9.62 (s, 1H), 7.63 (d, J=8 Hz, 1H), 7.30 (d, J=8.8 Hz, 1H), 7.15 (d, J=10.4 Hz, 1H), 6.40 (d, J=2.4 Hz, 1H), 6.35 (dd, J=8.8 Hz, 1H), 4.86 (s, 2H), 3.86 (s, 2H), 3.55 (s, 3H).

D,D,D-Methyl 2-(5-amino-2-(N-(1-hydroxy-1,3-dihydrobenzo[c][1,2]oxaborol-6-yl)sulfamoyl)phenyl)acetate

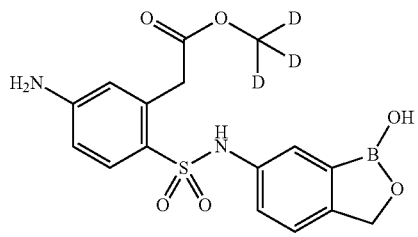 [SMILES: [2H]C([2H])([2H])OC(=O)Cc1cc(N)ccc1S(=O)(=O)Nc1ccc2c(c1)B(O)OC2]

To the suspension of 2-(5-amino-2-(N-(1-hydroxy-1,3-dihydrobenzo[c][1,2]oxaborol-6-yl)sulfamoyl)phenyl)acetic acid (1.81 g, 5 mmol) and CD$_3$OD (25 ml), added 5 drops of sulfuric acid. The mixture was heated 60° C. overnight. Concentrated, diluted with EtOAc, washed with NaHCO$_3$, then water and brine, dried over Na$_2$SO$_4$. Concentrated, got light brown solid as crude product. Added EtOAc (30 ml) and water (2 ml), sonicated for 1 hour, filtered and dried under high vacuum. Got 700 mg off white solid as product. MS calcd for (C$_{16}$H$_{14}$D$_3$BN$_2$O$_6$S): 379.11. MS found (ESI negative): (M–H)$^-$=378.1. $^1$H NMR (400 MHz, DMSO-d$_6$) δ (ppm): 9.87 (s, 1H), 9.16 (br, 1H), 7.47 (d, J=8.4 Hz, 1H), 7.39 (d, J=2 Hz, 1H), 7.19 (d, J=8 Hz, 1H), 7.08 (dd, J=8 Hz, 1H), 6.40 (d, J=8.4 Hz, 2H), 5.91 (br, 1H), 4.84 (s, 2H), 3.86 (s, 2H).

Trideuteromethyl 2-(5-amino-2-(N-(5-fluoro-1-hydroxy-1,3-dihydrobenzo[c][1,2]oxaborol-6-yl)sulfamoyl)phenyl)acetate

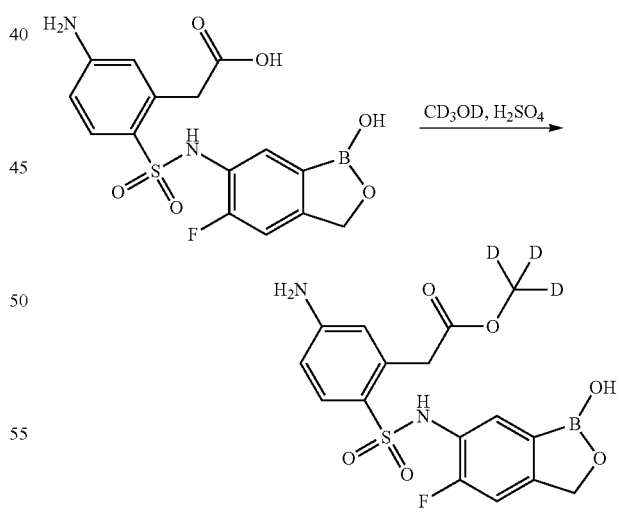

To a solution of 2-(5-amino-2-(N-(5-fluoro-1-hydroxy-1, 3-dihydrobenzo[c][1,2]oxaborol-6-yl)sulfamoyl)phenyl) acetic acid (0.5 g, 1.32 mmol) isopropanol (15 mL) was added 5 drops of concentrated sulfuric acid. The reaction was heated to reflux for 16 hrs then cooled to room temperature and added to 10 mL of water before evaporating all solvent under vacuum. The residue was partitioned between ethyl acetate and 1M HCl and the organic layer dried over Na$_2$SO$_4$.

Removal of solvent under vacuum provided crude material that was purified by precipitation from ethyl acetate/hexanes to yield 54 mg (10%) of the title compound as an off-white solid. MS calcd for ($C_{16}H_{13}D_3BFN_2O_6S$): 397.1. MS found (ESI negative): (M–H)⁻=396.1. ¹H NMR (DMSO-d₆) δ (ppm): 9.62 (s, 1H), 9.20 (bs, 1H), 7.62 (d, 1H), 7.30 (m, 1H), 7.15 (d, J=10 Hz, 1H), 6.36 (m, 2H), 5.91 (bs, 2H), 4.87 (s, 2H), 3.86 (s, 2H).

Ethyl 2-(2-(N-(1-hydroxy-1,3-dihydrobenzo[c][1,2]oxaborol-6-yl)sulfamoyl)-5-(2,2,2-trifluoroacetamido)phenyl)acetate

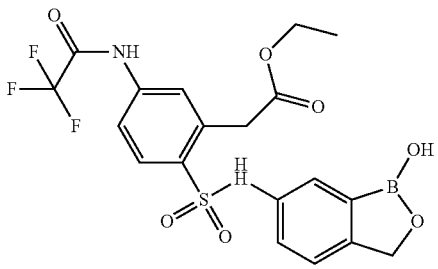

To a solution of 6-amino-3H-benzo[c][1,2]oxaborol-1-ol (0.7 g, 4.7 mmol), pyridine (1 mL, 12.4 mmol) in DCM (10 mL) was added ethyl 2-(2-(chlorosulfonyl)-5-(2,2,2-trifluoroacetamido)phenyl)acetate (1.5 g, 4 mmol). The reaction was stirred at r.t. for 2 hr and monitored by LC/MS. Purification: The solvent was removed and worked up with EtOAc and 1N HCl, brine, dried over Na₂SO₄. A portion of the crude material was purified by the preparative HPLC give the title product ethyl 2-(2-(N-(1-hydroxy-1,3-dihydrobenzo[c][1,2]oxaborol-6-yl)sulfamoyl)-5-(2,2,2-trifluoroacetamido)phenyl)acetate 18 mg as white powder ¹H NMR (400 MHz, DMSO-d₆) δ (ppm): 11.54 (s, 1H), 10.36 (s, 1H), 9.21 (bs, 1H), 7.85 (d, J=8 Hz, 1H), 7.71 (m, 2H), 7.44 (d, J=2 Hz, 1H), 7.25 (d, J=8.4 Hz, 1H), 7.12 (dd, J=8, 2 Hz, 1H), 4.87 (s, 2H), 4.06 (m, 4H), 1.17 (t, J=7.2 Hz, 3H); MS (ESI) m/z=485.1 (M–H, negative).

Ethyl 2-(5-amino-2-(N-(1-hydroxy-1,3-dihydrobenzo[c][1,2]oxaborol-6-yl)sulfamoyl)phenyl)acetate

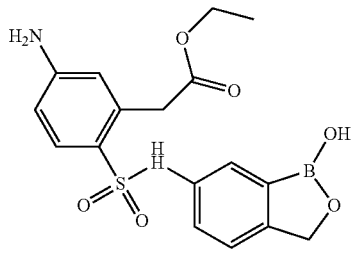

Ethyl 2-(2-(N-(1-hydroxy-1,3-dihydrobenzo[c][1,2]oxaborol-6-yl)sulfamoyl)-5-(2,2,2-trifluoroacetamido)phenyl)acetate (0.45 g, 0.92 mmol) and NH₃ (7M in MeOH, 5 mL) was heated to 80° C. for 2 hrs. The reaction was monitored by LC/MS. Purification: The solvent was removed in vacuo and the product was recrystallized from EtOAc/MeOH to give 194 mg of the title compound as a white solid (yield: 54%). ¹H NMR (400 MHz, DMSO-d₆) δ (ppm): 9.88 (s, 1H), 9.17 (bs, 1H), 7.48 (d, J=9.2 Hz, 1H), 7.41 (d, J=0.9 Hz, 1H), 7.21 (d, J=8 Hz, 1H), 7.10 (dd, J=8.4, 2 Hz, 1H), 6.41 (m, 2H), 5.93 (s, 2H), 4.86 (s, 2H), 4.05 (q, J=7.6 Hz, 2H), 3.87 (s, 2H), 1.17 (t, J=7.2 Hz, 3H); MS (ESI) m/z=389.1 (M–H, negative).

Ethyl 2-(2-(N-(5-fluoro-1-hydroxy-1,3-dihydrobenzo[c][1,2]oxaborol-6-yl)sulfamoyl)-5-(2,2,2-trifluoroacetamido)phenyl)acetate

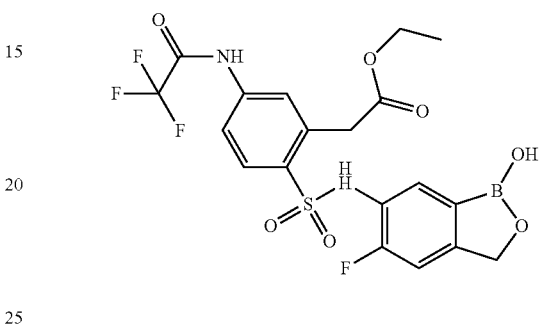

General Procedure 1: Starting Materials 6-amino-5-fluoro-3H-benzo[c][1,2]oxaborol-1-ol and ethyl 2-(2-(chlorosulfonyl)-5-(2,2,2-trifluoroacetamido)phenyl)acetate. ¹H NMR (400 MHz, DMSO-d₆) δ (ppm): 11.56 (s, 1H), 10.20 (s, 1H), 9.23 (bs, 1H), 7.73 (d, J=11.4 Hz, 1H), 7.69 (d, 2H, J=3.1 Hz), 7.63 (d, J=7.8 Hz, 1H), 7.20 (d, J=10.2 Hz, 1H), 4.89 (s, 2H), 4.06 (m, 4H), 1.17 (t, J=7.6 Hz, 3H); MS (ESI) m/z=503.0 (M–H, negative).

Ethyl 2-(5-amino-2-(N-(5-fluoro-1-hydroxy-1,3-dihydrobenzo[c][1,2]oxaborol-6-yl)sulfamoyl)phenyl)acetate

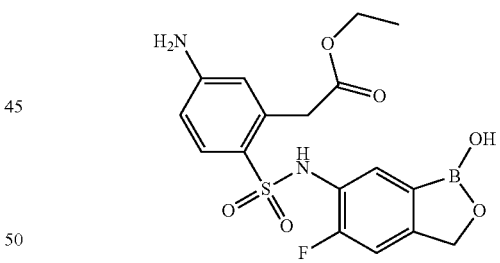

Ethyl 2-(2-(N-(5-fluoro-1-hydroxy-1,3-dihydrobenzo[c][1,2]oxaborol-6-yl)sulfamoyl)-5-(2,2,2-trifluoroacetamido)phenyl)acetate (0.25 g, 0.50 mmol) and NH₃ (7M in MeOH, 5 mL) was heated to 80° C. for 2 hrs. The reaction was monitored by LC/MS. Purification: The solvent was removed in vacuo and the product was recrystallized from EtOAc/MeOH to give 80 mg of the title compound as a white solid (yield: 40%). ¹H NMR (400 MHz, DMSO-d₆) δ (ppm): 9.62 (s, 1H), 9.27 (bs, 1H), 7.64 (d, J=8.2 Hz, 1H), 7.31 (d, J=8.8 Hz, 1H), 7.16 (d, J=10 Hz, 1H), 6.41 (d, J=2.4 Hz, 1H), 6.36 (dd, J=8.8, 2 Hz, 1H), 5.94 (s, 2H), 4.88 (s, 2H), 4.05 (q, J=7.6 Hz, 2H), 3.87 (s, 2H), 1.17 (t, J=7.2 Hz, 3H); MS (ESI) m/z=407.1 (M–H, negative).

Isopropyl 2-(5-amino-2-(N-(1-hydroxy-1,3-dihydrobenzo[c][1,2]oxaborol-6-yl)sulfamoyl)phenyl)acetate

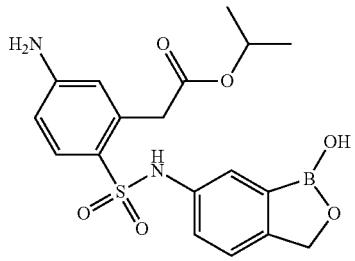 [SMILES: CC(C)OC(=O)Cc1cc(N)ccc1S(=O)(=O)Nc1ccc2c(c1)B(O)OC2]

To a solution of 2-(5-amino-2-(N-(1-hydroxy-1,3-dihydrobenzo[c][1,2]oxaborol-6-yl)sulfamoyl)phenyl)acetic acid (0.5 g, 1.38 mmol) in isopropanol (100 mL) was added 4 drops of concentrated sulfuric acid. The reaction was heated to reflux for 48 hrs then cooled to room temperature and added to 10 mL of water before evaporating all solvent under vacuum. The residue was partitioned between ethyl acetate and 1M HCl and the organic layer dried over $Na_2SO_4$. Removal of solvent under vacuum provided 357 mg (64%) of the title compound as a white solid. MS calcd for ($C_{18}H_{2}O_3N_2O_6S$): 404.1. MS found (ESI negative): (M−H)⁻=403.1. ¹H NMR (DMSO-d₆) δ (ppm): 9.84 (s, 1H), 9.15 (s, 1H), 7.40-7.47 (m, 2H), 7.19 (d, J=8.4, 1H), 7.10 (d, J=2.0 Hz, 1H), 6.37 (bs, 2H), 5.91 (bs, 2H), 4.85 (m, 3H), 3.83 (s, 1H), 1.16 (d, J=6.4, 6H).

tert-Butyl 2-(5-amino-2-(N-(1-hydroxy-1,3-dihydrobenzo[c][1,2]oxaborol-6-yl)sulfamoyl)phenyl)acetate

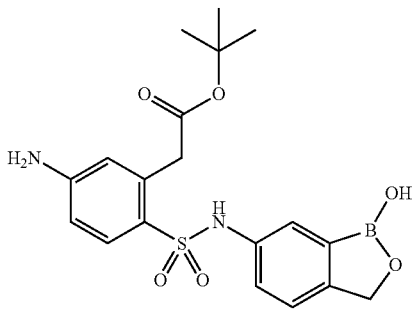 [SMILES: CC(C)(C)OC(=O)Cc1cc(N)ccc1S(=O)(=O)Nc1ccc2c(c1)B(O)OC2]

To the solution of 2-(5-amino-2-(N-(1-hydroxy-1,3-dihydrobenzo[c][1,2]oxaborol-6-yl)sulfamoyl)phenyl)acetic acid (2.2 g, 6 mmol) in dry THF (20 ml) under nitrogen, added the solution of tert-butyl 2,2,2-trichloroacetate (4.3 ml, 24 mmol) in dry DCM (10 ml), followed by $BF_3Et_2O$ (0.1 ml, 0.72 mmol). The reaction was stirred at rt overnight. Quenched the reaction with sodium bicarbonate (sat. in water), diluted with EtOAc, washed with 1N HCl, water and brine, dried over anhydrous sodium sulfate. Concentrated, the result was purified by flash chromatography with EtOAc and hexane. Got 650 mg light yellow solid as product. MS calcd for ($C_{19}H_{23}BN_2O_6S$): 418.14. MS found (ESI negative): (M−H)⁻=417.0. ¹H NMR (400 MHz, DMSO-d₆) δ (ppm): 9.83 (s, 1H), 7.46 (d, J=8.8 Hz, 1H), 7.40 (d, J=1.6 Hz, 1H), 7.19 (d, J=8 Hz, 1H), 7.09 (dd, J=8 Hz, 1H), 6.39 (d, J=6.8 Hz, 1H), 6.37 (s, 1H), 4.84 (s, 2H), 3.77 (s, 2H), 1.37 (s, 9H).

Methyl 3-(5-amino-2-(N-(1-hydroxy-1,3-dihydrobenzo[c][1,2]oxaborol-6-yl)sulfamoyl)phenyl)propanoate and

Ethyl 3-(5-amino-2-(N-(1-hydroxy-1,3-dihydrobenzo[c][1,2]oxaborol-6-yl)sulfamoyl)phenyl)propanoate

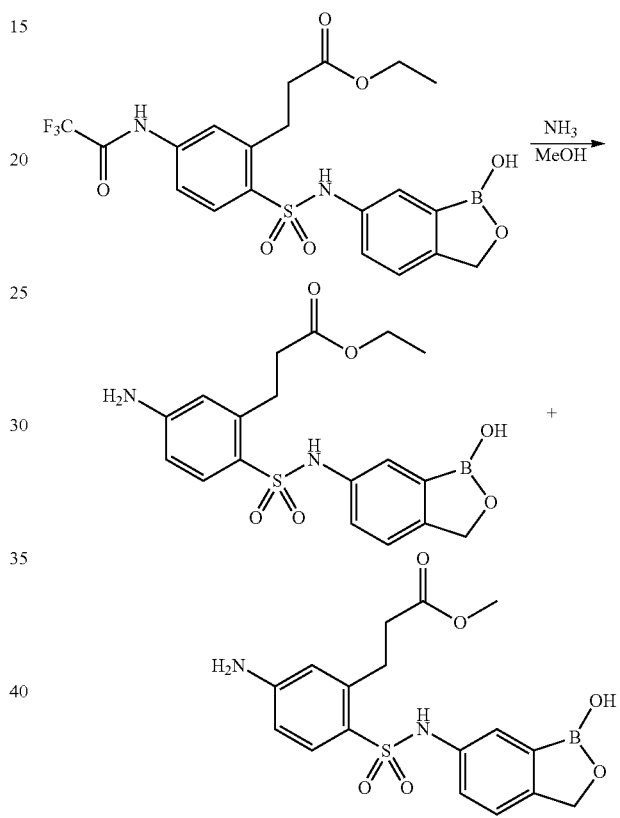

A solution of ethyl 3-(2-(N-(1-hydroxy-1,3-dihydrobenzo[c][1,2]oxaborol-6-yl)sulfamoyl)-5-(2,2,2-trifluoroacetamido)phenyl)propanoate (50 mg, 0.1 mmol) in 7M ammonium in MeOH (10 mL) was stirred in a sealed tube at 50° C. for 6 hours. After concentrated, the crude mixture was purified by prep HPLC (SunFire Prep C18 OBD 5 uM 30×50 mm column) to give ethyl 3-(5-amino-2-(N-(1-hydroxy-1,3-dihydrobenzo[c][1,2]oxaborol-6-yl)sulfamoyl)phenyl)propanoate as a white solid (22 mg, yield 54%) and methyl 3-(5-amino-2-(N-(1-hydroxy-1,3-dihydrobenzo[c][1,2]oxaborol-6-yl)sulfamoyl)phenyl)propanoate as a white solid (7.3 mg, 19%).

Methyl 3-(5-amino-2-(N-(1-hydroxy-1,3-dihydrobenzo[c][1, 2]oxaborol-6-yl)sulfamoyl)phenyl)propanoate MS calcd for ($C_{18}H_{21}BN_2O_6S$): 404.2. MS found (ESI negative): (M−H)⁻=403.1. ¹H NMR (DMSO-d₆) δ (ppm): 10.0 (s, 1H), 9.18 (bs, 1H), 7.51 (d, J=8.4 Hz, 1H), 7.40 (s, 1H), 7.20 (d, J=8.0 Hz, 1H), 7.09 (d, J=8.4 Hz, 1H), 6.38 (s, 1H), 6.35 (d, J=8.4 Hz, 1H), 4.84 (s, 2H), 4.05 (q, 2H), 3.05 (t, 2H), 2.49 (t, 2H), 1.16 (t, 3H)

Ethyl 3-(5-amino-2-(N-(1-hydroxy-1,3-dihydrobenzo[c][1,2]oxaborol-6-yl)sulfamoyl)phenyl)propanoate MS calcd for ($C_{17}H_{19}BN_2O_6S$): 390.2. MS found (ESI negative): (M−H)⁻=389.1. $^1H$ NMR (DMSO-$d_6$) δ (ppm): 10.0 (s, 1H), 9.18 (bs, 1H), 7.51 (d, J=8.8 Hz, 1H), 7.40 (s, 1H), 7.20 (d, J=8.0 Hz, 1H), 7.09 (d, J=8.4 Hz, 1H), 6.38 (s, 1H), 6.35 (d, J=8.8 Hz, 1H), 4.84 (s, 2H), 3.59 (s, 3H), 3.05 (t, 2H), 2.50 (t, 2H).

2-(5-Amino-2-(N-(1-hydroxy-1,3-dihydrobenzo[c][1,2]oxaborol-6-yl)sulfamoyl)phenyl)acetamide

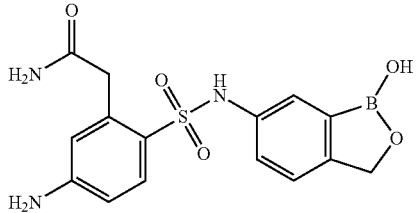 [SMILES: NC(=O)Cc1cc(N)ccc1S(=O)(=O)Nc1ccc2c(c1)B(O)OC2]

A mixture of methyl 2-(2-(N-(1-hydroxy-1,3-dihydrobenzo[c][1,2]oxaborol-6-yl)sulfamoyl)-5-(2,2,2-trifluoroacetamido)phenyl)acetate (0.5 g, 0.001 mol) and aq. $NH_3 \cdot H_2O$ (28%, 10 mL) in $CH_3OH$ was stirred at 50° C. over night. The mixture was concentrated and the residue dissolved in ethyl acetate and washed with brine, dried and concentrated, purified by column chromatography (PE:EA 5:1~1:3) to give the title compound, which was dissolved in MeCN, acidified with aq. HCl and freeze-dried to give the product as hydrochloride salt (200 mg, yield 53%). $^1HNMR$ DMSO-d6 400 MH. δ9.85 (s, 1H), 9.17 (s, 1H), 7.43-6.32 (m, 6H), 5.92 (s, 2H), 4.86 (s, 2H), 3.74 (s, 2H). LC-MS m/z 360 (M−H, negative); HPLC purity: 96.93% (220 nm), 99.27% (254 nm).

2-(5-Amino-2-(N-(1-hydroxy-1,3-dihydrobenzo[c][1,2]oxaborol-6-yl)sulfamoyl)phenyl)-N-methylacetamide

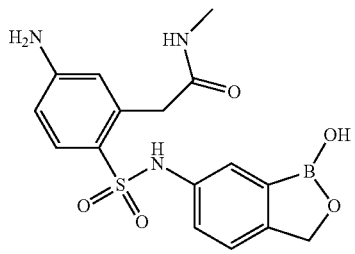 [SMILES: CNC(=O)Cc1cc(N)ccc1S(=O)(=O)Nc1ccc2c(c1)B(O)OC2]

To a stirred solution of 2-(5-amino-2-(N-(1-hydroxy-1,3-dihydrobenzo[c][1,2]oxaborol-6-yl)sulfamoyl)phenyl)acetic acid (860 mg, 2.37 mmol) and methylamine hydrochloride salt (0.34 g, 4.75 mmol) in 10 mL of DMF was added PyBOP (1300 mg, 2.49 mmol) and TEA (1.13 mL, 8.3 mmol). The reaction mixture was stirred for 16 hours. After water was added, the reaction mixture was extracted with ethyl acetate and washed with water, 1N HCl and brine. The organic layer was dried over $Na_2SO_4$ and concentrated. The crude residue was purified by prep HPLC (SunFire Prep C18 OBD 5 uM 30×50 mm column) to give the desired product as an offwhite powder (165 mg, yield 19%). MS calcd for ($C_{16}H_{18}BN_3O_5S$): 375.1. MS found (ESI negative): (M−H)⁻=374.1. $^1H$ NMR (400 MHz, DMSO-$d_6$) δ (ppm): 9.87 (s, 1H), 9.17 (bs, 1H), 7.93 (d, J=4.8 Hz, 1H), 7.41 (m, 2H), 7.22 (d, J=8 Hz, 1H), 7.11 (dd, J=8, 2 Hz, 1H), 6.45 (d, J=2.4 Hz, 1H)), 6.35 (d, J=8.8, 2 Hz, 1H), 4.87 (s, 2H), 3.77 (s, 2H), 2.63 (d, J=4.4 Hz, 3H).

2-(5-Amino-2-(N-(1-hydroxy-1,3-dihydrobenzo[c][1,2]oxaborol-6-yl)sulfamoyl)phenyl)-N-ethylacetamide

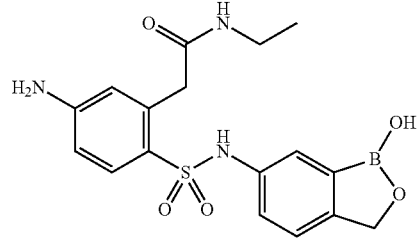 [SMILES: CCNC(=O)Cc1cc(N)ccc1S(=O)(=O)Nc1ccc2c(c1)B(O)OC2]

To the mixture of 2-(5-amino-2-(N-(1-hydroxy-1,3-dihydrobenzo[c][1,2]oxaborol-6-yl)sulfamoyl)phenyl)acetic acid (500 mg, 1.4 mmol) and ethyl amine (2.1 mg, 4.2 mmol) in DMF (5 ml), added PyBOP (730 mg, 1.4 mmol) then triethyl amine (0.4 ml, 3 mmol). Stirring was kept for 3 hours. Diluted with EtOAc, washed with 1N HCl, water and brine. Dried over anhydrous sodium sulfate. Concentrated, the residue was dissolved in DMSO and purified by prep HPLC (SunFire Prep C18 OBD 5 uM 30×50 mm column). The title compound was obtained as white powder. MS calcd for ($C_{17}H_{20}BN_3O_5S$): 389.12. MS found (ESI negative): (M−H)⁻=388.1. $^1H$ NMR (400 MHz, DMSO-$d_6$) δ (ppm): 9.86 (s, 1H), 9.15 (br, 1H), 7.98 (m, 1H), 7.41 (s, 1H), 7.39 (d, J=8.8 Hz, 1H), 7.21 (d, J=8 Hz, 1H), 7.09 (dd, J=8.4 Hz, 1H), 6.44 (d, J=2 Hz, 1H), 6.33 (dd, J=8.8 Hz, 1H), 4.85 (s, 2H), 3.75 (s, 2H), 3.09 (m, 1H), 1.02 (t, J=7.2 Hz, 3H).

2-(5-Amino-2-(N-(1-hydroxy-1,3-dihydrobenzo[c][1,2]oxaborol-6-yl)sulfamoyl)phenyl)-N-propylacetamide

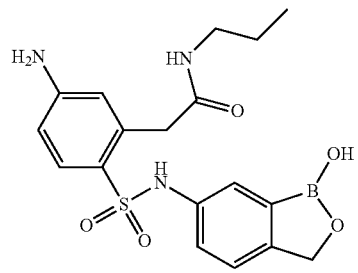 [SMILES: CCCNC(=O)Cc1cc(N)ccc1S(=O)(=O)Nc1ccc2c(c1)B(O)OC2]

To a stirred solution of 2-(5-amino-2-(N-(1-hydroxy-1,3-dihydrobenzo[c][1,2]oxaborol-6-yl)sulfamoyl)phenyl)acetic acid (360 mg, 1 mmol) and n-propylamine (0.6 mL, 6 mmol) in 10 mL of DMF was added PyBOP (780 mg, 1.5 mmol) and TEA (0.5 mL, 3.56 mmol). The reaction mixture was stirred for 16 hours. After water was added, the reaction mixture was extracted with ethyl acetate and washed with water, 1N HCl and brine. The organic layer was dried over $Na_2SO_4$ and concentrated. The crude residue was purified by prep HPLC (SunFire Prep C18 OBD 5 uM 30×50 mm column) to give the desired product as a white powder (207 mg, yield 51%). MS calcd for ($C_{18}H_{22}BN_3O_5S$): 403.1. MS found (ESI negative): (M−H)⁻=402.1. ¹H NMR (400 MHz, DMSO-d₆) δ (ppm): 9.89 (s, 1H), 9.17 (bs, 1H), 7.99 (t, J=5.6 Hz, 1H), 7.42 (m, 2H), 7.22 (d, J=8 Hz, 1H), 7.11 (dd, J=8, 2 Hz, 1H), 6.46 (d, J=2 Hz, 1H)), 6.35 (d, J=8.8, 2.4 Hz, 1H), 4.87 (s, 2H), 3.78 (s, 2H), 3.05 (m, 2H), 1.43 (m, 2H), 0.85 (t, J=7.2 Hz, 3H).

2-(5-Amino-2-(N-(1-hydroxy-1,3-dihydrobenzo[c][1,2]oxaborol-6-yl)sulfamoyl)phenyl)-N-butylacetamide

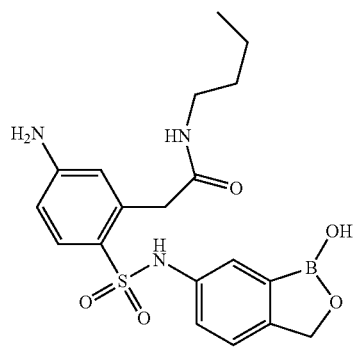 [SMILES: CCCCNC(=O)Cc1cc(N)ccc1S(=O)(=O)Nc1ccc2c(c1)B(O)OC2]

To a stirred solution of 2-(5-amino-2-(N-(1-hydroxy-1,3-dihydrobenzo[c][1,2]oxaborol-6-yl)sulfamoyl)phenyl)acetic acid (360 mg, 1 mmol) and n-butylamine (0.6 mL, 6 mmol) in 10 mL of DMF was added PyBOP (780 mg, 1.5 mmol) and TEA (0.5 mL, 3.56 mmol). The reaction mixture was stirred for 16 hours. After water was added, the reaction mixture was extracted with ethyl acetate and washed with water, 1N HCl and brine. The organic layer was dried over Na₂SO₄ and concentrated. The crude residue was first purified by ISCO CombiFlash Rf silica chromatography eluted with 88:10:2 chloroform:MeOH:H₂O to give the desired product as a yellow solid (228 mg, yield 54%). MS calcd for (C₁₉H₂₄BN₃O₅S): 417.2. MS found (ESI negative): (M−H)⁻=416.2. ¹H NMR (400 MHz, DMSO-d₆) δ (ppm): 9.88 (s, 1H), 9.17 (s, 1H), 7.96 (t, J=5.2 Hz, 1H), 7.42 (m, 2H), 7.22 (d, J=8 Hz, 1H), 7.11 (dd, J=8, 2 Hz, 1H), 6.46 (d, J=2.4 Hz, 1H), 6.35 (dd, J=2.4, 8.8 Hz, 1H), 5.93 (bs, 2H), 4.87 (s, 2H), 3.77 (s, 2H), 3.08 (m, 2H), 1.39 (m, 2H), 1.30 (m, 2H), 0.87 (t, J=7.2 Hz, 3H).

2-(5-Amino-2-(N-(1-hydroxy-1,3-dihydrobenzo[c][1,2]oxaborol-6-yl)sulfamoyl)phenyl)-N-sec-butylacetamide

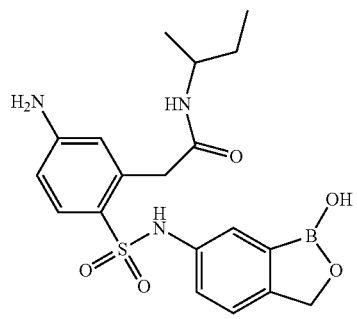 [SMILES: CCC(C)NC(=O)Cc1cc(N)ccc1S(=O)(=O)Nc1ccc2c(c1)B(O)OC2]

To a stirred solution of 2-(5-amino-2-(N-(1-hydroxy-1,3-dihydrobenzo[c][1,2]oxaborol-6-yl)sulfamoyl)phenyl)acetic acid (720 mg, 2 mmol) and sec-butylamine (0.7 mL, 7 mmol) in 20 mL of DMF was added PyBOP (1550 mg, 3 mmol) and TEA (3 mL, 15 mmol). The reaction mixture was stirred for 16 hours. After water was added, the reaction mixture was extracted with ethyl acetate and washed with water, 1N HCl and brine. The organic layer was dried over Na₂SO₄ and concentrated. The crude residue was first purified by preparative HPLC (SunFire Prep C18 OBD 5 uM 30×50 mm column) followed by ISCO CombiFlash Rf silica chromatography eluted with 88:10:2 chloroform:MeOH:H₂O to give the desired product as a yellow solid (100 mg, yield 13%). MS calcd for (C₁₉H₂₄BN₃O₅S): 417.2. MS found (ESI negative): (M−H)⁻=416.4. ¹H NMR (400 MHz, DMSO-d₆) δ (ppm): 9.90 (s, 1H), 9.17 (s, 1H), 7.84 (d, J=8 Hz, 1H), 7.44 (d, J=2 Hz, 1H), 7.40 (d, J=8.8 Hz, 1H), 7.22 (d, J=8 Hz, 1H), 7.10 (dd, J=8.4, 2 Hz, 1H), 6.48 (d, J=2.4 Hz, 1H), 6.34 (dd, J=8.8, 2.4 Hz, 1H), 5.93 (bs, 2H), 4.87 (s, 2H), 3.78 (s, 2H), 3.71 (m, 1H), 1.40 (m, 2H), 1.05 (d, J=6.4 Hz, 3H), 0.82 (t, J=7.2 Hz, 3H).

2-(5-Amino-2-(N-(1-hydroxy-1,3-dihydrobenzo[c][1,2]oxaborol-6-yl)sulfamoyl)phenyl)-N-butyl-N-methylacetamide

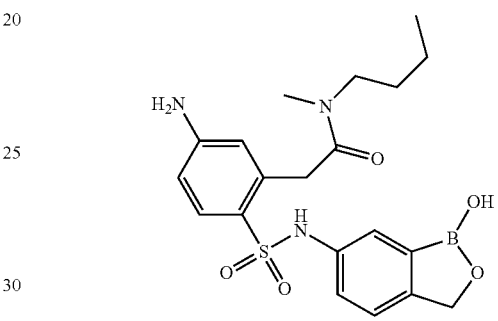

To a stirred solution of 2-(5-amino-2-(N-(1-hydroxy-1,3-dihydrobenzo[c][1,2]oxaborol-6-yl)sulfamoyl)phenyl)acetic acid (360 mg, 1 mmol) and n-butylmethylamine (0.6 mL, 6 mmol) in 10 mL of DMF was added PyBOP (780 mg, 1.5 mmol) and TEA (0.5 mL, 3.56 mmol). The reaction mixture was stirred for 16 hours. After water was added, the reaction mixture was extracted with ethyl acetate and washed with water, 1N HCl and brine. The organic layer was dried over Na₂SO₄ and concentrated. The crude residue was first purified by prep HPLC (SunFire Prep C18 OBD 5 uM 30×50 mm column) to give the desired product as a yellow solid (115 mg, yield 27%). MS calcd for (C₂₀H₂₆BN₃O₅S): 431.2. MS found (ESI negative): (M−H)⁻=430.1. ¹H NMR (400 MHz, DMSO-d₆) δ (ppm): 9.80 (s, 1H), 9.17 (bs, 1H), 7.45 (m, 2H), 7.22 (d, J=8 Hz, 1H), 7.11 (d, J=8, 2 Hz, 1H), 6.37 (d, J=8.4 Hz, 1H), 6.32 (s, 1H), 5.94 (bs, 2H), 4.87 (s, 2H), 3.77 (s, 2H), 3.15 (m, 2H), 2.85 (s, 3H), 1.39 (m, 2H), 1.30 (m, 2H), 0.87 (t, J=7.2 Hz, 3H).

2-(5-Amino-2-(N-(1-hydroxy-1,3-dihydrobenzo[c][1,2]oxaborol-6-yl)sulfamoyl)phenyl)-N-isobutylacetamide

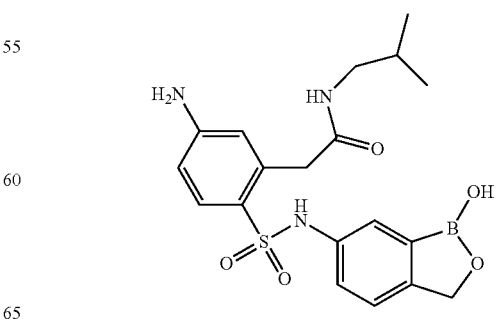

To a stirred solution of 2-(5-amino-2-(N-(1-hydroxy-1,3-dihydrobenzo[c][1,2]oxaborol-6-yl)sulfamoyl)phenyl)acetic acid (720 mg, 2 mmol) and isobutylamine (1.2 mL, 12 mmol) in 20 mL of DMF was added PyBOP (1550 mg, 3 mmol) and TEA (1 mL, 7 mmol). The reaction mixture was stirred for 16 hours. After water was added, the reaction mixture was extracted with ethyl acetate and washed with water, 1N HCl and brine. The organic layer was dried over $Na_2SO_4$ and concentrated. The crude residue was purified by ISCO CombiFlash Rf silica chromatography eluted with 88:10:2 chloroform:MeOH:$H_2O$ to give the desired product as a yellow solid (430 mg, yield 51%). MS calcd for ($C_{19}H_{24}BN_3O_5S$): 417.2. MS found (ESI negative): (M−H)$^-$=416.1. $^1$H NMR (400 MHz, DMSO-$d_6$) δ (ppm): 9.89 (s, 1H), 9.17 (bs, 1H), 7.96 (t, J=5.6 Hz, 1H), 7.41 (m, 2H), 7.22 (d, J=8.4 Hz, 1H), 7.10 (d, J=8 Hz, 1H), 6.47 (s, 1H), 6.34 (d, J=8 Hz, 1H), 5.93 (bs, 2H), 4.87 (s, 2H), 3.80 (s, 2H), 2.93 (t, J=6.4 Hz 2H), 1.72 (m, 1H), 0.85 (d, J=7.8 Hz, 6H).

2-(5-Amino-2-(N-(1-hydroxy-1,3-dihydrobenzo[c][1,2]oxaborol-6-yl)sulfamoyl)phenyl)-N-cyclopropylacetamide

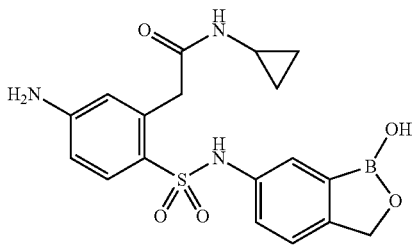 [SMILES: Nc1ccc(S(=O)(=O)Nc2ccc3c(c2)B(O)OC3)c(CC(=O)NC2CC2)c1]

To the mixture of 2-(5-amino-2-(N-(1-hydroxy-1,3-dihydrobenzo[c][1,2]oxaborol-6-yl)sulfamoyl)phenyl)acetic acid (500 mg, 1.4 mmol) and cyclopropyl amine (0.5 ml, 7 mmol) in DMF (5 ml), added PyBOP (730 mg, 1.4 mmol) then triethyl amine (0.4 ml, 3 mmol). Stirring was kept for 3 hours. Diluted with EtOAc, washed with 1N HCl, water and brine. Dried over anhydrous sodium sulfate. Concentrated, the residue was dissolved in DMSO and purified by prep HPLC (SunFire Prep C18 OBD 5 uM 30×50 mm column). The title compound was obtained as white powder. MS calcd for ($C_{18}H_{20}BN_3O_5S$): 401.12. MS found (ESI negative): (M−H)$^-$=400.1. $^1$H NMR (400 MHz, DMSO-$d_6$) δ (ppm): 9.84 (s, 1H), 8.14 (d, J=4 Hz, 1H), 7.43 (s, 1H), 7.42 (d, J=8.8 Hz, 1H), 7.24 (d, J=8.4 Hz, 1H), 7.11 (dd, J=8.4 Hz, 1H), 6.43 (d, J=2 Hz, 1H), 6.36 (dd, J=8.4 Hz, 1H), 4.88 (s, 2H), 3.74 (s, 2H), 2.67 (m, 1H), 0.64 (m, 2H), 0.44 (m, 2H).

2-(5-Amino-2-(N-(1-hydroxy-1,3-dihydrobenzo[c][1,2]oxaborol-6-yl)sulfamoyl)phenyl)-N-cyclobutylacetamide

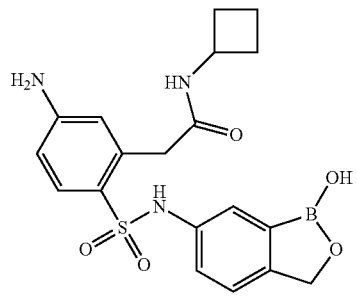 [SMILES: Nc1ccc(S(=O)(=O)Nc2ccc3c(c2)B(O)OC3)c(CC(=O)NC2CCC2)c1]

To a stirred solution of 2-(5-amino-2-(N-(1-hydroxy-1,3-dihydrobenzo[c][1,2]oxaborol-6-yl)sulfamoyl)phenyl)acetic acid (400 mg, 1.2 mmol) and cyclobutylamine (0.8 mL, 6 mmol) in 20 mL of DMF was added PyBOP (850 mg, 1.7 mmol) and TEA (1 mL, 7 mmol). The reaction mixture was stirred for 16 hours. After water was added, the reaction mixture was extracted with ethyl acetate and washed with water, 1N HCl and brine. The organic layer was dried over $Na_2SO_4$ and concentrated. The crude residue was purified by ISCO CombiFlash Rf silica chromatography eluted with 88:10:2 chloroform:MeOH:$H_2O$ to give the desired product as a yellow solid (250 mg, yield 54%). MS calcd for ($C_{19}H_{22}BN_3O_5S$): 415.1. MS found (ESI negative): (M−H)$^-$=414.2. $^1$H NMR (400 MHz, DMSO-$d_6$) δ (ppm): 9.85 (s, 1H), 9.17 (s, 1H), 8.28 (d, J=7.6 Hz, 1H), 7.42 (m, 2H), 7.22 (d, J=8.4 Hz, 1H), 7.10 (dd, J=8, 2 Hz, 1H), 6.44 (d, J=2.4 Hz, 1H), 6.34 (dd, J=8, 2 Hz, 1H), 5.93 (bs, 2H), 4.87 (s, 2H), 4.20 (m, 1H), 3.75 (s, 2H), 2.18 (m, 2H), 1.89 (m, 2H), 1.64 (m, 2H).

2-(5-Amino-2-(N-(1-hydroxy-1,3-dihydrobenzo[c][1,2]oxaborol-6-yl)sulfamoyl)phenyl)-N-cyclopentylacetamide

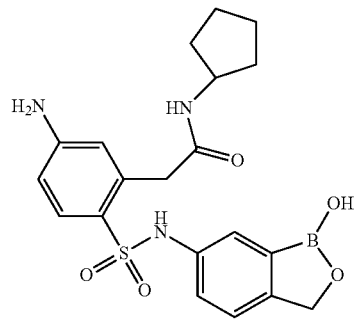 [SMILES: Nc1ccc(S(=O)(=O)Nc2ccc3c(c2)B(O)OC3)c(CC(=O)NC2CCCC2)c1]

To a stirred solution of 2-(5-amino-2-(N-(1-hydroxy-1,3-dihydrobenzo[c][1,2]oxaborol-6-yl)sulfamoyl)phenyl)acetic acid (360 mg, 1 mmol) and cyclopentylamine (0.6 mL, 6 mmol) in 10 mL of DMF was added PyBOP (780 mg, 1.5 mmol) and TEA (0.5 mL, 3.56 mmol). The reaction mixture was stirred for 16 hours. After water was added, the reaction mixture was extracted with ethyl acetate and washed with water, 1N HCl and brine. The organic layer was dried over $Na_2SO_4$ and concentrated. The crude residue was purified by prep HPLC (SunFire Prep C18 OBD 5 uM 30×50 mm column) to give the desired product as a white powder (27 mg, yield 6%). MS calcd for ($C_{20}H_{24}BN_3O_5S$): 429.2. MS found (ESI negative): (M−H)$^-$=428.2. $^1$H NMR (400 MHz, DMSO-$d_6$) δ (ppm): 9.89 (s, 1H), 9.17 (bs, 1H), 8.02 (d, J=7.2 Hz, 1H), 7.44 (m, 2H), 7.22 (d, J=8 Hz, 1H), 7.11 (d, J=8 Hz, 1H), 6.46 (s, 1H), 6.35 (d, J=8 Hz, 1H), 5.94 (bs, 2H), 4.87 (s, 2H), 4.02 (q, J=6.4 Hz, 1H), 3.77 (s, 2H), 1.81 (m, 2H), 1.64 (m, 2H), 1.51 (m, 2H), 1.39 (m, 2H).

2-(5-Amino-2-(N-(1-hydroxy-1,3-dihydrobenzo[c][1,2]oxaborol-6-yl)sulfamoyl)phenyl)-N-cyclohexylacetamide

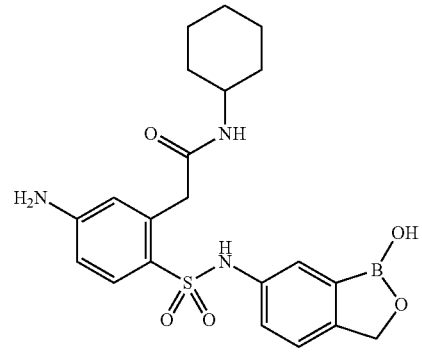 [SMILES: Nc1ccc(S(=O)(=O)Nc2ccc3c(c2)B(O)OC3)c(CC(=O)NC2CCCCC2)c1]

To the mixture of 2-(5-amino-2-(N-(1-hydroxy-1,3-dihydrobenzo[c][1,2]oxaborol-6-yl)sulfamoyl)phenyl)acetic acid (1.09 g, 3 mmol) and cyclohexyl amine (1.4 ml, 12 mmol) in DMF (10 ml), added PyBOP (1.56 g, 3 mmol) then triethyl amine (0.4 ml, 3 mmol). Stirring was kept for 3 hours. Diluted with EtOAc, washed with 1N HCl, water and brine. Dried over anhydrous sodium sulfate. Concentrated, the residue was dissolved in DMSO and purified by prep HPLC (SunFire Prep C18 OBD 5 uM 30×50 mm column). The title compound was obtained as light yellow powder. MS calcd for ($C_{21}H_{26}BN_3O_5S$): 443.17. MS found (ESI negative): $(M-H)^-$=442.2. $^1$H NMR (400 MHz, DMSO-$d_6$) δ (ppm): 9.87 (s, 1H), 7.90 (d, J=6 Hz, 1H), 7.41 (s, 1H), 7.39 (d, J=8.8 Hz, 1H), 7.20 (d, J=8 Hz, 1H), 7.08 (dd, J=8 Hz, 1H), 6.45 (d, J=2 Hz, 1H), 6.33 (dd, J=8.8 Hz, 1H), 4.85 (s, 2H), 3.75 (s, 2H), 3.55 (m, 1H), 1.80-1.50 (m, 5H), 1.30-1.10 (m, 5H).

4-Amino-2-(2-(azetidin-1-yl)-2-oxoethyl)-N-(1-hydroxy-1,3-dihydrobenzo[c][1,2]oxaborol-6-yl)benzenesulfonamide

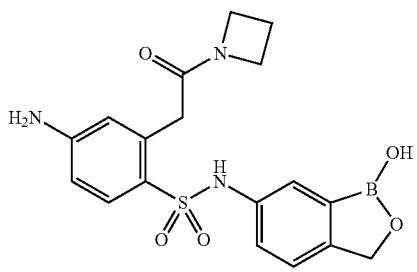 [SMILES: Nc1ccc(S(=O)(=O)Nc2ccc3c(c2)B(O)OC3)c(CC(=O)N2CCC2)c1]

To the solution of methyl 2-(2-(N-(1-hydroxy-1,3-dihydrobenzo[c][1,2]oxaborol-6-yl)sulfamoyl)-5-(2,2,2-trifluoroacetamido)phenyl)acetate (5.1 g, 1 mmol) in methanol, added NaOH (2.4 g, in 30 ml water). Stirred at rt for 2 days. Quenched the reaction with 1N HCl, extracted with EtOAc, washed with brine, dried over anhydrous sodium sulfate. Concentrated and got 3.5 g 2-(5-amino-2-(N-(1-hydroxy-1,3-dihydrobenzo[c][1,2]oxaborol-6-yl)sulfamoyl)phenyl) acetic acid bright yellow solid as crude product.

To the mixture of 2-(5-amino-2-(N-(1-hydroxy-1,3-dihydrobenzo[c][1,2]oxaborol-6-yl)sulfamoyl)phenyl)acetic acid (500 mg, 1.4 mmol) and azetidine hydrochloride (470 mg, 5 mmol) in DMF (5 ml), added PyBOP (730 mg, 1.4 mmol) then triethyl amine (1.1 ml, 8 mmol). Stirring was kept for 3 hours. Diluted with EtOAc, washed with 1N HCl, water and brine. Dried over anhydrous sodium sulfate. Concentrated, the residue was dissolved in DMSO and purified by prep HPLC (SunFire Prep C18 OBD 5 uM 30×50 mm column). The compound was obtained as white powder. MS calcd for ($C_{18}H_{20}BN_3O_5S$): 401.12. MS found (ESI negative): $(M-H)^-$=400.1. $^1$H NMR (400 MHz, DMSO-$d_6$) δ (ppm): 9.69 (s, 1H), 7.36 (d, J=1.6 Hz, 1H), 7.34 (d, J=8.8 Hz, 1H), 7.16 (d, J=8 Hz, 1H), 7.04 (dd, J=8.4 Hz, 1H), 6.34 (d, J=2.4 Hz, 1H), 6.30 (dd, J=8.8 Hz, 1H), 4.81 (s, 2H), 4.01 (t, J=7.2 Hz, 1H), 3.81 (t, J=7.6 Hz, 1H), 3.57 (s, 2H), 2.11 (m, 2H).

4-Amino-N-(1-hydroxy-1,3-dihydrobenzo[c][1,2]oxaborol-6-yl)-2-(2-oxo-2-(pyrrolidin-1-yl)ethyl)benzenesulfonamide

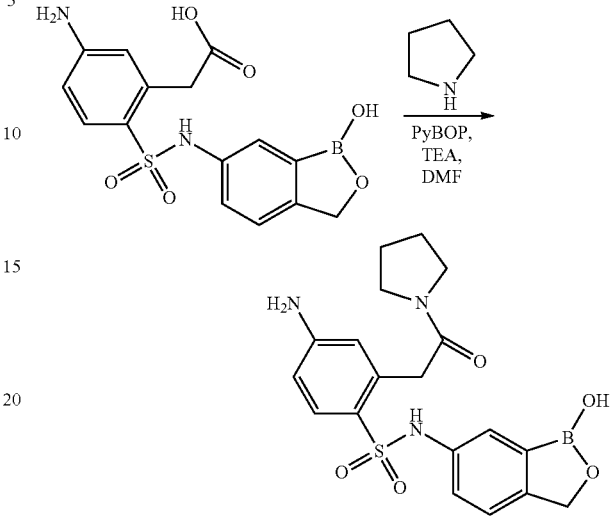

To a stirred solution of 2-(5-amino-2-(N-(1-hydroxy-1,3-dihydrobenzo[c][1,2]oxaborol-6-yl)sulfamoyl)phenyl)acetic acid (360 mg, 1 mmol) and pyrrolidine (0.5 mL, 6 mmol) in 10 mL of DMF was added PyBOP (780 mg, 1.5 mmol) and TEA (0.5 mL, 3.56 mmol). The reaction mixture was stirred for 16 hours. After water was added, the reaction mixture was extracted with ethyl acetate and washed with water, 1N HCl and brine. The organic layer was dried over $Na_2SO_4$ and concentrated. The crude residue was purified by prep HPLC (SunFire Prep C18 OBD 5 uM 30×50 mm column) to give the desired product as a white powder (28 mg, yield 7%). MS calcd for ($C_{19}H_{22}BN_3O_5S$): 415.1. MS found (ESI negative): $(M-H)^-$=414.1. $^1$H NMR (400 MHz, DMSO-$d_6$) δ (ppm): 9.77 (s, 1H), 9.17 (bs, 1H), 7.44 (m, 2H), 7.23 (d, J=8 Hz, 1H), 7.11 (dd, J=8, 2 Hz, 1H), 6.37 (m, 2H)), 4.87 (s, 2H), 3.82 (s, 2H), 3.32 (m, 4H), 1.81 (m, 4H).

2-(5-Amino-2-(N-(1-hydroxy-1,3-dihydrobenzo[c][1,2]oxaborol-6-yl)sulfamoyl)phenyl)-N-(prop-2-ynyl)acetamide

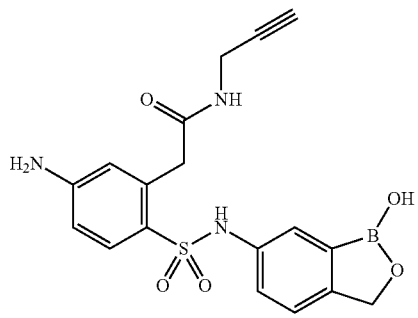 [SMILES: C#CCNC(=O)Cc1cc(N)ccc1S(=O)(=O)Nc1ccc2c(c1)B(O)OC2]

To the mixture of 2-(5-amino-2-(N-(1-hydroxy-1,3-dihydrobenzo[c][1,2]oxaborol-6-yl)sulfamoyl)phenyl)acetic acid (363 mg, 1 mmol) and propargyl amine (0.2 ml, 3 mmol) in DMF (5 ml), added PyBOP (520 mg, 1 mmol) then triethyl amine (0.3 ml, 2 mmol). Stirring was kept for 3 hours. Diluted with EtOAc, washed with 1N HCl, water and brine. Dried over anhydrous sodium sulfate. Concentrated, the residue was dissolved in DMSO and purified by prep HPLC (SunFire Prep C18 OBD 5 uM 30×50 mm column). The title compound was obtained as white powder. MS calcd for ($C_{18}H_{18}BN_3O_5S$): 399.11. MS found (ESI negative): (M−H)⁻=398.03. ¹H NMR (400 MHz, DMSO-d₆) δ (ppm): 9.80 (s, 1H), 9.1 (br, 1H), 8.42 (t, J=4.8 Hz, 1H), 7.44 (s, 1H), 7.43 (d, J=8.4 Hz, 1H), 7.22 (d, J=8 Hz, 1H), 7.13 (dd, J=8.4 Hz, 1H), 6.44 (d, J=2 Hz, 1H), 6.36 (dd, J=8.8 Hz, 1H), 4.87 (s, 2H), 3.91 (m, 2H), 3.80 (s, 2H).

2-(5-Amino-2-(N-(1-hydroxy-1,3-dihydrobenzo[c][1,2]oxaborol-6-yl)sulfamoyl)phenyl)-N-benzylacetamide

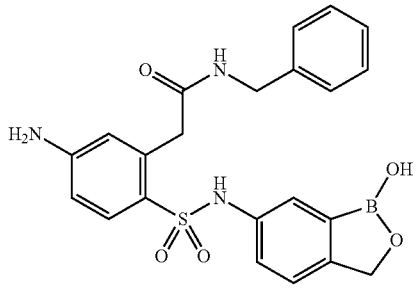 [SMILES: Nc1ccc(S(=O)(=O)Nc2ccc3c(c2)B(O)OC3)c(CC(=O)NCc2ccccc2)c1]

To the mixture of 2-(5-amino-2-(N-(1-hydroxy-1,3-dihydrobenzo[c][1,2]oxaborol-6-yl)sulfamoyl)phenyl)acetic acid (500 mg, 1.4 mmol) and benzyl amine (0.5 ml, 4.5 mmol) in DMF (5 ml), added PyBOP (730 mg, 1.4 mmol) then triethyl amine (0.4 ml, 3 mmol). Stirring was kept for 3 hours. Diluted with EtOAc, washed with 1N HCl, water and brine. Dried over anhydrous sodium sulfate. Concentrated, the residue was dissolved in DMSO and purified by prep HPLC (SunFire Prep C18 OBD 5 uM 30×50 mm column). The title compound was obtained as white powder. MS calcd for ($C_{22}H_{22}BN_3O_5S$): 451.14. MS found (ESI negative): (M−H)⁻=450.1. ¹H NMR (400 MHz, DMSO-d₆) δ (ppm): 9.78 (s, 1H), 9.15 (br, 1H), 8.38 (t, J=6 Hz, 1H), 7.37 (d, J=1.2 Hz, 1H), 7.36 (d, J=8.8 Hz, 1H), 7.30-7.10 (m, 6H), 7.01 (dd, J=8.4 Hz, 1H), 6.43 (d, J=2 Hz, 1H), 6.30 (dd, J=8.4 Hz, 1H), 4.80 (s, 2H), 4.25 (d, J=5.6 Hz, 2H), 3.79 (s, 2H).

2-(5-Amino-2-(N-(1-hydroxy-1,3-dihydrobenzo[c][1,2]oxaborol-6-yl)sulfamoyl)phenyl)-N-(3,3-difluorocyclobutyl)acetamide

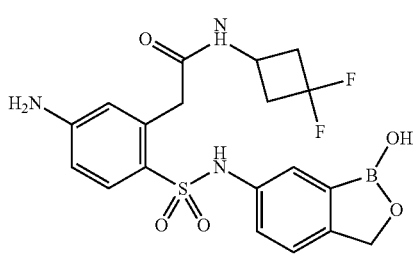 [SMILES: Nc1ccc(S(=O)(=O)Nc2ccc3c(c2)B(O)OC3)c(CC(=O)NC2CC(F)(F)C2)c1]

To the mixture of 2-(5-amino-2-(N-(1-hydroxy-1,3-dihydrobenzo[c][1,2]oxaborol-6-yl)sulfamoyl)phenyl)acetic acid (1.09 g, 3 mmol) and 3,3-difluorocyclobutyl amine hydrochloride (1 g, 7 mmol) in DMF (10 ml), added PyBOP (1.56 g, 3 mmol) then triethyl amine (1.8 ml, 12 mmol). Stirring was kept for 3 hours. Diluted with EtOAc, washed with 1N HCl, water and brine. Dried over anhydrous sodium sulfate. Concentrated, the residue was dissolved in DMSO and purified by prep HPLC (SunFire Prep C18 OBD 5 uM 30×50 mm column). The title compound was obtained as light yellow powder. MS calcd for ($C_{19}H_{20}BF_2N_3O_5S$): 451.12. MS found (ESI negative): (M−H)⁻=450.1. ¹H NMR (400 MHz, DMSO-d₆) δ (ppm): 9.79 (s, 1H), 9.15 (s, 1H), 8.48 (d, J=6.4 Hz, 1H), 7.43 (d, J=8.8 Hz, 1H), 7.39 (d, J=2 Hz, 1H), 7.20 (d, J=8.4 Hz, 1H), 7.09 (dd, J=8.4 Hz, 1H), 6.40 (d, J=2 Hz, 1H), 6.35 (dd, J=8.4 Hz, 1H), 5.92 (s, 2H), 4.85 (s, 2H), 4.05 (m, 1H), 3.75 (s, 2H), 2.89 (m, 2H), 2.59 (m, 2H).

4-Amino-2-(2-hydrazinyl-2-oxoethyl)-N-(1-hydroxy-1,3-dihydrobenzo[c][1,2]oxaborol-6-yl)benzenesulfonamide

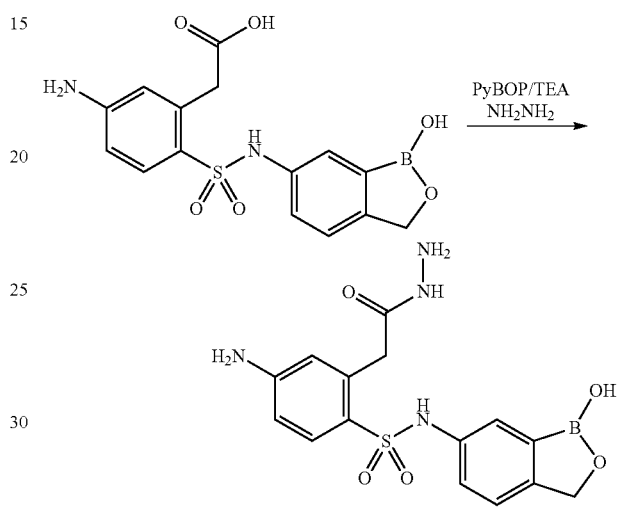

To a stirred solution of 2-(5-amino-2-(N-(1-hydroxy-1,3-dihydrobenzo[c][1,2]oxaborol-6-yl)sulfamoyl)phenyl)acetic acid (23.6 mg, 0.066 mmol) and hydrazine (6.3 uL, 0.13 mmol) in 1 mL of DMF were added PyBOP (69 mg, 0.13 mmol) and triethylamine (31 uL, 0.22 mmol). The reaction mixture was stirred at room temperature for 1 hour. The crude mixture was purified by prep HPLC (SunFire Prep C18 OBD 5 uM 30×50 mm column) to give the title compound as a white solid (5.0 mg, yield 16%). MS calcd for ($C_{15}H_{17}BN_4O_5S$): 376.1. MS found (ESI negative): (M−H)⁻=375.1. ¹H NMR (DMSO-d₆) δ (ppm): 10.4 (bs, 1H), 9.74 (s, 1H), 9.11 (bs, 1H), 7.38 (d, J=8.0 Hz, 1H), 7.36 (s, 1H), 7.17 (d, J=8.0 Hz, 1H), 7.06 (d, J=8.0 Hz, 1H), 6.34 (m, 2H), 5.89 (bs, 2H), 4.81 (s, 2H), 3.76 (s, 2H).

2-(5-Amino-2-(N-(1-hydroxy-1,3-dihydrobenzo[c][1,2]oxaborol-6-yl)sulfamoyl)phenyl)-N-methoxyacetamide

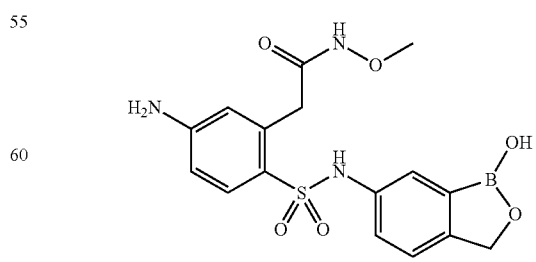

To a stirred solution of 2-(5-amino-2-(N-(1-hydroxy-1,3-dihydrobenzo[c][1,2]oxaborol-6-yl)sulfamoyl)phenyl)acetic acid (430 mg, 1.19 mmol) and methoxyamine hydrochloride (125 mg, 1.78 mmol) in 10 mL of DMF was added PyBOP (926 mg, 1.78 mmol) and TEA (496 uL, 3.56 mmol). The reaction mixture was stirred for 16 hours. After water was added, the reaction mixture was extracted with ethyl acetate and washed with water, 1N HCl and brine. The organic layer was dried over $Na_2SO_4$ and concentrated. The crude residue was purified by prep HPLC (SunFire Prep C18 OBD 5 uM 30×50 mm column) to give the desired product as a yellow solid (16.4 mg, yield 4%). Analytical data for title compound. MS calcd for ($C_{16}H_{18}BN_3O_6S$): 391.2. MS found (ESI negative): (M−H)$^-$=390.0. $^1$H NMR (DMSO-$d_6$) δ (ppm): 11.14 (s, 1H), 9.74 (s, 1H), 9.10 (bs, 1H), 7.36-7.40 (m, 2H), 7.16 (d, J=8.0 Hz, 1H), 7.05 (d, J=8.0 Hz, 1H), 6.36 (s, 1H), 6.31 (d, J=8.8 Hz, 1H), 4.80 (s, 2H), 3.58 (s, 2H), 3.56 (s, 3H).

N-(5-amino-2-(N-(1-hydroxy-1,3-dihydrobenzo[c] [1,2]oxaborol-6-yl)sulfamoyl)benzyl)acetamide

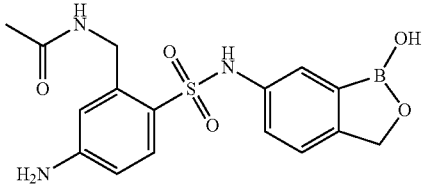 [SMILES: CC(=O)NCc1cc(N)ccc1S(=O)(=O)Nc1ccc2c(c1)B(O)OC2]

4-Amino-2-(aminomethyl)-N-(1-hydroxy-1,3-dihydrobenzo[c][1,2]oxaborol-6-yl)benzenesulfonamide To a solution of 2-cyano-N-(1-hydroxy-1,3-dihydrobenzo[c][1,2]oxaborol-6-yl)-4-nitrobenzenesulfonamide (1.077 g, 3 mmol) in MeOH/NH$_4$OH (100 ml/10 ml) was added Raney Ni (2 g) under nitrogen, then the solution was stirred under hydrogen atmosphere at room temperature for overnight. The mixture was filtered and the filtrate was concentrated to give title compound 4-amino-2-(aminomethyl)-N-(1-hydroxy-1,3-dihydrobenzo[c][1,2]oxaborol-6-yl)benzenesulfonamide (1.0 g, 100%) as a green solid. $^1$H NMR: DMSO 400 MHz. δ7.41 (d, J=14.0 Hz, 2H), 7.16 (d, J=8.0 Hz, 1H), 7.08 (d, J=8.0 Hz, 1H), 6.63 (s, 1H), 6.33 (d, J=8.4 Hz, 1H), 5.82 (brs, 2H), 4.84 (s, 2H), 3.95 (s, 2H).

N-(5-amino-2-(N-(1-hydroxy-1,3-dihydrobenzo[c] [1,2]oxaborol-6-yl)sulfamoyl)benzyl)acetamide A solution of 4-amino-2-(aminomethyl)-N-(1-hydroxy-1, 3-dihydrobenzo[c][1,2]oxaborol-6-yl)benzenesulfonamide (500 mg, 1.5 mmol) in pyridine (15 ml) was stirred at room temperature for 30 mins. DCM (40 ml) and acetic anhydride (168 mg, 1.65 mmol) was then added to the mixture. And it was stirred at room temperature for overnight. The mixture was concentrated in vacuo and the residue was purified by prep. HPLC (column: Luna 300×50.0 mm, 10 u; liquid phase: [A-H$_2$O+0.025% TFA; B-MeCN] B %: 10%-30%, 20 min) to give the title compound (226 mg, 40.2%) as a light yellow solid. $^1$H NMR: DMSO 400 MHz. δ9.99 (s, 1H), 9.19 (s, 1H), 8.24 (d, J=12.0 Hz, 1H), 7.52 (d, J=8.4 Hz, 1H), 7.43 (s, 1H), 7.21 (d, J=8.0 Hz, 1H), 7.12 (dd, J=10.0 Hz, 1H), 6.45 (s, 1H), 6.35 (dd, J=10.8 Hz, 1H), 5.95 (brs, 2H), 4.85 (s, 2H), 4.54 (s, 2H), 1.92 (s, 3H). ESI-MS m/z 374 (M−H, positive); HPLC purity: 90.13% (MaxPlot 190-370 nm), 96.33% (220 nm).

4-Amino-2-((3,3-dimethylureido)methyl)-N-(1-hydroxy-1,3-dihydrobenzo[c][1,2]oxaborol-6-yl)benzenesulfonamide and N-(5-amino-2-(N-(1-hydroxy-1,3-dihydrobenzo[c] [1,2]oxaborol-6-yl)sulfamoyl)benzyl)-2,2,2-trifluoroacetamide

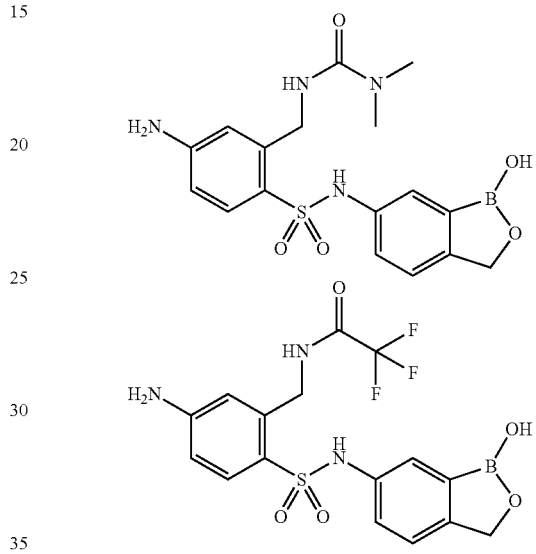

To a stirred solution of 4-amino-2-(aminomethyl)-N-(1-hydroxy-1,3-dihydrobenzo[c][1,2]oxaborol-6-yl)benzenesulfonamide (208 mg, 0.465 mmol) in 3 mL of pyridine was added dimethylcarbamic chloride (64 uL, 0.698 mmol). The reaction mixture was stirred at room temperature for 16 hours. After pyridine was removed in vacuo, the crude residue was purified by prep HPLC (SunFire Prep C18 OBD 5 uM 30×50 mm column) to give 4-amino-2-((3,3-dimethylureido) methyl)-N-(1-hydroxy-1,3-dihydrobenzo[c][1,2]oxaborol-6-yl)benzenesulfonamide as a yellow solid (16 mg, yield 9%), and N-(5-amino-2-(N-(1-hydroxy-1,3-dihydrobenzo[c] [1,2]oxaborol-6-yl)sulfamoyl)benzyl)-2,2,2-trifluoroacetamide (149.5 mg, yield 75%).

4-Amino-2-((3,3-dimethylureido)methyl)-N-(1-hydroxy-1,3-dihydrobenzo[c][1,2]oxaborol-6-yl)benzenesulfonamide: MS calcd for ($C_{17}H_{21}BN_4O_5S$): 404.2. MS found (ESI negative): (M−H)$^-$=403.1. $^1$H NMR (DMSO-$d_6$) δ (ppm): 10.06 (s, 1H), 9.18 (bs, 1H), 7.53 (d, J=8.8 Hz, 1H), 7.45 (s, 1H), 7.21 (d, J=8.0 Hz, 1H), 7.13 (d, J=8.0 Hz, 1H), 6.75 (t, 1H), 6.53 (s, 1H), 6.36 (d, J=8.4 Hz, 1H), 4.86 (s, 2H), 4.57 (d, J=5.6 Hz, 2H), 2.76 (s, 6H).

N-(5-amino-2-(N-(1-hydroxy-1,3-dihydrobenzo[c][1,2] oxaborol-6-yl)sulfamoyl)benzyl)-2,2,2-trifluoroacetamide: MS calcd for ($C_{16}H_{15}BN_3O_5F_3S$): 429.2. MS found (ESI negative): (M−H)$^-$=428.0. $^1$H NMR (DMSO-$d_6$) δ (ppm): 10.05 (s, 1H), 9.86 (t, 1H), 9.18 (bs, 1H), 7.55 (d, J=8.0 Hz, 1H), 7.44 (s, 1H), 7.22 (d, J=8.4 Hz, 1H), 7.13 (d, J=8.4 Hz, 1H), 6.39 (d, J=8.8 Hz, 1H), 6.34 (s, 1H), 4.85 (s, 2H), 4.69 (d, J=6 Hz, 2H).

N-(5-Amino-2-(N-(1-hydroxy-1,3-dihydrobenzo[c][1,2]oxaborol-6-yl)sulfamoyl)phenethyl)-2,2,2-trifluoroacetamide

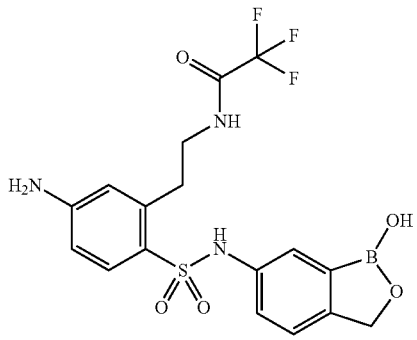 [SMILES: Nc1ccc(S(=O)(=O)Nc2ccc3c(c2)B(O)OC3)c(CCNC(=O)C(F)(F)F)c1]

General procedure 1: 6-aminobenzo[c][1,2]oxaborol-1(3H)-ol (600 mg, 4 mmol), 4-(2,2,2-trifluoroacetamido)-2-(2-(2,2,2-trifluoroacetamido)ethyl)benzene-1-sulfonyl chloride (1.7 g, 4 mmol), pyridine (0.4 ml, 5 mmol), rt, 1 hour. Removed solvent, the crude was dissolved in MeOH (20 ml), treated with ammonia (2 ml, 7N in MeOH), heated at 60° C. for 2 hours in a sealed tube. After cooled down to rt, concentrated, the result solid was purified by prep HPLC (SunFire Prep C18 OBD 5 uM 30×50 mm column). Characterization data for N-(5-Amino-2-(N-(1-hydroxy-1,3-dihydrobenzo[c][1,2]oxaborol-6-yl)sulfamoyl)phenethyl)-2,2,2-trifluoroacetamide: MS calcd for ($C_{14}H_{17}BF_3N_3O_5S$): 443.09. MS found (ESI negative): (M−H)⁻=442.1. $^1$H NMR (400 MHz, DMSO-$d_6$) δ (ppm): 9.91 (s, 1H), 9.46 (m, 1H), 7.52 (d, J=8.8 Hz, 1H), 7.40 (d, J=2 Hz, 1H), 7.20 (d, J=8.4 Hz, 1H), 7.10 (dd, J=8 Hz, 1H), 6.37 (s, 1H), 6.35 (d, J=6.8 Hz, 1H), 4.84 (s, 2H), 3.37 (q, J=14 Hz, 2H), 3.01 (t, J=7.6 Hz, 2H).

N-(5-Amino-2-(N-(5-fluoro-1-hydroxy-1,3-dihydrobenzo[c][1,2]oxaborol-6-yl)sulfamoyl)phenethyl)-2,2,2-trifluoroacetamide

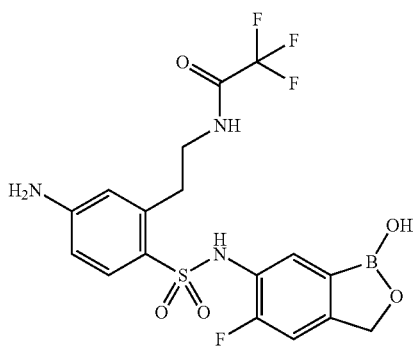 [SMILES: Nc1ccc(S(=O)(=O)Nc2cc3c(cc2F)COB3O)c(CCNC(=O)C(F)(F)F)c1]

General procedure 1: 6-amino-5-fluorobenzo[c][1,2]oxaborol-1(3H)-ol (250 mg, 1.5 mmol), 4-(2,2,2-trifluoroacetamido)-2-(2-(2,2,2-trifluoroacetamido)ethyl)benzene-1-sulfonyl chloride (640 mg, 1.5 mmol), pyridine (0.15 ml, 1.8 mmol), rt, 0.5 hour. Removed solvent, the crude was dissolved in MeOH (5 ml), treated with ammonia (2 ml, 7N in MeOH), heated at 60° C. for 2 hours in a sealed tube. After cooled down to rt, concentrated, the result solid was purified by prep HPLC (SunFire Prep C18 OBD 5 uM 30×50 mm column). MS calcd for ($C_{17}H_{16}BF_4N_3O_5S$): 461.08. MS found (ESI negative): (M−H)⁻=460.1. $^1$H NMR (400 MHz, DMSO-$d_6$) δ (ppm): 9.61 (s, 1H), 9.45 (m, 1H), 7.63 (d, J=8 Hz, 1H), 7.35 (d, J=8.4 Hz, 1H), 7.17 (d, J=8.8 Hz, 1H), 6.40 (d, J=1.6 Hz, 1H), 6.33 (dd, J=8.4 Hz, 1H), 4.86 (s, 2H), 3.40 (q, J=13.6 Hz, 2H), 3.03 (t, J=7.6 Hz, 2H).

4-Amino-2-(cyclopropanesulfonamidomethyl)-N-(1-hydroxy-1,3-dihydrobenzo[c][1,2]oxaborol-6-yl)benzenesulfonamide

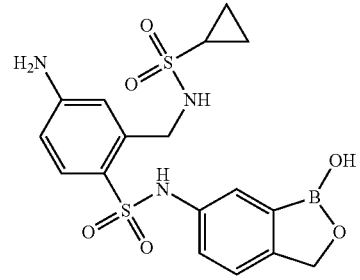 [SMILES: Nc1ccc(S(=O)(=O)Nc2ccc3c(c2)B(O)OC3)c(CNS(=O)(=O)C2CC2)c1]

To a stirred solution of 4-amino-2-(aminomethyl)-N-(1-hydroxy-1,3-dihydrobenzo[c][1,2]oxaborol-6-yl)benzenesulfonamide (708 mg, 2.1 mmol) and triethylamine (1 mL, 7 mmol) in 100 mL of DCM was added cyclopropanesulfonyl chloride (0.3 g, 2.2 mmol). The reaction mixture was stirred at room temperature for 16 hours. After the majority of the solvent was removed under vacuum, the reaction mixture was extracted with ethyl acetate and washed with water, 1N HCl and brine. The organic layer was dried over $Na_2SO_4$ and concentrated, the crude residue was purified by prep HPLC (SunFire Prep C18 OBD 5 uM 30×50 mm column) to give the desired product as a yellow solid (45 mg, yield 5%). MS calcd for ($C_{17}H_{20}BN_3O_6S_2$): 437.1. MS found (ESI negative): (M−H)⁻=336.1. $^1$H NMR (400 MHz, DMSO-$d_6$) δ (ppm): 10.04 (s, 1H), 9.17 (bs, 1H), 7.55 (d, J=8.8 Hz, 1H), 7.50 (t, J=6.4 Hz, 1H), 7.44 (d, J=1.6 Hz, 1H), 7.22 (d, J=8.8 Hz, 1H), 7.11 (dd, J=8, 1.6 Hz, 1H), 6.83 (d, J=2.4 Hz, 1H), 6.40 (dd, J=8.4, 2.4 Hz, 1H), 4.86 (s, 2H), 4.44 (d, J=6.4 Hz, 2H), 2.60 (m, 1H), 0.92 (m, 4H).

4-Amino-2-(cyclohexanesulfonamidomethyl)-N-(1-hydroxy-1,3-dihydrobenzo[c][1,2]oxaborol-6-yl)benzenesulfonamide

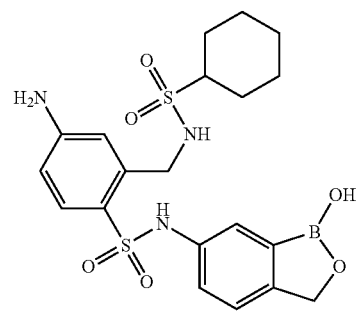 [SMILES: Nc1ccc(S(=O)(=O)Nc2ccc3c(c2)B(O)OC3)c(CNS(=O)(=O)C2CCCCC2)c1]

To a stirred solution of 4-amino-2-(aminomethyl)-N-(1-hydroxy-1,3-dihydrobenzo[c][1,2]oxaborol-6-yl)benzenesulfonamide (0.6 g, 1.8 mmol) and triethylamine (0.7 mL, 5 mmol) in 100 mL of DCM was added cyclohexanesulfonyl chloride (0.3 g, 2.2 mmol). The reaction mixture was stirred at room temperature for 16 hours. After majority of the solvent was removed under vacuum, the reaction mixture was extracted with ethyl acetate and washed with water, 1N HCl and brine. The organic layer was dried over $Na_2SO_4$ and concentrated, the crude residue was purified by prep HPLC (SunFire Prep C18 OBD 5 uM 30×50 mm column) to give the desired product as a yellow powder (112 mg, yield 13%). MS calcd for ($C_{20}H_{26}BN_3O_6S_2$): 479.1. MS found (ESI negative): $(M-H)^-$=478.0. $^1$H NMR (400 MHz, DMSO-$d_6$) δ (ppm): 10.03 (s, 1H), 9.17 (bs, 1H), 7.54 (d, J=8.4 Hz, 1H), 7.44 (d, J=2 Hz, 1H), 7.33 (t, J=6.4 Hz, 1H), 7.22 (d, J=8.4 Hz, 1H), 7.10 (dd, J=8, 2 Hz, 1H), 6.81 (d, J=2 Hz, 1H), 6.40 (dd, J=8.8, 2.4 Hz, 1H), 4.86 (s, 2H), 4.44 (d, J=6.4 Hz, 2H), 2.93 (m, 1H), 2.02 (m, 2H), 1.80 (m, 2H), 1.64 (m, 1H), 1.33 (m, 5H).

Methyl 5-amino-2-(N-(1-hydroxy-1,3-dihydrobenzo [c][1,2]oxaborol-6-yl)sulfamoyl)benzylcarbamate and Methyl 3-(methoxycarbonylamino)methyl)-4-(N-(1-hydroxy-1,3-dihydrobenzo[c][1,2]oxaborol-6-yl) sulfamoyl)phenylcarbamate

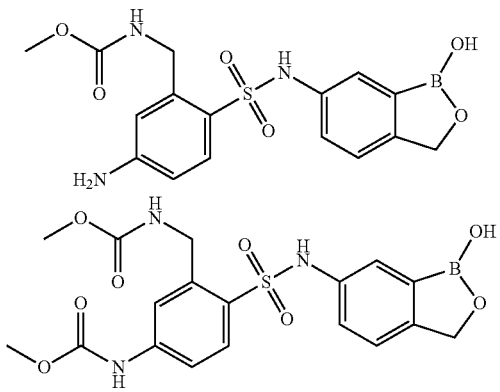

A solution of 4-amino-2-(aminomethyl)-N-(1-hydroxy-1, 3-dihydrobenzo[c][1,2]oxaborol-6-yl)benzenesulfonamide (832.5 mg, 2.5 mmol) in pyridine (20 ml) was stirred at room temperature for 30 mins. Methyl chloroformate (708.5 mg, 7.5 mmol) was then added to the mixture and it was stirred at room temperature for overnight. The solution was concentrated in vacuo and the residue was purified by prep. HPLC (column: Luna 300×50.0 mm, 10 u; liquid phase: [A-$H_2O$+ 0.025% TFA; B-MeCN] B %: 5%-45%, 30 min) to give methyl 5-amino-2-(N-(1-hydroxy-1,3-dihydrobenzo[c][1,2] oxaborol-6-yl)sulfamoyl)benzylcarbamate (208 mg, 21.28%) as a yellow solid and methyl 3-(methoxycarbonylamino)methyl)-4-(N-(1-hydroxy-1,3-dihydrobenzo[c][1,2] oxaborol-6-yl)sulfamoyl)phenylcarbamate (445 mg, 39.64%) as an orange solid.

Methyl 5-amino-2-(N-(1-hydroxy-1,3-dihydrobenzo[c] [1,2]oxaborol-6-yl)sulfamoyl)benzylcarbamate $^1$H NMR: DMSO 400 MHz. δ10.03 (s, 1H), 9.20 (brs, 1H), 7.56-7.50 (m, 2H), 7.45 (s, 1H), 7.22 (d, J=8.4 Hz, 1H), 7.13 (dd, J=10.4 Hz, 1H), 6.50 (s, 1H), 6.37 (dd, J=10.8 Hz, 1H), 5.90 (brs, 2H), 4.86 (s, 2H), 4.51 (s, 2H), 3.58 (s, 3H). ESI-MS m/z 390 (M–H, positive); HPLC purity: 94.43% (MaxPlot 190-370 nm), 97.83% (220 nm).

Meth 3-(methoxycarbonylamino)methyl)-4-(N-(1-hydroxy-1,3-dihydrobenzo[c][1,2]oxaborol-6-yl)sulfamoyl) phenylcarbamate $^1$H NMR: DMSO 400 MHz δ10.34 (s, 1H), 10.10 (s, 1H), 9.22 (brs, 1H), 7.80 (d, J=9.2 Hz, 1H), 7.63 (d, J=11.6 Hz, 1H), 7.52-7.47 (m, 3H), 7.24 (d, J=8.4 Hz, 1H), 7.15 (dd, J=10.0 Hz, 1H), 4.87 (s, 2H), 4.59 (s, 2H), 3.67 (s, 3H), 3.60 (s, 3H). ESI-MS m/z 448 (M–H, positive); HPLC purity: 98.13% (MaxPlot 190-370 nm), 99.41% (220 nm).

Ethyl 5-amino-2-(N-(1-hydroxy-1,3-dihydrobenzo[c] [1,2]oxaborol-6-yl)sulfamoyl)benzylcarbamate

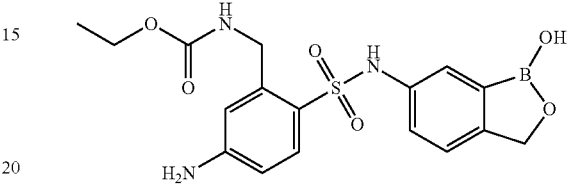

To a solution of 4-amino-2-(aminomethyl)-N-(1-hydroxy-1,3-dihydrobenzo[c][1,2]oxaborol-6-yl)benzenesulfonamide (500 mg, 0.89 mmol) and TEA (360 mg, 3.6 mmol) in THF (200 mL) at –20° C. was slowly added ethyl chloroformate (97.5 mg, 0.89 mmol) in THF (10 mL). Then the mixture was stirred at room temperature for 2 hrs. The mixture was concentrated in vacuo and the residue was purified by prep-HPLC (column: Luna 300×50.0 mm, 10 u; liquid phase: [A-$H_2O$+0.025% TFA; B-MeCN] B %: 10%-35%, 25 min) to give the title compound (240 mg, 58%) as TFA salt. $^1$H NMR DMSO 400 MHz δ 9.99 (s, 1H), 7.52 (d, J=8.8 Hz, 1H), 7.42 (q, 3H), 7.20 (d, J=8.0 Hz, 1H), 7.11 (dd, $J_{1=8.0}$ Hz, $J_2$=2.0 Hz, 1H), 6.48 (s, 1H), 6.35 (q, 1H), 4.84 (s, 2H), 4.50 (s, 2H), 4.00 (q, 2H), 1.17 (t, 3H).

Propyl 5-amino-2-(N-(1-hydroxy-1,3-dihydrobenzo [c][1,2]oxaborol-6-yl)sulfamoyl)benzylcarbamate

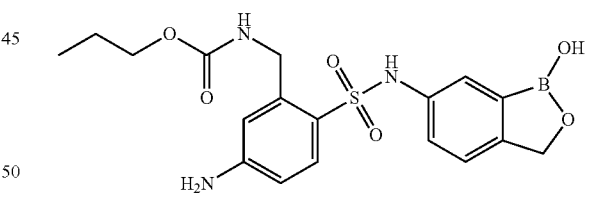

To a solution of 4-amino-2-(aminomethyl)-N-(1-hydroxy-1,3-dihydrobenzo[c][1,2]oxaborol-6-yl)benzenesulfonamide (500 mg, 0.89 mmol) and TEA (360 mg, 3.6 mmol) in THF (200 mL) at –20° C. was slowly added propyl chloroformate (108 mg, 0.89 mmol) in THF (10 mL). Then the mixture was stirred at room temperature for 2 hrs. The mixture was concentrated in vacuo and the residue was purified by prep-HPLC (column: Luna 300×50.0 mm, 10 u; liquid phase: [A-$H_2O$+0.025% TFA; B-MeCN] B %: 15%-40%, 25 min) to give the title compound (246 mg, 46%) as TFA salt. $^1$H NMR DMSO 400 MHz δ 9.99 (s, 1H), 7.52 (d, J=8.4 Hz, 1H), 7.42 (s, 2H), 7.20 (d, J=8.0 Hz, 1H), 7.11 (dd, $J_1$=8.0 Hz, $J_2$=2.0 Hz, 1H), 6.48 (s, 1H), 6.35 (q, 1H), 4.84 (s, 2H), 4.50 (s, 2H), 3.93 (q, 2H), 1.57 (q, 2H), 0.63 (t, 3H).

Isopropyl 5-amino-2-(N-(1-hydroxy-1,3-dihydrobenzo[c][1,2]oxaborol-6-yl)sulfamoyl)benzylcarbamate

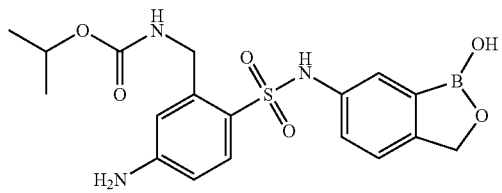 [SMILES: CC(C)OC(=O)NCc1cc(N)ccc1S(=O)(=O)Nc1ccc2c(c1)B(O)OC2]

To a solution of 4-amino-2-(aminomethyl)-N-(1-hydroxy-1,3-dihydrobenzo[c][1,2]oxaborol-6-yl)benzenesulfonamide (500 mg, 0.89 mmol) and TEA (360 mg, 3.6 mmol) in THF (200 mL) at −20° C. was slowly added iso-propyl chloroformate (97.5 mg, 0.89 mmol) in THF (10 mL). Then the mixture was stirred at room temperature for 2 hrs. The mixture was concentrated in vacuo and the residue was purified by prep-HPLC (column: Gemini 300×50.0 mm, 10 u; liquid phase: [A-H$_2$O+0.04% NH$_3$OH; B-MeCN] B %: 10%-35%, 25 min) to give the title compound (230 mg, 43%). $^1$H NMR DMSO 400 MHz δ 9.17 (s, 1H), 7.53 (d, J=8.4 Hz, 1H), 7.44 (d, J=2.0 Hz, 1H), 7.33 (q, 1H), 7.20 (d, J=8.4 Hz, 1H), 7.12 (q, 1H), 6.47 (s, 1H), 6.36 (q, 1H), 6.00 (s, 2H), 4.85 (s, 2H), 4.77 (q, 1H), 4.50 (s, 2H), 1.19 (d, J=6.0 Hz, 6H).

Isobutyl 5-amino-2-(N-(1-hydroxy-1,3-dihydrobenzo[c][1,2]oxaborol-6-yl)sulfamoyl)benzylcarbamate

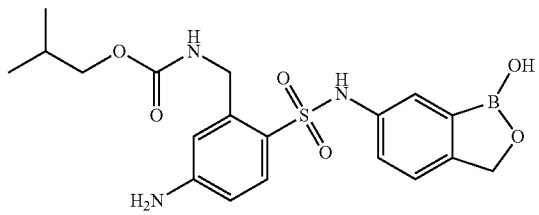 [SMILES: CC(C)COC(=O)NCc1cc(N)ccc1S(=O)(=O)Nc1ccc2c(c1)B(O)OC2]

To a solution of 4-amino-2-(aminomethyl)-N-(1-hydroxy-1,3-dihydrobenzo[c][1,2]oxaborol-6-yl)benzenesulfonamide (500 mg, 0.89 mmol) and TEA (360 mg, 3.6 mmol) in THF (200 mL) at −20° C. was slowly added iso-butyl chloroformate (121 mg, 0.89 mmol) in THF (10 mL). Then the mixture was stirred at room temperature for 2 hrs. The mixture was concentrated in vacuo and the residue was purified by prep-HPLC (column: Luna 300×50.0 mm, 10 u; liquid phase: [A-H$_2$O+0.025% TFA; B-MeCN] B %: 15%-40%, 25 min) to give the title compound (185 mg, 38%) as TFA salt. $^1$H NMR DMSO 400 MHz δ 9.98 (s, 1H), 7.52 (d, J=8.8 Hz, 1H), 7.43 (q, 2H), 7.20 (d, J=8.8 Hz, 1H), 7.11 (q, 1H), 6.48 (s, 1H), 6.35 (q, 1H), 4.84 (s, 2H), 4.50 (s, 2H), 3.75 (d, J=7.2 Hz, 2H), 1.84 (q, 1H), 0.88 (q, 6H).

Pentan-3-yl 5-amino-2-(N-(1-hydroxy-1,3-dihydrobenzo[c][1,2]oxaborol-6-yl)sulfamoyl)benzylcarbamate

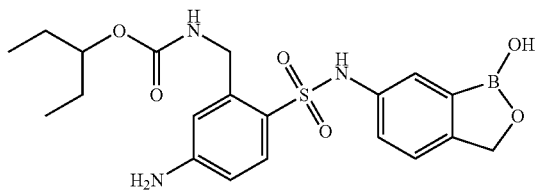 [SMILES: CCC(CC)OC(=O)NCc1cc(N)ccc1S(=O)(=O)Nc1ccc2c(c1)B(O)OC2]

To a solution of 4-amino-2-(aminomethyl)-N-(1-hydroxy-1,3-dihydrobenzo[c][1,2]oxaborol-6-yl)benzenesulfonamide (500 mg, 0.89 mmol) and TEA (360 mg, 3.6 mmol) in THF (200 mL) at −20° C. was slowly added 3-pentyl chloroformate (147 mg, 0.89 mmol) in THF (10 mL). Then the mixture was stirred at room temperature for 2 hrs. The mixture was concentrated in vacuo and the residue was purified by prep-HPLC (column: Luna 300×50.0 mm, 10 u; liquid phase: [A-H$_2$O+0.025% TFA; B-MeCN] B %: 17%-42%, 25 min) to give the title compound (230 mg, 43%) as TFA salt. $^1$H NMR: DMSO 400 MHz δ 9.97 (s, 1H), 7.53 (d, J=8.4 Hz, 1H), 7.35 (q, 1H), 7.20 (d, J=8.4 Hz, 1H), 7.11 (J=8.4 Hz, 1H), 6.47 (s, 1H), 6.35 (q, 1H), 4.88 (s, 2H), 4.50 (q, 3H), 1.50 (q, 4H), 0.84 (t, 6H).

Benzyl 5-amino-2-(N-(1-hydroxy-1,3-dihydrobenzo[c][1,2]oxaborol-6-yl)sulfamoyl)benzylcarbamate

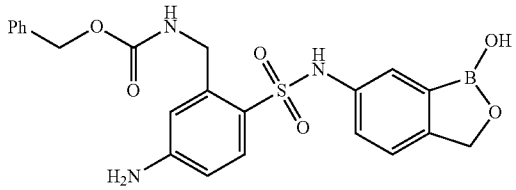 [SMILES: Nc1ccc(S(=O)(=O)Nc2ccc3c(c2)B(O)OC3)c(CNC(=O)OCc2ccccc2)c1]

To a solution of 4-amino-2-(aminomethyl)-N-(1-hydroxy-1,3-dihydrobenzo[c][1,2]oxaborol-6-yl)benzenesulfonamide (500 mg, 0.89 mmol) and TEA (360 mg, 3.6 mmol) in THF (200 mL) at −20° C. was slowly added CbzCl (151 mg, 0.89 mmol) in THF (10 mL). Then the mixture was stirred at room temperature for 2 hrs. The mixture was concentrated in vacuo and the residue was purified by prep-HPLC (column: Luna 300×50.0 mm, 10 u; liquid phase: [A-H2O+0.025% TFA; B-MeCN] B %: 15%-40%, 25 min) to give the title compound (220 mg, 42%) as TFA salt. $^1$H NMR: DMSO 400 MHz δ 9.97 (s, 1H), 7.63 (t, J=7.2 Hz, 1H), 7.55 (q, 1H), 7.42 (q, 1H), 7.37 (q, 3H), 7.32 (q, 3H), 7.30 (q, 3H), 6.52 (s, 1H), 6.37 (q, 1H), 5.05 (s, 2H), 4.83 (s, 2H), 4.53 (s, 2H).

4-Amino-N-(1-hydroxy-1,3-dihydrobenzo[c][1,2]oxaborol-6-yl)-2-(methylsulfonylmethyl)benzenesulfonamide

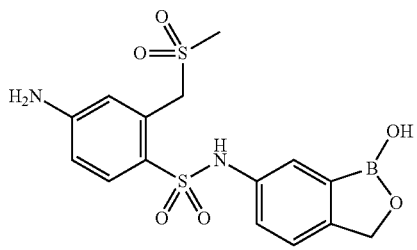 [SMILES: CS(=O)(=O)Cc1cc(N)ccc1S(=O)(=O)Nc1ccc2c(c1)B(O)OC2]

To a stirred solution of 3-(methylsulfonylmethyl)aniline (2.0 g, 10.8 mmol) and triethylamine (4.5 mL, 32.3 mmol) in 100 mL of CH$_2$Cl$_2$ was added 2,2,2-trifluoroacetic anhydride (3.0 mL, 21.6 mmol) dropwise. The reaction mixture was stirred for 16 hours. After the mixture was concentrated, the residue was purified by ISCO CombiFlash Rf silica chromatography eluted with 0-50% ethyl acetate in hexane to give the desired compound as a yellow solid (2.8 g, yield 92%).

2,2,2-Trifluoro-N-(3-(methylsulfonylmethyl)phenyl)acetamide (1.5 g, 4.0 mmol) was mixed with chlorosulfonic acid (3 mL) at 0° C., and the mixture was stirred at room temperature for 16 hours. As the starting material was consumed as indicated by LC/MS, the mixture was added dropwise to ice-water. The mixture was extracted with dichloromethane. The organic layer was dried over Na$_2$SO$_4$ and concentrated to give the desired product as a yellow residue (1.6 g, yield 88%).

To a stirred solution of 2-(methylsulfonylmethyl)-4-(2,2,2-trifluoroacetamido)benzene-1-sulfonyl chloride (680 mg, 1.8 mmol) and 6-aminobenzo[c][1,2]oxaborol-1(3H)-ol (400 mg, 2.7 mmol) in 10 mL of ACN was added pyridine (290 uL, 3.6 mmol) dropwise. The reaction mixture was stirred at room temperature for 16 hours. After the mixture was concentrated, the residue was extracted with ethyl acetate and washed with water, 1N HCl and brine. The organic layer was dried over Na$_2$SO$_4$ and concentrated. A solution of this crude compound in 7M ammonium in MeOH (10 mL) was stirred in a sealed tube at 50° C. for 4 hours. After concentrated, the crude mixture was purified by prep HPLC (SunFire Prep C18 OBD 5 uM 30×50 mm column) to give the title compound as a white solid (498 mg, yield 70%). MS calcd for (C$_{15}$H$_{17}$BN$_2$O$_6$S$_2$): 396.2. MS found (ESI negative): (M−H)$^-$=395.1. $^1$H NMR (DMSO-d$_6$) δ (ppm): 9.95 (s, 1H), 9.20 (bs, 1H), 7.54 (d, J=8.8 Hz, 1H), 7.41 (s, 1H), 7.21 (d, J=8.4 Hz, 1H), 7.07 (d, J=8.0 Hz, 1H), 6.72 (s, 1H), 6.47 (d, J=8.8 Hz, 1H), 4.85 (s, 2H), 4.71 (s, 2H), 2.82 (s, 3H).

4-Amino-2-(ethylsulfonylmethyl)-N-(1-hydroxy-1,3-dihydrobenzo[c][1,2]oxaborol-6-yl)benzenesulfonamide To a stirred suspension of 1-(bromomethyl)-3-nitrobenzene (40 g; 0.18 mol) and iron powder (31 g; 0.55 mol) in EtOH (1000 mL) was added concentrated HCl (33.8 g, 0.93 mol) at r.t. The mixture was stirred at 85° C. for 2 hrs, cooling to r.t. and filtered. The filtrate was evaporated and the residue was solved in EtOAc and washed with brine, dried (Na$_2$SO$_4$) and concentrated to give the 3-(bromomethyl)aniline (30 g, 87% yield) as a yellow solid. $^1$H NMR: (400 MHz, MeOD) δ 7.59-7.56 (m, 1H), 7.54 (t, 1H), 7.39 (d, 1H), 7.38-7.34 (m, 1H), 4.73 (s, 2H).

To a solution of 3-(bromomethyl)aniline (20 g, 0.11 mol) and Et$_3$N (54.3 g, 0.54 mol) in dry DCM (150 mL) was added acetyl chloride (12.6 g, 0.16 mol) at 0° C. The reaction mixture was stirred at r.t. for 3 hrs. Then water was added, the organic layer was separated and washed with water. The organics was dried over Na$_2$SO$_4$ and concentrated to give the desired product N-(3-(bromomethyl)phenyl)acetamide (10 g, 41% yield). $^1$H NMR: (400 MHz, CDCl$_3$) δ 7.81 (s, 1H), 7.62 (s, 1H), 7.42 (d, 1H), 7.32-7.28 (m, 1H), 7.13 (d, 1H), 4.55 (s, 2H), 2.12 (s, 3H).

To a solution of N-(3-(bromomethyl)phenyl)acetamide (6.6 g, 29 mmol) in CH$_3$CN (50 mL) and water (10 mL) was added K$_2$CO$_3$ (6 g, 43 mmol) and EtSH (1.79 g, 29 mmol). The mixture was stirred at r.t. overnight. After removal of the solvent, the residue was extracted with EtOAc, dried and concentrated to give the crude product. The crude was purified by silica gel chromatography (petroleum ether:EtOAc=1:0 to 10:1) to give N-(3-(ethylthiomethyl)phenyl)acetamide (3.4 g, 56% yield) as a light yellow solid. $^1$H NMR: (400 MHz, CDCl$_3$) δ 7.81 (s, 1H), 7.41 (s, 1H), 7.34 (d, 1H), 7.22-7.17 (m, 1H), 7.01 (d, 1H), 3.61 (s, 2H), 2.41-2.34 (m, 2H), 2.11 (s, 3H), 1.24 (t, 3H).

To a solution of N-(3-(ethylthiomethyl)phenyl)acetamide (1 g, 5 mmol) in DCM (10 mL) was added mCPBA (2.4 g, 14 mol). The reaction mixture was stirred at 40° C. overnight. Then water was added, the organic layer was separated and washed with an aqueous of NaHCO$_3$, dried over Na$_2$SO$_4$, concentrated and purified by silica gel chromatography (petroleum ether:EtOAc=1:0 to 5:1) to give N-(3-(ethylsulfonylmethyl)phenyl)acetamide (1 g, 87% yield) as a white solid. $^1$H NMR: (400 MHz, CDCl$_3$) δ 7.84 (s, 1H), 7.61 (s, 1H), 7.41 (d, 1H), 7.24 (t, 1H), 7.14 (d, 1H), 4.14 (s, 2H), 2.90-2.85 (m, 2H), 2.12 (s, 3H), 1.34 (t, 3H).

To N-(3-(ethylsulfonylmethyl)phenyl)acetamide (1 g, 4 mmol) was added HOSO$_2$Cl (4.8 g) dropwise at 0° C. The mixture was stirred at r.t. for 3 hrs. The reaction mixture was diluted with DCM and washed with water, the organics was dried over Na$_2$SO$_4$, concentrated under reduced pressure to give 4-acetamido-2-(ethylsulfonylmethyl)benzene-1-sulfonyl chloride (0.8 g, yield 57%).

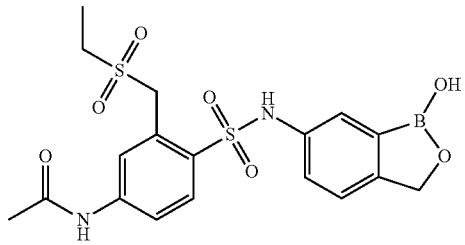 [SMILES: CCS(=O)(=O)Cc1cc(NC(C)=O)ccc1S(=O)(=O)Nc1ccc2c(c1)B(O)OC2]

To a solution of 6-amino-3H-benzo[c][1,2]oxaborol-1-ol (0.7 g, 5 mmol) and NMM (1.43 g, 14 mmol) in CH$_3$CN (50 mL) was added a solution of 4-acetamido-2-(ethylsulfonylmethyl)benzene-1-sulfonyl chloride (1.6 g, 5 mmol) in CH$_3$CN (50 mL) dropwise at 0° C. The reaction mixture was stirred at room temperature for 2 hrs, then the reaction solution was concentrated in vacuo, the residue was diluted with water and extracted with EtOAc, the organics was dried over Na$_2$SO$_4$, concentrated in vacuo to give the compound 7 (0.72 g, yield 34%).

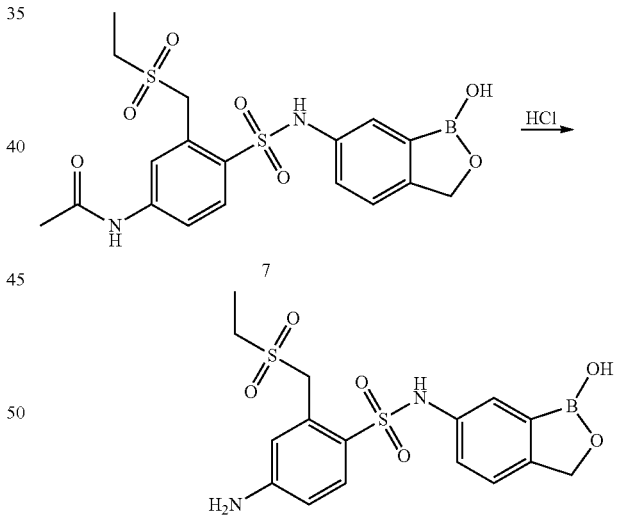

Compound 7 (0.7 g, 1 mmol) was dissolved in concentrated HCl (25 mL) and stirred at r.t. overnight. The reaction mixture was neutralized and concentrated, the residue was extracted with MeOH and concentrated in vacuo to give the crude product. The crude product was purified by prep-HPLC (column: Luna 300×50.0 mm, 10μ; liquid phase: [A-H$_2$O+0.05% TFA, B—CH$_3$CN] B %: 12%-42%, 25 min), concentrated, acidified with HCl and freeze-dried to give the title compound (0.22 g, yield 34%) as HCl salt. $^1$H NMR: (400 MHz, DMSO-d6) δ 9.87 (s, 1H), 7.52 (d, 1H), 7.41 (s, 1H), 7.22 (d, 1H), 7.08 (t, 1H), 6.73 (d, 1H), 6.48 (d, 1H), 4.85 (s, 2H), 4.70 (s, 2H), 3.01 (d, 2H), 1.12 (t, 3H).

4-Amino-N-(1-hydroxy-1,3-dihydrobenzo[c][1,2] oxaborol-6-yl)-2-(propylsulfonylmethyl)benzenesulfonamide

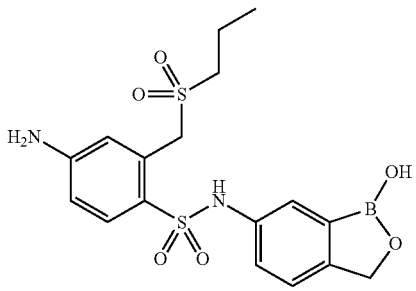 [SMILES: CCCS(=O)(=O)Cc1cc(N)ccc1S(=O)(=O)Nc1ccc2c(c1)B(O)OC2]

A solution of 1-(chloromethyl)-3-nitrobenzene (10.0 g, 58.1 mmol) in DMF (30 mL) was stirred at room temperature, then sodium propane-1-thiolate (5.7 g, 58.1 mmol) was added, followed by stirring at 60° C. overnight. After water was added, the aqueous layer was extracted with ethyl acetate 3 times. The combined organic phase was washed with brine, dried over sodium sulfate and concentrated to give (3-nitrobenzyl)(propyl)sulfane (11.2 g, yield 91%).

A solution compound (3-nitrobenzyl)(propyl)sulfane (7.5 g, 35.3 mmol) and m-CPBA (18.4 g, 106.5 mmol) in DCM (50 mL) was stirred at room temperature overnight. The reaction mixture was washed with saturated sodium thiosulfate, NaHCO$_3$, and water. The combined organic phase was washed with brine, dried over sodium sulfate and concentrated to give compound 1-nitro-3-(propylsulfonylmethyl)benzene (6.1 g, yield 71%).

To a stirred solution of 1-nitro-3-(propylsulfonylmethyl)benzene (2.0 g, 8.2 mmol) in 20 ml, of MeOH was added Pd/C (10 wt. % on activated carbon, 400 mg). The reaction mixture was allowed to hydrogenate at room temperature under hydrogen at 50 psi for 1 hour. After the mixture was filtered through a pad of Celite, the reaction was concentrated in vacuo. The residue was purified by ISCO CombiFlash Rf silica chromatography eluted with 0-50% ethyl acetate in hexane to give the desired compound 3-(propylsulfonylmethyl)aniline as a yellow residue (1.7 g, yield 97%).

To a stirred solution of 3-(propylsulfonylmethyl)aniline (1.7 g, 8.0 mmol) and triethylamine (3.3 mL, 23.9 mmol) in 20 mL of CH$_2$Cl$_2$ was added 2,2,2-trifluoroacetic anhydride (2.2 mL, 15.9 mmol) dropwise. The reaction mixture was stirred for 16 hours. After the mixture was concentrated, the residue was purified by ISCO CombiFlash Rf silica chromatography eluted with 0-50% ethyl acetate in hexane to give the desired compound as a yellow solid (2.3 g, yield 93%).

2,2,2-Trifluoro-N-(3-(propylsulfonylmethyl)phenyl)acetamide (1.3 g, 4.2 mmol) was mixed with chlorosulfonic acid (3 mL) at 0° C., and the mixture was stirred at room temperature for 16 hours. As the starting material was consumed as indicated by LC/MS, the mixture was added dropwise to ice-water. The mixture was extracted with dichloromethane. The organic layer was dried over Na$_2$SO$_4$ and concentrated to give the desired product as a yellow residue (1.5 g, yield 88%).

To a stirred solution of 2-(propylsulfonylmethyl)-4-(2,2,2-trifluoroacetamido)benzene-1-sulfonyl chloride (700 mg, 1.7 mmol) and 6-aminobenzo[c][1,2]oxaborol-1(3H)-ol (384 mg, 2.58 mmol) in 10 mL of ACN was added pyridine (278 uL, 3.4 mmol) dropwise. The reaction mixture was stirred at room temperature for 16 hours. After the mixture was concentrated, the residue was extracted with ethyl acetate and washed with water, 1N HCl and brine. The organic layer was dried over Na$_2$SO$_4$ and concentrated. A solution of this crude compound in 7M ammonium in MeOH (10 mL) was stirred in a sealed tube at 50° C. for 4 hours. After concentrated, the crude mixture was purified by prep HPLC (SunFire Prep C18 OBD 5 uM 30×50 mm column) to give the title compound as an off-white solid (428 mg, yield 59%). MS calcd for (C$_{17}$H$_{21}$BN$_2$O$_6$S$_2$): 424.3. MS found (ESI negative): (M−H)$^-$=423.1. $^1$H NMR (DMSO-d$_6$) δ (ppm): 9.88 (s, 1H), 9.20 (bs, 1H), 7.52 (d, J=8.8 Hz, 1H), 7.41 (s, 1H), 7.21 (d, J=8.4 Hz, 1H), 7.08 (d, J=8.0 Hz, 1H), 6.73 (s, 1H), 6.47 (d, J=8.4 Hz, 1H), 4.86 (s, 2H), 4.69 (s, 2H), 2.97 (t, 2H), 1.61 (m, 2H), 0.89 (s, 3H).

4-Amino-N-(1-hydroxy-1,3-dihydrobenzo[c][1,2] oxaborol-6-yl)-2-(2-(methylsulfonyl)ethyl)benzenesulfonamide A solution of 1-(bromomethyl)-3-nitrobenzene (30 g, 0.14 mol) in DMF (200 mL) was heated to 70° C., then sodium cyanide (17 g, 0.21 mol) was added slowly. The reaction mixture was stirred at 70° C. for 5 hours. The reaction was terminated by addition of water. The aqueous layer was extracted with ethyl acetate 3 times. The combined organic phase was washed with brine, dried over sodium sulfate. The crude product was purified by silica gel column chromatography (petroleum ether/ethyl acetate=10:1) to give 2-(3-nitrophenyl)acetonitrile (12.5 g, yield 33%). $^1$H NMR: 400 MHz CDCl$_3$ δ 8.15-8.14 (m, 2H), 7.66-7.64 (m, 1H), 7.56-7.52 (m, 1H), 3.82 (s, 2H).

A solution of 2-(3-nitrophenyl)acetonitrile (11 g, 68 mmol) in MeOH/HCl (300 mL, 4M), was stirred at room temperature overnight. The solvent was evaporated, saturated sodium bicarbonate was added, and the aqueous layer was extracted with ethyl acetate 3 times. The combined organic phase was washed with brine, dried over sodium sulfate and concentrated to give methyl 2-(3-nitrophenyl)acetate (12 g, yield 92%). $^1$H NMR: 400 MHz CDCl$_3$ δ 8.16-8.14 (m, 2H), 7.64-7.62 (m, 1H), 7.53-7.51 (m, 1H), 3.75 (s, 2H), 3.73 (s, 3H).

A solution of methyl 2-(3-nitrophenyl)acetate (12 g, 62 mmol) in THF (100 ml) was cooled to 0° C., then MeOH (10 mL) was added slowly, followed by stirring at room temperature overnight. Water was added to terminate the reaction. The aqueous layer was extracted with ethyl acetate 3 times. The combined organic phase was washed with brine, dried over sodium sulfate and concentrated to give 2-(3-nitrophenyl)ethanol (9 g, yield 90%). $^1$H NMR: 400 MHz CDCl$_3$ δ 8.11-8.07 (m, 2H), 7.59-7.56 (m, 1H), 7.49-7.45 (m, 1H), 3.94-3.91 (m, 2H), 2.99-2.96 (m, 2H).

A solution of 2-(3-nitrophenyl)ethanol (9 g, 53.8 mmol) in DCM (100 mL) was cooled to 0° C., then pyridine (22.7 g, 287 mmol) was dropwise added to the reaction solution. Then methylsulfonylchloride was added slowly dropwise, followed by stirring at room temperature for one hour. Water was added to terminate the reaction. The aqueous layer was extracted by ethyl acetate 3 times. The combined organic phase was washed with brine, dried over sodium sulfate and concentrated to give 3-nitrophenethyl methanesulfonate (13 g, yield 98%). $^1$H NMR: 400 MHz CDCl$_3$ δ 8.13-8.10 (m, 2H), 7.60-7.53 (m, 1H), 7.53-7.47 (m, 1H), 4.48-4.45 (m, 2H), 3.19-3.15 (m, 2H), 2.95 (s, 3H).

A solution of 3-nitrophenethyl methanesulfonate (6 g, 24.5 mmol) in DMF (30 mL) was stirred at room temperature, then sodium methyl mercaptide (22 g, 20%) was added, followed by stirring at 70° C. overnight. Water was added to terminate the reaction. The aqueous layer was extracted with ethyl acetate 3 times. The combined organic phase was washed with brine, dried over sodium sulfate and concentrated to give methyl(3-nitrophenethyl)sulfane (4.4 g, yield 91%). $^1$H NMR: 400 MHz CDCl₃ δ 8.09-8.07 (m, 2H), 7.53-7.56 (m, 1H), 7.49-7.45 (m, 1H), 3.03-2.99 (m, 2H), 2.81-2.78 (m, 2H), 2.16 (s, 3H).

A mixture of methyl(3-nitrophenethyl)sulfane (4.4 g, 22 mmol) and iron powder (3.75 g, 67 mmol) in MeOH was stirred at room temperature, then aqueous HCl (20 g, 36.5%) was added slowly, then the mixture solution was heated to reflux for 3 hours. The solvent was evaporated, and saturated sodium bicarbonate was added, the aqueous layer was extracted with ethyl acetate 3 times. The combined organic phase was washed with brine, dried over sodium sulfate and concentrated to give 3-(2-(methylthio)ethyl)aniline (3.5 g, yield 94%). ¹H NMR: 400 MHz CDCl₃ δ 7.11-7.07 (m, 1H), 6.63-6.61 (m, 1H), 6.56-6.54 (m, 1H), 3.64 (s, 2H), 2.83-2.71 (m, 4H), 2.13 (s, 3H).

A solution of 3-(2-(methylthio)ethyl)aniline (4 g, 24 mmol) in DCM (100 mL) was cooled to 0° C., then triethylamine (19.6 mL, 143 mmol) was dropwise added to the reaction solution. Then trifluoroaceticanhydride (10.2 mL, 72 mmol) was added slowly dropwise, followed by stirring at room temperature for 3 hours. Water was added to terminate the reaction. The aqueous layer was extracted with ethyl acetate 3 times. The combined organic phase was washed with brine, dried over sodium sulfate and concentrated to give 2,2,2-trifluoro-N-(3-(2-(methylthio)ethyl)phenyl)acetamide (6 g, yield 95%). ¹H NMR: 400 MHz CDCl₃ δ 7.98-7.97 (s, 1H), 7.65 (s, 1H), 7.47-7.46 (m, 1H), 7.42-7.39 (m, 1H), 7.10-7.08 (m, 1H), 3.13-3.10 (m, 2H), 2.92-2.88 (m, 2H), 2.11 (s, 3H).

A solution of 2,2,2-trifluoro-N-(3-(2-(methylthio)ethyl) phenyl)acetamide (4 g, 15 mmol) and m-CPBA (7.9 g, 45 mmol) in DCM (30 mL) was heated to reflux overnight. Aqueous solution of sodium thiosulfate (10 mL) was added. The solid was filtered from the mixture solution. The aqueous layer was extracted by ethyl acetate 3 times. The combined organic phase was washed with brine, dried over sodium sulfate and concentrated to give 2,2,2-trifluoro-N-(3-(2-(methylsulfonyl)ethyl)phenyl)acetamide (4 g, yield 89%). ¹H NMR: 400 MHz CDCl₃ δ 7.85 (s, 1H), 7.50-7.49 (m, 1H), 7.36-7.28 (m, 2H), 7.07-7.05 (m, 1H), 3.26-3.22 (m, 2H), 3.14-3.10 (m, 2H), 2.79 (s, 3H).

Chlorosulfonic acid (5.8 g, 49 mmol) was cooled to 0° C., then 2,2,2-trifluoro-N-(3-(2-(methylsulfonyl)ethyl)phenyl) acetamide (2 g, 6.8 mmol) was added slowly. The reaction mixture was allowed to warm to room temperature. Two hours later, the reaction was poured onto ice. The aqueous layer was extracted with ethyl acetate 3 times. The combined organic phase was washed with brine, dried over sodium sulfate. The crude product was purified by pre-HPLC (column: Luna 300×50.0 mm, 10 um; liquid phase: [A-H₂O+ 0.05% TFA; B-MeCN] B %: 0%-27%, 23 min) to give 2-(2-(methylsulfonyl)ethyl)-4-(2,2,2-trifluoroacetamido) benzenesulfonic acid (1.1 g, yield 28%).

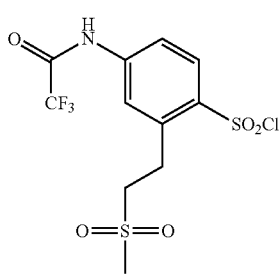

2-(2-(Methylsulfonyl)ethyl)-4-(2,2,2-trifluoroacetamido) benzenesulfonic acid (1.1 g, 2.9 mmol) was dissolved in SOCl₂ (30 mL), and the reaction was heated to reflux overnight. The solvent was evaporated to give crude product of compound 11 (1.2 g, crude).

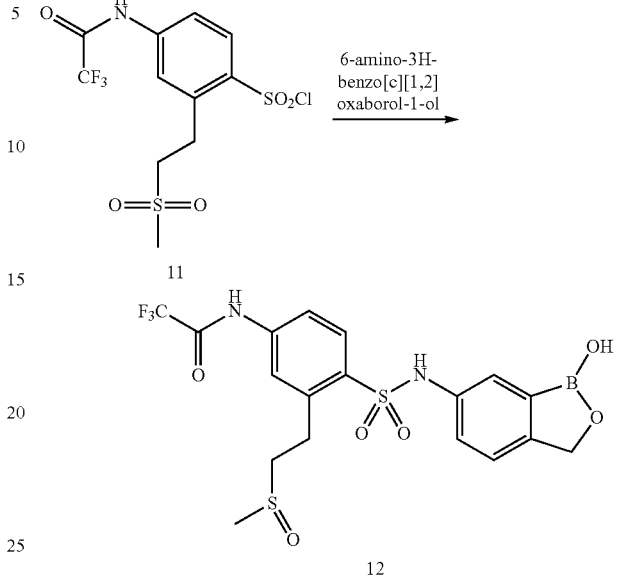

A solution of 6-amino-3H-benzo[c][1,2]oxaborol-1-ol (0.27 g, 2.4 mmol) and N-methylmorpholine (0.54 g, 5 mmol) in MeCN (50 mL) was added compound 11 (1.1 g, 2.8 mmol) at 0° C., then the solution was stirred at room temperature overnight. The mixture was concentrated in vacuo, and ethyl acetate and water was added to the residue. The organic layer was dried over Na₂SO₄ and concentrated to give the crude product of compound 12 (0.8 g, crude).

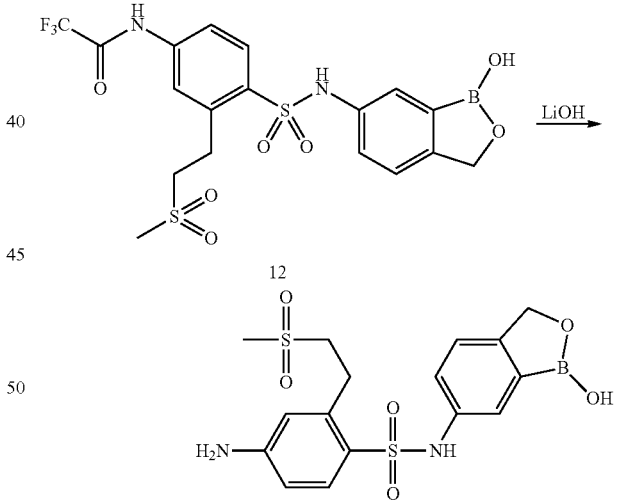

A mixture of crude compound 12 (0.8 g, 1.6 mmol) and LiOH.H₂O (0.21 g, 4.8 mmol) in MeOH (30 mL) and water (10 ml) was stirred at room temperature overnight. Then the reaction solution was neutralized by HCl (1M), then solvent was evaporated. The residue was purified by pre-HPLC (column: Luna 300×50.0 mm, 10 um; liquid phase: [A-H₂O+ 0.05% TFA; B-MeCN] B %: 10%-40%, 24 min), concentrated, acidified with HCl and freeze-dried to give compound (0.23 g, yield 36%) as HCl salt. ¹H NMR: 400 MHz DMSO-d6 δ 10.00 (s, 1H), 7.48-7.46 (m, 1H), 7.41 (s, 1H), 7.22-7.20 (m, 1H), 7.12-7.09 (m, 1H), 6.45-6.44 (m, 1H), 6.38-6.36 (m, 1H), 4.84 (s, 1H), 3.28-3.23 (m, 2H), 3.18-3.13 (m, 2H), 3.00 (s, 3H).

4-Amino-N-(1-hydroxy-1,3-dihydrobenzo[c][1,2]oxaborol-6-yl)-2-(2-(methylsulfinyl)ethyl)benzenesulfonamide

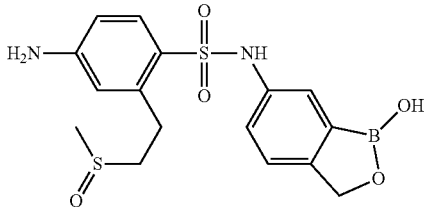 [SMILES: CS(=O)CCc1cc(N)ccc1S(=O)(=O)Nc1ccc2c(c1)B(O)OC2]

Chlorosulfonic acid (26.5 g, 227 mmol) was cooled to 0° C., then 2,2,2-trifluoro-N-(3-(2-(methylthio)ethyl)phenyl)acetamide (3 g, 11.3 mmol) was added slowly, followed by stirring at room temperature overnight. The reaction mixture was poured onto ice, the mixture was filtered and the filter cake was collected as 2-(2-(methylsulfinyl)ethyl)-4-(2,2,2-trifluoroacetamido)benzene-1-sulfonyl chloride (1 g, crude), which was used quickly for the next step reaction.

To a solution of 6-amino-3H-benzo[c][1,2]oxaborol-1-ol (0.59 g, 3.9 mmol) and N-methylmorpholine (2.53 g, 25 mmol) in MeCN (70 mL) was added 2-(2-(methylsulfinyl)ethyl)-4-(2,2,2-trifluoroacetamido)benzene-1-sulfonyl chloride (1 g, crude, 2.6 mmol) in MeCN (20 mL) at 0° C., then the solution was stirred at room temperature overnight. The mixture was concentrated in vacuo, and ethyl acetate and water was added to the residue. The organic layer was dried over $Na_2SO_4$ and concentrated to give the crude product. The residue was purified by prep-HPLC (column: Luna 300×50.0 mm, 10 um; liquid phase: [A-$H_2O$+0.05% TFA; B-MeCN] B %: 30%-60%, 25 min) to give 2,2,2-trifluoro-N-(4-(N-(1-hydroxy-1,3-dihydrobenzo[c][1,2]oxaborol-6-yl)sulfamoyl)-3-(2-(methylsulfinyl)ethyl)phenyl)acetamide (0.3 g, yield 32%).

A mixture of crude compound 14 (0.3 g, 0.6 mmol) and $LiOH.H_2O$ (0.12 g, 3 mmol) in MeOH (30 mL) and water (10 ml) was stirred at room temperature overnight. Then the reaction solution was neutralized by HCl (1 M), then solvent was evaporated. The residue was purified by pre-HPLC (column: Luna 300×50.0 mm, 10 um; liquid phase: [A-$H_2O$+0.05% TFA; B-MeCN] B %: 5%-35%, 23 min), concentrated, acidified with HCl and freeze-dried to give the title compound (0.18 g, yield 81%) as HCl salt. $^1$H NMR: 400 MHz DMSO δ10.01 (s, 1H), 7.56-7.54 (m, 1H), 7.43 (s, 1H), 7.23-7.21 (m, 1H), 7.14-7.11 (m, 1H), 6.52-6.51 (m, 1H), 6.48-6.43 (m, 1H), 4.85 (s, 2H), 3.18-3.13 (m, 2H), 2.97-2.91 (m, 1H), 2.86-2.81 (m, 1H), 2.56 (s, 3H).

4-Amino-N-(1-hydroxy-1,3-dihydrobenzo[c][1,2]oxaborol-6-yl)-2-((2-oxooxazolidin-3-yl)methyl)benzenesulfonamide To a cooled suspension of 4-amino-2-(aminomethyl)-N-(1-hydroxy-1,3-dihydrobenzo[c][1,2]oxaborol-6-yl)benzenesulfonamide (1.0 g, 2.3 mmol) in DCM (40 ml) was added a solution of chloroethyl formate chloride (0.329 g, 2.3 mmol) in DCM (40 ml) dropwise at 0° C. over 1 h. The rxn mix was washed with $H_2O$, brine, dried over $MgSO_4$, filtered, and concentrated in reduced pressure to dryness.

The crude intermediate was dissolved in THF, then NaH (3 eq) was added and stirred at rt for 24 hrs. The rxn was quenched with $H_2O$ and extracted with EtOAc, dried over $MgSO_4$, filtered, concentrated in reduced pressure to dryness, then purified by Prep-HPLC and prep-TLC to give the desired product (35 mg). $^1$H NMR (400 MHz, $CD_3CN$) δ (ppm): 8.18 (brs, 1H), 7.66 (d, J=8.4 Hz, 1H), 7.48 (d, J=2.0 Hz, 1H), 7.28 (d, J=8.4 Hz, 1H), 7.17 (dd, J=2.0, 8.4 Hz, 1H), 6.83 (s, 1H), 6.63 (d, J=2.4 Hz, 1H), 6.54 (dd, J=2.4, 8.8 Hz, 1H), 4.95 (s, 2H), 4.88 (brs, 2H), 4.66 (s, 2H), 4.33 (t, J=7.2 Hz, 2H), 3.50 (t, J=7.2 Hz, 2H). MS (ESI) m/z=402 (M−1).

(Z)-2,2,2-Trifluoro-N-(4-(N-(1-hydroxy-1,3-dihydrobenzo[c][1,2]oxaborol-6-yl)sulfamoyl)-3-((2-oxodihydrofuran-3(2H)-ylidene)methyl)phenyl)acetamide

(Z)-4-Amino-N-(1-hydroxy-1,3-dihydrobenzo[c][1,2]oxaborol-6-yl)-2-((2-oxodihydrofuran-3(2H)-ylidene)methyl)benzenesulfonamide

2,2,2-Trifluoro-N-(4-(N-(1-hydroxy-1,3-dihydrobenzo[c][1,2]oxaborol-6-yl)sulfamoyl)-3-((2-oxotetrahydrofuran-3-yl)methyl)phenyl)acetamide

4-Amino-N-(1-hydroxy-1,3-dihydrobenzo[c][1,2]oxaborol-6-yl)-2-((2-oxotetrahydrofuran-3-yl)methyl)benzenesulfonamide

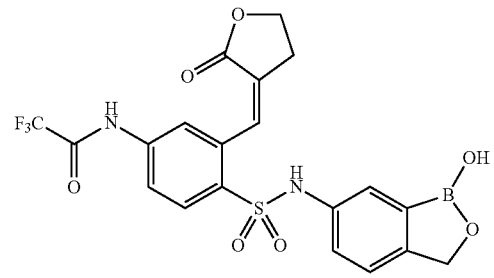

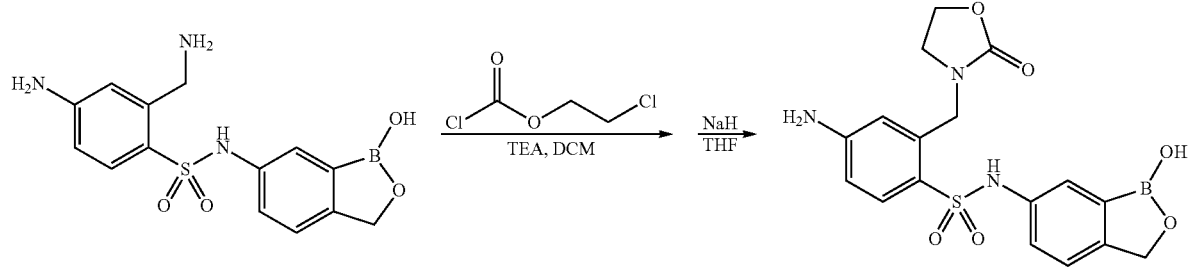

-continued

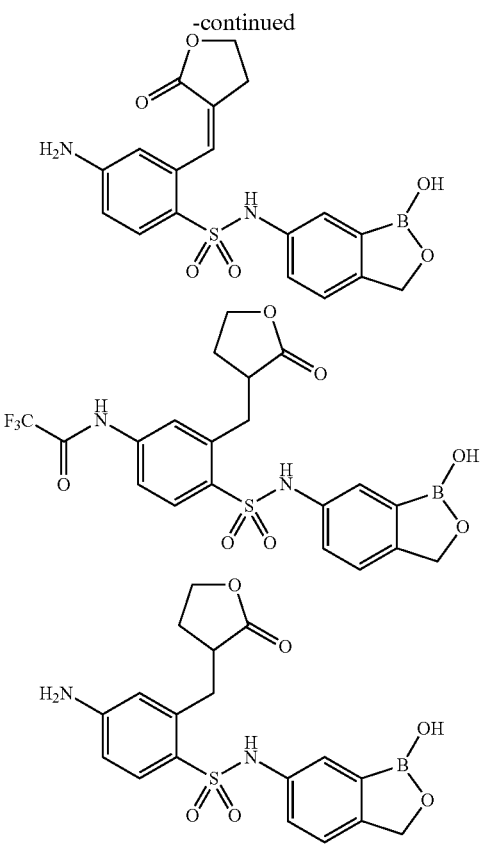

The reaction mixture of 2,2,2-trifluoro-N-(3-iodophenyl) acetamide (160 mg, 0.52 mmol), 3-methylenedihydrofuran-2(3H)-one (62 mg, 0.63 mmol), Pd(OAc)$_2$ (33 mg, 0.015 mmol) and KOAc (200 mg, 2.04 mmol) in NMP (2 mL) was degassed and heated to 110° C. for 12 hrs. The mixture was extracted with EtOAc and washed with H$_2$O, brine, dried over MgSO$_4$, filtered, concentrated in reduced pressure to dryness, and recrystallized in MeOH to give desired intermediate (Z)-2,2,2-trifluoro-N-(3-((2-oxodihydrofuran-3(2H)-ylidene) methyl)phenyl)acetamide (120 mg). $^1$H NMR (400 MHz, DMSO-d$_6$) δ (ppm): 11.4 (s, 1H), 7.96 (s, 1H), 7.74 (dt, J=7.6, 1.6 Hz, 1H), 7.51 (7, J=7.6 Hz, 1H), 7.28 (d, J=8.4 Hz, 1H), 7.47 (dt, J=7.6, 1.6 Hz, 1H), 7.38 (t, J=2.8 Hz, 1H), 4.43 (t, J=7.2 Hz, 2H), 3.24 (dt, J=2.8, 7.2 Hz, 2H). MS (ESI) m/z=284 (M−1).

Intermediate (Z)-2-((2-oxodihydrofuran-3(2H)-ylidene) methyl)-4-(2,2,2-trifluoroacetamido)benzene-1-sulfonyl chloride was made in same procedure of 2-bromo-4-(2,2,2-trifluoroacetamido)benzene-1-sulfonyl chloride in the synthesis of 4-amino-N-(1-hydroxy-1,3-dihydrobenzo[c][1,2] oxaborol-6-yl)-2-(2-ethoxyethyl)benzenesulfonamide.

The crude intermediate (Z)-2-((2-oxodihydrofuran-3(2H)-ylidene)methyl)-4-(2,2,2-trifluoroacetamido)benzene-1-sulfonyl chloride (2.85 g, 10 mmol) and 6-aminobenzo[c][1,2] oxaborol-1(3H)-ol (1.5 g, 10 mmol) was suspended in CAN (50 ml), followed by the addition of pyridine (3 ml) dropwise. After stirred at rt for 3 hrs, the mixture was poured into ice-H$_2$O and extracted with EtOAc, washed with H$_2$O, brine, dried over MgSO$_4$, filtered, concentrated in reduced pressure to dryness. The crude product was treated with DCM to give (Z)-2,2,2-trifluoro-N-(4-(N-(1-hydroxy-1,3-dihydrobenzo [c][1,2]oxaborol-6-yl)sulfamoyl)-3-((2-oxodihydrofuran-3 (2H)-ylidene)methyl)phenyl)acetamide as a solid (3.4 g). $^1$H NMR (400 MHz, DMSO-d$_6$) δ (ppm): 11.63 (s, 1H), 10.34 (s, 1H), 9.18 (s, 1H), 8.00 (d, J=8.4 Hz, 1H), 7.87 (s, 1H), 7.87 (dd, J=8.4, 1.6 Hz, 1H), 7.82 (t, J=2.8 Hz, 1H), 7.34 (d, J=1.6 Hz, 1H), 7.21 (d, J=8.4 Hz, 1H), 7.07 (dd, J=8.4, 1.6 Hz, 1H), 4.85 (s, 2H), 4.28 (t, J=7.2 Hz, 2H), 2.88 (dt, J=2.8, 7.2 Hz, 2H). MS (ESI) m/z=495 (M−1).

(Z)-2,2,2-Trifluoro-N-(4-(N-(1-hydroxy-1,3-dihydrobenzo[c][1,2]oxaborol-6-yl)sulfamoyl)-3-((2-oxodihydrofuran-3(2H)-ylidene)methyl)phenyl)acetamide (200 mg) was hydrogenated with Pd/C (10%, 50 mg) in MeOH (20 ml) at 30 psi for 2 hrs. The reaction mixture was filtered, concentrated in reduced pressure to dryness. The crude product was treated with DCM to give 2,2,2-trifluoro-N-(4-(N-(1-hydroxy-1,3-dihydrobenzo[c][1,2]oxaborol-6-yl)sulfamoyl)-3-((2-oxotetrahydrofuran-3-yl)methyl)phenyl)acetamide as a solid. $^1$H NMR (400 MHz, CD$_3$OD) δ (ppm): 7.92 (d, J=8.6 Hz, 1H), 7.75 (d, J=2.4 Hz, 1H), 7.64 (dd, J=8.2, 2.4 Hz, 1H), 7.28 (s, 1H), 7.22 (d, J=8.2 Hz, 1H), 7.17 (dd, J=8.2, 2.0 Hz, 1H), 4.95 (s, 2H), 4.36 (dt, J=8.8, 2.8 Hz, 1H), 4.19 (m, 1H), 3.53 (m, 1H), 3.06 (m, 2H), 2.22 (m, 1H), 2.04 (m, 1H). MS (ESI) m/z=497 (M−1).

4-Amino-N-(1-hydroxy-1,3-dihydrobenzo[c][1,2]oxaborol-6-yl)-2-((2-oxotetrahydrofuran-3-yl)methyl)benzenesulfonamide and (Z)-4-Amino-N-(1-hydroxy-1,3-dihydrobenzo[c][1,2]oxaborol-6-yl)-2-((2-oxodihydrofuran-3 (2H)-ylidene)methyl)benzenesulfonamide were prepared in same procedure of 4-amino-N-(1-hydroxy-1,3-dihydrobenzo [c][1,2]oxaborol-6-yl)-2-(2-ethoxyethyl)benzenesulfonamide in Scheme 1.

(Z)-4-Amino-N-(1-hydroxy-1,3-dihydrobenzo[c][1,2]oxaborol-6-yl)-2-((2-oxodihydrofuran-3(2H)-ylidene)methyl) benzenesulfonamide: $^1$H NMR (400 MHz, CD$_3$OD) δ (ppm): 7.77 (d, J=1.6 Hz, 1H), 7.63 (dd, J=8.0, 1.6 Hz, 1H), 7.52 (d, J=8.0 Hz, 2H), 6.85 (dd, J=2.0, 8.8 Hz, 1H), 6.58 (d, J=2.0 Hz, 1H), 5.67 (d, J=3.6 Hz, 1H), 5.11 (s, 2H), 4.17 (m, 2H), 2.21 (m, 2H), 1.80 (m, 1H). MS (ESI) m/z=399 (M−1).

4-Amino-N-(1-hydroxy-1,3-dihydrobenzo[c][1,2]oxaborol-6-yl)-2-((2-oxotetrahydrofuran-3-yl)methyl)benzenesulfonamide: $^1$H NMR (400 MHz, DMSO) δ (ppm): 9.98 (s, 1H), 9.17 (s, 1H), 7.52 (d, J=8.8 Hz, 1H), 7.41 (d, J=2.0 Hz, 1H), 7.19 (d, J=8.0 Hz, 1H), 7.11 (dd, J=8.4, 2.0 Hz, 1H), 6.44 (d, J=2.0 Hz, 1H), 6.36 (dd, J=8.4, 2.0 Hz, 1H), 5.87 (s, 2H), 4.84 (s, 2H), 4.26 (dt, J=8.8, 2.8 Hz, 1H), 4.09 (m, 1H), 3.28 (m, 1H), 2.86-3.06 (m, 2H), 2.22 (m, 1H), 2.04 (m, 1H), 1.88 (m, 1H). MS (ESI) m/z=401 (M−1).

2,2,2-Trifluoro-N-(4-(N-(1-hydroxy-1,3-dihydrobenzo[c][1,2]oxaborol-6-yl)sulfamoyl)-3-(oxazol-2-ylmethyl)phenyl)acetamide and 4-Amino-N-(1-hydroxy-1,3-dihydrobenzo[c][1,2] oxaborol-6-yl)-2-(oxazol-2-ylmethyl)benzenesulfonamide

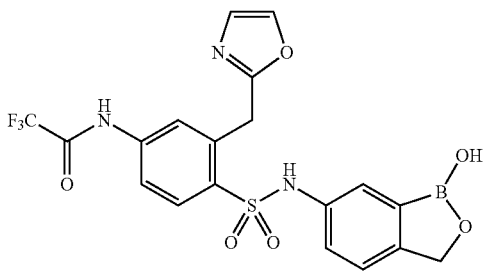

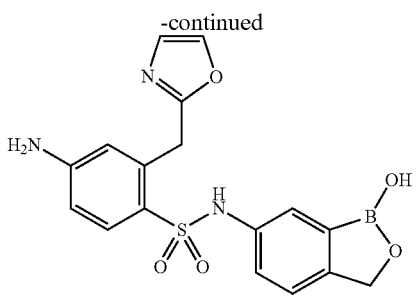

To a stirred solution of 2-(3-nitrophenyl)acetic acid (5.8 g, 32 mmol) and 2,2-dimethoxyethanamine (3.7 g, 35.2 mmol) in 50 mL of DMF was added HATU (12.2 g, 32 mmol) and DIEA (11.2 mL, 64 mmol). The reaction mixture was stirred for 16 hours. After water was added, the reaction mixture was extracted with ethyl acetate and washed with water, 0.5N HCl and brine. The organic layer was dried over $Na_2SO_4$ and concentrated to give the desired compound as a yellow residue (8.6 g, yield 100%).

To a stirred solution of N-(2,2-dimethoxyethyl)-2-(3-nitrophenyl)acetamide (8.6 g, 32 mmol) in 50 mL of dioxane was added concentrated HCl (20 mL). The reaction mixture was stirred at room temperature for 3 hours. The reaction mixture was extracted with ethyl acetate and washed with water, 0.5N HCl and brine. The organic layer was dried over $Na_2SO_4$ and concentrated. The residue was purified by ISCO CombiFlash Rf silica chromatography eluted with 50-100% ethyl acetate and hexane to give the desired compound as a yellow glassy material (3.1 g, yield 44%).

2-(3-Nitrophenyl)-N-(2-oxoethyl)acetamide (3.1 g, 14 mmol) was mixed with 25 g of Eaton's reagent. The reaction mixture was stirred at 100° C. for 3 days. After cooled down, the reaction mixture was poured slowly to ice-water. The mixture was extracted with ethyl acetate and washed with 0.5N HCl, $NaHCO_3$ solution and brine. The organic layer was dried over $Na_2SO_4$ and concentrated to give a yellow residue. The residue was purified by ISCO CombiFlash Rf silica chromatography eluted with 0-20% MeOH in dichloromethane to give the desired compound as a yellow residue (1.1 g, yield 39%).

To a stirred solution of 2-(3-nitrobenzyl)oxazole (1.0 g, 4.9 mmol) in 20 mL of MeOH was added Pd/C (10 wt. % on activated carbon, 250 mg). The flask was evacuated quickly and filled with hydrogen three times. A hydrogen balloon was then placed on the reaction flask. The reaction mixture was allowed to stir at room temperature under hydrogen for 2 hours. After the mixture was filtered through a pad of Celite, the reaction was concentrated in vacuo to give a yellow residue that was used directly for the next step. To a stirred solution of 3-(oxazol-2-ylmethyl)aniline (0.85 g, 4.9 mmol) and TEA (2.4 mL, 17.3 mmol) in 10 mL of $CH_2Cl_2$ was added 2,2,2-trifluoroacetic anhydride (1.6 mL, 11.5 mmol) dropwise. The reaction mixture was stirred at room temperature for 3 hours. After the mixture was concentrated, the residue was purified by ISCO CombiFlash Rf silica chromatography eluted with 0-50% ethyl acetate in hexane to give the desired compound as a yellow solid (1.1 g, yield 83%).

2,2,2-Trifluoro-N-(3-(oxazol-2-ylmethyl)phenyl)acetamide (1.1 g, 4.1 mmol) was mixed with chlorosulfonic acid (3 mL) at 0° C., and the mixture was stirred at room temperature for 3 hours. As the starting material was consumed as indicated by LC/MS, the mixture was added dropwise to ice-water. The mixture was extracted with dichloromethane. The organic layer was dried over $Na_2SO_4$ and concentrated to give the desired product as a yellow residue (450 mg, yield 30%).

To a stirred solution of 2-(oxazol-2-ylmethyl)-4-(2,2,2-trifluoroacetamido)benzene-1-sulfonyl chloride (450 mg, 1.2 mmol) and 6-aminobenzo[c][1,2]oxaborol-1(3H)-ol (212 mg, 1.42 mmol) in 10 mL of ACN was added pyridine (228 uL, 2.8 mmol) dropwise. The reaction mixture was stirred at room temperature for 3 hours. After the mixture was concentrated, the residue was extracted with ethyl acetate and washed with water, 1N HCl and brine. The organic layer was dried over $Na_2SO_4$ and concentrated to give the desired compound as a yellow residue (540 mg, yield 92%). A small portion of the crude mixture was purified by prep HPLC (SunFire Prep C18 OBD 5 uM 30×50 mm column) to give the title compound as a yellow solid.

2,2,2-Trifluoro-N-(4-(N-(1-hydroxy-1,3-dihydrobenzo[c][1,2]oxaborol-6-yl)sulfamoyl)-3-(oxazol-2-ylmethyl)phenyl)acetamide: MS calcd for ($C_{19}H_{15}BN_3O_6F_3S$): 481.2. MS found (ESI negative): (M−H)⁻=480.1. $^1$H NMR (DMSO-$d_6$) δ (ppm): 11.46 (s, 1H), 10.39 (s, 1H), 9.18 (bs, 1H), 7.97 (s, 1H), 7.86 (d, J=8.8 Hz, 1H), 7.70 (d, J=8.8 Hz, 1H), 7.48 (s, 1H), 7.41 (s, 1H), 7.20 (d, J=8.4 Hz, 1H), 7.10 (s, 1H), 7.08 (d, J=8.0 Hz, 1H), 4.81 (s, 2H), 4.48 (s, 2H)

A solution of 2,2,2-trifluoro-N-(4-(N-(1-hydroxy-1,3-dihydrobenzo[c][1,2]oxaborol-6-yl)sulfamoyl)-3-(oxazol-2-ylmethyl)phenyl)acetamide (460 mg, 0.95 mmol) in 7M ammonium in MeOH (10 mL) was stirred in a sealed tube at 50° C. for 3 hours. After concentrated, the crude mixture was purified by prep HPLC (SunFire Prep C18 OBD 5 uM 30×50 mm column) to give the title compound as a yellow solid (340 mg, yield 92%).

4-Amino-N-(1-hydroxy-1,3-dihydrobenzo[c][1,2]oxaborol-6-yl)-2-(oxazol-2-ylmethyl)benzenesulfonamide: MS calcd for ($C_{17}H_{16}BN_3O_5S$): 385.2. MS found (ESI negative): (M−H)⁻=384.1. $^1$H NMR (DMSO-$d_6$) δ (ppm): 9.95 (s, 1H), 9.18 (bs, 1H), 7.95 (s, 1H), 7.49 (d, J=8.8 Hz, 1H), 7.38 (s, 1H), 7.17 (d, J=8.4 Hz, 1H), 7.09 (s, 1H), 7.06 (d, J=8.4 Hz, 1H), 6.33 (d, J=8.8 Hz, 1H), 6.10 (s, 1H), 4.80 (s, 2H), 4.31 (s, 2H).

2,2,2-Trifluoro-N-(4-(N-(1-hydroxy-1,3-dihydrobenzo[c][1,2]oxaborol-6-yl)sulfamoyl)-3-((4-methyloxazol-2-yl)methyl)phenyl)acetamide and 4-Amino-N-(1-hydroxy-1,3-dihydrobenzo[c][1,2]oxaborol-6-yl)-2-((4-methyloxazol-2-yl)methyl)benzenesulfonamide

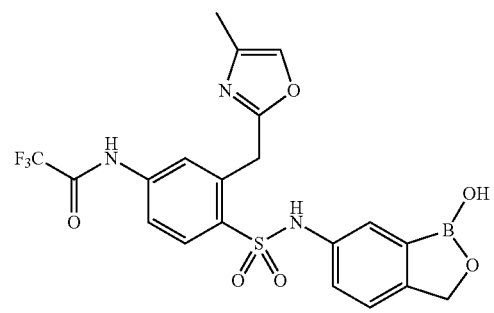

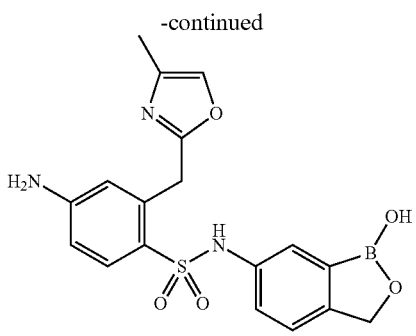

To a stirred solution of 2-(3-nitrophenyl)acetic acid (2.61 g, 14.4 mmol) and 2-aminopropan-1-ol (1.30 g, 17.2 mmol) in 40 mL of DMF was added EDC (3.30 g, 17.2 mmol) and HOBt (2.32, 17.2 mmol). The reaction mixture was stirred for 16 hours. After water was added, the reaction mixture was extracted with ethyl acetate and washed with water, 0.5N HCl and brine. The organic layer was dried over $Na_2SO_4$ and concentrated. The residue was purified by ISCO CombiFlash Rf silica chromatography eluted with 0-10% MeOH in dichloromethane to give the desired compound as a white solid (3.43 g, yield 100%).

To a stirred solution of N-(1-hydroxypropan-2-yl)-2-(3-nitrophenyl)acetamide (3.8 g, 16.0 mmol) in 100 mL of dichloromethane was added Dess-Martin periodinane (10.1 g, 23.9 mmol). The reaction mixture was stirred at room temperature for 2 hours. The reaction mixture was washed with $Na_2S_2O_3$ and $NaHCO_3$ solution. The organic layer was dried over $Na_2SO_4$ and concentrated. The residue was purified by ISCO CombiFlash Rf silica chromatography eluted with 0-5% MeOH in dichloromethane to give the desired compound as a yellow residue (2.84 g, yield 75%).

2-(3-Nitrophenyl)-N-(1-oxopropan-2-yl)acetamide (2.84 g, 12.0 mmol) was mixed with 25 g of Eaton's reagent. The reaction mixture was stirred at 100° C. for 4 days. After cooled down, the reaction mixture was poured slowly to ice-water. The mixture was extracted with ethyl acetate and washed with 0.5N HCl, $NaHCO_3$ solution and brine. The organic layer was dried over $Na_2SO_4$ and concentrated to give a yellow residue. The residue was purified by ISCO CombiFlash Rf silica chromatography eluted with 0-20% MeOH in dichloromethane to give the desired compound as a yellow residue (1.08 g, yield 41%).

To a stirred solution of 4-methyl-2-(3-nitrobenzyl)oxazole (1.0 g, 4.6 mmol) in 10 mL of MeOH was added Pd/C (10 wt. % on activated carbon, 200 mg). The flask was evacuated quickly and filled with hydrogen three times. A hydrogen balloon was then placed on the reaction flask. The reaction mixture was allowed to stir at room temperature under hydrogen for 2 hours. After the mixture was filtered through a pad of Celite, the reaction was concentrated in vacuo to give the desired compound that was used directly for the next step. To a stirred solution of 3-((4-methyloxazol-2-yl)methyl)aniline (1.0 g, 4.6 mmol) and TEA (1.92 mL, 13.7 mmol) in 10 mL of $CH_2Cl_2$ was added 2,2,2-trifluoroacetic anhydride (1.27 mL, 9.1 mmol) dropwise. The reaction mixture was stirred at room temperature for 3 hours. After the mixture was concentrated, the residue was purified by ISCO CombiFlash Rf silica chromatography eluted with 0-50% ethyl acetate in hexane to give the desired compound as a yellow solid (0.28 g, yield 22%).

2,2,2-Trifluoro-N-(3-((4-methyloxazol-2-yl)methyl)phenyl)acetamide (0.28 g, 0.99 mmol) was mixed with chlorosulfonic acid (3 mL) at 0° C., and the mixture was stirred at room temperature for 3 hours. As the starting material was consumed as indicated by LC/MS, the mixture was added dropwise to ice-water. The mixture was extracted with dichloromethane. The organic layer was dried over $Na_2SO_4$ and concentrated to give the desired product as a yellow residue (180 mg, yield 48%).

To a stirred solution of 2-((4-methyloxazol-2-yl)methyl)-4-(2,2,2-trifluoroacetamido)benzene-1-sulfonyl chloride (180 mg, 0.47 mmol) and 6-aminobenzo[c][1,2]oxaborol-1(3H)-ol (106 mg, 0.71 mmol) in 10 mL of ACN was added pyridine (114 uL, 1.41 mmol) dropwise. The reaction mixture was stirred at room temperature for 3 hours. After the mixture was concentrated, the residue was extracted with ethyl acetate and washed with water, 1N HCl and brine. The organic layer was dried over $Na_2SO_4$ and concentrated to give the desired compound as a yellow residue (236 mg, yield 94%). A small portion of the crude mixture was purified by prep HPLC (SunFire Prep C18 OBD 5 uM 30×50 mm column) to give the title compound as a yellow solid. 2,2,2-Trifluoro-N-(4-(N-(1-hydroxy-1,3-dihydrobenzo[c][1,2]oxaborol-6-yl)sulfamoyl)-3-((4-methyloxazol-2-yl)methyl)phenyl)acetamide MS calcd for ($C_{20}H_{17}BN_3O_6F_3S$): 495.2. MS found (ESI negative): (M–H)$^−$=494.1. $^1$H NMR (DMSO-$d_6$) δ (ppm): 11.51 (s, 1H), 10.43 (s, 1H), 9.20 (s, 1H), 7.91 (d, J=8.8 Hz, 1H), 7.77 (s, J=8.8 Hz, 1H), 7.69 (s, 1H), 7.53 (s, 1H), 7.44 (s, 1H), 7.24 (d, J=8.4 Hz, 1H), 7.12 (d, J=8.0 Hz, 1H), 4.86 (s, 2H), 4.47 (s, 2H), 2.01 (s, 3H).

A solution of 2,2,2-trifluoro-N-(4-(N-(1-hydroxy-1,3-dihydrobenzo[c][1,2]oxaborol-6-yl)sulfamoyl)-3-((4-methyloxazol-2-yl)methyl)phenyl)acetamide (200 mg, 0.40 mmol) in 7M ammonium in MeOH (10 mL) was stirred in a sealed tube at 50° C. for 4 hours. After concentrated, the crude mixture was purified by prep HPLC (SunFire Prep C18 OBD 5 uM 30×50 mm column) to give the title compound as a yellow solid (59 mg, yield 37%). 4-Amino-N-(1-hydroxy-1,3-dihydrobenzo[c][1,2]oxaborol-6-yl)-2-((4-methyloxazol-2-yl)methyl)benzenesulfonamide MS calcd for ($C_{18}H_{18}BN_3O_5S$): 399.2. MS found (ESI negative): (M–H)$^−$=398.1. $^1$H NMR (DMSO-$d_6$) δ (ppm): 9.93 (s, 1H), 9.10 (s, 1H), 7.62 (s, 1H), 7.48 (d, J=8.8 Hz, 1H), 7.37 (s, 1H), 7.16 (d, J=8.0 Hz, 1H), 7.05 (d, J=8.0 Hz, 1H), 6.33 (d, J=8.8 Hz, 1H), 6.12 (s, 1H), 4.80 (s, 2H), 4.25 (s, 2H), 1.98 (s, 3H)

4-Amino-N-(1-hydroxy-1,3-dihydrobenzo[c][1,2]oxaborol-6-yl)-2-((5-methyloxazol-2-yl)methyl)benzenesulfonamide

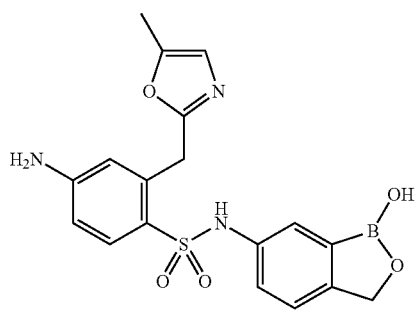 [SMILES: Cc1cnc(Cc2cc(N)ccc2S(=O)(=O)Nc2ccc3c(c2)B(O)OC3)o1]

To the solution of 3-aminophenylacetic acid (10 g, 66 mmol) and trifluoroacetic anhydride (9.2 ml, 66 ml) in DCM (200 ml) at 0° C., added triethyl amine (27 ml, 0.2 mol) slowly. The temperature was raised to room temperature after addition. The reaction was worked up 2 hours later, quenched with 1N HCl, washed with water and brine, and dried over anhydrous sodium sulfate. Concentrated to get crude 2-(3-(2,2,2-trifluoroacetamido)phenyl)acetic acid as white solid. Used for next step without further purification.

To the mixture of 2-(3-(2,2,2-trifluoroacetamido)phenyl)acetic acid (2.96 g, 12 mmol), propargylamine (0.97 ml, 15 mmol), HATU (4.5 g, 12 mmol) in acetonitrile (50 ml), added DIPEA (5.2 ml, 30 mmol) slowly. Stirring was kept 2 hours at room temperature. Removed solvent, extracted with EtOAc, washed with 1N HCl, water and brine, dried over sodium sulfate. Concentrated to get 1.42 g 2,2,2-trifluoro-N-(3-(2-oxo-2-(prop-2-ynylamino)ethyl)phenyl)acetamide as white solid.

To the solution of 2,2,2-trifluoro-N-(3-(2-oxo-2-(prop-2-ynylamino)ethyl)phenyl)acetamide (1.42 g, 5 mmol) in acetic acid (50 ml), added mercury acetate (175 mg, 0.55 mmol), then heated to reflux for 3 hours. Removed solvent, extracted with EtOAc, washed with water and brine, dried over anhydrous sodium sulfate. Concentrated, the result solid was purified by flash chromatography with EtOAc and hexane (0~50%). Got 570 mg 2,2,2-trifluoro-N-(3-((5-methyloxazol-2-yl)methyl)phenyl)acetamide as white solid.

Mixed 2,2,2-trifluoro-N-(3-((5-methyloxazol-2-yl)methyl)phenyl)acetamide with chlorosulfonyl acid (2 ml) at 0° C. Stirring was kept for 3 hours while temperature slow rise to rt. The result was transferred to a mixture of ice and water under strong stirring, filtered, washed with water, dried under vacuum. Got 275 mg 2-((5-methyloxazol-2-yl)methyl)-4-(2,2,2-trifluoroacetamido)benzene-1-sulfonyl chloride as off white solid.

General procedure 1: 6-aminobenzo[c][1,2]oxaborol-1(3H)-ol (110 g, 0.74 mmol), 2-((5-methyloxazol-2-yl)methyl)-4-(2,2,2-trifluoroacetamido)benzene-1-sulfonyl chloride (270 mg, 0.7 mmol), pyridine (0.09, 1 mmol), rt, 3 hours. Removed solvent, the crude was dissolved in MeOH (15 ml), treated with ammonia (4 ml, 7N in MeOH), heated at 60° C. for 5 hours in a sealed tube. After cooled down to rt, concentrated, the result solid was purified by prep HPLC (SunFire Prep C18 OBD 5 uM 30×50 mm column). The title compound (160 mg, 0.4 mmol) was obtained as white powder. MS calcd for ($C_{18}H_{18}BN_3O_5S$): 399.11. MS found (ESI positive): $(M+H)^+$=400.1. $^1$H NMR (400 MHz, DMSO-$d_6$) δ (ppm): 9.99 (s, 1H), 9.17 (s, 1H), 7.55 (d, J=8.8 Hz, 1H), 7.42 (d, J=2 Hz, 1H), 7.22 (d, J=8.4 Hz, 1H), 7.12 (dd, J=8 Hz, 1H), 6.73 (s, 1H), 6.38 (dd, J=8.8 Hz, 1H), 6.18 (d, J=2 Hz, 1H), 5.94 (s, 2H), 4.84 (s, 2H), 4.29 (s, 1H), 2.20 (s, 3H).

2,2,2-Trifluoro-N-(4-(N-(1-hydroxy-1,3-dihydrobenzo[c][1,2]oxaborol-6-yl)sulfamoyl)-3-((5-methyl-1,3,4-oxadiazol-2-yl)methyl)phenyl)acetamide 4-Amino-N-(1-hydroxy-1,3-dihydrobenzo[c][1,2]oxaborol-6-yl)-2-((5-methyl-1,3,4-oxadiazol-2-yl)methyl)benzenesulfonamide

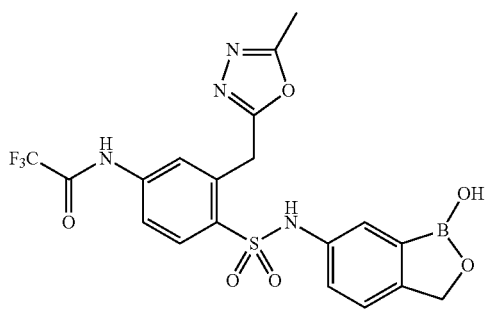

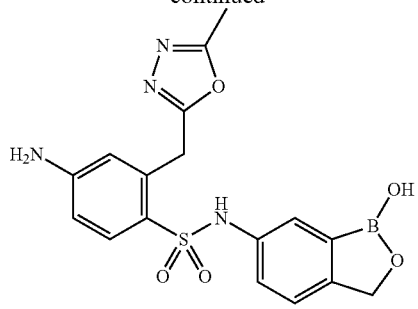

To a stirred solution of 2-(3-nitrophenyl)acetic acid (5.0 g, 27.6 mmol) and hydrazine (2 mL, 41.4 mmol) in 10 mL of DMF were added HATU (15.7 g, 41.4 mmol) and DIEA (14.5 mL, 82.8 mmol). The reaction mixture was stirred at room temperature for 16 hours. After water was added, the reaction mixture was extracted with ethyl acetate and washed with water, 1N HCl and brine. The organic layer was dried over $Na_2SO_4$ and concentrated. The residue was purified by ISCO CombiFlash Rf silica chromatography eluted with 0-10% ethyl acetate in hexane to give the desired compound as a white solid (4.0 g, yield 74%).

To a stirred solution of 2-(3-nitrophenyl)acetohydrazide (2.0 g, 10.3 mmol) in 20 ml, of HOAc was added 1,1,1-triethoxyethane (9.4 mL, 51.2 mmol). The reaction mixture was refluxed for 3 hours. After cooled down, the reaction mixture was concentrated in vacuo to remove the volatile. The residue was purified by ISCO CombiFlash Rf silica chromatography eluted with 0-50% ethyl acetate in hexane to give the desired compound as a yellow oil (1.0 g, yield 45%).

To a stirred solution of 2-methyl-5-(3-nitrobenzyl)-1,3,4-oxadiazole (1.0 g, 4.56 mmol) in 30 mL of MeOH was added Pd/C (10 wt. % on activated carbon, 400 mg). The flask was evacuated quickly and filled with hydrogen three times. A hydrogen balloon was then placed on the reaction flask. The reaction mixture was allowed to stir at room temperature under hydrogen for 2 hours. After the mixture was filtered through a pad of Celite, the reaction was concentrated in vacuo to give the desired compound as a yellow oil (0.86 g, yield 100%).

To a stirred solution of 3-((5-methyl-1,3,4-oxadiazol-2-yl)methyl)aniline (0.86 g, 4.55 mmol) and triethylamine (1.9 mL, 13.7 mmol) in 10 mL of $CH_2Cl_2$ was added 2,2,2-trifluoroacetic anhydride (1.26 mL, 9.1 mmol) dropwise. The reaction mixture was stirred for 16 hours. After the mixture was concentrated, the residue was purified by ISCO CombiFlash Rf silica chromatography eluted with 0-80% ethyl acetate in hexane to give the desired compound as a yellow solid (0.8 g, yield 62%).

2,2,2-Trifluoro-N-(3-((5-methyl-1,3,4-oxadiazol-2-yl)methyl)phenyl)acetamide (0.6 g, 2.1 mmol) was mixed with chlorosulfonic acid (3 mL) at 0° C., and the mixture was stirred at room temperature for 3 hours. As the starting material was consumed as indicated by LC/MS, the mixture was added dropwise to ice-water. After filtered, the resulting residue was dried in vacuo to give the desired compound as a yellow residue (0.3 g, yield 37%).

To a stirred solution of 2-((5-methyl-1,3,4-oxadiazol-2-yl)methyl)-4-(2,2,2-trifluoroacetamido)benzene-1-sulfonyl chloride (300 mg, 0.78 mmol) and 6-aminobenzo[c][1,2]oxaborol-1(3H)-ol (194 mg, 1.3 mmol) in 5 mL of ACN was added pyridine (1.26 mL, 9.1 mmol) dropwise. The reaction mixture was stirred at room temperature for 3 hours. After the mixture was concentrated, the residue was extracted with ethyl acetate and washed with water, 1N HCl and brine. The organic layer was dried over $Na_2SO_4$ and concentrated to give the desired compound as a yellow solid (318 mg, yield 82%).

MS calcd for ($C_{19}H_{16}BN_4O_6F_3S$): 496.2, MS found (ESI negative): (M−H)⁻=495.1. ¹H NMR (DMSO-d₆) δ (ppm): 11.5 (s, 1H), 10.5 (s, 1H), 9.20 (s, 1H), 7.93 (d, J=8.8 Hz, 1H), 7.80 (s, J=8.4 Hz, 1H), 7.59 (s, 1H), 7.44 (s, 1H), 7.25 (d, J=8.0 Hz, 1H), 7.12 (d, J=8.0 Hz, 1H), 4.86 (s, 2H), 4.59 (s, 2H), 2.40 (s, 3H)

A solution of 2,2,2-trifluoro-N-(4-(N-(1-hydroxy-1,3-dihydrobenzo[c][1,2]oxaborol-6-yl)sulfamoyl)-3-((5-methyl-1,3,4-oxadiazol-2-yl)methyl)phenyl)acetamide (300 mg, 0.60 mmol) in 7M ammonium in MeOH (10 mL) was stirred in a sealed tube at 50° C. for 16 hours. After concentrated, the crude mixture was purified by prep HPLC (SunFire Prep C18 OBD 5 uM 30×50 mm column) to give the title compound as a yellow solid (90 mg, yield 37%). MS calcd for ($C_{14}H_{17}BN_4O_5S$): 400.2. MS found (ESI negative): (M−H)⁻=399.1. ¹H NMR (DMSO-d₆) δ (ppm): 10.0 (s, 1H), 9.20 (bs, 1H), 7.56 (d, J=8.8 Hz, 1H), 7.42 (s, 1H), 7.22 (d, J=8.4 Hz, 1H), 7.11 (d, J=8.4 Hz, 1H), 6.41 (d, J=8.4 Hz, 1H), 6.26 (s, 1H), 4.85 (s, 2H), 4.41 (s, 2H), 2.39 (s, 3H)

N-(3-((5-Ethyl-1,3,4-oxadiazol-2-yl)methyl)-4-(N-(1-hydroxy-1,3-dihydrobenzo[c][1,2]oxaborol-6-yl)sulfamoyl)phenyl)-2,2,2-trifluoroacetamide 4-Amino-2-((5-ethyl-1,3,4-oxadiazol-2-yl)methyl)-N-(1-hydroxy-1,3-dihydrobenzo[c][1,2]oxaborol-6-yl)benzenesulfonamide

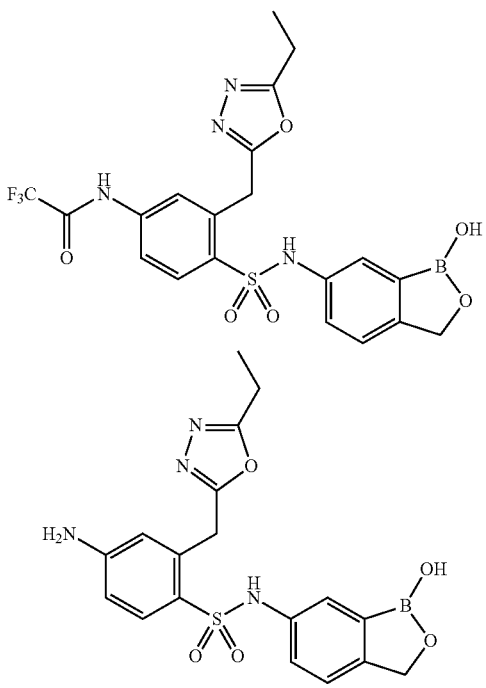

To a stirred solution of 2-(3-nitrophenyl)acetohydrazide (1.0 g, 4.74 mmol) in 10 mL of HOAc was added 1,1,1-triethoxypropane (4.7 mL, 23.7 mmol). The reaction mixture was refluxed for 3 hours. After cooled down, the reaction mixture was concentrated in vacuo to remove the volatile. The residue was purified by ISCO CombiFlash Rf silica chromatography eluted with 0-50% ethyl acetate in hexane to give the desired compound as a yellow oil (1.1 g, yield 100%).

To a stirred solution of 2-ethyl-5-(3-nitrobenzyl)-1,3,4-oxadiazole (1.1 g, 4.72 mmol) in 40 mL of MeOH was added Pd/C (10 wt. % on activated carbon, 400 mg). The flask was evacuated quickly and filled with hydrogen three times. A hydrogen balloon was then placed on the reaction flask. The reaction mixture was allowed to stir at room temperature under hydrogen for 3 hours. After the mixture was filtered through a pad of Celite, the reaction was concentrated in vacuo to give the desired compound as a yellow residue (1.0 g, yield 100%).

To a stirred solution of 3-((5-ethyl-1,3,4-oxadiazol-2-yl)methyl)aniline (1.0 g, 4.92 mmol) and triethylamine (2.1 mL, 14.8 mmol) in 20 mL of CH₂Cl₂ was added 2,2,2-trifluoroacetic anhydride (1.37 mL, 9.85 mmol) dropwise. The reaction mixture was stirred for 16 hours. After the mixture was concentrated, the residue was purified by ISCO CombiFlash Rf silica chromatography eluted with 0-80% ethyl acetate in hexane to give the desired compound as a yellow solid (1.0 g, yield 68%).

N-(3-((5-ethyl-1,3,4-oxadiazol-2-yl)methyl)phenyl)-2,2,2-trifluoroacetamide (0.7 g, 2.34 mmol) was mixed with chlorosulfonic acid (3.2 mL) at 0° C., and the mixture was stirred at room temperature for 2 hours. As the starting material was consumed as indicated by LC/MS, the mixture was added dropwise to ice-water. After filtered, the resulting residue was dried in vacuo to give the desired compound as a yellow residue (0.34 g, yield 37%).

To a stirred solution of 2-((5-ethyl-1,3,4-oxadiazol-2-yl)methyl)-4-(2,2,2-trifluoroacetamido)benzene-1-sulfonyl chloride (335 mg, 0.84 mmol) and 6-aminobenzo[c][1,2]oxaborol-1(3H)-ol (125 mg, 0.84 mmol) in 5 mL of ACN was added pyridine (205 uL, 2.53 mmol) dropwise. The reaction mixture was stirred at room temperature for 3 hours. After the mixture was concentrated, the residue was extracted with ethyl acetate and washed with water, 1N HCl and brine. The organic layer was dried over Na₂SO₄ and concentrated to give the desired compound as a yellow solid (390 mg, yield 91%).

A solution of N-(3-((5-ethyl-1,3,4-oxadiazol-2-yl)methyl)-4-(N-(1-hydroxy-1,3-dihydrobenzo[c][1,2]oxaborol-6-yl)sulfamoyl)phenyl)-2,2,2-trifluoroacetamide (390 mg, 0.76 mmol) in 7M ammonium in MeOH (10 mL) was stirred in a sealed tube at 50° C. for 16 hours. After concentrated, the crude mixture was purified by prep HPLC (SunFire Prep C18 OBD 5 uM 30×50 mm column) to give the title compound as a yellow solid (204 mg, yield 64%). MS calcd for ($C_{18}H_{19}BN_4O_5S$): 414.2, MS found (ESI negative): (M−H)⁻=413.1. ¹H NMR (DMSO-d₆) δ (ppm): 10.0 (s, 1H), 9.16 (bs, 1H), 7.56 (d, J=8.8 Hz, 1H), 7.42 (s, 1H), 7.22 (d, J=8.0 Hz, 1H), 7.11 (d, J=8.4 Hz, 1H), 6.42 (d, J=8.8 Hz, 1H), 6.26 (s, 1H), 4.85 (s, 2H), 4.42 (s, 2H), 2.75 (q, 2H), 1.19 (t, 3H).

2,2,2-Trifluoro-N-(4-(N-(1-hydroxy-1,3-dihydrobenzo[c][1,2]oxaborol-6-yl)sulfamoyl)-3-((5-propyl-1,3,4-oxadiazol-2-yl)methyl)phenyl)acetamide 4-Amino-N-(1-hydroxy-1,3-dihydrobenzo[c][1,2]oxaborol-6-yl)-2-((5-propyl-1,3,4-oxadiazol-2-yl)methyl)benzenesulfonamide

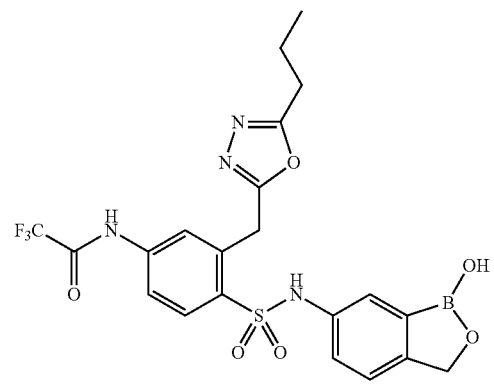

-continued

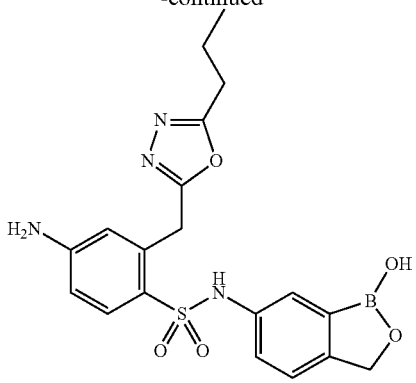

To a stirred solution of 2-(3-nitrophenyl)acetohydrazide (1.1 g, 5.6 mmol) in 10 mL of HOAc was added 1,1,1-trimethoxybutane (4.1 mL, 26.1 mmol). The reaction mixture was refluxed for 3 hours. After cooled down, the reaction mixture was concentrated in vacuo to remove the volatile to give the desired compound as a yellow oil (1.4 g, yield 100%).

To a stirred solution of 2-(3-nitrobenzyl)-5-propyl-1,3,4-oxadiazole (1.4 g, 5.6 mmol) in 40 mL of MeOH was added Pd/C (10 wt. % on activated carbon, 400 mg). The flask was evacuated quickly and filled with hydrogen three times. A hydrogen balloon was then placed on the reaction flask. The reaction mixture was allowed to stir at room temperature under hydrogen for 2 hours. After the mixture was filtered through a pad of Celite, the reaction was concentrated in vacuo to give the desired compound as a yellow residue (1.2 g, yield 100%).

To a stirred solution of 3-((5-propyl-1,3,4-oxadiazol-2-yl)methyl)aniline (1.2 g, 5.53 mmol) and triethylamine (1.8 mL, 12.9 mmol) in 20 mL of $CH_2Cl_2$ was added 2,2,2-trifluoroacetic anhydride (2.7 mL, 19.4 mmol) dropwise. The reaction mixture was stirred for 16 hours. After the mixture was concentrated, the residue was purified by ISCO CombiFlash Rf silica chromatography eluted with 0-80% ethyl acetate in hexane to give the desired compound as a yellow solid (1.6 g, yield 92%).

2,2,2-trifluoro-N-(3-((5-propyl-1,3,4-oxadiazol-2-yl)methyl)phenyl)acetamide (1.6 g, 5.11 mmol) was mixed with chlorosulfonic acid (3.2 mL) at 0° C., and the mixture was stirred at room temperature for 2 hours. As the starting material was consumed as indicated by LC/MS, the mixture was added dropwise to ice-water. After filtered, the resulting residue was dried in vacuo to give the desired compound as a yellow residue (0.43 g, yield 20%).

To a stirred solution of 2-((5-propyl-1,3,4-oxadiazol-2-yl)methyl)-4-(2,2,2-trifluoroacetamido)benzene-1-sulfonyl chloride (430 mg, 1.05 mmol) and 6-aminobenzo[c][1,2]oxaborol-1(3H)-ol (234 mg, 1.57 mmol) in 5 mL of ACN was added pyridine (253 uL, 3.13 mmol) dropwise. The reaction mixture was stirred at room temperature for 16 hours. After the mixture was concentrated, the residue was extracted with ethyl acetate and washed with water, 1N HCl and brine. The organic layer was dried over $Na_2SO_4$ and concentrated to give the desired compound as a yellow solid (410 mg, yield 75%).

A solution of 2,2,2-trifluoro-N-(4-(N-(1-hydroxy-1,3-dihydrobenzo[c][1,2]oxaborol-6-yl)sulfamoyl)-3-((5-propyl-1,3,4-oxadiazol-2-yl)methyl)phenyl)acetamide (390 mg, 0.74 mmol) in 7M ammonium in MeOH (10 mL) was stirred in a sealed tube at 50° C. for 4 hours. After concentrated, the crude mixture was purified by prep HPLC (SunFire Prep C18 OBD 5 uM 30×50 mm column) to give the title compound as a yellow solid (195 mg, yield 62%). MS calcd for ($C_{19}H_{21}BN_4O_5S$): 428.3. MS found (ESI negative): (M−H)$^-$=427.1. $^1$H NMR (DMSO-d$_6$) δ (ppm): 10.0 (s, 1H), 9.12 (bs, 1H), 7.51 (d, J=8.4 Hz, 1H), 7.37 (s, 1H), 7.17 (d, J=8.0 Hz, 1H), 7.05 (d, J=8.4 Hz, 1H), 6.36 (d, J=8.8 Hz, 1H), 6.21 (s, 1H), 4.80 (s, 2H), 4.37 (s, 2H), 2.65 (q, 2H), 1.55 (m, 2H), 0.83 (t, 3H).

4-Amino-N-(1-hydroxy-1,3-dihydrobenzo[c][1,2]oxaborol-6-yl)-2-((3-methyl-1,2,4-oxadiazol-5-yl)methyl)benzenesulfonamide 6-Amino-2-(6-(1-hydroxy-1,3-dihydrobenzo[c][1,2]oxaborole)-1,1-dioxide-2H-1,2-benzothiazin-3(4H)-one

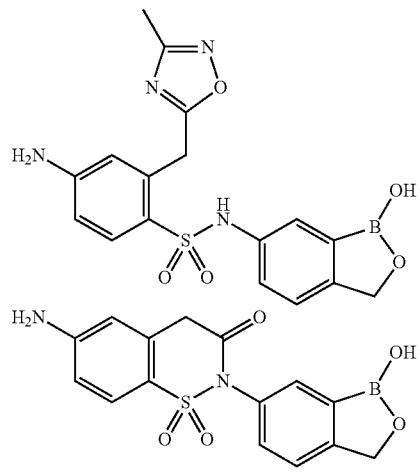

To a stirred solution of 2-(5-amino-2-(N-(1-hydroxy-1,3-dihydrobenzo[c][1,2]oxaborol-6-yl)sulfamoyl)phenyl)acetic acid (1.0 g, 2.76 mmol) and (E)-N'-hydroxyacetimidamide (490 mg, 6.62 mmol) in 10 mL of DMF was added EDC (1.27 g, 6.62 mmol) and HOBt (894 mg, 6.62 mmol). The reaction mixture was stirred for 3 hours. After water was added, the reaction mixture was extracted with ethyl acetate and washed with water, 1N HCl and brine. The organic layer was dried over $Na_2SO_4$ and concentrated. The residue was purified by ISCO CombiFlash Rf silica chromatography eluted with 0-60% MeOH in dichloromethane to give the desired compound as a yellow residue (50 mg, yield 4%).

A solution of (Z)—N'-(2-(5-amino-2-(N-(1-hydroxy-1,3-dihydrobenzo[c][1,2]oxaborol-6-yl)sulfamoyl)phenyl)acetoxy)acetimidamide (50 mg, 0.12 mmol) in 1 mL of DMF was stirred at 140° C. for 30 min. The crude mixture was purified by prep HPLC (SunFire Prep C18 OBD 5 uM 30×50 mm column) to give the desired compound as a yellow solid (6 mg, yield 13%), and cyclized product (5 mg, yield 12%).

4-Amino-N-(1-hydroxy-1,3-dihydrobenzo[c][1,2]oxaborol-6-yl)-2-((3-methyl-1,2,4-oxadiazol-5-yl)methyl)benzenesulfonamide: MS calcd for ($C_{17}H_{17}BN_4O_5S$): 400.2. MS found (ESI negative): (M−H)$^-$=399.1. $^1$H NMR (DMSO-d$_6$) δ (ppm): 10.0 (s, 1H), 9.18 (bs, 1H), 7.53 (d, J=8.8 Hz, 1H), 7.40 (s, 1H), 7.21 (d, J=8.4 Hz, 1H), 7.07 (d, J=8.4 Hz, 1H), 6.43 (d, J=8.4 Hz, 1H), 6.37 (s, 1H), 4.85 (s, 2H), 4.46 (s, 2H), 2.23 (s, 3H)

6-Amino-2-(6-(1-hydroxy-1,3-dihydrobenzo[c][1,2]oxaborole)-1,1-dioxide-2H-1,2-benzothiazin-3(4H)-one: MS calcd for ($C_{15}H_{13}BN_2O_5S$): 344.2. MS found (ESI negative): (M−H)$^-$=343.1. $^1$H NMR (DMSO-d$_6$) δ (ppm): 9.18 (bs, 1H), 7.61 (s, 1H), 7.52-7.61 (m, 2H), 7.31 (d, J=8.0 Hz, 1H), 6.62-6.66 (m, 2H), 6.38 (bs, 1H), 5.05 (s, 2H), 4.18 (s, 2H).

2,2,2-Trifluoro-N-(4-(N-(1-hydroxy-1,3-dihydrobenzo[c][1,2]oxaborol-6-yl)sulfamoyl)-3-((5-methyl-1,2,4-oxadiazol-3-yl)methyl)phenyl)acetamide and 4-Amino-N-(1-hydroxy-1,3-dihydrobenzo[c][1,2]oxaborol-6-yl)-2-((5-methyl-1,2,4-oxadiazol-3-yl)methyl)benzenesulfonamide

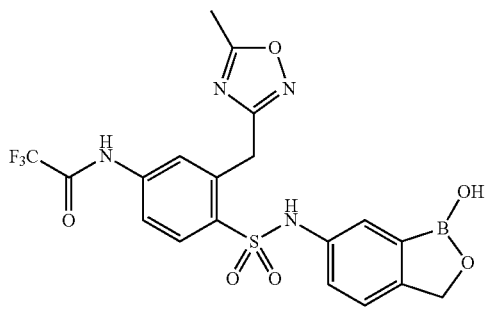

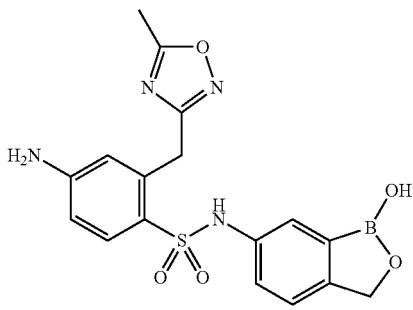

To a stirred solution of hydroxylamine hydrochloride (10.7 g, 154 mmol) in 25 mL of DMSO was added 25% NaOMe methanol solution dropwise. Subsequently, 2-(3-nitrophenyl)acetonitrile (5.0 g, 30.8 mmol) in 25 mL of DMSO was added slowly. The reaction mixture was stirred at 100° C. for 4 hours. After cooled down, water was added. The reaction mixture was extracted with ethyl acetate and washed with brine. The organic layer was dried over $Na_2SO_4$ and concentrated to give the desired compound as a brown residue (5.1 g, yield 85%).

To a stirred solution of (Z)—N'-hydroxy-2-(3-nitrophenyl)acetimidamide (5.0 g, 25.6 mmol) in 50 mL of DMF was added acetyl chloride (20 mL). The reaction mixture was stirred at room temperature for 16 hours. After water was added, the reaction mixture was extracted with ethyl acetate and washed with brine. The organic layer was dried over $Na_2SO_4$ and concentrated. The residue obtained was stirred at 150° C. for 16 hours. After the solvent was removed in vacuo, the residue was purified by ISCO CombiFlash Rf silica chromatography eluted with 0-40% ethyl acetate and hexane to a yellow residue. This residue was further purified by prep HPLC (SunFire Prep C18 OBD 5 uM 30×50 mm column) to give the title compound as a white solid (1.1 g, yield 18%).

To a stirred solution of 5-methyl-3-(3-nitrobenzyl)-1,2,4-oxadiazole (1.0 g, 4.6 mmol) in 40 mL of THF was added Lindlar catalyst (0.7 g). The flask was evacuated quickly and filled with hydrogen three times. A hydrogen balloon was then placed on the reaction flask. The reaction mixture was allowed to stir at room temperature under hydrogen for 4 hours. After the mixture was filtered through a pad of Celite, the reaction was concentrated in vacuo to give a yellow residue that was used directly for the next step. To a stirred solution of 3-((5-methyl-1,2,4-oxadiazol-3-yl)methyl)aniline and TEA (1.9 mL, 13.7 mmol) in 30 mL of $CH_2Cl_2$ was added 2,2,2-trifluoroacetic anhydride (1.3 mL, 9.1 mmol) dropwise. The reaction mixture was stirred at room temperature for 2 hours. After the mixture was concentrated, the residue was purified by ISCO CombiFlash Rf silica chromatography eluted with 0-40% ethyl acetate in hexane to give the desired compound as a yellow solid (0.8 g, yield 62%).

2,2,2-trifluoro-N-(3-((5-methyl-1,2,4-oxadiazol-3-yl)methyl)phenyl)acetamide (0.8 g, 2.8 mmol) was mixed with chlorosulfonic acid (3 mL) at 0° C., and the mixture was stirred at room temperature for 3 hours. As the starting material was consumed as indicated by LC/MS, the mixture was added dropwise to ice-water. The mixture was extracted with dichloromethane. The organic layer was dried over $Na_2SO_4$ and concentrated to give the desired product as a yellow residue (490 mg, yield 46%).

To a stirred solution of 2-((5-methyl-1,2,4-oxadiazol-3-yl)methyl)-4-(2,2,2-trifluoroacetamido)benzene-1-sulfonyl chloride (490 mg, 1.3 mmol) and 6-aminobenzo[c][1,2]oxaborol-1(3H)-ol (627 mg, 4.21 mmol) in 10 mL of ACN was added pyridine (680 uL, 8.4 mmol) dropwise. The reaction mixture was stirred at room temperature for 3 hours. After the mixture was concentrated, the residue was extracted with ethyl acetate and washed with water, 1N HCl and brine. The organic layer was dried over $Na_2SO_4$ and concentrated to give the desired compound as a yellow residue (555 mg, yield 88%). A small portion of the crude mixture was purified by prep HPLC (SunFire Prep C18 OBD 5 uM 30×50 mm column) to give the title compound as a yellow solid.

2,2,2-Trifluoro-N-(4-(N-(1-hydroxy-1,3-dihydrobenzo[c][1,2]oxaborol-6-yl)sulfamoyl)-3-((5-methyl-1,2,4-oxadiazol-3-yl)methyl)phenyl)acetamide MS calcd for ($C_{19}H_{16}BN_4O_6F_3S$): 496.2. MS found (ESI negative): (M−H)⁻=495.1. $^1$H NMR (DMSO-$d_6$) δ (ppm): 11.5 (s, 1H), 10.5 (s, 1H), 9.20 (bs, 1H), 7.93 (d, J=8.8 Hz, 1H), 7.80 (s, J=8.4 Hz, 1H), 7.59 (s, 1H), 7.44 (s, 1H), 7.25 (d, J=8.0 Hz, 1H), 7.12 (d, J=8.0 Hz, 1H), 4.86 (s, 2H), 4.59 (s, 2H), 2.40 (s, 3H)

A solution of 2,2,2-trifluoro-N-(4-(N-(1-hydroxy-1,3-dihydrobenzo[c][1,2]oxaborol-6-yl)sulfamoyl)-3-(oxazol-2-ylmethyl)phenyl)acetamide (510 mg, 1.03 mmol) in 7M ammonium in MeOH (10 mL) was stirred in a sealed tube at 50° C. for 3 hours. After concentrated, the crude mixture was purified by prep HPLC (SunFire Prep C18 OBD 5 uM 30×50 mm column) to give the title compound as a yellow solid (284 mg, yield 69%).

4-Amino-N-(1-hydroxy-1,3-dihydrobenzo[c][1,2]oxaborol-6-yl)-2-((5-methyl-1,2,4-oxadiazol-3-yl)methyl)benzenesulfonamide MS calcd for ($C_{17}H_{17}BN_4O_5S$): 400.2. MS found (ESI negative): (M−H)⁻=399.1. $^1$H NMR (DMSO-$d_6$) δ (ppm): 11.4 (s, 1H), 10.4 (s, 1H), 9.16 (bs, 1H), 7.87 (d, J=8.8 Hz, 1H), 7.72 (s, J=8.8 Hz, 1H), 7.48 (s, 1H), 7.40 (s, 1H), 7.19 (d, J=8.0 Hz, 1H), 7.09 (d, J=8.4 Hz, 1H), 4.81 (s, 2H), 4.40 (s, 2H), 2.47 (s, 3H).

4-Amino-2-((3-ethyl-1,2,4-oxadiazol-5-yl)methyl)-N-(1-hydroxy-1,3-dihydrobenzo[c][1,2]oxaborol-6-yl)benzenesulfonamide

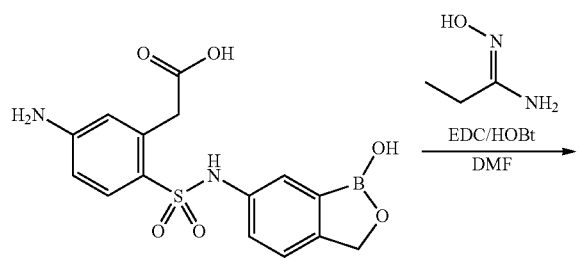

dried over $Na_2SO_4$ and concentrated. The residue was purified by prep HPLC (SunFire Prep C18 OBD 5 uM 30×50 mm column) to give the title compound as a yellow solid (6 mg, yield 13%), and cyclized product (7 mg, yield 1%). 4-Amino-N-(1-hydroxy-1,3-dihydrobenzo[c][1,2]oxaborol-6-yl)-2-((3-ethyl-1,2,4-oxadiazol-5-yl)methyl)benzenesulfonamide: MS calcd for ($C_{18}H_{19}BN_4O_5S$): 414.24. MS found (ESI negative): (M–H)⁻=413.1. ¹H NMR (DMSO-$d_6$) δ (ppm): 10.0 (s, 1H), 9.18 (bs, 1H), 7.55 (d, J=8.8 Hz, 1H), 7.41 (s, 1H), 7.22 (d, J=8 Hz, 1H), 7.08 (dd, J=8, 2 Hz, 1H), 6.45 (dd, J=8.8, 2 Hz, 1H, 6.39 (d, J=3 Hz, 1H), 4.86 (s, 2H), 4.48 (s, 2H), 2.63 (q, J=7.6 Hz 2H), 1.17 (t, J=7.6 Hz, 3H).

4-Amino-2-(furan-2-yl)-N-(1-hydroxy-1,3-dihydrobenzo[c][1,2]oxaborol-6-yl)benzenesulfonamide

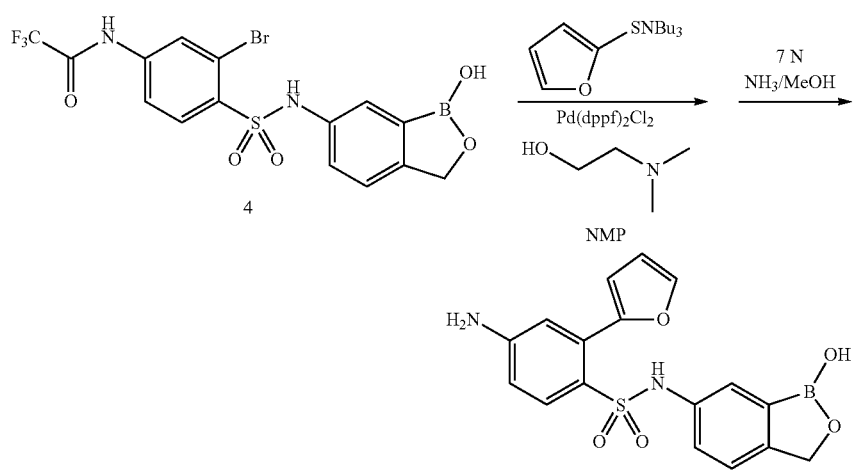

-continued

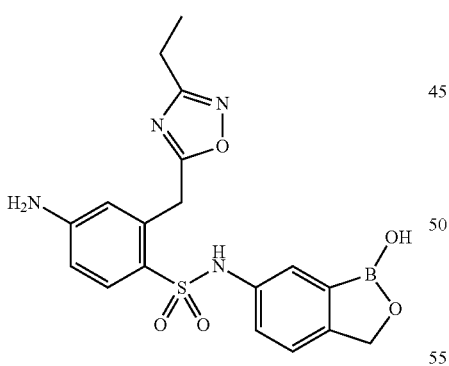

To a stirred solution of 2-(5-amino-2-(N-(1-hydroxy-1,3-dihydrobenzo [c][1,2]oxaborol-6-yl)sulfamoyl)phenyl)acetic acid (0.5 g, 1.4 mmol) and (E)-N'-hydroxypropionimidamide (0.19 mL, 2.1 mmol) in 10 mL of DMF was added EDC (0.5 g, 3.6 mmol) and HOBt (700 mg, 3.6 mmol). The reaction mixture was stirred for 24 hours. After water was added, the reaction mixture was extracted with ethyl acetate and washed with water, 1N HCl and brine. The organic layer was 4-Amino-2-(furan-2-yl)-N-(1-hydroxy-1,3-dihydrobenzo[c][1,2]oxaborol-6-yl)benzenesulfonamide was prepared in same procedure as in the synthesis of 4-amino-N-(1-hydroxy-1,3-dihydrobenzo[c][1,2]oxaborol-6-yl)-2-(2-ethoxyethyl)benzenesulfonamide. ¹H NMR (400 MHz, DMSO-$d_6$) δ (ppm): 9.48 (s, 1H), 7.70 (d, J=1.6 Hz, 1H), 7.54 (d, J=8.8 Hz, 1H), 7.31 (d, J=2.0 Hz, 1H), 7.14 (d, J=8.0 Hz, 1H), 6.99 (dd, J=2.0, 8.0 Hz, 1H), 6.81 (d, J=3.6 Hz, 1H), 6.67 (d, J=2.0 Hz, 1H), 6.51 (dd, J=2.0, 3.2 Hz, 1H), 6.42 (dd, J=2.4, 8.8 Hz, 1H), 4.79 (s, 2H). MS (ESI) m/z=369 (M–1).

2,4-Diamino-N-(1-hydroxy-1,3-dihydro-benzo[c][1,2]oxaborol-6-yl)-benzenesulfonamide hydrochloride

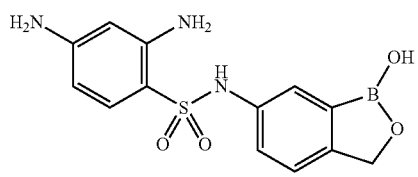 [SMILES: Nc1ccc(S(=O)(=O)Nc2ccc3c(c2)B(O)OC3)c(N)c1]

N-(1-Hydroxy-1,3-dihydro-benzo[c][1,2]oxaborol-6-yl)-2,4-dinitro-benzenesulfonamide General Procedure 1: 6-Amino-3H-benzo[c][1,2]oxaborol-1-ol (1.0 g, 6.7 mmol), 2,4-dinitrobenzenesulfonyl chloride (2.1 g, 8.0 mmol), NMM (2.9 mL, 26.8 mmol), and MeCN (20 mL) at rt O/N. The mixture was concentrated in vacuo. H₂O (5 mL) and EtOAc (25 mL) were added to the residue and the mixture was stirred until a clear biphasic solution was observed. The aqueous layer was loaded onto an Isolute HM-N column and left to stand for 10 min. The organic layer was then eluted through the column. The column was then further washed with EtOAc (20 mL). The organic fractions were concentrated in vacuo and the residue was dissolved in MeOH and loaded onto a pre-column (silica, 12 g). Purification by flash chromatography (20-100% EtOAc/hexane) gave a yellow solid; yield: 1.69 g (67%). Recrystallization from MeOH/MeCN/H₂O and then again from MeCN/H₂O gave the title compound as a yellow solid (20 mg). mp 149-150° C.; ¹H NMR (400 MHz, DMSO-d₆) δ (ppm): 11.01 (bs, 1H), 9.27 (s, 1H), 8.88-8.87 (m, 1H), 8.60-8.56 (m, 1H), 8.18-8.16 (m, 1H), 7.52-7.51 (m, 1H), 7.35-7.33 (m, 1H), 7.24-7.22 (m, 1H), 4.91 (s, 2H); MS (ESI) m/z=378 (M−1, negative); HPLC purity: 97.20% (MaxPlot 200-400 nm), 97.04% (220 nm).

2,4-Diamino-N-(1-hydroxy-1,3-dihydro-benzo[c][1,2]oxaborol-6-yl)-benzenesulfonamide hydrochloride A suspension of N-(1-hydroxy-1,3-dihydro-benzo[c][1,2]oxaborol-6-yl)-2,4-dinitro-benzenesulfonamide (1.6 g, 4.2 mmol), 10% Pd/C (500 mg), and abs. EtOH (150 mL) was shaken in a Parr apparatus at rt under an atmosphere of H₂ (50 psi) for 3 h. The mixture was filtered through Celite (washing with EtOH) and then a 0.2 μM filter. The filtrate was concentrated in vacuo at 40° C. and the residue was recrystallized (MeCN/H₂O) to give a brown solid. Prep HPLC of a portion of this material [30-70% MeCN/0.1% HCO₂H (aq)], followed by isolation of the major fraction by concentration in vacuo, addition of 1 M HCl, and lyophilization (2×) gave the title compound. ¹H NMR (400 MHz, DMSO-d₆) δ (ppm): 10.04 (s, 1H), 7.45-7.44 (m, 1H), 7.34-7.32 (m, 1H), 7.24-7.22 (m, 1H), 7.16-7.14 (m, 1H), 6.16 (s, 1H), 6.07-6.04 (m, 1H), 4.86 (s, 2H); MS (ESI) m/z=318 (M−1, negative); HPLC purity: 99.43% (MaxPlot 200-400 nm), 98.29% (220 nm).

2-(5-Amino-2-(N-(5-fluoro-1-hydroxy-1,3-dihydrobenzo[c][1,2]oxaborol-6-yl)sulfamoyl)phenyl)acetamide

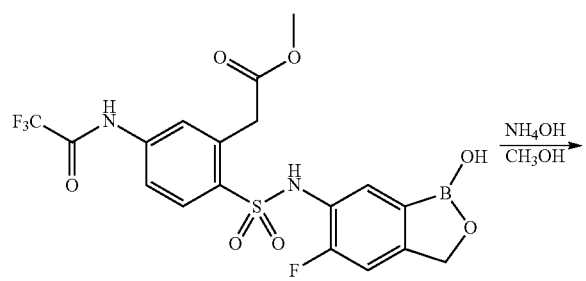

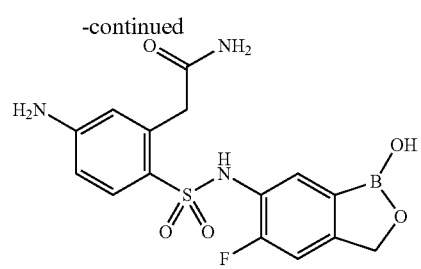

To the solution of methyl 2-(2-(N-(5-fluoro-1-hydroxy-1,3-dihydrobenzo[c][1,2]oxaborol-6-yl)sulfamoyl)-5-(2,2,2-trifluoroacetamido)phenyl)acetate (480 mg, 1 mmol) in methanol (5 ml), added ammonia hydroxide (2 ml), heated at 100° C. in a sealed tube overnight. The result mixture was concentrated, then dissolved in DMSO and purified by prep HPLC (SunFire Prep C18 OBD 5 uM 30×50 mm column). The title compound was obtained as yellow solid. MS calcd for (C₁₅H₁₅BN₃O₅FS): 379.17. MS found (ESI negative): (M−H)⁻=378.1. ¹H NMR (400 MHz, DMSO-d₆) δ (ppm): 9.64 (s, 1H), 9.20 (bs, 1H), 7.53 (d, J=8 Hz, 1H), 7.34 (s, 1H), 7.25 (d, J=8.8 Hz, 1H), 7.13 (d, J=10.4 Hz, 1H), 7.04 (s, 1H), 6.45 (d, J=2 Hz, 1H), 6.29 (dd, J=8.8 Hz, 1H), 4.82 (s, 2H).

4-Amino-2-(3-ethylureido)-N-(1-hydroxy-1,3-dihydrobenzo[c][1,2]oxaborol-6-yl)benzenesulfonamide

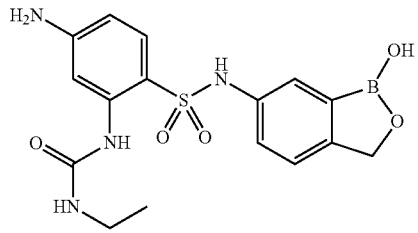 [SMILES: CCNC(=O)Nc1cc(N)ccc1S(=O)(=O)Nc1ccc2c(c1)B(O)OC2]

N-(1-hydroxy-1,3-dihydrobenzo[c][1,2]oxaborol-6-yl)-2,4-dinitrobenzenesulfonamide Using General Procedure 1: 6-amino-3H-benzo[c][1,2]oxaborol-1-ol (4.9 g, 32.6 mmol), 2,4-dinitro-benzenesulfonyl chloride (9.8 g, 36.8 mmol), pyridine (18 mL), methylene chloride (100 ml), 0° C.-rt, O/N. Purification: precipitation from hot H₂O. The title compound was recrystallized from ethyl acetate as a light-orange solid (9.5 g). ¹H NMR (400 MHz, DMSO-d₆) δ ppm 11.0 (s, 1H), 9.27 (s, 1H), 8.88 (d, Hz, 1H), 8.58 (dd, J=2.2, 8.6 Hz, 1H), 8.17 (d, J=8.6 Hz, 1H), 7.51 (d, Hz, 1H), 7.34 (d, J=8.3 Hz, 1H), (dd, J=1.9, 8.3 Hz, 1H), 4.91 (s, 2H); MS (ESI) m/z=378 (M−1, negative).

2,4-Diamino-N-(1-hydroxy-1,3-dihydrobenzo[c][1,2]oxaborol-6-yl)benzene sulfonamide To a solution of N-(1-hydroxy-1,3-dihydrobenzo[c][1,2]oxaborol-6-yl)-2,4-dinitrobenzenesulfonamide (0.43 g, 1.14 mmol) was added Raney-Ni (100 mg), following by degas and replacement of air with H₂. The reaction mixture was hydrogenated at room temperature for 2 hours. Once the reaction was completed (LC/MS), the mixture was filtered through Celite®. The filtrate was concentrated in vacuo to give a gummy material. The crude product was recrystallized in MeOH to give the title compound as an off-white solid (0.32 g). $^1$H NMR (400 MHz, DMSO-d$_6$) δ ppm 9.77 (s, 1H), 9.15 (s, 1H), 7.41 (s, 1H), 7.10~7.18 (m, 3H), 5.72~5.73 (m, 2H), 5.60 (s, 1H), 5.52 (s, 2H), 4.84 (s, 2H); MS (ESI) m/z=318 (M−1, negative); HPLC purity: 99.6% (MaxPlot 200-400 nm), 99.3% (220 nm).

4-Amino-2-(3-ethylureido)-N-(1-hydroxy-1,3-dihydrobenzo[c][1,2]oxaborol-6-yl)benzenesulfonamide To a solution of 2,4-diamino-N-(1-hydroxy-1,3-dihydrobenzo[c][1,2]oxaborol-6-yl)benzenesulfonamide (1.0 g, 3.13 mmol) in DMF (15 ml) was added isocyanatoethane (0.5 g, 7.0 mmol) dropwise at room temperature. The reaction mixture was stirred at room temperature overnight, diluted with ethyl acetate and washed with H$_2$O, brine. The organic fraction was then dried (MgSO$_4$) and concentrated in vacuo. The residue was purified by Prep-HPLC to give the title compound as a white powder (0.3 g). $^1$H NMR (400 MHz, DMSO-d$_6$) δ ppm 9.87 (s, 1H), 9.17 (s, 1H), 7.99 (s, 1H), 7.43 (d, J=1.6 Hz, 1H), 7.34 (d, J=2.0 Hz, 1H), 7.31 (d, J=8.4 Hz, 1H), 7.24 (d, J=8.0 Hz, 1H), 7.12 (dd, J=2.0, 8.4 Hz, 1H), 7.02 (t, J=5.2 Hz, 1H), 6.08 (dd, J=2.0, 8.4 Hz, 1H), 5.88 (s, 2H), 4.87 (s, 2H), 3.04~3.11 (m, 2H), 1.07 (t, J=7.2 Hz, 3H); MS (ESI) m/z=389 (M−1, negative); HPLC purity: 93.6% (MaxPlot 200-400 nm), 90.3% (220 nm).

Methyl 5-amino-2-(N-(1-hydroxy-1,3-dihydrobenzo [c][1,2]oxaborol-6-yl)sulfamoyl)phenylcarbamate

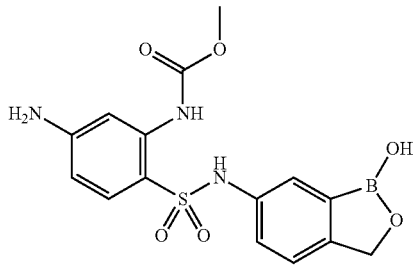 [SMILES: COC(=O)Nc1cc(N)ccc1S(=O)(=O)Nc1ccc2c(c1)B(O)OC2]

To the mixture of methyl 2-(3-aminophenyl)acetate (8 g, 50 mmol) and triethyl amino (7 ml, 50 mmol) in DCM (50 ml) at 0° C., added trifluoroacetic acid anhydride (6.95 ml, 50 mmol) slowly, stirred for 2 hours at rt after addition. Removed solvent, diluted with EtOAc, washed with water and brine, dried over Na$_2$SO$_4$. Concentrated to give light yellow solid used for next step without further purification.

The crude methyl 3-(2,2,2-trifluoroacetamido)phenylcarbamate (8.1 g, 31 mmol) was added to chlorosulphonyl acid (40 ml) at 0° C. in portion, stirred at rt after addition overnight. The reaction mixture was slowly poured onto ice/water under stirring, the result suspension was filtered and washed with cold water. Leave it for air dry. 6.7 g off white solid as product.

General procedure 1: 6-aminobenzo[c][1,2]oxaborol-1 (3H)-ol (1.5 g, 10 mmol), methyl 2-(chlorosulfonyl)-5-(2,2, 2-trifluoroacetamido)phenyl carbamate (3.6 g, 10 mmol), pyridine (0.9, 11 mmol), rt, 0.5 hour. Removed solvent, the crude (450 mg) was dissolved in MeOH (5 ml), treated with ammonia (2 ml, 7N in MeOH), heated at 100° C. for 2 hours in a sealed tube. After cooled down to rt, concentrated, the result solid was purified by prep HPLC (SunFire Prep C18 OBD 5 uM 30×50 mm column). The title compound was obtained as light yellow powder. MS calcd for (C$_{16}$H$_{17}$BN$_2$O$_6$S): 376.19. MS found (ESI negative): (M−H)$^-$=375.0. $^1$H NMR (400 MHz, DMSO-d$_6$) δ (ppm): 9.87 (s, 1H), 7.47 (d, J=8.4 Hz, 1H), 7.39 (d, J=2 Hz, 1H), 7.19 (d, J=8.4 Hz, 1H), 7.08 (dd, J=8 Hz, 1H), 6.40 (d, J=2.4 Hz, 1H), 6.38 (s, 1H), 4.84 (s, 2H), 3.86 (s, 2H), 3.54 (s, 3H).

Methyl 5-amino-2-(N-(5-fluoro-1-hydroxy-1,3-dihydrobenzo[c][1,2]oxaborol-6-yl)sulfamoyl)phenylcarbamate

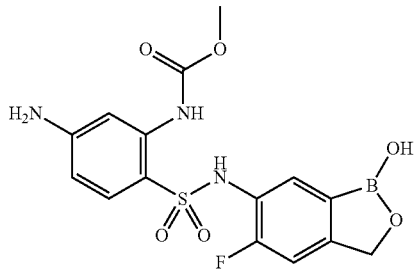 [SMILES: COC(=O)Nc1cc(N)ccc1S(=O)(=O)Nc1cc2c(cc1F)COB2O]

To the mixture of 2-chloro-5-nitroaniline (34.5 g, 0.2 mmol) and methyl chloroformate (19.4 ml, 0.25 mol) in THF (250 ml) under nitrogen, added NaH (5 g, 40% in mineral oil, 0.25 mol). Stirred at rt overnight. Quenched the reaction with water, removed solvent, extracted with EtOAc, washed with water and brine, dried over Na$_2$SO$_4$. Concentrated, the result solid was purified by flash chromatography with EtOAc and hexane (20%). Got methyl 2-chloro-5-nitrophenylcarbamate (17 g) as off white solid.

To the mixture of methyl 2-chloro-5-nitrophenylcarbamate (11.5 g, 50 mmol) and benzyl mercaptane (6.5 ml, 55 mmol) in DMF (150 ml), added potassium carbonate (16.6 g, 120 mmol). Heated at 90° C. for 12 hours. Removed solvent, extracted with EtOAc, washed with water and brine, dried over Na$_2$SO$_4$. Concentrated to get crude methyl 2-(benzylthio)-5-nitrophenylcarbamate as product.

To the solution of methyl 2-(benzylthio)-5-nitrophenylcarbamate (6.4 g, 20 mmol) in CCl$_4$ and water (55 ml, 10:1), bubbled chlorine gas for 10 minutes, then bubbled with nitrogen for another 10 minutes. Extracted with DCM, washed with water and brine, dried over Na$_2$SO$_4$. Concentrated to get methyl 2-(chlorosulfonyl)-5-nitrophenylcarbamate as light yellow oil.

General Procedure 1: 6-amino-5-fluorobenzo[c][1,2]oxaborol-1(3H)-ol (660 mg, 4 mmol), crude methyl 2-(chlorosulfonyl)-5-nitrophenylcarbamate (1.2 g, 4 mmol), pyridine (1.5 ml, 16 mmol), rt, 1 hour. Removed solvent and got the crude product as solid. The crude was dissolved in MeOH (25 ml), added Pd/C (1.5 g, 10 wt %), charged with hydrogen under 50 psi for 1 hour. Filtered through celite, concentrated, the residue was purified by prep HPLC (SunFire Prep C18 OBD 5 uM 30×50 mm column). The title compound (100 mg) was obtained as off white powder. MS calcd for (C$_{15}$H$_{15}$BFN$_3$O$_6$S): 395.08. MS found (ESI negative): (M−H)$^-$=394.1. $^1$H NMR (400 MHz, DMSO-d$_6$) δ (ppm): 9.16 (s, 1H), 7.59 (d, J=8 Hz, 1H), 7.27 (d, J=8.8 Hz, 1H), 7.20 (d, J=1.6 Hz, 1H), 7.10 (m, 1H), 6.15 (d, J=9.2 Hz, 1H), 5.78 (s, 2H), 4.84 (s, 2H), 3.57 (s, 3H).

Ethyl 5-amino-2-(N-(1-hydroxy-1,3-dihydrobenzo[c][1,2]oxaborol-6-yl)sulfamoyl)phenylcarbamate

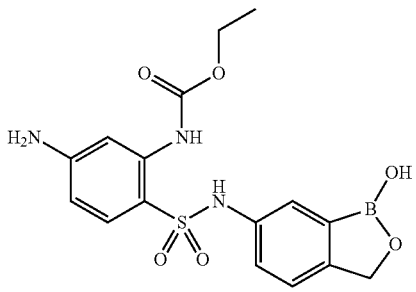 [SMILES: CCOC(=O)Nc1cc(N)ccc1S(=O)(=O)Nc1ccc2c(c1)B(O)OC2]

To the solution of 2-chloro-5-nitroaniline (17.3 g, 0.1 mol) in DCM (200 ml) at 0° C., added trifluoroacetic anhydride (13.9 ml, 0.1 mol), followed by triethyl amine (20.9 ml, 0.15 mol). Removed ice bath and stirred at rt for 1 hour. Washed with 1N HCl, water and brine, dried over $Na_2SO_4$. Concentrated to get crude N-(2-chloro-5-nitrophenyl)-2,2,2-trifluoroacetamide as light yellow solid.

To the mixture of N-(2-chloro-5-nitrophenyl)-2,2,2-trifluoroacetamide (13.4 g, 50 mmol) and benzyl mercaptane (5.9 ml, 50 mmol) in DMF (200 ml), added $K_2CO_3$ (27.6 g, 0.2 mol). Heated at 100° C. for 2 days. Removed most solvent, extracted with EtOAc, washed with 1N HCl, water and brine, dried over $Na_2SO_4$. Concentrated to get 17.5 g N-(2-(benzylthio)-5-nitrophenyl)-2,2,2-trifluoroacetamide as yellow solid.

To the solution of N-(2-(benzylthio)-5-nitrophenyl)-2,2,2-trifluoroacetamide (17.5 g, 49 mmol) in methanol (100 ml), added ammonia (15 ml, 7N in $CH_3OH$). The reaction was heated at 60° C. for 2 hours. Then concentrated, extracted with EtOAc, washed with water and brine, dried over $Na_2SO_4$. Concentrated to give 11.5 g 2-(benzylthio)-5-nitroaniline as product.

To the solution of 2-(benzylthio)-5-nitroaniline (2.61 g, 10 mmol) in DMF (10 ml), added ethyl chloroformate (1.05 ml, 1 1mmol), followed by DIPEA (2.1 ml, 12 mmol). Stirred for 4 hours. Diluted with EtOAc, washed with water and brine, dried over $Na_2SO_4$. Concentrated to give ethyl 2-(benzylthio)-5-nitrophenylcarbamate as product.

To the suspension of ethyl 2-(benzylthio)-5-nitrophenylcarbamate (662 mg, 2 mmol) in carbon tetrachloride and water (22 ml, 10:1), bubbled chlorine gas for 15 minutes. Then bubbled with nitrogen for 10 minutes. The result was extracted with DCM, washed with water and brine, dried over $Na_2SO_4$. Concentrated to get crude ethyl 2-(chlorosulfonyl)-5-nitrophenylcarbamate and used without further purification.

General procedure 1: 6-aminobenzo[c][1,2]oxaborol-1(3H)-ol (300 g, 2 mmol), ethyl 2-(chlorosulfonyl)-5-nitrophenylcarbamate, pyridine (0.3 ml, 4 mmol), rt, 1 hour. Removed solvent, the crude was dissolved in MeOH (20 ml), added Pd/C (0.5 g, 10 wt %), charged with hydrogen under 50 psi for 1 hour. Filtered through celite, concentrated, the residue was purified by prep HPLC (SunFire Prep C18 OBD 5 uM 30×50 mm column). The title compound (150 mg) was obtained as white powder. MS calcd for ($C_{16}H_{18}BN_3O_6S$): 391.10. MS found (ESI negative): $(M-H)^-$=390.1. $^1H$ NMR (400 MHz, DMSO-$d_6$) δ (ppm): 9.99 (s, 1H), 8.54 (s, 1H), 7.44 (d, J=2 Hz, 1H), 7.30 (d, J=8.8 Hz, 1H), 7.24 (m, 2H), 7.06 (dd, J=8.8 Hz, 1H), 6.17 (dd, J=8.8 Hz, 1H), 4.87 (s, 2H), 4.04 (q, J=14 Hz, 2H), 1.17 (t, J=7.2 Hz, 3H).

Ethyl 5-amino-2-(N-(5-fluoro-1-hydroxy-1,3-dihydrobenzo[c][1,2]oxaborol-6-yl)sulfamoyl)phenylcarbamate

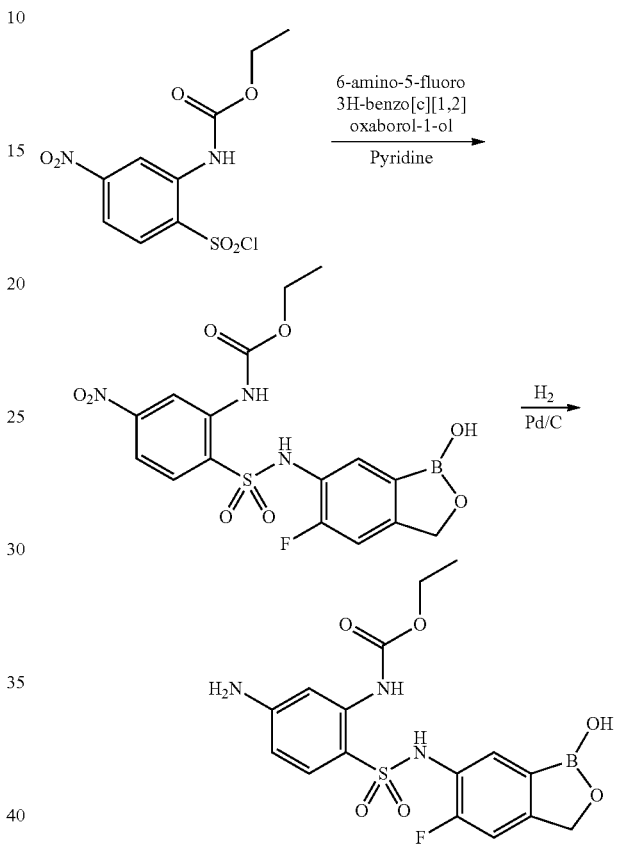

To a stirred solution of 6-amino-5-fluoro-3H-benzo[c][1,2]oxaborol-1-ol (0.4 g, 3 mmol) and pyridine (2 mL) in 10 mL of DCM was added ethyl 2-(chlorosulfonyl)-5-nitrophenylcarbamate (0.4 g, 2 mmol) in portion. The reaction mixture was stirred at room temperature for 3 hours. After the mixture was concentrated, the residue was extracted with ethyl acetate and washed with water, 1N HCl and brine. The organic layer was dried over $Na_2SO_4$ and concentrated to give the crude product as a yellow solid (150 mg).

To a stirred solution of ethyl 2-(N-(5-fluoro-1-hydroxy-1,3-dihydrobenzo[c][1,2]oxaborol-6-yl)sulfamoyl)-5-nitrophenylcarbamate (0.15 g, 0.34 mmol) in 10 mL of MeOH: EtOAc was added Pd/C (10 wt. % on activated carbon, 50 mg), followed by charging with hydrogen under 50 psi for 2 hour. The crude was filtered through celite, concentrated, the residue was purified by prep HPLC (SunFire Prep C18 OBD 5 uM 30×50 mm column) to give the title compound ethyl 5-amino-2-(N-(5-fluoro-1-hydroxy-1,3-dihydrobenzo[c][1,2]oxaborol-6-yl)sulfamoyl)phenylcarbamate as light yellow solid (114 mg). MS calcd for ($C_{16}H_{17}BFN_3O_6S$): 409.1. MS found (ESI negative): $(M-H)^-$=408.1. $^1H$ NMR (400 MHz, DMSO-$d_6$) δ (ppm): 9.84 (s, 1H), 9.30 (s, 1H), 8.49 (s, 1H), 7.65 (d, J=8 Hz, 1H), 7.24 (m, 2H), 7.20 (d, J=10 Hz, 1H), 6.18 (dd, J=8.8, 2 Hz, 1H), 6.09 (bs, 2H), 4.89 (s, 2H), 4.01 (q, J=7.2 Hz, 2H), 1.17 (t, J=7.2 Hz, 3H).

Isopropyl 5-amino-2-(N-(1-hydroxy-1,3-dihydrobenzo[c][1,2]oxaborol-6-yl)sulfamoyl)phenylcarbamate

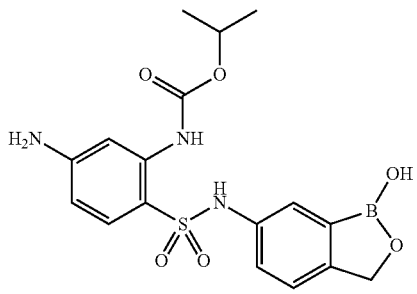 [SMILES: CC(C)OC(=O)Nc1cc(N)ccc1S(=O)(=O)Nc1ccc2c(c1)B(O)OC2]

To the mixture of 2-chloro-5-nitroaniline (8.6 g, 50 mmol) and isobutyl chloroformate (50 ml, 1M in toluene) in DCM (200 ml), added N-methyl morpholine (6.6 ml, 60 mmol). Heated to reflux for 2 days. Removed solvent, extracted with EtOAc, washed with water and brine, dried over $Na_2SO_4$. Concentrated, the result solid was purified by flash chromatography with EtOAc and hexane (20%). Got 1.3 g isopropyl 2-chloro-5-nitrophenylcarbamate as an off white solid.

To the mixture of isopropyl 2-chloro-5-nitrophenylcarbamate (1.3 g, 5 mmol) and benzyl mercaptane (0.6 ml, 5 mmol) in DMF (15 ml), added potassium carbonate (2.1 g, 15 mmol). Heated at 90° C. for 12 hours. Removed solvent, extracted with EtOAc, washed with water and brine, dried over $Na_2SO_4$. Concentrated to get crude isopropyl 2-(benzylthio)-5-nitrophenylcarbamate (1.2 g) as product.

To the solution of isopropyl 2-(benzylthio)-5-nitrophenylcarbamate (1.2 g, 0.35 mmol) in $CCl_4$ and water (11 ml, 10:1), bubbled chlorine gas for 10 minutes, the bubbled with nitrogen for another 10 minutes. Extracted with DCM, washed with water and brine, dried over $Na_2SO_4$. Concentrated to get isopropyl 2-(chlorosulfonyl)-5-nitrophenylcarbamate as light yellow oil.

General Procedure 1: 6-aminobenzo[c][1,2]oxaborol-1(3H)-ol (75 mg, 0.5 mmol), isopropyl 2-(chlorosulfonyl)-5-nitrophenylcarbamate (160 mg, 0.5 mmol), pyridine (0.2 ml, 2 mmol), rt, 1 hour. Removed solvent and got the crude product as solid. The crude was dissolved in MeOH (15 ml), added Pd/C (0.5 g, 10 wt %), charged with hydrogen under 50 psi for 1 hour. Filtered through celite, concentrated, the residue was purified by prep HPLC (SunFire Prep C18 OBD 5 uM 30×50 mm column). The title compound (70 mg) was obtained as white powder. MS calcd for ($C_{17}H_{20}BN_3O_6S$): 405.12. MS found (ESI negative): (M-H)$^-$=404.1. $^1$H NMR (400 MHz, DMSO-$d_6$) δ (ppm): 10.01 (s, 1H), 8.52 (s, 1H), 7.43 (d, J=2 Hz, 1H), 7.31~7.23 (m, 3H), 7.08 (dd, J=8 Hz, 1H), 6.40 (dd, J=8.4 Hz, 1H), 4.86 (s, 2H), 4.78 (m, 1H), 1.21 (d, J=6 Hz, 6H).

Isopropyl 5-amino-2-(N-(5-fluoro-1-hydroxy-1,3-dihydrobenzo[c][1,2]oxaborol-6-yl)sulfamoyl)phenylcarbamate

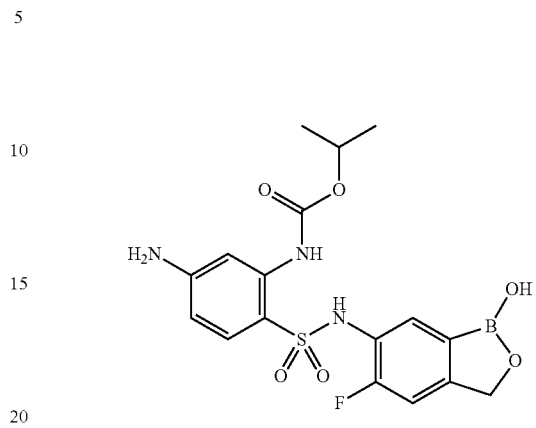

To the mixture of 2-chloro-5-nitroaniline (8.6 g, 50 mmol) and isobutyl chloroformate (50 ml, 1M in toluene) in DCM (200 ml), added N-methyl morpholine (6.6 ml, 60 mmol). Heated to reflux for 2 days. Removed solvent, extracted with EtOAc, washed with water and brine, dried over $Na_2SO_4$. Concentrated, the result solid was purified by flash chromatography with EtOAc and hexane (20%). Got 1.3 g isopropyl 2-chloro-5-nitrophenylcarbamate as off white solid.

To the mixture of isopropyl 2-chloro-5-nitrophenylcarbamate (1.3 g, 5 mmol) and benzyl mercaptane (0.6 ml, 5 mmol) in DMF (15 ml), added potassium carbonate (2.1 g, 15 mmol). Heated at 90° C. for 12 hours. Removed solvent, extracted with EtOAc, washed with water and brine, dried over $Na_2SO_4$. Concentrated to get crude isopropyl 2-(benzylthio)-5-nitrophenylcarbamate (1.2 g) as product.

To the solution of isopropyl 2-(benzylthio)-5-nitrophenylcarbamate (1.2 g, 0.35 mmol) in $CCl_4$ and water (11 ml, 10:1), bubbled chlorine gas for 10 minutes, the bubbled with nitrogen for another 10 minutes. Extracted with DCM, washed with water and brine, dried over $Na_2SO_4$. Concentrated to get isopropyl 2-(chlorosulfonyl)-5-nitrophenylcarbamate as light yellow oil.

General Procedure 1: 6-amino-5-fluorobenzo[c][1,2]oxaborol-1(3H)-ol (84 mg, 0.5 mmol), isopropyl 2-(chlorosulfonyl)-5-nitrophenylcarbamate (160 mg, 0.5 mmol), pyridine (0.2 ml, 2 mmol), rt, 1 hour. Removed solvent and got the crude product as solid. The crude was dissolved in MeOH (15 ml), added Pd/C (0.5 g, 10 wt %), charged with hydrogen under 50 psi for 1 hour. Filtered through celite, concentrated, the residue was purified by prep HPLC (SunFire Prep C18 OBD 5 uM 30×50 mm column). The title compound (70 mg) was obtained as white powder. MS calcd for ($C_{17}H_{19}BFN_3O_6S$): 423.11. MS found (ESI negative): (M-H)$^-$=422.0. $^1$H NMR (400 MHz, DMSO-$d_6$) δ (ppm): 9.82 (s, 1H), 8.46 (s, 1H), 7.63 (d, J=8 Hz, 1H), 7.29 (d, J=2 Hz, 1H), 7.24 (d, J=8.8 Hz, 1H), 7.19 (d, J=10 Hz, 1H), 6.17 (dd, J=8.4 Hz, 1H), 4.87 (s, 2H), 4.74 (m, 1H), 1.17 (d, J=6.4 Hz, 6H).

N-(5-Amino-2-(N-(1-hydroxy-1,3-dihydrobenzo[c][1,2]oxaborol-6-yl)sulfamoyl)phenyl)-2,2,2-trifluoroacetamide

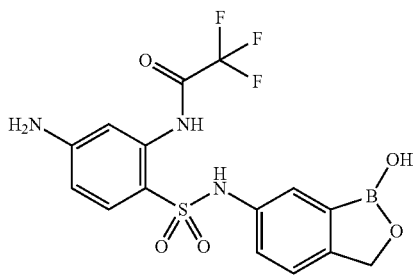 [SMILES: Nc1ccc(S(=O)(=O)Nc2ccc3c(c2)B(O)OC3)c(NC(=O)C(F)(F)F)c1]

To the mixture of 2-chloro-5-nitroaniline (17.3 g, 100 mmol) and trifluoroacetic anhydride (13.9 ml, 100 ml) in DCM (200 ml) at 0° C., added triethyl amine (20.9 ml, 150 mmol). The temperature was raised to rt after addition, stirring was kept for 1 hour. Removed solvent, extracted with EtOAc, washed with water and brine, dried over $Na_2SO_4$. Concentrated, the result solid was used for next step without further purification.

To the mixture of isopropyl N-(2-chloro-5-nitrophenyl)-2,2,2-trifluoroacetamide (13.4 g, 50 mmol) and benzyl mercaptane (5.9 ml, 50 mmol) in DMF (200 ml), added potassium carbonate (27.6 g, 200 mmol). Heated at 90° C. for 12 hours. Removed solvent, extracted with EtOAc, washed with water and brine, dried over $Na_2SO_4$. Concentrated to get crude N-(2-(benzylthio)-5-nitrophenyl)-2,2,2-trifluoroacetamide (17.5 g) as yellow solid.

To the solution of N-(2-(benzylthio)-5-nitrophenyl)-2,2,2-trifluoroacetamide (10.7 g, 30 mmol) in $CCl_4$ and water (150 ml, 5:1), bubbled chlorine gas for 15 minutes, the bubbled with nitrogen for another 10 minutes. Extracted with DCM, washed with water and brine, dried over $Na_2SO_4$. Concentrated to get 4-nitro-2-(2,2,2-trifluoroacetamido)benzene-1-sulfonyl chloride as orange oil.

General Procedure 1: 6-aminobenzo[c][1,2]oxaborol-1(3H)-ol (2.98 g, 20 mmol), 4-nitro-2-(2,2,2-trifluoroacetamido)benzene-1-sulfonyl chloride (6.65 g, 20 mmol), pyridine (1.62 ml, 20 mmol), rt, 1 hour. Removed solvent and got the crude product as solid. The crude (230 mg, 0.5 mmol) was dissolved in MeOH (20 ml), added Pd/C (0.5 g, 10 wt %), charged with hydrogen under 50 psi for 1 hour. Filtered through celite, concentrated, the residue was purified by prep HPLC (SunFire Prep C18 OBD 5 uM 30×50 mm column). The title compound (103 mg) was obtained as white powder. MS calcd for ($C_{17}H_{20}BN_3O_6S$): 415.06. MS found (ESI negative): $(M-H)^- = 414.1$ Example 2

LeuRS IC50 Testing

Experiments were performed in 96-well microtiter plates, using 80 μL reaction mixtures containing 50 mM HEPES-KOH (pH 8.0), 30 mM $MgCl_2$ and 30 mM KCl, 13 μM [$^{14}$C]leucine (306 mCi/mmol, Perkin-Elmer), 15 uM total E. coli tRNA (Roche, Switzerland), 0.02% (w/v) BSA, 1 mM DTT, 0.2 pM LeuRs and 4 mM ATP at 30° C. Reactions were started by the addition of 4 mM ATP. After 7 minutes, reactions were quenched and tRNA was precipitated by the addition of 50 μL of 10% (w/v) TCA and transferred to 96-well nitrocellulose membrane filter plates (Millipore Multiscreen HTS, MSHAN4B50). Each well was then washed three times with 100 μL of 5% TCA. Filter plates were then dried under a heat lamp and the precipitated [$^{14}$C]leucine tRNA$^{Leu}$ were quantified by liquid scintillation counting using a Wallac MicroBeta Trilux model 1450 liquid scintillation counter (PerkinElmer, Waltham Mass.).

To determine the inhibitor concentration which reduces enzyme activity by 50% ($IC_{50}$), increasing concentrations of inhibitor were incubated with LeuRS enzyme, tRNA and leucine for 20 minutes. Reactions were initiated by the addition of 4 mM ATP and stopped after 7 minutes then precipitated and counted to quantify radioactivity.

Biochemical testing results for exemplary compounds of the invention are provided in FIG. 1.

Example 3

Antibacterial MIC Testing

All MIC testing of bacteria followed the Clinical and Laboratory Standards Institute (CLSI) guidelines for antimicrobial testing of aerobic bacteria (Methods for Dilution Antimicrobial Susceptibility Tests for Bacteria That Grow Aerobically; Approved Standard—Seventh Edition)(M07-A7) and anaerobic bacteria (Methods for Antimicrobial Susceptibility Testing of Anaerobic Bacteria; Approved Standard—Seventh Edition) (M11-A7).

Antibacterial MIC testing results for exemplary compounds of the invention are provided in FIG. 1.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound, or a salt thereof, having a structure which is

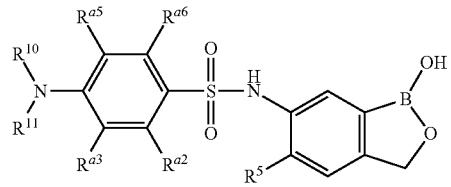

wherein $R^5$ is H or halogen,
one of $R^{a2}$, $R^{a3}$, $R^{a5}$ and $R^{a6}$ is —NHC(O)OR$^{30}$ or alkyl substituted with —C(O)OR$^{30}$ or alkyl substituted with —S(O)$_2$R$^{30}$ or alkyl substituted with halogen or alkyl substituted with hydroxy or alkyl substituted with cyano or alkyl substituted with —NHC(O)OR$^{30}$ or alkyl substituted with unsubstituted oxazolyl or alkyl substituted with alkyl substituted oxazolyl or alkyl substituted with unsubstituted oxadiazolyl or alkyl substituted with alkyl substituted oxadiazolyl or alkyl substituted with —C(O)NHR$^{35}$, wherein R$^{30}$ is unsubstituted alkyl and R$^{35}$ is unsubstituted alkyl or unsubstituted cycloalkyl,
and the remaining members of $R^{a2}$, $R^{a3}$, $R^{a5}$ and $R^{a6}$ are H, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl wherein each hydrogen in said compound, or a salt thereof, is independently H or D.

2. The compound of claim 1, having a structure which is

[Chemical structure diagram showing a benzenesulfonamide with $R^{10}$, $R^{11}$, $R^{a2}$, $R^5$ substituents connected to a benzoxaborole with OH group]

wherein $R^5$ is or halogen, $R^{a2}$ is —NHC(O)OR$^{30}$ or alkyl substituted with —C(O)OR$^{30}$ or alkyl substituted with —S(O)$_2$R$^{30}$ or alkyl substituted with halogen or alkyl substituted with hydroxy or alkyl substituted with cyano or alkyl substituted with —NHC(O)OR$^{30}$ or alkyl substituted with unsubstituted oxazolyl or alkyl substituted with alkyl substituted oxazolyl or alkyl substituted with unsubstituted oxadiazolyl or alkyl substituted with alkyl substituted oxadiazolyl or alkyl substituted with —C(O)NHR$^{35}$, wherein $R^{30}$ is unsubstituted alkyl and $R^{35}$ is unsubstituted alkyl or unsubstituted cycloalkyl, $R^{10}$ and $R^{11}$ are independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl wherein each hydrogen in said $R^{a2}$ or said $R^5$ is independently H or D.

3. The compound of claim 1, wherein $R^5$ is H.

4. The compound of claim 1, wherein $R^5$ is F.

5. The compound of claim 1, having a structure which is

[Chemical structure diagram showing H$_2$N-substituted benzenesulfonamide with $R^{a2}$, $R^5$ substituents connected to benzoxaborole with OH group]

6. The compound of claim 5, wherein $R^{a2}$ is CH$_2$NHC(O)OR$^{30}$ or CH$_2$C(O)OR$^{30}$ or CH$_2$S(O)$_2$R$^{30}$ or CH$_2$CN or CH$_2$C(O)NHR$^{35}$ or methyl substituted with unsubstituted oxazolyl or methyl substituted with alkyl substituted oxazolyl or methyl substituted with unsubstituted oxadiazolyl or methyl substituted with alkyl substituted oxadiazolyl, wherein $R^{30}$ is unsubstituted alkyl and $R^{35}$ is unsubstituted alkyl or unsubstituted cycloalkyl.

7. The compound of claim 6, wherein each hydrogen in said $R^{30}$ or said $R^{35}$ is independently H or D.

8. The compound of claim 6, wherein $R^{a2}$ is CH$_2$NHC(O)OR$^{30}$ or CH$_2$C(O)OR$^{30}$ or CH$_2$S(O)$_2$R$^{30}$, and $R^{30}$ is CH$_3$ or CH$_2$CH$_3$ or CH$_2$CH$_2$CH$_3$ or CH(CH$_3$)$_2$ or CH$_2$CH$_2$CH$_2$CH$_3$ or C(CH$_3$)$_3$ or C(CH$_3$)(CH$_2$CH$_3$)

wherein each hydrogen in said $R^{a2}$ is independently H or D.

9. The compound of claim 6, wherein $R^{a2}$ is CH$_2$NHC(O)OR$^{30}$ or CH$_2$C(O)OR$^{30}$ or CH$_2$S(O)$_2$R$^{30}$, and $R^{30}$ is CH$_3$ or CD$_2$H or CDH$_2$ or CH$_2$CH$_3$ or CH$_2$CD$_3$ or CH$_2$CD$_2$H or CH$_2$CDH$_2$ or CH$_2$CH$_2$CH$_3$ or CH$_2$CH$_2$CD$_3$ or CH$_2$CH$_2$CD$_2$H or CH$_2$CH$_2$CDH$_2$ or CH(CH$_3$)$_2$ or CH(CD$_3$)$_2$ or CH(CD$_3$)(CH$_3$) or CH$_2$CH$_2$CH$_2$CH$_3$ or CH$_2$CH$_2$CH$_2$CD$_3$ or CH$_2$CH$_2$CH$_2$CD$_2$H or CH$_2$CH$_2$CH$_2$CDH$_2$ or C(CH$_3$)$_3$ or C(CD$_3$)$_3$ or C(CD$_3$)(CH$_3$)$_2$ or C(CD$_3$)$_2$(CH$_3$) or CH(CH$_3$)(CH$_2$CH$_3$) or CH(CD$_3$)(CH$_2$CH$_3$) or CH(CH$_3$)(CH$_2$CD$_3$) or CH(CD$_3$)(CH$_2$CD$_3$).

10. The compound of claim 6, wherein $R^{a2}$ is CH$_2$NHC(O)OCH$_3$ or CH$_2$C(O)OCH$_3$ or CH$_2$S(O)$_2$CH$_3$.

11. The compound of claim 6, wherein $R^5$ is H and $R^{a2}$ is CH$_2$C(O)OR$^{30}$, and $R^{30}$ is CH$_3$ or CH$_2$CH$_3$ or CH$_2$CH$_2$CH$_3$ or CH(CH$_3$)$_2$ or CH$_2$CH$_2$CH$_2$CH$_3$ or C(CH$_3$)$_3$ or CH(CH$_3$)(CH$_2$CH$_3$), wherein each hydrogen in said $R^{a2}$ is independently H or D.

12. The compound of claim 6, wherein $R^5$ is H and $R^{a2}$ is CH$_2$C(O)OR$^{30}$, and $R^{30}$ is CH$_3$ or CD$_3$ or CD$_2$H or CDH$_2$ or CH$_2$CH$_3$ or CH$_2$CD$_3$ or CH$_2$CD$_2$H or CH$_2$CDH$_2$.

13. The compound of claim 1, wherein $R^{a2}$ is CH$_2$C(O)NHR$^{35}$, wherein $R^{35}$ is cyclobutyl or cyclopentyl or cyclohexyl.

14. The compound of claim 1, wherein $R^{a2}$ is CH$_2$CH$_2$F or CH$_2$CH$_2$OH or —NHC(O)OR$^{30}$, wherein $R^{30}$ is methyl or ethyl or propyl or isopropyl or butyl or t-butyl or isobutyl.

15. The compound of claim 1, wherein $R^{2a}$ is methyl substituted with 4-methyloxazol-2-yl or methyl substituted with 5-methyloxazol-2-yl or methyl substituted with 5-propyl-1,3,4-oxadiazol-2-yl or methyl substituted with 5-methyl-1,3,4-oxadiazol-2-yl.

16. A combination comprising:
a) the compound of claim 1, or a pharmaceutically acceptable salt thereof; and
b) a therapeutically active agent.

17. A pharmaceutical formulation comprising:
a) the compound of claim 1 or the combination of claim 16, or a pharmaceutically acceptable salt thereof; and
b) a pharmaceutically acceptable excipient.

18. A method of killing or inhibiting the growth of a bacteria, said method comprising:
contacting said bacteria with an effective amount of the compound of claim 1 or the combination of claim 16, or a pharmaceutically acceptable salt thereof, thereby killing or inhibiting the growth of the bacteria.

19. A method of treating a bacterial infection comprising:
administering to an animal suffering from said infection an effective amount of the compound of claim 1, or a pharmaceutically acceptable salt thereof, thereby treating the bacterial infection.

20. The compound of claim 1, which is D,D,D-Methyl 2-(5-amino-2-(N-(1-hydroxy-1,3-dihydrobenzo[c][1,2]oxaborol-6-yl)sulfamoyl)phenyl)acetate.

21. The compound of claim 1, which is
4-Amino-N-(1-hydroxy-1,3-dihydrobenzo[c][1,2]oxaborol-6-yl)-2-(propylsulfonylmethyl)benzenesulfonamide;
4-Amino-2-(ethylsulfonylmethyl)-N-(1-hydroxy-1,3-dihydrobenzo[c][1,2]oxaborol-6-yl)benzenesulfonamide; or
4-Amino-N-(1-hydroxy-1,3-dihydrobenzo[c][1,2]oxaborol-6-yl)-2-(methylsulfonylmethyl)benzenesulfonamide.

22. The compound of claim 1, which is
Methyl 2-(5-amino-2-(N-(5-fluoro-1-hydroxy-1,3-dihydrobenzo[c][1,2]oxaborol-6-yl)sulfamoyl)phenyl)acetate;
Methyl 2-(5-amino-2-((1-hydroxy-1,3-dihydrobenzo[c][1,2]oxaborol-6-yl)methylsulfonyl)phenyl)acetate;
Isopropyl 2-(5-amino-2-(N-(1-hydroxy-1,3-dihydrobenzo[c][1,2]oxaborol-6-yl)sulfamoyl)phenyl)acetate;

Ethyl 2-(5-amino-2-(N-(5-fluoro-1-hydroxy-1,3-dihydrobenzo[c][1,2]oxaborol-6-yl)sulfamoyl)phenyl)acetate;
Ethyl 2-(5-amino-2-(N-(1-hydroxy-1,3-dihydrobenzo[c][1,2]oxaborol-6-yl)sulfamoyl)phenyl)acetate; or
tert-Butyl 2-(5-amino-2-(N-(1-hydroxy-1,3-dihydrobenzo[c][1,2]oxaborol-6-yl)sulfamoyl)phenyl)acetate.

23. The compound of claim 1, which is
Methyl-amino-2-(N-(1-hydroxy-1,3-dihydrobenzo[c][1,2]oxaborol-6-yl)sulfamoyl)phenylcarbamate;
Isopropyl 5-amino-2-(N-(1-hydroxy-1,3-dihydrobenzo[c][1,2]oxaborol-6-yl)sulfamoyl)phenylcarbamate;
Ethyl 5-amino-2-(N-(1-hydroxy-1,3-dihydrobenzo[c][1,2]oxaborol-6-yl)sulfamoyl)phenylcarbamate;
Isopropyl 5-amino-2-(N-(1-hydroxy-1,3-dihydrobenzo[c][1,2]oxaborol-6-yl)sulfamoyl)benzylcarbamate;
Propyl 5-amino-2-(N-(1-hydroxy-1,3-dihydrobenzo[c][1,2]oxaborol-6-yl)sulfamoyl)benzylcarbamate;
Isopropyl 5-amino-2-(N-(5-fluoro-1-hydroxy-1,3-dihydrobenzo[c][1,2]oxaborol-6-yl)sulfamoyl)phenylcarbamate; or
Ethyl 5-amino-2-(N-(5-fluoro-1-hydroxy-1,3-dihydrobenzo[c][1,2]oxaborol-6-yl)sulfamoyl)phenylcarbamate.

24. The compound of claim 1, which is
4-Amino-N-(1-hydroxy-1,3-dihydrobenzo[c][1,2]oxaborol-6-yl)-2-((5-methyl-1,2,4-oxadiazol-3-yl)methyl)benzenesulfonamide;
4-Amino-N-(1-hydroxy-1,3-dihydrobenzo[c][1,2]oxaborol-6-yl)-2-(oxazol-2-ylmethyl)benzenesulfonamide;
4-Amino-N-(1-hydroxy-1,3-dihydrobenzo[c][1,2]oxaborol-6-yl)-2-((5-methyloxazol-2-yl)methyl)benzenesulfonamide; or
4-Amino-N-(1-hydroxy-1,3-dihydrobenzo[c][1,2]oxaborol-6-yl)-2-((5-propyl-1,3,4-oxadiazol-2-yl)methyl)benzenesulfonamide.

25. The compound of claim 1, which is
4-Amino-2-(2-fluoroethyl)-N-(1-hydroxy-1,3-dihydrobenzo[c][1,2]oxaborol-6-yl)benzenesulfonamide;
4-Amino-N-(1 hydroxy-1,3-dihydrobenzo[c][1,2]oxaborol-6-yl)-2-(2-hydroxyethyl)benzenesulfonamide;
4-Amino-N-(5-fluoro-1-hydroxy-1,3-dihydrobenzo[c][1,2]oxaborol-6-yl)-2-(2-hydroxyethyl)benzenesulfonamide;
Isopropyl 5-amino-2-(N-(1-hydroxy-1,3-dihydrobenzo[c][1,2]oxaborol-6-yl)sulfamoyl)benzylcarbamate;
Propyl 5-amino-2-(N-(1-hydroxy-1,3-dihydrobenzo[c][1,2]oxaborol-6-yl)sulfamoyl)benzylcarbamate;
4-Amino-2-(cyanomethyl)-N-(1-hydroxy-1,3-dihydrobenzo[c][1,2]oxaborol-6-yl)benzenesulfonamide;
Isobutyl 5-amino-2-(N-(1-hydroxy-1,3-dihydrobenzo[c][1,2]oxaborol-6-yl)sulfamoyl)benzylcarbamate;
2-(5-Amino-2-(N-(1-hydroxy-1,3-dihydrobenzo[c][1,2]oxaborol-6-yl)sulfamoyl)phenyl)-N-cyclopentylacetamide;
Methyl 5-amino-2-(N-(1-hydroxy-1,3-dihydrobenzo[c][1,2]oxaborol-6-yl)sulfamoyl)benzylcarbamate;
Ethyl 5-amino-2-(N-(1-hydroxy-1,3-dihydrobenzo[c][1,2]oxaborol-6-yl)sulfamoyl)benzylcarbamate;
2-(5-Amino-2-(N-(1-hydroxy-1,3-dihydrobenzo[c][1,2]oxaborol-6-yl)sulfamoyl)phenyl)-N-cyclobutylacetamide; or
2-(5-Amino-2-(N-(1-hydroxy-1,3-dihydrobenzo[c][1,2]oxaborol-6-yl)sulfamoyl)phenyl)-N-cyclohexylacetamide.

\* \* \* \* \*